(12) United States Patent
Chessari et al.

(10) Patent No.: US 8,530,469 B2
(45) Date of Patent: *Sep. 10, 2013

(54) THERAPEUTIC COMBINATIONS OF HYDROXYBENZAMIDE DERIVATIVES AS INHIBITORS OF HSP90

(75) Inventors: Gianni Chessari, Cambridge (GB); Miles Stuart Congreve, Cambridge (GB); Martyn Frederickson, Cambridge (GB); Christopher William Murray, Cambridge (GB); Eva Figueroa Navarro, Cambridge (GB); Alison Jo-Anne Woolford, Cambridge (GB); Maria Grazia Carr, Luton (GB); Robert Downham, Cambridge (GB); Michael Alistair O'Brien, Herts (GB); Theresa Rachel Phillips, Macclesfield (GB); Andrew James Woodhead, Cambridge (GB)

(73) Assignee: Astex Therapeutics Ltd., Cambridge (GB)

( * ) Notice: Subject to any disclaimer, the term of this patent is extended or adjusted under 35 U.S.C. 154(b) by 31 days.

This patent is subject to a terminal disclaimer.

(21) Appl. No.: 13/271,678

(22) Filed: Oct. 12, 2011

(65) Prior Publication Data
US 2012/0251545 A1 Oct. 4, 2012

Related U.S. Application Data

(60) Continuation of application No. 12/707,260, filed on Feb. 17, 2010, now abandoned, which is a division of application No. 11/680,805, filed on Mar. 1, 2007, now Pat. No. 7,700,625, which is a continuation of application No. PCT/GB2006/001382, filed on Apr. 13, 2006.

(60) Provisional application No. 60/777,989, filed on Mar. 1, 2006, provisional application No. 60/670,897, filed on Apr. 13, 2005.

(30) Foreign Application Priority Data

Apr. 13, 2005 (GB) .................................. 0507474.5
Mar. 1, 2006 (GB) .................................. 0604111.5

(51) Int. Cl.
| | | |
|---|---|---|
| A61K 31/4035 | (2006.01) |
| A61K 31/47 | (2006.01) |
| A61K 31/496 | (2006.01) |
| A61K 31/5377 | (2006.01) |
| C07D 209/04 | (2006.01) |
| C07D 215/00 | (2006.01) |
| C07D 217/00 | (2006.01) |
| C07D 227/00 | (2006.01) |
| C07D 241/00 | (2006.01) |
| C07D 265/30 | (2006.01) |
| C07D 401/02 | (2006.01) |
| C07D 471/00 | (2006.01) |

(52) U.S. Cl.
USPC ............... 514/235.2; 514/235.5; 514/253.01; 514/254.09; 514/278; 514/300; 514/302; 514/309; 514/312; 514/323; 514/416; 544/124; 544/144; 544/360; 544/373; 546/113; 546/115; 546/146; 546/16; 546/168; 546/19; 546/201; 548/470

(58) Field of Classification Search
None
See application file for complete search history.

(56) References Cited

U.S. PATENT DOCUMENTS
| | | |
|---|---|---|
| 4,582,909 A | 4/1986 | Butler et al. |
| 4,760,064 A | 7/1988 | Tominaga et al. |
| 5,310,951 A | 5/1994 | Djuric et al. |

(Continued)

FOREIGN PATENT DOCUMENTS
| | | |
|---|---|---|
| DE | 19955283 | 5/2001 |
| DE | 10 2004 049 078 | 4/2006 |

(Continued)

OTHER PUBLICATIONS

UK Patent Office Search Report for GB 0604111.5.

(Continued)

*Primary Examiner* — Kamal Saeed
*Assistant Examiner* — Nyeemah A Grazier
(74) *Attorney, Agent, or Firm* — Vedder Price P.C.; Thomas J. Kowalski; Samuel Megerditchian

(57) ABSTRACT

The invention provides a combination comprising an Hsp90 inhibitor compound of the formula (VII):

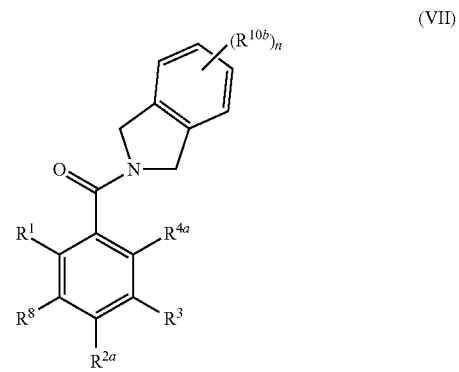

or tautomer or salt thereof and one or more therapeutic agents selected from topoisomerase I inhibitors; antimetabolites; tubulin targeting agents; DNA binder and topoisomerase II inhibitors; alkylating agents; monoclonal antibodies; antihormones; signal transduction inhibitors; proteasome inhibitors; DNA methyl transferases; cytokines; retinoids and HDAC or HAT modulators.

21 Claims, No Drawings

(56) References Cited

U.S. PATENT DOCUMENTS

| | | | |
|---|---|---|---|
| 5,332,735 | A | 7/1994 | Rault et al. |
| 6,469,024 | B2 | 10/2002 | Li et al. |
| 7,208,630 | B2 | 4/2007 | Blagg et al. |
| 7,229,986 | B2 | 6/2007 | Ishihara et al. |
| 7,425,633 | B2 | 9/2008 | Jiaang |
| 7,577,114 | B2 | 8/2009 | Hsieh |
| 7,700,625 | B2 | 4/2010 | Chessari et al. |
| 7,754,725 | B2 | 7/2010 | Chessari et al. |
| 8,101,648 | B2 | 1/2012 | Chessari |
| 8,106,057 | B2 | 1/2012 | Chessari et al. |
| 2003/0158177 | A1 | 8/2003 | Ishihara et al. |
| 2003/0203898 | A1 | 10/2003 | Haning et al. |
| 2004/0039038 | A1 | 2/2004 | Bernardon et al. |
| 2004/0253228 | A1 | 12/2004 | Srivastava et al. |
| 2004/0259877 | A1 | 12/2004 | Muto et al. |
| 2005/0037922 | A1 | 2/2005 | Bickers et al. |
| 2006/0019958 | A1 | 1/2006 | Muto et al. |
| 2006/0019961 | A1 | 1/2006 | Mahaney |
| 2006/0084647 | A1 | 4/2006 | Wang et al. |
| 2006/0089495 | A1 | 4/2006 | Blagg et al. |
| 2006/0100257 | A1 | 5/2006 | Muto et al. |
| 2006/0111409 | A1 | 5/2006 | Muto et al. |
| 2006/0122243 | A1 | 6/2006 | Muto et al. |
| 2006/0173188 | A1 | 8/2006 | Seki et al. |
| 2006/0178381 | A1 | 8/2006 | Jolidon et al. |
| 2006/0183902 | A1 | 8/2006 | Baxter et al. |
| 2007/0042997 | A1 | 2/2007 | Ital et al. |
| 2007/0184516 | A1 | 8/2007 | Maraheil et al. |
| 2007/0185059 | A1 | 8/2007 | Muto et al. |
| 2007/0259871 | A1 | 11/2007 | Chessari et al. |
| 2007/0265268 | A1 | 11/2007 | Kitamura et al. |
| 2008/0090880 | A1 | 4/2008 | Eggenweiler et al. |
| 2008/0306054 | A1 | 12/2008 | Chessari |
| 2009/0215742 | A1 | 8/2009 | Funk et al. |
| 2010/0092474 | A1* | 4/2010 | Gallagher et al. ......... 424/141.1 |
| 2010/0152184 | A1 | 6/2010 | Congreve et al. |
| 2010/0179145 | A1* | 7/2010 | Gallagher et al. ......... 514/235.2 |
| 2011/0105501 | A1* | 5/2011 | Gallagher et al. ......... 514/235.2 |

FOREIGN PATENT DOCUMENTS

| | | |
|---|---|---|
| EP | 347168 | 12/1989 |
| EP | 353753 | 2/1990 |
| EP | 0474403 | 3/1992 |
| EP | 0486386 | 5/1992 |
| EP | 0500336 | 8/1992 |
| EP | 0722723 | 7/1996 |
| EP | 1283199 | 2/2003 |
| EP | 1352650 | 10/2003 |
| EP | 1510207 | 3/2005 |
| EP | 1510210 | 3/2005 |
| EP | 1512396 | 3/2005 |
| EP | 1514544 | 3/2005 |
| EP | 1642880 | 4/2006 |
| EP | 1704856 | 9/2006 |
| EP | 1852112 | 11/2007 |
| JP | 49010506 | 1/1974 |
| JP | 09194450 | 7/1997 |
| WO | WO 91/08205 | 6/1991 |
| WO | WO 92/17467 | 10/1992 |
| WO | WO 97/26884 | 7/1997 |
| WO | WO 97/35999 | 10/1997 |
| WO | WO 97/36876 | 10/1997 |
| WO | WO 97/39750 | 10/1997 |
| WO | WO 97/47270 | 12/1997 |
| WO | WO 98/40385 | 9/1998 |
| WO | WO 98/45255 | 10/1998 |
| WO | WO 98/47885 | 10/1998 |
| WO | WO 98/50036 | 11/1998 |
| WO | WO 99/21422 | 5/1999 |
| WO | WO 99/29705 | 6/1999 |
| WO | WO 00/59867 | 10/2000 |
| WO | WO 01/36351 | 5/2001 |
| WO | WO 01/60369 | 8/2001 |
| WO | WO 01/87834 | 11/2001 |
| WO | WO 01/87887 | 11/2001 |
| WO | WO 01/90053 | 11/2001 |
| WO | WO 02/12210 | 2/2002 |
| WO | WO 02/18319 | 3/2002 |
| WO | WO 03/051877 | 6/2003 |
| WO | WO 03/053366 | 7/2003 |
| WO | WO 03/055860 | 7/2003 |
| WO | WO 03/086282 | 10/2003 |
| WO | WO 03/103665 | 12/2003 |
| WO | WO 2004/005295 | 1/2004 |
| WO | WO 2004/007501 | 1/2004 |
| WO | WO 2004/035571 | 4/2004 |
| WO | WO 2004/072051 | 8/2004 |
| WO | WO 2004/074283 | 9/2004 |
| WO | WO 2004/096757 | 11/2004 |
| WO | WO 2005/000300 | 1/2005 |
| WO | WO 2005/000839 | 1/2005 |
| WO | WO 2005/007151 | 1/2005 |
| WO | WO 2005/009940 | 2/2005 |
| WO | WO 2005/012297 | 2/2005 |
| WO | WO 2005/012541 | 2/2005 |
| WO | WO 2005/016889 | 2/2005 |
| WO | WO 2005/023818 | 3/2005 |
| WO | WO 2005/037214 | 4/2005 |
| WO | WO 2005/047249 | 5/2005 |
| WO | WO 2005/000778 | 6/2005 |
| WO | WO 2005/063222 | 7/2005 |
| WO | WO 2006/015123 | 2/2006 |
| WO | WO 2006/023778 | 3/2006 |
| WO | WO 2006/047740 | 5/2006 |
| WO | WO 2006/051808 | 5/2006 |
| WO | WO 2006/055760 | 5/2006 |
| WO | WO 2006/070195 | 7/2006 |
| WO | WO 2006/082001 | 8/2006 |
| WO | WO 2006/088193 | 8/2006 |
| WO | WO 2006/109085 | 10/2006 |
| WO | WO 2006/117669 | 11/2006 |
| WO | WO 2006/125119 | 11/2006 |
| WO | WO 2007/050124 | 5/2007 |
| WO | WO 2008/044027 | 4/2008 |
| WO | WO 2008/044029 | 4/2008 |
| WO | WO 2008/044034 | 4/2008 |
| WO | WO 2008/044041 | 4/2008 |
| WO | WO 2008/044045 | 4/2008 |
| WO | WO 2008/044054 | 4/2008 |
| WO | WO 2008/053319 | 5/2008 |

OTHER PUBLICATIONS

International Search Report for PCT/GB2006/001382.
Brown, Michael E. "Chapter 5: Thermoptometry", *Introduction to Thermal Analysis: Techniques and Applications, Second Edition*, Netherlands, 2001.
UK Patent Office Search Report for GB 0507474.5.
Bryn et al., Solid State Chemistry of Drugs, 2nd edition, 1999, pp. 233-247.
Chemical Abstracts, Accession No. 81:120448 (Abstract of JP 49010506, Mar. 11, 1994).
Y. Otani et al., "An Evaluation of Amide Group Planarity in 7-azabicyclo[2.2.1]Heptane Amids. Low Amide Bond Barrier in Solution." *J. Amer. Chem. Soc.*, 125(49), 15191-15199, 1983.
Golub et al., Molecular Classification of Cancer: Class Discovery and Class Prediction by Gene Expression Monitoring. Science. Oct. 15, 1999;286(5439):531-7.
Lala et al., Role of Nitric Oxide in Tumor Progression: Lessons From Experimental Tumors. Cancer Metastasis Rev. Mar. 1998:17 (1):91-106.
Mahaney et al., Synthesis and Activity of a New Class of Pathway-Selective Estrogen Receptor Ligands: Hydroxybenzoyl-3,4-dihydroquinoxalin-2(1H)-ones. Bioorg Med Chem. May 15, 2006;14(10):3455-66.
Madsen et al., Glucose-6-Phosphatase Catalytic Enzyme Inhibitors: Synthesis and In Vitro Evaluation of Novel 4,5,6,7-tetrahydrothieno[3,2-c]-and -[2,3c]pyridines. Bioorg Med Chem. Sep. 2000;8(9):2277-89.
Vippagunta et al., Adv. Drug Delivery Reviews (2001) vol. 48, p. 3-26.
Dymock, et al., Expert Opin. Ther. Patents (2004) vol. 14, p. 837-847.

Kubinyi et al., 3D QSAR in Drug Design: Ligand-Protein Interactions and Molecular Similarity, Springer (988)vol. 2-3, 800 pages, TOC and pp. 243-244 provided.
Bohonowych et al., Journal of Oncology, vol. 2010, pp. 1-17 (2010).
Stephen Neidle Ed,. Cancer Drug Design and Discovery, Elsevier/Academic Press, 2008, pp. 427-431.
Gura, Science, Nov. 7, 1997, vol. 278, No. 5340, pp. 1041-1042.
Roberts et al, JAMA, 292(17): 2130-2140 (2004).
Ju huai-qiang et al: "Synthesis and in vitro anti-HSV-1 activity of a novel Hsp90 inhibitor BJ-B11.", Bioorganic & Medicinal Chemistry Letters Mar. 15, 2011, vol. 21, No. 6, p. 1675-1677.
Galam, et al. Bioog. Med. Chem. (2007) vol. 15, p. 1939-1946.
Wermuth, The Practice of Medicinal Chemistry, 2d ed. (2003) 768 pages, Chapters 9-10 provided.
ABSTRACT: JP 9-221476: Hidenori, et al, Preparation and Formulation of Benzazepine Derivatives and analogs as Pharmaceuticals With Affinity for Vasopressin Receptors, STN Database Accession No. 127:248027.
Hunter et al., "Cdc37: a protein kinase chaperone?," Trends in Cell Biology, vol. 7, Apr. 1997, pp. 157-162.

* cited by examiner

THERAPEUTIC COMBINATIONS OF HYDROXYBENZAMIDE DERIVATIVES AS INHIBITORS OF HSP90

CROSS REFERENCE TO RELATED APPLICATIONS

This application is a continuation of U.S. Ser. No. 12/707,260 filed Feb. 17, 2010, now abandoned which is a divisional of U.S. Ser. No. 11/680,805, filed Mar. 1, 2007, now U.S. Pat. No. 7,700,625 which is a continuation of PCT International Application PCT/GB/2006/001382, filed Apr. 13, 2006, and published under PCT Article 21(2) in English as WO 2006/109085 on Oct. 19, 2006. PCT/GB/2006/001382 claimed benefit of priority from British application 0604111.5 and from U.S. Provisional application 60/777,989, both filed Mar. 1, 2006; and from British application 0507474.5 and from U.S. Provisional application 60/670,897, both filed Apr. 13, 2005. The entire contents of each of the prior applications are incorporated herein by reference.

FIELD OF THE INVENTION

This invention relates to compounds that inhibit or modulate the activity of the heat shock protein Hsp90, to the use of the compounds in the treatment or prophylaxis of disease states or conditions mediated by Hsp90, and to novel compounds having Hsp90 inhibitory or modulating activity. Also provided are pharmaceutical compositions containing the compounds and novel chemical intermediates.

BACKGROUND OF THE INVENTION

In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major form Hsp90α and minor form Hsp90β. Hsp90 binds proteins at a late stage of folding and is distinguished from other Hsps in that most of its protein substrates are involved in signal transduction. Hsp90 has a distinct ATP binding site, including a Bergerat fold characteristic of bacterial gyrase, topoisomerases and histidine kinases. It has been shown that ATP bound at the N-terminal pocket of Hsp90 is hydrolysed. This ATPase activity results in a conformational change in Hsp90 that is required to enable conformational changes in the client protein.

A dimerization domain and a second ATP binding site, which may regulate ATPase activity, is found near the c-terminus of Hsp90. Dimerization of HSP90 appears critical for ATP hydrolysis. Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind HSP90. A simplified model has emerged in which ATP binding to the amino terminal pocket alters Hsp90 conformation to allow association with a multichaperone complex. First the client protein is bound to an Hsp70/Hsp40 complex. This complex then associates with Hsp90 via Hop. When ADP is replaced by ATP, the conformation of Hsp90 is altered, Hop and Hsp70 are released and a different set of co-chaperones is recruited including p50cdc37 and p23. ATP hydrolysis results in the release of these co-chaperones and the client protein from the mature complex. Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al., 1997. J Biol. Chem., 272: 23834-23850).

Despite Hsp90 being ubiquitously expressed, GA has a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec *J. Med. Chem.* 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

There is some evidence that Hsp90 is found primarily within "activated" multichaperone complexes in the tumour cells as opposed to "latent" complexes in normal cells. One component of the multichaperone complex is the cdc37 co-chaperone. Cdc37 binds Hsp90 at the base of the ATP binding site and could affect the off rates of inhibitors bound to Hsp90 in the "activated" state (Roe et. al., *Cell* 116, (2004), pp. 87-98). The client protein bound to the Hsp90-Hsp70 form of the chaperone complex is believed to be more susceptible to ubiquitination and targeting to the proteasome for degradation. E3 ubiquitin ligases have been identified with chaperone interacting motifs and one of these (CHIP) was shown to promote the ubiquitination and degradation of Hsp90 client proteins (Connell et al., 2001. Xu et al., 2002).

Hsp90 Client Proteins

The number of reported Hsp90 client proteins now exceeds 100. Since many of its client proteins are involved in cell signalling proliferation and survival, Hsp90 has received major interest as an oncology target. Two groups of client proteins, cell signalling protein kinases and transcription factors, in particular suggest Hsp90 regulation may have potential benefit as an anticancer therapy.

Hsp90 protein kinase client proteins implicated in cell proliferation and survival include the following:

c-Src

Cellular Src (c-Src) is a receptor tyrosine kinase, required for mitogenesis initiated by multiple growth factor receptors, including the receptors for epidermal growth factor receptor (EGFR), platelet-derived growth factor receptor (PDGFR), colony stimulating factor-1 (CSF-1R), and the basic fibroblast growth factor (bFGFR). C-Src is also overexpressed and activated in many of the same human carcinomas that overexpress EGFR and ErbB2. Src is also required for the maintenance of normal bone homeostasis through its regulation of osteoclast function.

p185erbB2

ErbB2 (Her2/neu) is a receptor tyrosine kinase overexpressed in a variety of malignancies including breast, ovarian, prostate, and gastric cancers. ErbB2 was originally identified as an oncogene and inhibition of Hsp90 results in the polyubiquitination and degradation of erbB2.

Polo Mitotic Kinase

Polo-like kinases (Plks) are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase.

Akt (PKB)

Akt is involved in pathways that regulate cell growth by stimulating cell proliferation and suppressing apoptosis. Hsp90 inhibition by ansamycins results in a reduction in the Akt half life through ubiquitination and proteasomal degradation. Binding of cdc37 to Hsp90 is also required for the down-regulation of Akt. Following ansamycin treatment cancer cells arrest in the G2/M phase of the cell cycle 24 hours after treatment and proceed to apoptosis 24-48 hours later. Normal cells also arrest 24 hours after ansamycin treatment, but do not proceed on to apoptosis.

c-Raf, B-RAF, Mek

The RAS-RAF-MEK-ERK-MAP kinase pathway mediates cellular responses to growth signals. RAS is mutated to an oncogenic form in approximately 15% of human cancers. The three RAF genes are serine/threonine kinases that are regulated by binding RAS.

EGFR

The epidermal growth factor receptor (EGFR) is implicated in cell growth, differentiation, proliferation, survival, apoptosis, and migration. Overexpression of EGFR has been found in many different cancers and activating mutations of its kinase domain appear to be pathogenic in a subset of adenocarcinoams of the lung.

Flt3

FMS-like tyrosine kinase 3 (FLT3) is a receptor tyrosine kinase involved in cell proliferation, differentiation and apoptosis. Flt3 activation also leads to the activation of phosphatidylinositol 3-kinase (PI3K) and RAS signal-transduction cascades.

c-Met c-met is a receptor tyrosine kinase which binds hepatocyte growth factor (HGF) and regulates both cell motility and cell growth. c-met is overexpressed in tumours, including thyroid, stomach, pancreatic and colon cancer. HGF is also detected around the tumours, including liver metastases. This suggests that c-met and HGF play an important role in invasion and metastasis.

Cdk1, Cdk2, Cdk4, Cdk6

Cdk1, Cdk2, Cdk4, and Cdk6 drive the cell cycle. The activity of CDKs is regulated by their binding to specific subunits such as cyclins, inhibitory and assembly factors. The substrate specificity and timing of CDK activities is dictated by their interaction with specific cyclins. Cdk4/cyclin D and Cdk6/cyclin D are active in the G1 phase, Cdk2/cyclin E and Cdk2/cyclin A in S phase, and Cdc2/cyclin A and Cdc2/cyclin B in G2/M phase.

Cyclin-dependent kinase type 4 (CDK4), plays a key role in allowing cells to traverse G1 to S-phase transition of the cell cycle and is constitutively activated in many human cancers. The CDK4 activator, cyclin D1, is overexpressed and a CDK4 inhibitor, p16, is deleted in a variety of human tumours.

Cdk1/Cdk2 inhibitors have been developed which reversibly block normal cells in either the G1/S-phase or at the G2/M border. G2/M arrest is generally less well tolerated by the cells and consequently, they undergo apoptotic cell death. Since Hsp90 also is known to affect cell survival pathways this effect may be further amplified with an Hsp90 inhibitor.

Wee-1

The Wee-1 protein kinase carries out the inhibitory phosphorylation of CDC2 on tyrosine 15 (Tyr15). This is required for activation of the G2-phase checkpoint in response to DNA damage.

Hsp90 transcription factors implicated in cell proliferation and survival include the following:

Mutant p53

P53 is a tumour suppressor protein that causes cell cycle arrest and induces apoptosis. P53 is mutated in approximately half of all cancers. Mutant p53 associates with Hsp90 and is down-regulated in cancer lines treated with Hsp90 inhibitors, while wild type p53 levels were unaffected.

Progesterone Receptor/Estrogen Receptor/Androgen Receptor

In the absence of hormones, Progesterone and androgen receptors are bound by Hsp90 in an inactive form. Upon binding with their cognate hormones, the receptors undergo conformational changes and dissociation from hsp90. The ligand bound receptors are then capable of dimerisation, phosphorylation, and nuclear translocation. The activated receptors then bind to hormone-response elements (HREs) within the regulatory regions of target genes involved in maintaining cell proliferation.

Hif-1a

Hypoxia inducible factor-1a (HIF-1a) is a transcription factor that controls the expression of genes which play a role in angiogenesis. HIF-1a is expressed in the majority of metastases and is known to associate with Hsp90. Ansamycin treatment of renal carcinoma cell lines leads to the ubiquitination and proteasomal degradation of HIF-1a.

Hsp90 inhibitors are capable of affecting a large number of targets significant to signal transduction in tumour cell proliferation. Signal transduction inhibitors which regulate the activities of a single target, may not be as efficacious due to signalling pathway redundancy and the rapid development of resistance.

By regulating multiple targets involved in cell signalling and cell proliferation HSP90 inhibitors may prove beneficial in the treatment of a wide spectrum of proliferative disorders.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

PRIOR ART

EP 0474403 (Eli Lilly) discloses a class of 4-hydroxy benzamide derivatives for treating inflammatory bowel disease.

EP 0722723 (Eli Lilly) discloses a class of 4-hydroxy benzamide derivatives for treating multiple sclerosis.

EP 0500336 (University of Colorado Foundation) discloses a class of 4-hydroxy benzamide derivatives for treating type I diabetes.

WO 00/59867 (Pharmacor) discloses hydroxyphenyl derivatives for use as HIV integrase inhibitors.

JP 09194450 (Fujirebio) discloses ortho-hydroxybenzamide derivatives as pharmaceutical intermediates.

EP 0486386 discloses substituted benzoyl proline derivatives.

WO 2005/012297 (Janssen) discloses 4-hydroxy-3-fluorobenzoic acid piperidine amide as an intermediate in the preparation of compounds having LTA4 hydrolase modulating activity.

WO 2005/000839 (Tanabe)) discloses 4-hydroxy-3-bromobenzoic acid morpholine amide as an intermediate in the preparation of acylaminobenzofuran compounds.

The use of hydroxybenzamide derivatives as synthetic intermediates is disclosed in U.S. Pat. No. 5,310,951, JP 49010506, WO 01/36351, WO 98/45255 and WO 97/35999.

EP 0347 168 (Ono Pharmaceutical Co.) discloses para-substituted phenyl esters of pivalic acid as elastase inhibitors. One particular compound disclosed in this document is the 3-hydroxy-4-[(N-methyl-N-phenyl)carbamoyl phenyl ester of pivalic acid.

EP 0353753 (Takeda) discloses substituted benzoic acid amide compounds having glutamate receptor inhibiting activity.

US 2005/0037922 (Bayer Cropscience) discloses various hydroxylated benzoic acid dimethylamides and diethylamides as crop safeners.

WO 2005/009940 (Leo Pharma) discloses aminobenzophenone compounds stated to be useful in the treatment of inflammatory diseases and cancers.

WO 99/29705 (Glycomed et al) disclose a class of glycomimetic compounds having a number of possible uses including the treatment of cancer. One compound specifically disclosed in WO 99/29705 is the compound 2-(2-hydroxy-benzoyl)-1,2,3,4-tetrahydro-isoquinoline-3-carboxylic acid.

SUMMARY OF THE INVENTION

The invention provides compounds that have Hsp90 inhibiting or modulating activity and which it is envisaged will be useful in preventing or treating disease states or conditions mediated by Hsp90.

Thus, for example, it is envisaged that the compounds of the invention will be useful in alleviating or reducing the incidence of cancer.

In a first aspect, the invention provides a compound of the formula (I):

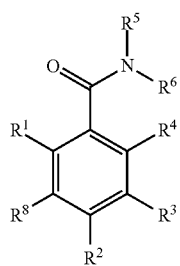

(I)

or salts, tautomers, solvates and N-oxides thereof; wherein:
$R^1$ is hydroxy or hydrogen;
$R^2$ is hydroxy; methoxy or hydrogen; provided that at least one of $R^1$ and $R^2$ is hydroxy;
$R^3$ is selected from hydrogen; halogen; cyano; $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group —(O)$_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
or $R^3$ and $R^4$ together form a monocyclic carbocyclic or heterocyclic ring of 5 to 7 ring members;
$R^5$ and $R^6$ together with the nitrogen atom to which they are attached form a bicyclic heterocyclic group having 8 to 12 ring members of which up to 5 ring members are heteroatoms selected from oxygen, nitrogen and sulphur; wherein the bicyclic heterocyclic group is optionally substituted by one or more substituents $R^{10}$;
$R^8$ is selected from hydrogen and fluorine; and
$R^{10}$ is selected from:
halogen;
hydroxy;
trifluoromethyl;
cyano;
nitro;
carboxy;
amino;
mono- or di-$C_{1-4}$ hydrocarbylamino;
carbocyclic and heterocyclic groups having from 3 to 12 ring members; and
a group $R^a$-$R^b$; wherein:
$R^a$ is a bond, O, CO, $X^1C(X^2)$, $C(X^2)X^1$, $X^1C(X^2)X^1$, S, SO, SO$_2$, NR$^c$, SO$_2$NR$^c$ or NR$^c$SO$_2$; and
$R^b$ is selected from hydrogen; carbocyclic and heterocyclic groups having from 3 to 12 ring members; and $C_{1-12}$ hydrocarbyl (such as $C_{1-10}$ hydrocarbyl) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), and carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, SO$_2$, NR$^c$, $X^1C(X^2)$, $C(X^2)X^1$ or $X^1C(X^2)X^1$;
$R^c$ is selected from $R^b$, hydrogen and $C_{1-4}$ hydrocarbyl; and
$X^1$ is O, S or NR$^c$ and $X^2$ is =O, =S or =NR$^c$;
but excluding the compound 2-(2-hydroxy-benzoyl)-1,2,3,4-tetrahydro-isoquinoline-3-carboxylic acid.

The invention also provides inter alia:
A compound of the formula (I), (II), (III), (IV), (V), (VI), (VIa), (VII), (VIIa) or (VIIb) or any sub-groups or examples thereof as defined herein for use in the prophylaxis or treatment of a disease state or condition mediated by Hsp90.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by Hsp90.

A method for the prophylaxis or treatment of a disease state or condition mediated by Hsp90, which method comprises administering to a subject in need thereof a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in alleviating or reducing the incidence of a disease state or condition mediated by Hsp90.

The use of a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease state or condition mediated by Hsp90.

A method for alleviating or reducing the incidence of a disease state or condition mediated by Hsp90, which method comprises administering to a subject in need thereof a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in treating a disease or condition comprising or arising from abnormal cell growth in a mammal.

The use of a compound of the formula (I), (II), (III), (IV), (V), (VI), (VIa), (VII), (VIIa) or (VIIb) or any sub-groups or examples thereof as defined herein for the manufacture of a medicament for treating a disease or condition comprising or arising from abnormal cell growth in a mammal.

A method for treating a disease or condition comprising or arising from abnormal cell growth in a mammal, which method comprises administering to the mammal a compound of the formula (I), (II), (III), (IV), (V), (VI), (VIa), (VII), (VIIa) or (VIIb) or any sub-groups or examples thereof as defined herein in an amount effective in inhibiting abnormal cell growth.

A compound of the formula (I), (II), (III), (IV), (V), (VI), (VIa), (VII), (VIIa) or (VIIb) or any sub-groups or examples thereof as defined herein for use in alleviating or reducing the incidence of a disease or condition comprising or arising from abnormal cell growth in a mammal.

The use of a compound of the formula (I), (II), (III), (IV), (V), (VI), (VIa), (VII), (VIIa) or (VIIb) or any sub-groups or examples thereof as defined herein for the manufacture of a medicament for alleviating or reducing the incidence of a disease or condition comprising or arising from abnormal cell growth in a mammal.

A method for alleviating or reducing the incidence of a disease or condition comprising or arising from abnormal cell growth in a mammal, which method comprises administering to the mammal a compound of the formula (I), (II), (III), (IV), (V), (VI), (VIa), (VII), (VIIa) or (VIIb) or any sub-groups or examples thereof as defined herein in an amount effective in inhibiting abnormal cell growth.

A method for treating a disease or condition comprising or arising from abnormal cell growth in a mammal, the method comprising administering to the mammal a compound of the formula (I), (II), (III), (IV), (V), (VI), (VIa), (VII), (VIIa) or (VIIb) or any sub-groups or examples thereof as defined herein in an amount effective to inhibit Hsp90 activity.

A method for alleviating or reducing the incidence of a disease or condition comprising or arising from abnormal cell growth in a mammal, the method comprising administering to the mammal a compound of the formula (I), (II), (III), (IV), (V), (VI), (VIa), (VII), (VIIa) or (VIIb) or any sub-groups or examples thereof as defined herein in an amount effective to inhibit Hsp90 activity.

A compound of the formula (I), (II), (III), (IV), (V), (VI), (VIa), (VII), (VIIa) or (VIIb) or any sub-groups or examples thereof as defined herein for use as an inhibitor of Hsp90.

A method of inhibiting Hsp90, which method comprises contacting the Hsp90 with an Hsp90-inhibiting compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in modulating a cellular process (for example cell division) by inhibiting the activity of Hsp90.

A method of modulating a cellular process (for example cell division) by inhibiting the activity of Hsp90 using a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of a disease state as described herein.

The use of a compound of the formula (I), (II), (III), (IV), (V), (VI), (VIa), (VII), (VIIa) or (VIIb) or any sub-groups or examples thereof as defined herein for the manufacture of a medicament, wherein the medicament is for any one or more of the uses defined herein.

A pharmaceutical composition comprising a compound of the formula (I), (II), (III), (IV), (V), (VI), (VIa), (VII), (VIIa) or (VIIb) or any sub-groups or examples thereof as defined herein and a pharmaceutically acceptable carrier.

A pharmaceutical composition comprising a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for oral administration.

A pharmaceutical composition comprising a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for parenteral administration, for example by intravenous (i.v.) administration.

A pharmaceutical composition comprising a compound of the formula (I), (II), (III), (IV), (V), (VI), (VIa), (VII), (VIIa) or (VIIb) or any sub-groups or examples thereof as defined herein and a pharmaceutically acceptable carrier in a form suitable for intravenous (i.v.) administration by injection or infusion.

A compound of the formula (I), (II), (III), (IV), (V), (VI), (VIa), (VII), (VIIa) or (VIIb) or any sub-groups or examples thereof as defined herein for use in medicine.

A compound as defined herein for any of the uses and methods set forth above, and as described elsewhere herein.

A compound of the formula (I), (II), (III), (IV), (V), (VI), (VIa), (VII), (VIIa) or (VIIb) or any sub-groups or examples thereof as defined herein for use in treatment or prophylaxis of a disease state or condition in a patient who has been screened and has been determined as suffering from, or being at risk of suffering from, a disease or condition which would be susceptible to treatment with a compound having activity against Hsp90.

The use of a compound of the formula (I), (II), (III), (IV), (V), (VI), (VIa), (VII), (VIIa) or (VIIb) or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against Hsp90.

A method for the diagnosis and treatment of a disease state or condition mediated by Hsp90, which method comprises (i) screening a patient to determine whether a disease or condition from which the patient is or may be suffering is one which would be susceptible to treatment with a compound having activity against Hsp90; and (ii) where it is indicated that the disease or condition from which the patient is thus susceptible, thereafter administering to the patient a compound of the formula (I), (II), (III), (IV), (V), (VI), (VIa), (VII), (VIIa) or (VIIb) or any sub-groups or examples thereof as defined herein.

General Preferences and Definitions

In this section, as in all other sections of this application, unless the context indicates otherwise, references to a compound of formula (I) includes all subgroups of formula (I) as defined herein, including formulae (II), (III), (IV), (V), (VI), (VIa), (VII), (VIIa) and (VIIb) and the term 'subgroups' includes all preferences, embodiments, examples and particular compounds defined herein.

Moreover, a reference to a compound of formula (I), (II), (III), (IV), (V), (VI), (VIa), (VII), (VIIa) or (VIIb) and subgroups thereof includes ionic forms, salts, solvates, isomers, tautomers, N-oxides, esters, prodrugs, isotopes and protected forms thereof, as discussed below: —preferably, the salts or tautomers or isomers or N-oxides or solvates thereof: —and more preferably, the salts or tautomers or N-oxides or solvates thereof.

The following general preferences and definitions shall apply to each of $R^1$ to $R^8$, $R^{10}$, $R^a$, $R^b$, $R^e$, $X^1$ and $X^2$ and their various sub-groups, sub-definitions, examples and embodiments unless the context indicates otherwise.

Any references to formula (I) herein shall also be taken to refer to and any sub-group of compounds within formula (I) and any preferences and examples thereof unless the context requires otherwise.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, for example 5 to 7, and preferably 5 or 6 ring members. Examples of bicyclic groups are those containing 8, 9, 10, 11 and 12 ring members, and more usually 9 or 10 ring members.

The term "bicyclic" as used herein refers to groups that have two rings joined together in such as way that at least one ring member is shared by both rings. Thus, the bicyclic group can be a fused ring (two ring members shared by both rings), spirocyclic (one ring member shared by both rings) or a bridged ring (three or more ring members shared by both rings).

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The terms "fully saturated" and "saturated" refer to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

One sub-group of bicyclic heteroaryl groups consists of groups (a) to (e) and (g) to (o) above.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzfuranyl, benzthienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1, 2, 3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), In one sub-set of heterocyclic groups, the heterocyclic groups contain cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

One preferred sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Another sub-set of non-aromatic heterocyclic groups consists of pyrrolidine, piperidine, morpholine, thiomorpholine, thiomorpholine S,S-dioxide, piperazine and N-alkyl piperazines such as N-methyl piperazine.

One particular sub-set of heterocyclic groups consists of pyrrolidine, piperidine, morpholine and N-alkyl piperazines (e.g. N-methyl piperazine), and optionally thiomorpholine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carboyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example Advanced Organic Chemistry, by Jerry March, 4$^{th}$ Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-12}$ hydrocarbyl group (such as a $C_{1-10}$ hydrocarbyl group) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, $SO_2$, $NR^c$, $X^1C(X^2)$, $C(X^2)X^1$ or $X^1C(X^2)X^1$;

$R^c$ is selected from $R^b$, hydrogen and $C_{1-4}$ hydrocarbyl; and $X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on the same or adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group.

Examples of such linked substituent groups include:

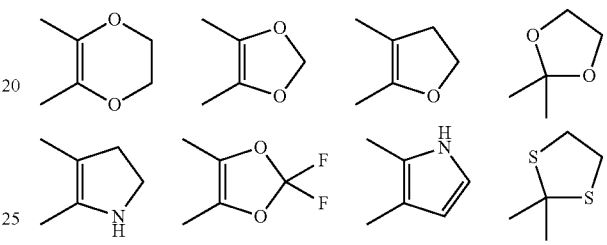

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

The prefix "$C_{x-y}$" (where x and y are integers) as used herein refers to the number of carbon atoms in a given group. Thus, a $C_{1-4}$ hydrocarbyl group contains from 1 to 4 carbon atoms, and a $C_{3-6}$ cycloalkyl group contains from 3 to 6 carbon atoms, and so on.

The term "acyclic hydrocarbyl" (e.g. as in "acyclic $C_{1-5}$ hydrocarbyl") as used herein refers to non-cyclic hydrocarbyl groups and in particular to alkyl, alkenyl and alkynyl groups as defined herein.

The term "mono- or di-$C_{1-5}$ hydrocarbylamino" as used herein refers to a monosubstituted or disubstituted amine group bearing either one or two hydrocarbyl substituent groups that each contain from 1 to 5 carbon atoms.

Preferred non-aromatic hydrocarbyl groups are saturated groups such as alkyl and cycloalkyl groups.

Generally by way of example, the hydrocarbyl groups can have up to ten carbon atoms (and more typically up to eight carbon atoms), unless the context requires otherwise. Within the sub-set of hydrocarbyl groups having 1 to 10 carbon atoms, particular examples are $C_{1-8}$ hydrocarbyl groups or $C_{1-6}$ hydrocarbyl groups, such as $C_{1-4}$ hydrocarbyl groups (e.g. $C_{1-3}$ hydrocarbyl groups or $C_{1-2}$ hydrocarbyl groups or $C_{2-3}$ hydrocarbyl groups or $C_{2-4}$ hydrocarbyl groups), specific examples being any individual value or combination of values selected from $C_1$, $C_2$, $C_3$, $C_4$, $C_5$, $C_6$, $C_7$, $C_8$, $C_9$ and $C_{10}$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups or $C_{2-3}$ alkyl groups or $C_{2-4}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 10 carbon atoms, more typically 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 10 carbon atoms, more typically 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 10 carbon atoms, more typically 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups having 2 to 10 carbon atoms, more typically 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

The terms $C_{1-12}$ hydrocarbyl, $C_{1-10}$ hydrocarbyl and $C_{1-8}$ hydrocarbyl as used herein encompasses alkyl, alkenyl, alkynyl, cycloalkyl, cycloalkenyl, phenyl, benzyl and phenylethyl groups wherein the preferences for and examples of each of the aforesaid groups are as defined above. Within this definition, particular hydrocarbyl groups are alkyl, cycloalkyl, phenyl, benzyl and phenylethyl (e.g. 1-phenylethyl or 2-phenylethyl) groups, one subset of hydrocarbyl groups consisting of alkyl and cycloalkyl groups and in particular $C_{1-4}$ alkyl and cycloalkyl groups such as methyl, ethyl, n-propyl, isopropyl, n-butyl, isobutyl, tert-butyl, cyclopropyl and cyclobutyl.

The term $C_{1-4}$ hydrocarbyl as used herein encompasses alkyl, alkenyl, alkynyl, cycloalkyl and cycloalkenyl groups wherein the preferences for and examples of the aforesaid groups are as defined above. Within this definition, particular C1-4 hydrocarbyl groups are alkyl and cycloalkyl groups, such as methyl, ethyl, n-propyl, isopropyl, n-butyl, isobutyl, tert-butyl, cyclopropyl and cyclobutyl.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members, more usually 5 to 6 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom. Thus, in an oxa-$C_{4-6}$ cycloalkyl group, there will be from 3 to 5 carbon ring members and an oxygen ring member. For example, an oxa-cyclohexyl group is a tetrahydropyranyl group.

The definition "$R^a$-$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, OC($NR^c$), SC($NR^c$), $NR^cC(NR^c)$, C(O)O, C(O)S, C(O)$NR^c$, C(S)O, C(S)S, C(S)$NR^c$, C($NR^c$)O, C($NR^c$)S, C($NR^c$)$NR^c$, OC(O)O, SC(O)O, $NR^cC(O)O$, OC(S)O, SC(S)O, $NR^cC(S)O$, OC($NR^c$)O, SC($NR^c$)O, $NR^cC(NR^c)O$, OC(O)S, SC(O)S, $NR^cC(O)S$, OC(S)S, SC(S)S, $NR^cC(S)S$, OC($NR^c$)S, SC($NR^c$)S, $NR^cC(NR^c)S$, OC(O)$NR^c$, SC(O)$NR^c$, $NR^cC(O)$ $NR^c$, OC(S)$NR^c$, SC(S)$NR^c$, $NR^cC(S)NR^c$, OC($NR^c$)$NR^c$, SC($NR^c$)$NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-10}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-10}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-10}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$ alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-10}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for $R^1$ to $R^{10}$ $R^1$ & $R^2$ $R^1$ is hydroxy or hydrogen; and $R^2$ is hydroxy, methoxy or hydrogen; provided that at least one of $R^1$ and $R^2$ is hydroxy.

Preferably, $R^1$ is hydroxy or hydrogen; and $R^2$ is hydroxy or hydrogen; provided that at least one of $R^1$ and $R^2$ is hydroxy.

In one embodiment, $R^1$ is hydroxy and $R^2$ is hydrogen or methoxy, preferably hydrogen.

In another embodiment, $R^1$ is hydrogen and $R^2$ is hydroxy.

In a further embodiment, $R^1$ is hydroxy and $R^2$ is hydroxy or methoxy.

In a preferred embodiment, $R^1$ and $R^2$ are both hydroxy.

$R^8$ $R^8$ is selected from hydrogen and fluorine. Preferably $R^8$ is hydrogen.

$R^3$ $R^3$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members.

In one sub-group of compounds, $R^3$ is selected from hydrogen, halogen, cyano, $C_{1-5}$ hydrocarbyl and $C_{1-5}$ hydrocarbyloxy; wherein the $C_{1-5}$ hydrocarbyl moiety in each instance is optionally substituted by one or more substituents selected from hydroxy, halogen, $C_{1-2}$ alkoxy and amino.

In another sub-group of compounds, $R^3$ is selected from halogen (e.g. chlorine or bromine), $C_{1-5}$ alkyl and $C_{3-4}$ cycloalkyl.

More typically, $R^3$ is selected from hydrogen, chlorine, $C_{1-5}$ hydrocarbyl and $C_{1-5}$ hydrocarbyloxy.

Particular groups $R^3$ include hydrogen, $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

A further sub-group of substituents $R^3$ consists of $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

When only one of $R^1$ and $R^2$ is hydroxy, $R^3$ may be other than hydrogen.

In one particular embodiment, $R^1$ and $R^2$ are both hydroxy and $R^3$ is hydrogen.

In a further particular embodiment, $R^3$ is selected from isopropyl and tert-butyl.

In one general embodiment, $R^3$ is other than halogen.

In another general embodiment, $R^3$ may be other than fluorine.

In a further general embodiment, $R^3$ may be other than fluorine or methoxy.

$R^4$

In one embodiment, $R^4$ is selected from hydrogen; a group $-(O)_n-R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members.

In one sub-group of compounds, $R^4$ is selected from hydrogen; a group $-(O)_n-R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the $C_{1-5}$ hydrocarbyl moiety in each instance is optionally substituted by one or more substituents selected from hydroxy, halogen, $C_{1-2}$ alkoxy and amino.

Within this sub-group, $R^4$ is more typically selected from hydrogen, methoxy, halogen (e.g. fluorine or chlorine), cyano; hydroxy; amino and $C_{3-6}$ cycloalkyl.

More particularly, $R^4$ can be selected from a sub-set $R^{4a}$ wherein the sub-set $R^{4a}$ consists of hydrogen, methoxy, fluorine and chlorine.

Preferably $R^4$ is hydrogen.

In another embodiment, $R^3$ and $R^4$ together form a carbocyclic or heterocyclic ring of 5 to 7 ring members. The carbocyclic and heterocyclic groups can be any of the groups listed above in General Definitions and Preferences section but one particular group is a group wherein $R^3$ and $R^4$ together with the phenyl ring form a dihydrobenzofuran group.

Particular examples of the phenyl ring containing the moieties $R^1$, $R^2$, $R^3$ and $R^4$ are as set out in Table 1. The point of attachment to the carbonyl group is indicated by means of an asterisk.

TABLE 1

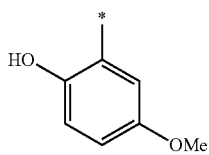

A1

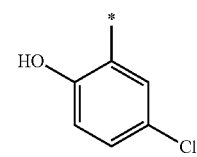

A2

TABLE 1-continued

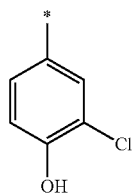

A3

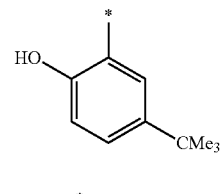

A4

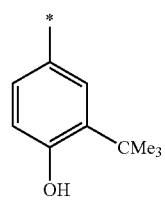

A5

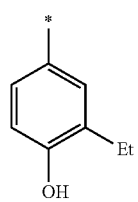

A6

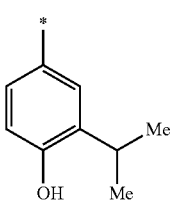

A7

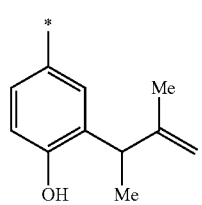

A8

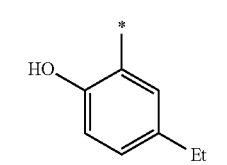

A9

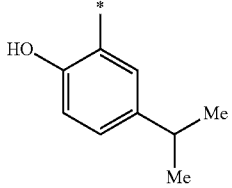

A10

TABLE 1-continued

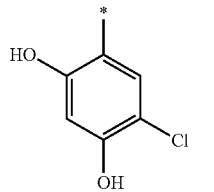 A11

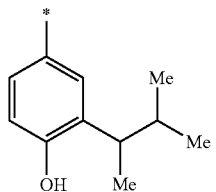 A12

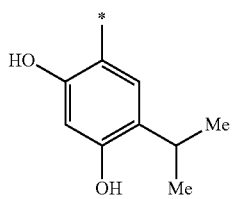 A13

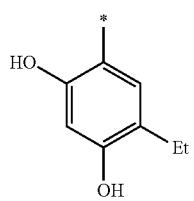 A14

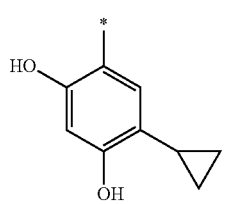 A15

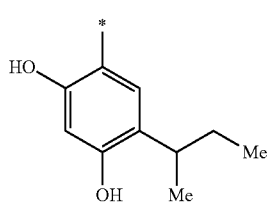 A16

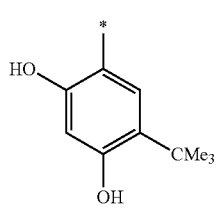 A17

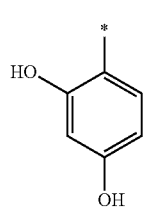 A18

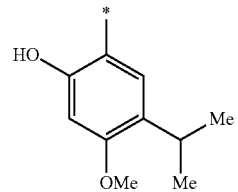 A19

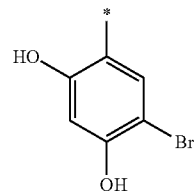 A20

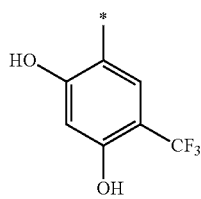 A21

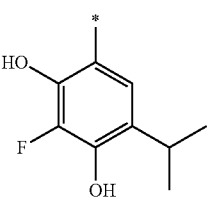 A22

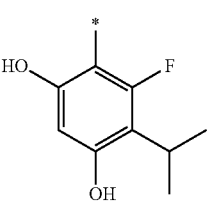 A23

In one embodiment, the phenyl moiety is selected from groups A1 to A21.

In another embodiment, the phenyl moiety is selected from groups A1 to A18.

Preferred phenyl moieties include groups A5, A7, A11, A13, A14, A15, A16, A11 and A18.

Particularly preferred phenyl moieties are A5, A7, A13, A14 and A17.

Particularly preferred phenyl moieties are A11 and A13.

One particularly preferred phenyl moiety is group A13.

$R^5$ & $R^6$ $R^5$ and $R^6$ together with the nitrogen atom to which they are attached form a bicyclic heterocyclic group having up to 12 ring members of which up to 5 ring members are heteroatoms selected from oxygen, nitrogen and sulphur.

The bicyclic groups can be any of the groups listed above in the General Preferences and Definitions section or listed below in the Particular and Preferred Sub-groups section, and such groups may be unsubstituted or substituted by one or more substituents $R^{10}$ as defined herein.

The bicyclic heterocyclic group is typically a fused ring bicyclic group or a spirocylic group and more typically is a fused ring bicyclic group. Particular fused ring systems of interest in the context of the invention are 5.6 and 6.6 fused ring systems. In the bicyclic heterocyclic groups, one of the rings may be a heterocyclic ring and the other may be a carbocyclic ring, or both rings may be heterocyclic.

In one sub-group of compounds, one of the rings of the bicyclic heterocyclic group is non-aromatic and other is aromatic. Preferably the nitrogen atom of the group $NR^5R^6$ forms part of the non-aromatic ring. Particular examples of such groups are dihydroindole, dihydroisoindole, tetrahydroquinoline and tetrahydroisoquinoline groups.

More particular examples of such groups are dihydroindole, dihydroisoindole, tetrahydroquinoline and tetrahydroisoquinoline groups, but wherein the tetrahydroisoquinoline group bears no substituent groups on the non-aromatic ring thereof.

The bicyclic heterocyclic rings are optionally substituted by one or more substituent groups $R^{10}$ as defined herein.

In one embodiment, the bicyclic heterocyclic ring is substituted by 1, 2 or 3 substituent groups $R^{10}$ as defined herein.

In another embodiment, the bicyclic heterocyclic ring is substituted by 1 or 2 substituent groups $R^{10}$ as defined herein.

The substituent group or groups $R^{10}$ may be attached to either or both of the two rings making up the bicyclic heterocyclic group. In one embodiment, the ring containing the nitrogen atom of the group $NR^5R^6$ does not bear any substituents $R^{10}$. In another embodiment, the ring containing the nitrogen atom of the group $NR^5R^6$ bears a substituent $R^{10}$ but the substituent is other than a carboxylic acid group.

In one sub-group of compounds, the bicyclic heterocyclic group is unsubstituted or is substituted by one, two or three (preferably one or two) substituents selected from a group $R^{10a}$ consisting of halogen, hydroxy, amino and a group $R^a$-$R^b$ where $R^a$ is selected from a bond, O, CO, C(O)O, C(O)NR$^c$, NR$^c$C(O), NR$^c$C(O)O, NR$^c$, SO, SO$_2$, SONR$^c$, and SO$_2$NR$^c$; and $R^b$ is selected from hydrogen; carbocyclic and heterocyclic groups having 5 or 6 ring members; and $C_{1-10}$ hydrocarbyl (e.g. $C_{1-8}$ hydrocarbyl such as $C_{1-8}$ alkyl or $C_{3-7}$ cycloalkyl) optionally substituted by one or more substituents selected from hydroxy, oxo, amino, mono- or di-$C_{1-8}$ non-aromatic hydrocarbylamino, (e.g. mono- or di-$C_{1-4}$ hydrocarbylamino), carboxy, and carbocyclic and heterocyclic groups having from 3 to 7 ring members, and wherein one or more of the carbon atoms of the $C_{1-8}$ hydrocarbyl group may optionally be replaced by O, S, C(O)O, C(O)NR$^c$ or NR$^c$.

Within this sub-group of compounds and sub-groups, preferences and examples thereof, where it is stated that one or more of the carbon atoms of the $C_{1-8}$ hydrocarbyl group may optionally be replaced by O, S, C(O)O, C(O)NR$^c$ or NR$^c$, the orientation of the ester and amide groups may be in either direction unless indicated to the contrary.

In the above sub-groups, when $R^b$ is a carbocyclic or heterocyclic group, the carbocyclic or heterocyclic group may be substituted by one or more substituents $R^{10}$ as defined herein. For example, when $R^b$ is a carbocyclic or heterocyclic group, the carbocyclic or heterocyclic group may be substituted by one or more substituents selected from CO$_2R^{14}$ wherein $R^{14}$ is hydrogen or $C_{1-6}$ alkyl; $C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], CH$_2$[sol], C(O)[sol], OCH$_2$CH$_2$[sol] or OCH$_2$CH$_2$CH$_2$[sol] where [sol] is as defined below.

In a more particular sub-group, the bicyclic heterocyclic group is unsubstituted or is substituted by one, two or three (preferably one or two) substituents selected from a group $R^{10b}$ consisting of halogen, OH, NH$_2$, CH$_2$OH, CH$_2$NH$_2$, O—$C_{1-6}$-alkyl, NH—$C_{1-6}$ alkyl, aryl, heteroaryl, $C_{3-7}$ cycloalkyl, heterocyclyl, O-heteroaryl, O—$C_{3-7}$ cycloalkyl,
O-heterocycloalkyl, C(=O)$C_{1-6}$ alkyl, C(=O)O$C_{1-6}$ alkyl, C(=O)NH$_2$, C(=O)NH$C_{1-6}$ alkyl, C(=O)N($C_{1-6}$ alkyl)$_2$, NH($C_{1-6}$ alkyl), N($C_{1-6}$ alkyl)$_2$, NC(=O)$C_{1-6}$ alkyl, $C_6$ aryl, O$C_6$ aryl, C(=O)$C_6$aryl, C(=O)O$C_6$aryl, C(=O)NH$_2$, C(=O)NH$C_6$aryl, C(=O)N($C_6$ aryl)$_2$, NH($C_6$ aryl), N($C_6$ aryl)$_2$, NC(=O)$C_6$ aryl, $C_{5-6}$ heterocyclyl, O$C_{5-6}$ heterocyclyl, C(=O)$C_{5-6}$ heterocyclyl, C(=O)O$C_{5-6}$ heterocyclyl, C(=O)NH$C_{5-6}$ heterocyclyl, C(=O)N($C_{5-6}$ heterocyclyl)$_2$, NH($C_{5-6}$ heterocyclyl), N($C_{5-6}$ heterocyclyl)$_2$, NC(=O)$C_{5-6}$ heterocyclyl, C(=O)NH$C_{1-6}$ alkyl, $C_{5-6}$ aryl, S(=O)$C_{1-6}$ alkyl, S(=O)N—$C_{1-6}$ alkyl and SO$_2$N—$C_{1-6}$ alkyl; and a group [sol], CH$_2$[sol], or OCH$_2$CH$_2$[sol] where [sol] is selected from the following groups

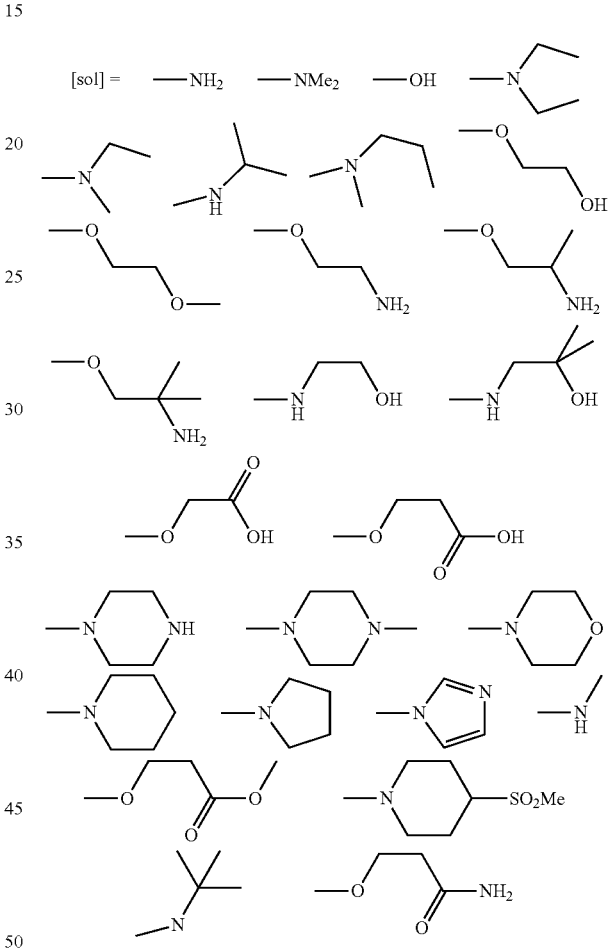

In another sub-group of compounds, the bicyclic ring is unsubstituted or is substituted by 1, 2 or 3 (e.g. 1 or 2, for example 1) groups $R^{10c}$ where $R^{10c}$ is a group [sol], CH$_2$[sol] or OCH$_2$CH$_2$[sol] where [sol] is selected from the following groups

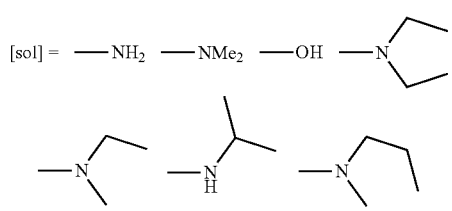

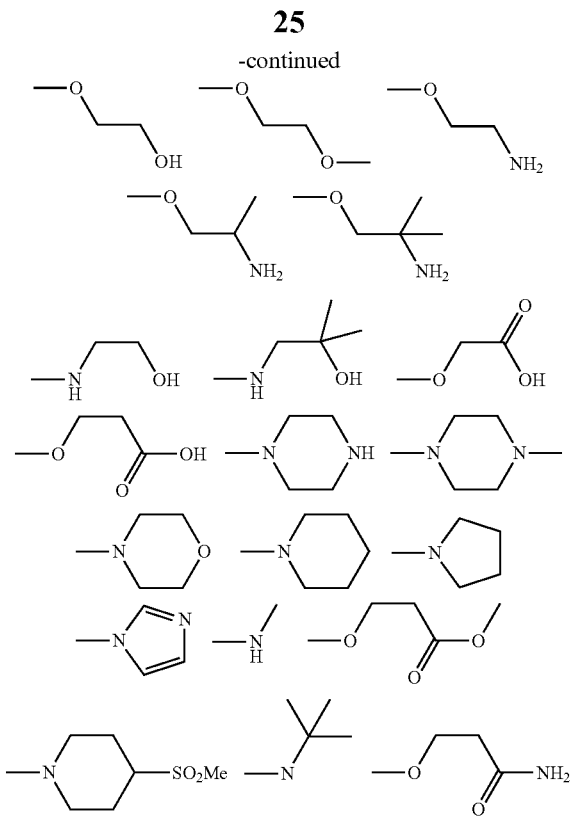

and wherein (i) $R^{10c}$ is optionally further selected from a group $OCH_2CH_2CH_2[sol]$ and/or (ii) [sol] is further selected from $NHR^{11}$ wherein $R^{11}$ is $COR^{12}$ or $R^{12}$ and $R^{12}$ is $C_{1-4}$ alkyl, aryl or aryl-$C_{1-4}$ alkyl.

In another sub-group of compounds, the bicyclic ring is unsubstituted or is substituted by one or two substituents $R^{10c}$ where $R^{10cc}$ is selected from:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], C(O)[sol], $OCH_2CH_2$[sol] or $OCH_2CH_2CH_2$[sol] where [sol] is selected from the following groups

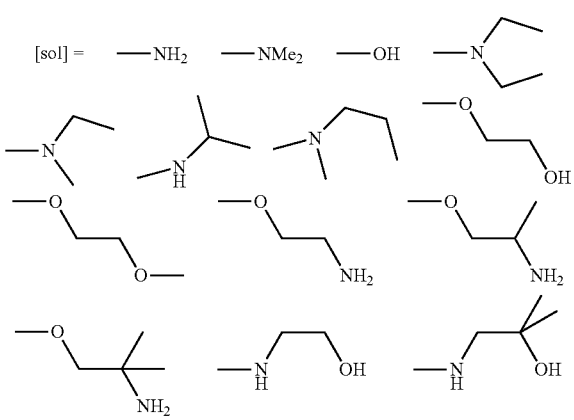

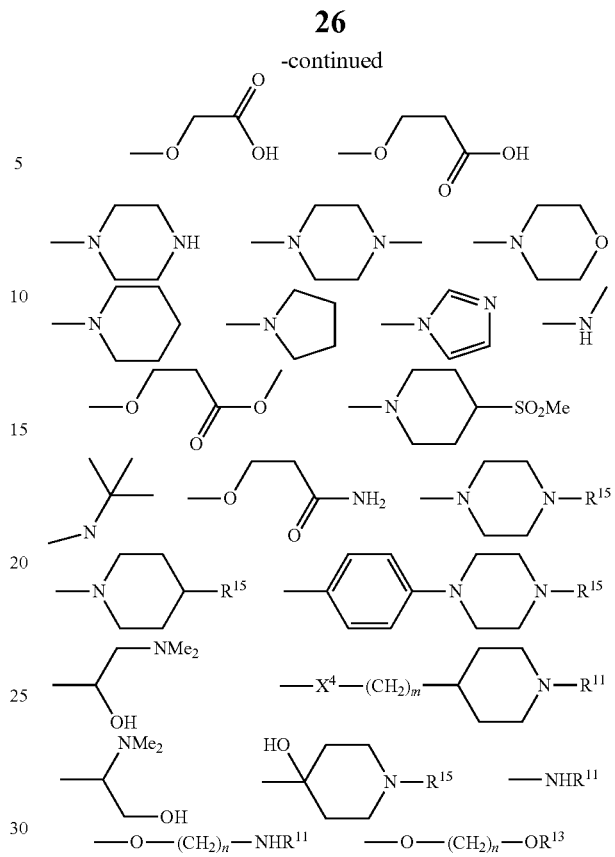

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In a further sub-group of compounds, the bicyclic ring is unsubstituted or is substituted by one or two substituents $R^{10ccc}$ where $R^{10ccc}$ is selected from:

a group [sol] or $CH_2$[sol] where [sol] is selected from the following groups:

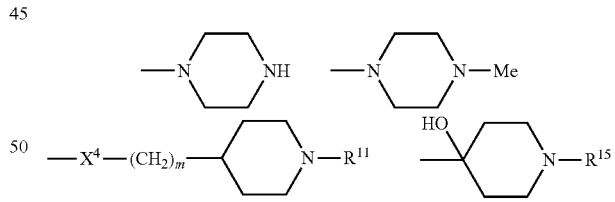

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In another sub-group of compounds, where $R^{10b}$ or $R^{10c}$ or $R^{10cc}$ is a group [sol], $CH_2$[sol], $OCH_2CH_2$[sol] or $OCH_2CH_2CH_2$[sol] and [sol] contains a primary or secondary amine group, the primary or secondary amine group can be derivatised to form an acyl derivative such as an amide, carbamate or urea. For example, the amine group can be derivatised to form a carbamate such as a $C_{1-4}$alkyloxycarbonylamino group, or a benzyloxycarbonylamino group.

In one sub-group of compounds, $R^5$ and $R^6$ together with the nitrogen atom to which they are attached form an optionally substituted dihydroisoindole group wherein the optional substituents are selected from groups $R^{10}$, $R^{10a}$, $R^{10b}$, $R^{10c}$ and $R^{10}$ and sub-groups and examples thereof as defined herein.

Particular examples of the group $NR^5R^6$ are shown in Table 2. The point of attachment to the carbonyl group is shown by means of an asterisk.

TABLE 2

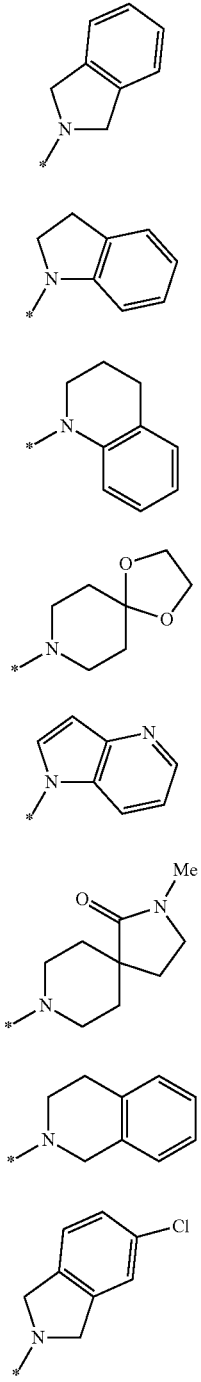

B8

B13

B14

B20

B26

B29

B30

B35

TABLE 2-continued

B36

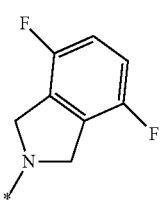

B37

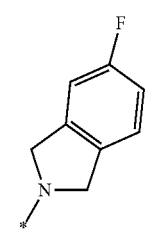

B38

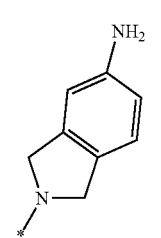

B39

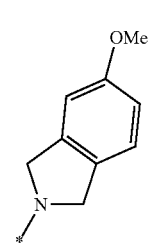

B40

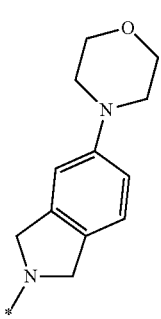

B41

TABLE 2-continued
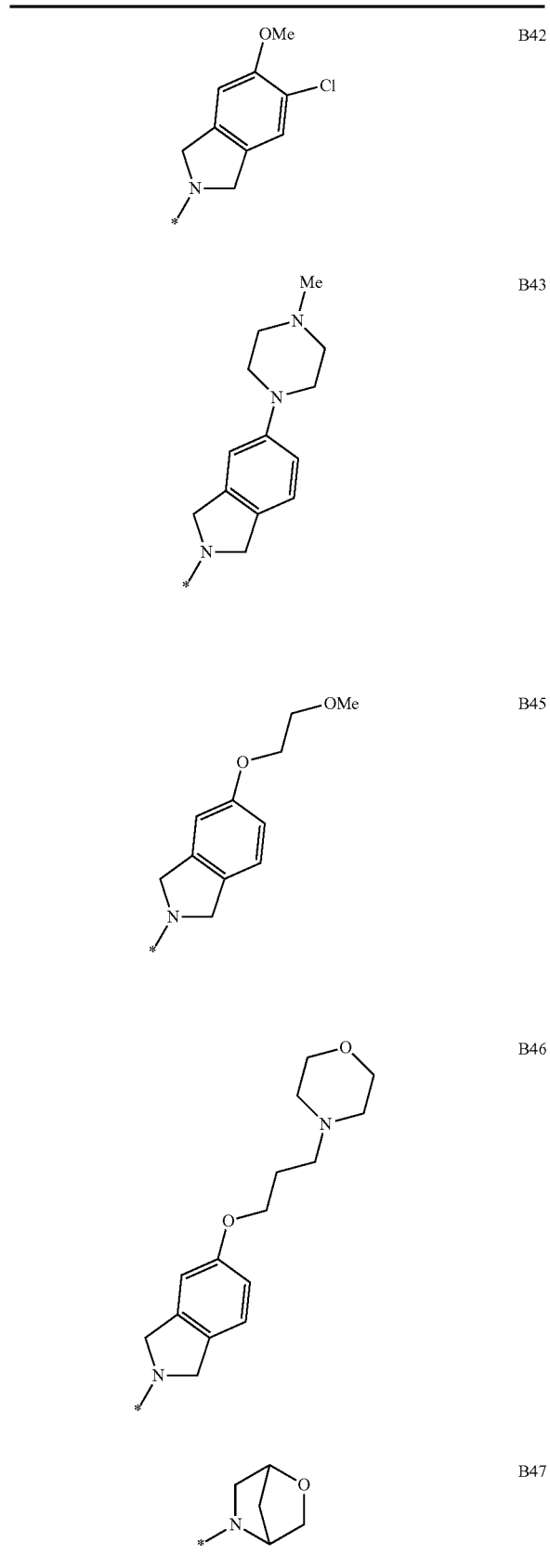
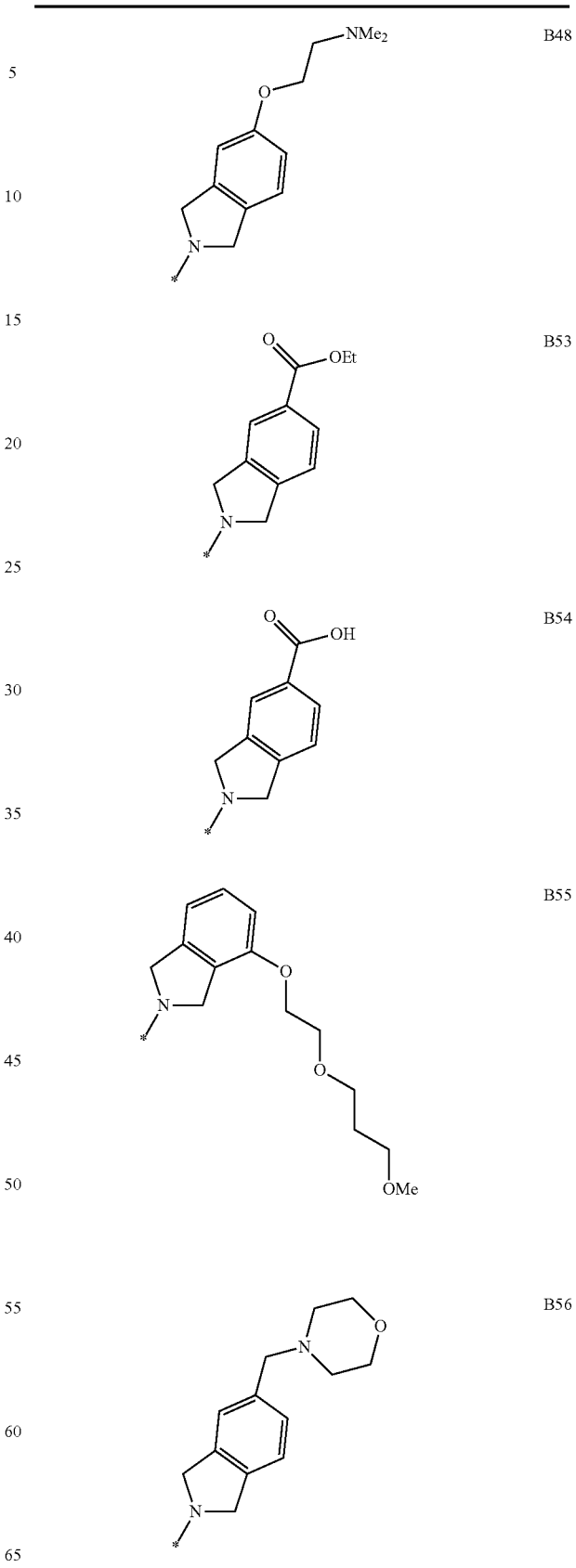

TABLE 2-continued
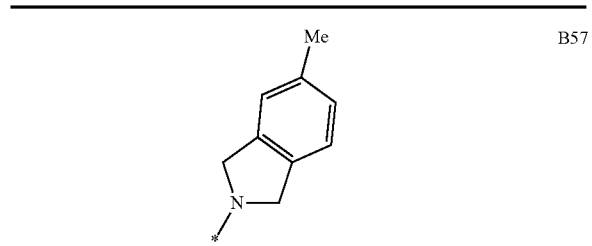 B57
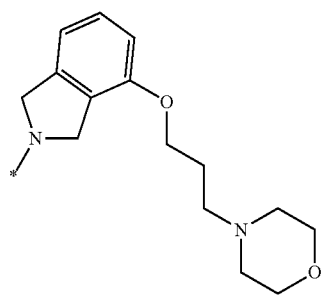 B58
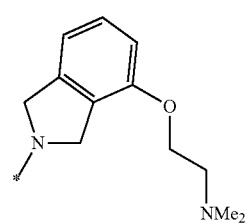 B59
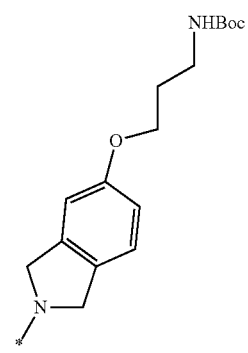 B60
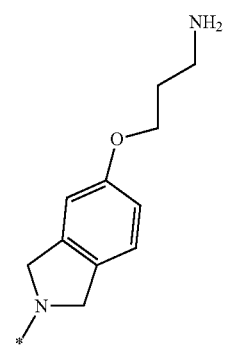 B61
TABLE 2-continued
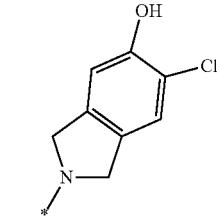 B62
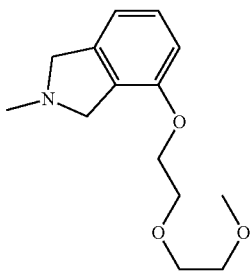 [SMILES: COCCOCCOc1cccc2c1CN(C)C2] B71
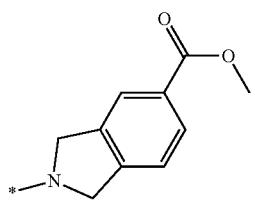 B72
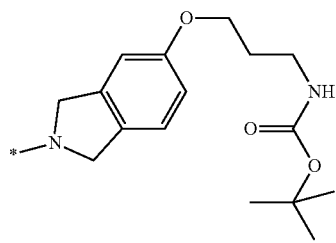 B73
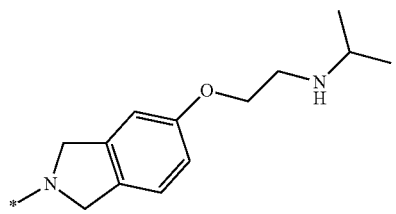 B74
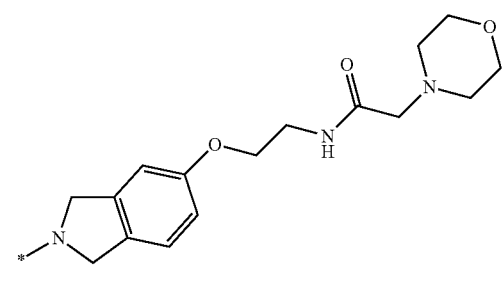 B75

TABLE 2-continued
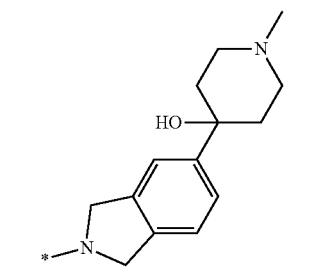 B76
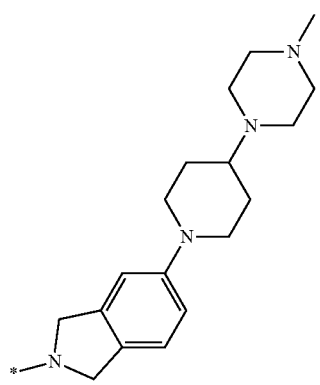 B77
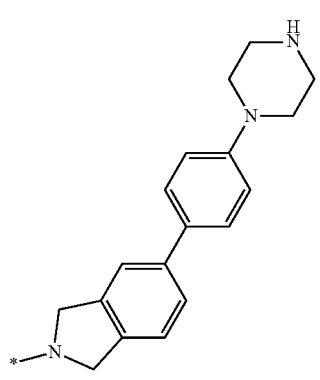 B78
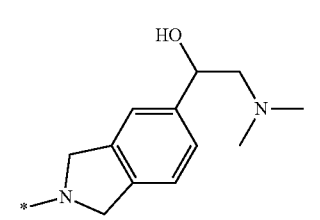 B79
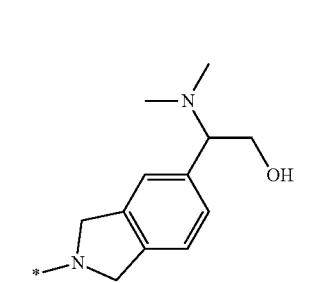 B80
TABLE 2-continued
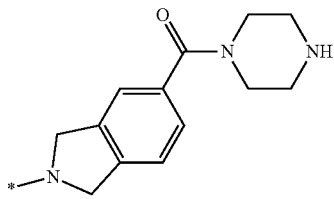 B81
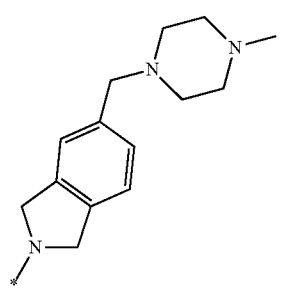 B82
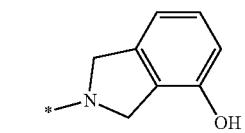 B83
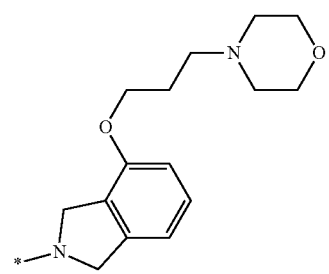 B84
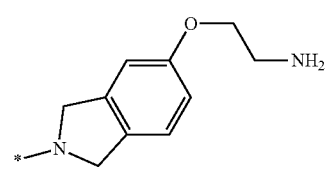 B85
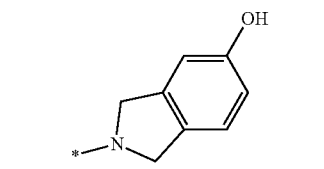 B86
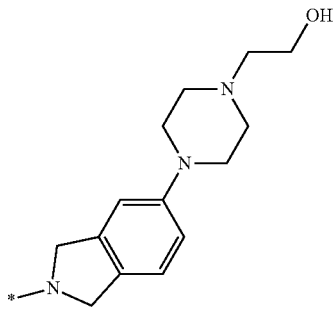 B87

TABLE 2-continued
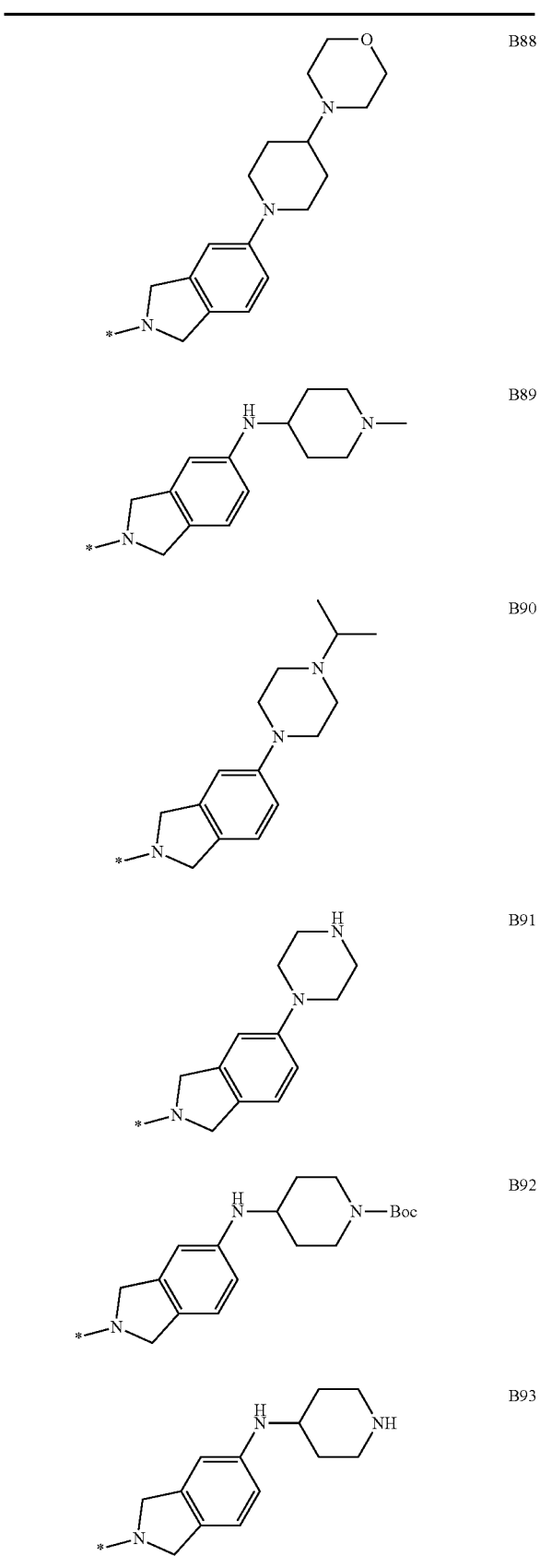
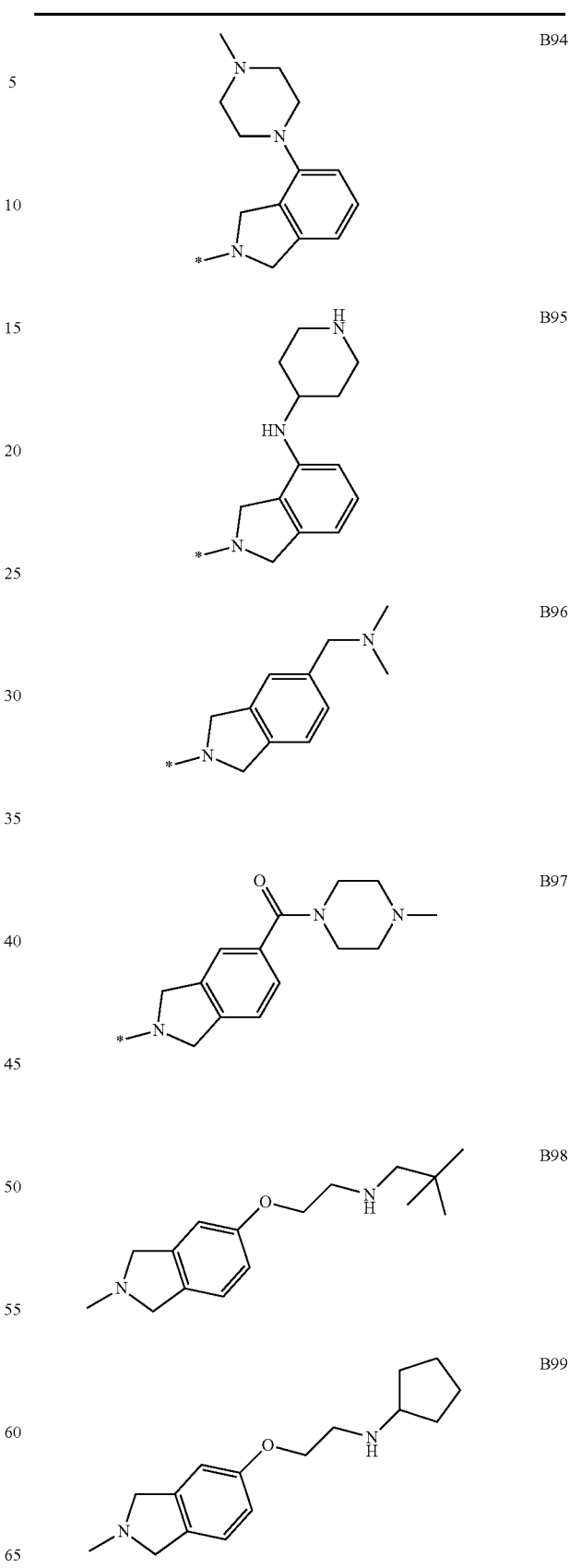

TABLE 2-continued

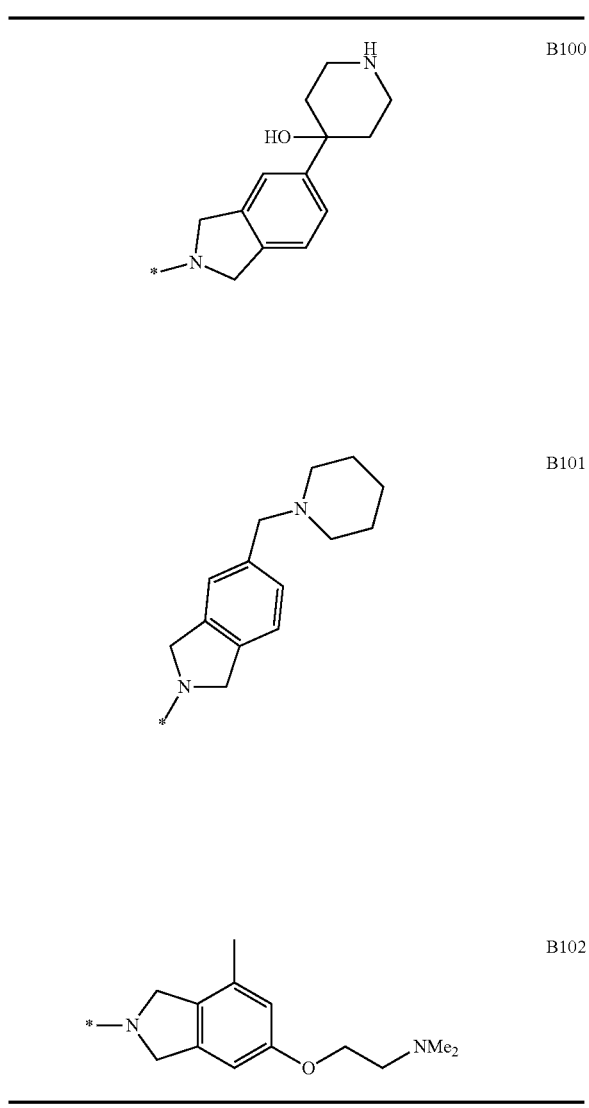

B100

B101

B102

One set of preferred groups NR$^5$R$^6$ consists of or includes groups B8 and B30.

Another preferred group NR$^5$R$^6$ is group B8.

A further set of preferred groups NR$^5$R$^6$ consists of groups B8, B35, B36, B37, B38, B39, B40, B41, B42, B43, B45, B46, B48, B53, B54, B55, B55, B57, B58, B59, B60, B61 and B62.

A further set of preferred groups NR$^5$R$^6$ consists of groups B8, B35, B36, B37, B38, B39, B40, B41, B42, B43, B45, B46, B48, B53, B54, B55, B56, B57, B58, B59, B60, B61 and B62

Another set of preferred groups consists of B8, B35, B36, B37, B38, B39, B40, B41, B42, B43, B45, B46, B48, B53, B54, B55, B56, B57, B58, B59, B60, B61, B62, B71, B72, B74, B75, B76, B77, B78, B79, B80, B81, B82, B83, B85, B86, B87, B93, B94, B95, B97, B98, B99, B100 and B101.

A further sub-set of groups NR$^5$R$^6$ consists of B43, B46, B48, B76, B82, B89, B91 and B96. Within this sub-set, more preferred groups are groups B43, B46, B48, B76, B82, B89 and B91, with B76, B82 and B89 being particularly preferred.

Particular and Preferred Sub-Groups

One sub-group of novel compounds of the invention can be represented by the general formula (II):

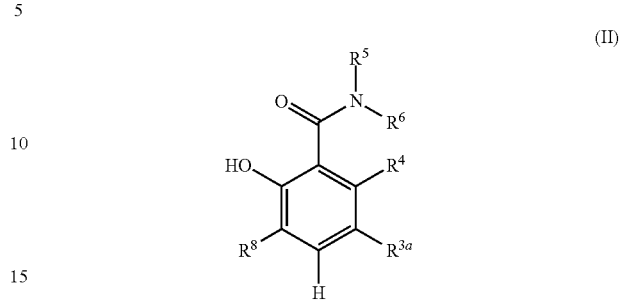

(II)

or salts, tautomers, solvates and N-oxides thereof; wherein:
R$^{3a}$ is selected from hydrogen, halogen, cyano, C$_{1-5}$ hydrocarbyl and C$_{1-5}$ hydrocarbyloxy; wherein the C$_{1-5}$ hydrocarbyl and C$_{1-5}$ hydrocarbyloxy moieties are each optionally substituted by one or more substituents selected from hydroxy, halogen, C$_{1-2}$ alkoxy, amino, mono- and di-C$_{1-2}$ alkylamino, and aryl and heteroaryl groups of 5 to 12 ring members;
R$^4$ is selected from hydrogen; a group —(O)$_n$—R$^7$ where n is 0 or 1 and R$^7$ is an acyclic C$_{1-5}$ hydrocarbyl group or a monocyclic carbocyclic or heterocyclic group having 3 to 7 ring members; halogen; cyano; hydroxy; amino; and mono- or di-C$_{1-5}$ hydrocarbyl-amino, wherein the acyclic C$_{1-5}$ hydrocarbyl group and the mono and di-C$_{1-5}$ hydrocarbylamino moieties in each instance are optionally substituted by one or more substituents selected from hydroxy, halogen, C$_{1-2}$ alkoxy, amino, mono- and di-C$_{1-2}$ alkylamino, and aryl and heteroaryl groups of 5 to 12 ring members;
or R$^{3a}$ and R$^4$ together form a monocyclic carbocyclic or heterocyclic ring of 5 to 7 ring members;
R$^5$ and R$^6$ together with the nitrogen atom to which they are attached form a bicyclic group having up to 12 ring members (e.g. 8-12 ring members or 9-10 ring members) of which up to 5 ring members are heteroatoms selected from oxygen, nitrogen and sulphur; and
R$^8$ is selected from hydrogen and fluorine.

Another sub-group of novel compounds of the invention can be represented by the formula (III):

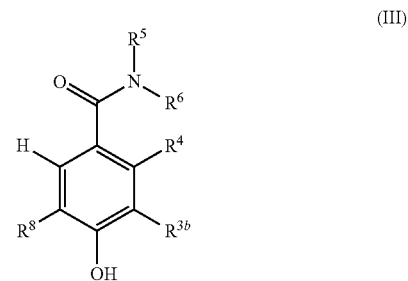

(III)

or salts, tautomers, solvates and N-oxides thereof; wherein:
R$^{3b}$ is selected from hydrogen, halogen, cyano, C$_{1-5}$ hydrocarbyl and C$_{1-5}$ hydrocarbyloxy; wherein the C$_{1-5}$ hydrocarbyl and C$_{1-5}$ hydrocarbyloxy moieties are each optionally substituted by one or more substituents selected from hydroxy, halogen, C$_{1-2}$ alkoxy, amino, mono- and di-C$_{1-2}$ alkylamino, and aryl and heteroaryl groups of 5 to 12 ring members;

$R^4$ is selected from hydrogen; a group $—(O)_n—R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;

or $R^{3b}$ and $R^4$ together form a monocyclic carbocyclic or heterocyclic ring of 5 to 7 ring members;

$R^5$ and $R^6$ together with the nitrogen atom to which they are attached form a bicyclic group having from up to 12 ring members (e.g. 8-12 ring members or 9-10 ring members) of which up to 5 ring members are heteroatoms selected from oxygen, nitrogen and sulphur; and $R^8$ is selected from hydrogen and fluorine.

A further sub-group of novel compounds of the invention can be represented by the formula (IV):

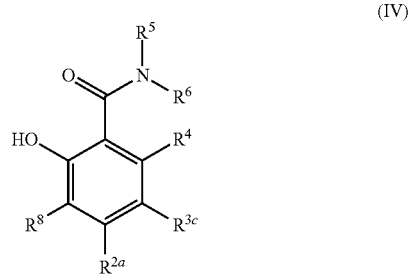

(IV)

or salts, tautomers, solvates and N-oxides thereof; wherein:
$R^{2a}$ is selected from hydroxy and methoxy (and is preferably hydroxy);
$R^{3c}$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group $—(O)_n—R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
or $R^{3c}$ and $R^4$ together form a monocyclic carbocyclic or heterocyclic ring of 5 to 7 ring members;
$R^5$ and $R^6$ together with the nitrogen atom to which they are attached form a bicyclic group having up to 12 ring members (e.g. 8-12 ring members or 9-10 ring members) of which up to 5 ring members are heteroatoms selected from oxygen, nitrogen and sulphur; and
$R^8$ is selected from hydrogen and fluorine.

Within formulae (II), (III) and (IV), particular sub-groups of compounds are those wherein $NR^5R^6$ forms a bicyclic ring of up 10 ring members (e.g. 9 or 10 ring members, preferably 9 ring members) of which up to 5 ring members are heteroatoms selected from O, N and S, the monocylic or bicyclic ring being optionally substituted by up to three substituent groups $R^{10}$, $R^{10a}$, $R^{10b}$, $R^{10c}$ and $R^{10cc}$ as defined herein, more typically up to two substituents, for example up to one substituent.

More particular substituents for the bicyclic heterocyclic group $NR^5R^6$ are those forming part of a sub-group $R^{10d}$ which consists of the members of sub-group $R^{10c}$ and fluoro, chloro, bromo, trifluoromethyl, difluoromethoxy, trifluoromethoxy, cyano, methyl, ethyl, cyclopropyl, hydroxy, methylsulphonyl, amino, methylamino, dimethylamino, methoxy, ethoxy, hydroxymethyl, hydroxyethyl, ethoxycarbonyl, methoxycarbonyl, aminocarbonyl, oxo, methoxymethyl, carboxy, phenyl, $C_{1-2}$ alkoxycarbonyl, aminocarbonyl, acetyl, methylsulphonyl and pyridyl. Within this sub-group, one sub-set of substituents includes methyl, ethyl, chloro, fluoro, hydroxy, methylsulphonyl, amino, methylamino, dimethylamino, cyano, methoxy, ethoxy, hydroxymethyl, cyclopropyl, hydroxyethyl, ethoxycarbonyl, methoxycarbonyl, aminocarbonyl, oxo, methoxymethyl and acetyl.

For example, $NR^5R^6$ can form a 5.6 or 6.6 fused bicyclic ring of 9 or ten ring members of which 1 to 3 are heteroatoms, the bicyclic ring being optionally substituted by one or more substituents $R^{10}$ or $R^{10a}$ or $R^{10b}$ or $R^{10c}$ or $R^{10cc}$ or $R^{10d}$ and sub-groups (sub-sets) and examples thereof as defined herein.

Within this sub-group, examples of fused bicyclic rings are those in which a non-aromatic ring such as a pyrrolidine, piperidine, piperazine or morpholine ring is fused to a 6-membered aryl or heteroaryl ring such as a benzene or pyridine ring, and wherein a nitrogen atom present in the non-aromatic ring is bonded to the carbonyl group in formulae (II), (III) or (IV).

Particular fused bicyclic rings include dihydroindole, dihydroisoindole, tetrahydroquinoline and tetrahydroisoquinoline, and aza-analogues thereof in which one or two carbon ring members in the aromatic ring are replaced by nitrogen.

One sub-group of bicyclic heterocyclic groups formed by $NR^5R^6$ consists of dihydroisoindole optionally substituted by one or more (e.g. 1, 2 or 3) optional substituents selected from groups $R^{10}$, $R^{10a}$, $R^{10b}$ and $R^{10c}$ or $R^{10cc}$ and or $R^{10d}$ and sub-groups (sub-sets) and examples thereof as defined herein.

Preferred compounds are those wherein the group $R^{3a}$ or $R^{3b}$ or $R^{3e}$ is selected from hydrogen, halogen and $C_{1-5}$ alkyl; wherein the $C_{1-5}$ alkyl moiety in each instance is optionally substituted by one or more substituents selected from hydroxy, halogen, $C_{1-2}$ alkoxy and amino.

More preferably, the group $R^{3a}$ or $R^{3b}$ or $R^{3c}$ is hydrogen or a $C_{3-5}$ alkyl group optionally substituted by one or more substituents selected from hydroxy, halogen, $C_{1-2}$ alkoxy and amino. In particular, the group $R^{3a}$ or $R^{3b}$ or $R^{3c}$ is selected from hydrogen and isopropyl, sec-butyl, tert-butyl and 1,2-dimethylpropyl groups.

Another sub-group of compounds of the invention is represented by formula (V):

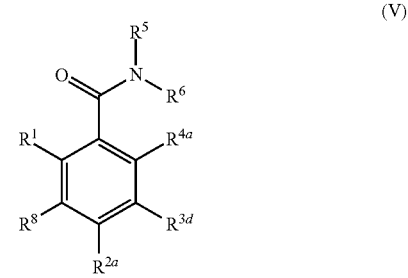

(V)

or salts, tautomers, solvates and N-oxides thereof;

wherein $R^1$ is hydrogen or hydroxy; $R^{2a}$ is hydroxy or methoxy; provided that at least one of $R^1$ and $R^{2a}$ is hydroxy; $R^{3d}$ is selected from ethyl and secondary and tertiary alkyl groups of 3 to 6 carbon atoms; $R^{4a}$ is selected from hydrogen, fluorine, chlorine and methoxy; and $R^5$, $R^6$ and $R^8$ are as defined herein; provided that when $R^1$ and $R^2$ are both hydroxy, then $R^{3d}$ can additionally be selected from hydrogen.

In one embodiment, when $R^1$ and $R^2$ are both hydroxy, $R^{3d}$ is hydrogen.

In another embodiment, $R^{3d}$ is ethyl or a secondary or tertiary alkyl group. Particularly preferred alkyl groups $R^{3d}$ are ethyl, isopropyl and tert-butyl, and in particular isopropyl.

Within formulae (II) to (V), preferred groups $NR^5R^6$ are dihydroisoindole groups which may be substituted or unsubstituted by one, two or three groups $R^{10}$, $R^{10a}$ or $R^{10b}$ or $R^{10c}$ or $R^{10cc}$ or $R^{10d}$ and sub-groups (sub-sets) and examples thereof as defined herein but, in one particular embodiment, are unsubstituted.

Another preferred sub-set of compounds can be represented by formula (VI):

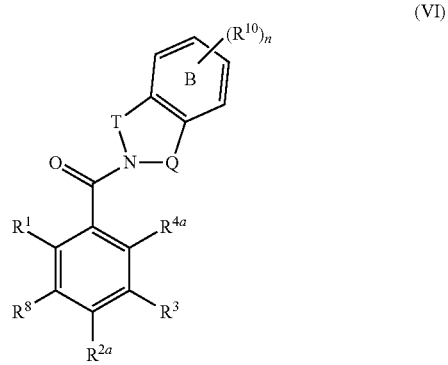

(VI)

or salts, tautomers, solvates and N-oxides thereof;
wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10})_j$ and Q is a group $(CHR^{10})_k$ where j and k are each 0, 1, 2 or 3 provided that the sum of j and k is 2 or 3; n is 0, 1, 2 or 3 and $R^3$, $R^{4a}$, $R^8$ and $R^{10}$ are as defined herein.

Another preferred sub-set of compounds can be represented by formula (VIa):

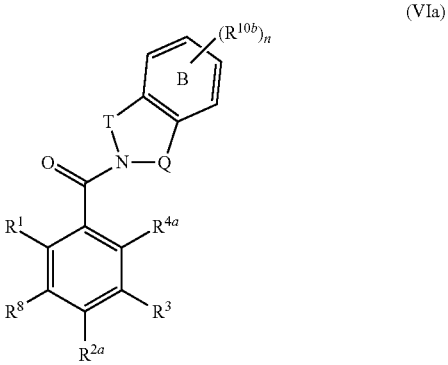

(VIa)

or salts, tautomers, solvates and N-oxides thereof;
wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10b})_j$ and Q is a group $(CHR^{10b})_k$ where j and k are each 0, 1, 2 or 3 provided that the sum of j and k is 2 or 3; n is 0, 1, 2 or 3 and $R^3$, $R^{4a}$, $R^8$ and $R^{10b}$ are as defined herein.

In one sub-group of compounds within formula (VI) or formula (VIa), $R^1$ is hydrogen.

In another subgroup of compounds within formula (VI) or formula (VIa), $R^1$ is hydroxy.

In formula (VI), examples of the bicyclic group:

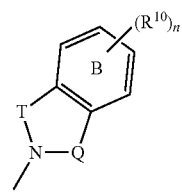

include the groups C1 to C6 below.

C1

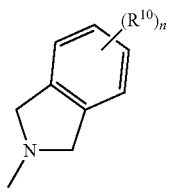

C2

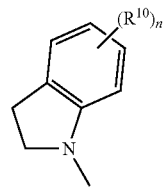

C3

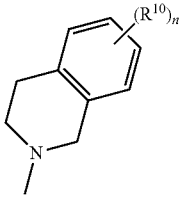

C4

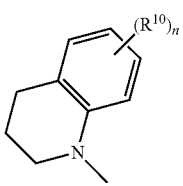

C5

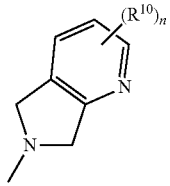

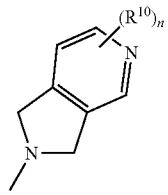

Preferred groups are groups C1, C5 and C6

In the groups C1 to C6, the moiety $R^{10}$ can be a group $R^{10}$ as hereinbefore defined or can be a group $R^{10b}$, $R^{10c}$, $R^{10cc}$ or $R^{10ccc}$ as defined herein. In each case, n is preferably 1, 2 or 3, and more preferably is 1 or 2, e.g. 1.

A currently preferred group is group C1.

Within formula (VI), one particular group of compounds can be represented by the formula (VII):

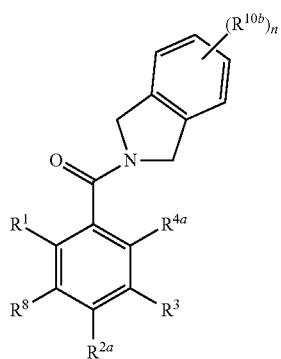

(VII)

or salts, tautomers, solvates and N-oxides thereof;
wherein $R^1$, $R^{2a}$, $R^3$, $R^{4a}$, $R^8$ and $R^{10b}$ are as defined herein and n is 0, 1 2 or 3 (more preferably 0, 1 or 2, e.g. 0 or 1), and provided that at least one of $R^1$ and $R^{2a}$ is hydroxy.

Within formulae (VI) and (VII), the substituent $R^3$ is preferably a group $R^{3d}$ as defined herein and/or the substituent $R^{10b}$ is either absent (n=0) or is selected from groups $R^{10c}$ and $R^{10d}$ and sub-groups (sub-sets) and examples thereof as defined herein. Preferably $R^1$ and $R^{2a}$ are both hydroxy.

One particular group of compounds of the invention within formula (VII) is represented by the formula (VIIa):

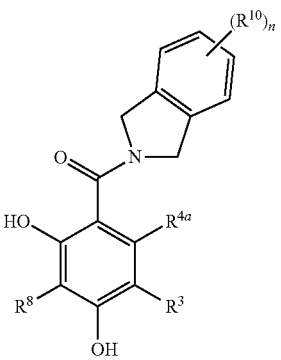

(VIIa)

or salts, tautomers, solvates and N-oxides thereof;
wherein $R^3$ is selected from hydrogen, halogen, $C_{1-5}$ alkyl, $C_{2-5}$ alkenyl and $C_{3-4}$ cycloalkyl groups; $R^{4a}$ is selected from hydrogen, fluorine, chlorine and methoxy; $R^8$ is hydrogen or fluorine; n is 0, 1 2 or 3; and $R^{10}$ is as defined herein.

Within formula (VIIa), $R^{10}$ can be selected from, for example, one, two or three groups $R^{10a}$ or $R^{10b}$ or $R^{10c}$ or $R^{10cc}$ or $R^{10d}$ and sub-groups (sub-sets) and examples thereof as defined herein.

One preferred group of compounds of the invention within formula (VII) is represented by the formula (VIIb):

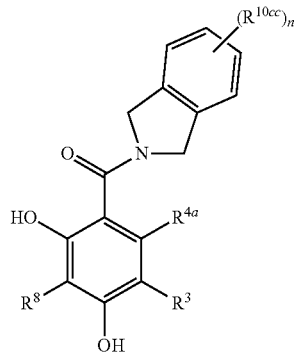

(VIIb)

or salts, tautomers, solvates and N-oxides thereof;
wherein $R^3$ is selected from hydrogen, halogen, $C_{1-5}$ alkyl, $C_{2-5}$ alkenyl and $C_{3-4}$ cycloalkyl groups; $R^{4a}$ is selected from hydrogen, fluorine, chlorine and methoxy; $R^8$ is hydrogen or fluorine; n is 0, 1 2 or 3; and $R^{10cc}$ is selected from:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2$[sol], $C(O)$[sol], $OCH_2CH_2$[sol] or $OCH_2CH_2CH_2$[sol] where [sol] is selected from the following groups -continued

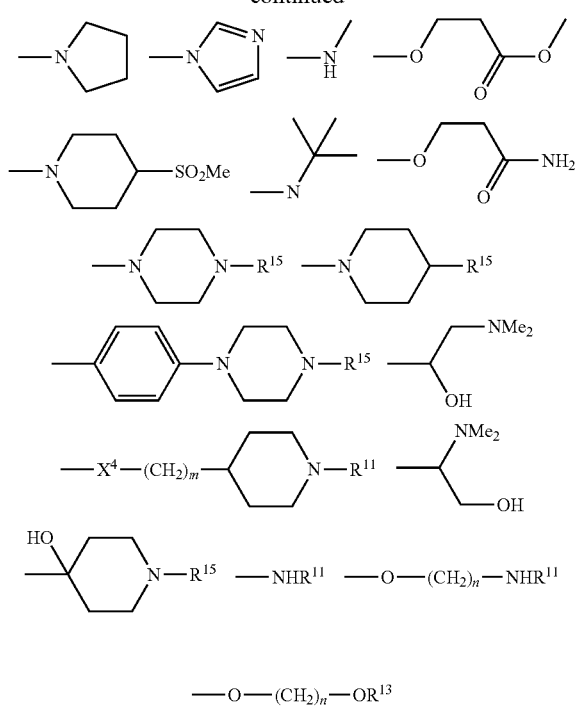

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In a further embodiment, the compound can be an aza- or diaza-analogue of the compounds of formulae (VI), (VII) and (VIIa) as defined herein wherein one or two of the carbon atoms of the benzene ring attached to the five membered ring is replaced by nitrogen.

For example, the group:

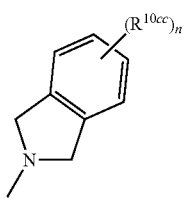

in the compound of formula (VIIa)

may be replaced by:

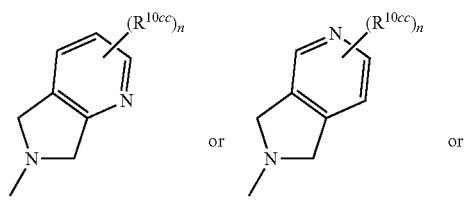

or

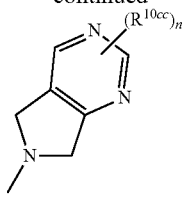

In each of formulae (VI), (VIa), (VII), (VIIa) and (VIIb) and sub-groups thereof as defined herein, n is preferably 1, 2 or 3, and more preferably is 1 or 2. In one embodiment, n is 1.

Specific compounds of the invention include:

(5-chloro-2-hydroxy-phenyl)-(1,3-dihydro-isoindol-2-yl)-methanone;
(3-tert-butyl-4-hydroxy-phenyl)-(2,3-dihydro-indol-1-yl)-methanone;
(3-tert-butyl-4-hydroxy-phenyl)-(3,4-dihydro-2H-quinolin-1-yl)-methanone;
(3,4-dihydro-1H-isoquinolin-2-yl)-(4-hydroxy-3-isopropyl-phenyl)-methanone;
(1,3-dihydro-isoindol-2-yl)-(2,4-dihydroxy-5-isopropyl-phenyl)-methanone;
(3-tert-butyl-4-hydroxy-phenyl)-(1,4-dioxa-8-aza-spiro[4.5]dec-8-yl)-methanone;
(3-tert-butyl-4-hydroxy-phenyl)-(1,3-dihydro-isoindol-2-yl)-methanone;
(3-tert-butyl-4-hydroxy-phenyl)-pyrrolo[3,2-b]pyridin-1-yl-methanone;
8-(3-tert-butyl-4-hydroxy-benzoyl)-2-methyl-2,8-diaza-spiro[4.5]decan-1-one;
(1,3-dihydro-isoindol-2-yl)-(4-hydroxy-3-isopropyl-phenyl)-methanone;
(3-tert-butyl-4-hydroxy-phenyl)-(3,4-dihydro-1H-isoquinolin-2-yl)-methanone;
(1,3-dihydro-isoindol-2-yl)-(5-ethyl-2,4-dihydroxy-phenyl)-methanone;
(5-cyclopropyl-2,4-dihydroxy-phenyl)-(1,3-dihydro-isoindol-2-yl)-methanone;
(5-sec-butyl-2,4-dihydroxy-phenyl)-(1,3-dihydro-isoindol-2-yl)-methanone;
(1,3-dihydro-isoindol-2-yl)-(2,4-dihydroxy-phenyl)-methanone;
(5-chloro-1,3-dihydro-isoindol-2-yl)-(2,4-dihydroxy-5-isopropyl-phenyl)-methanone;
[5-(3-amino-propoxy)-1,3-dihydro-isoindol-2-yl]-(2,4-dihydroxy-5-isopropyl-phenyl)-methanone;
(5-Bromo-2,4-dihydroxy-phenyl)-(1,3-dihydro-isoindol-2-yl)-methanone;
(1,3-Dihydro-isoindol-2-yl)-(2,4-dihydroxy-5-trifluoromethyl-phenyl)-methanone;
(2,4-Dihydroxy-5-isopropyl-phenyl)-{4-[2-(2-methoxy-ethoxy)-ethoxy]-1,3-dihydro-isoindol-2-yl}methanone;
(2,4-Dihydroxy-5-isopropyl-phenyl)-[4-(2-dimethylamino-ethoxy)-1,3-dihydro-isoindol-2-yl]-methanone;
(2,4-Dihydroxy-5-isopropyl-phenyl)-[4-(3-morpholin-4-yl-propoxy)-1,3-dihydro-isoindol-2-yl]methanone;
(3-sec-Butyl-4-hydroxy-phenyl)-(1,3-dihydro-isoindol-2-yl)-methanone;
(5-tert-Butyl-2,4-dihydroxy-phenyl)-(1,3-dihydro-isoindol-2-yl)-methanone;
(5-Chloro-2,4-dihydroxy-phenyl)-(1,3-dihydro-isoindol-2-yl)-methanone;
(1,3-Dihydro-isoindol-2-yl)-(2-hydroxy-5-isopropyl-4-methoxy-phenyl)-methanone;

(4,7-difluoro-1,3-dihydro-isoindol-2-yl)-(2,4-dihydroxy-5-isopropyl-phenyl)-methanone;
(2,4-dihydroxy-5-isopropyl-phenyl)-(5-fluoro-1,3-dihydro-isoindol-2-yl)-methanone;
(1,3-dihydro-isoindol-2-yl)-(3-fluoro-2,4-dihydroxy-5-isopropyl-phenyl)-methanone;
(1,3-dihydro-isoindol-2-yl)-(2-fluoro-4,6-dihydroxy-3-isopropyl-phenyl)-methanone;
(2,4-dihydroxy-5-isopropyl-phenyl)-(4-fluoro-1,3-dihydro-isoindol-2-yl)-methanone hydrochloride;
(5-chloro-6-methoxy-1,3-dihydro-iso-indol-2-yl)-(2,4-dihydroxy-5-isopropyl-phenyl)-methanone;
(2,4-dihydroxy-5-isopropyl-phenyl)-[5-(2-methoxy-ethoxy)-1,3-dihydro-isoindol-2-yl]-methanone;
(2,4-dihydroxy-5-isopropyl-phenyl)-[5-(3-morpholin-4-yl-propoxy)-1,3-dihydro-isoindol-2-yl]-methanone;
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-(2-oxa-5-aza-bicyclo[2.2.1]hept-5-yl)-methanone;
(3,4-dihydro-1H-isoquinolin-2-yl)-(2,4-dihydroxy-5-isopropyl-phenyl)-methanone;
(5-amino-1,3-dihydro-isoindol-2-yl)-(2,4-dihydroxy-5-isopropyl-phenyl)-methanone;
(2,4-dihydroxy-5-isopropyl-phenyl)-(5-methoxy-1,3-dihydro-isoindol-2-yl)-methanone;
(2,4-dihydroxy-5-isopropyl-phenyl)-(5-morpholin-4-yl-1,3-dihydro-isoindol-2-yl)-methanone;
(2,4-dihydroxy-5-isopropyl-phenyl)-[5-(4-methyl-piperazin-1-yl)-1,3-dihydro-isoindol-2-yl]-methanone;
2-(2,4-dihydroxy-5-isopropyl-benzoyl)-2,3-dihydro-1H-isoindole-5-carboxylic acid methyl ester;
2-(2,4-dihydroxy-5-isopropyl-benzoyl)-2,3-dihydro-1H-isoindole-5-carboxylic acid;
(2,4-dihydroxy-5-isopropyl-phenyl)-(5-morpholin-4-ylmethyl-1,3-dihydro-isoindol-2-yl)-methanone;
{3-[2-(2,4-dihydroxy-5-isopropyl-benzoyl)-2,3-dihydro-1H-isoindol-5-yloxy]-propyl}-carbamic acid tert-butyl ester;
(2,4-dihydroxy-5-isopropyl-phenyl)-(5-methyl-1,3-dihydro-isoindol-2-yl)-methanone;
(2,4-dihydroxy-5-isopropyl-phenyl)-[5-(2-isopropylamino-ethoxy)-1,3-dihydro-isoindol-2-yl]-methanone;
N-{2-[2-(2,4-dihydroxy-5-isopropyl-benzoyl)-2,3-dihydro-1H-isoindol-5-yloxy]-ethyl}-2-morpholin-4-yl-acetamide;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-{5-[4-(4-methyl-piperazin-1-yl)-piperidin-1-yl]-1,3-dihydro-isoindol-2-yl}-methanone;
(2,4-dihydroxy-5-isopropyl-phenyl)-[5-(4-piperazin-1-yl-phenyl)-1,3-dihydro-isoindol-2-yl]-methanone;
2,4-dihydroxy-5-isopropyl-phenyl)-[5-(1-dimethylamino-2-hydroxy-ethyl)-1,3-dihydro-isoindol-2-yl]-methanone;
dihydroxy-5-isopropyl-phenyl)-[5-(2-dimethylamino-1-hydroxy-ethyl)-1,3-dihydro-isoindol-2-yl]-methanone;
(2,4-dihydroxy-5-isopropyl-phenyl)-[5-(piperazine-1-carbonyl)-1,3-dihydro-isoindol-2-yl]-methanone hydrochloride;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[4-(3-morpholin-4-yl-propoxy)-1,3-dihydro-isoindol-2-yl]methanone;
[5-(2-Amino-ethoxy)-1,3-dihydro-isoindol-2-yl]-(2,4-dihydroxy-5-isopropyl-phenyl)-methanone;
(2,4-Dihydroxy-5-isopropyl-phenyl)-(5-hydroxy-1,3-dihydro-isoindol-2-yl)-methanone;
(2,4-Dihydroxy-5-isopropyl-phenyl)-{5-[4-(2-hydroxy-ethyl)-piperazin-1-yl]-1,3-dihydro-isoindol-2-yl}-methanone;
(2,4-Dihydroxy-5-isopropyl-phenyl)-[5-(4-morpholin-4-yl-piperidin-1-yl)-1,3-dihydro-isoindol-2-yl]-methanone;
(2,4-Dihydroxy-5-isopropyl-phenyl)-[5-(1-methyl-piperidin-4-ylamino)-1,3-dihydro-isoindol-2-yl]-methanone;
(2,4-Dihydroxy-5-isopropyl-phenyl)-[5-(4-isopropyl-piperazin-1-yl)-1,3-dihydro-isoindol-2-yl]-methanone;
(2,4-Dihydroxy-5-isopropyl-phenyl)-(5-piperazin-1-yl-1,3-dihydro-isoindol-2-yl)-methanone;
4-[2-(2,4-Dihydroxy-5-isopropyl-benzoyl)-2,3-dihydro-1H-isoindol-5-ylamino]-piperidine-1-carboxylic acid tert-butyl ester;
(2,4-dihydroxy-5-isopropyl-phenyl)-[5-(piperidin-4-ylamino)-1,3-dihydro-isoindol-2-yl]-methanone;
(2,4-dihydroxy-5-isopropyl-phenyl)-[4-(4-methyl-piperazin-1-yl)-1,3-dihydro-isoindol-2-yl]-methanone;
(2,4-dihydroxy-5-isopropyl-phenyl)-[4-(piperidin-4-ylamino)-1,3-dihydro-isoindol-2-yl]-methanone;
(2,4-Dihydroxy-5-isopropyl-phenyl)-(5-dimethylaminomethyl-1,3-dihydroisoindol-2-yl)-methanone;
(2,4-Dihydroxy-5-isopropyl-phenyl)-[5-(4-methyl-piperazine-1-carbonyl)-1,3-dihydro-isoindol-2-yl]-methanone;
(2,4-Dihydroxy-5-isopropyl-phenyl)-{5-[2-(2,2-dimethyl-propylamino)-ethoxy]-1,3-dihydro-isoindol-2-yl}-methanone;
[5-(2-Cyclopentylamino-ethoxy)-1,3-dihydro-isoindol-2-yl]-(2,4-dihydroxy-5-isopropyl-phenyl)-methanone;
(2,4-Dihydroxy-5-isopropyl-phenyl)-(5-piperidin-1-ylmethyl-1,3-dihydro-isoindol-2-yl)-methanone;
(2,4-Dihydroxy-5-isopropyl-phenyl)-[5-(4-hydroxypiperidin-4-yl)-1,3-dihydro-isoindol-2-yl]-methanone;
(5-Chloro-2,4-dihydroxy-phenyl)-[5-(4-methyl-piperazin-1-yl)-1,3-dihydro-isoindol-2-yl]-methanone; and
(5-chloro-6-hydroxy-1,3-dihydro-isoindol-2-yl)-(2,4-dihydroxy-5-isopropyl-phenyl)-methanone;
(2,4-dihydroxy-5-isopropyl-phenyl)-[5-(4-methyl-piperazin-1-yl)-1,3-dihydro-isoindol-2-yl]-methanone;
(5-chloro-2,4-dihydroxy-phenyl)-[5-(4-methyl-piperazin-1-yl)-1,3-dihydro-isoindol-2-yl]methanone;
(2,4-dihydroxy-5-isopropyl-phenyl)-[5-(2-dimethylamino-ethoxy)-7-methyl-1,3-dihydro-isoindol-2-yl]-methanone;
and salts, solvates, N-oxides and tautomers thereof.

Preferred individual compounds of the formula (I) are:
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-[5-(4-methyl-piperazin-1-yl)-1,3-dihydro-isoindol-2-yl]-methanone;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[5-(1-methyl-piperidin-4-ylamino)-1,3-dihydro-isoindol-2-yl]-methanone;
(2,4-dihydroxy-5-isopropyl-phenyl)-(5-piperazin-1-yl-1,3-dihydro-isoindol-2-yl)-methanone;
(2,4-dihydroxy-5-isopropyl-phenyl)-(5-dimethylaminomethyl-1,3-dihydroisoindol-2-yl)-methanone;
or salts, solvates, N-oxides and tautomers thereof.

A particularly preferred set of individual compounds consists of:

(2,4-dihydroxy-5-isopropyl-phenyl)-[5-(4-hydroxy-1-methyl-piperidin-4-yl)-1,3-dihydro-isoindol-2-yl]-methanone;

(2,4-dihydroxy-5-isopropyl-phenyl)-[5-(4-methyl-piperazin-1-ylmethyl)-1,3-dihydro-isoindol-2-yl]-methanone; and (2,4-dihydroxy-5-isopropyl-phenyl)-[5-(1-methyl-piperidin-4-ylamino)-1,3-dihydro-isoindol-2-yl]-methanone;

or salts, solvates or tautomers thereof.

For the avoidance of doubt, it is to be understood that each general and specific preference, embodiment and example of the group $R^1$ may be combined with each general and specific preference, embodiment and example of the groups $R^2$ and/or $R^3$ and/or $R^4$ and/or $R^4$ and/or $R^5$ and/or $R^6$ and/or $R^{10}$ and/or Q and/or T and/or sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Salts, Solvates, Tautomers, Isomers, N-Oxides, Esters, Prodrugs and Isotopes

A reference to a compound of the formulae (I) and sub-groups thereof also includes ionic forms, salts, solvates, isomers, tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof.

Many compounds of the formula (I) can exist in the form of salts, for example acid addition salts or, in certain cases salts of organic and inorganic bases such as phenolate, carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

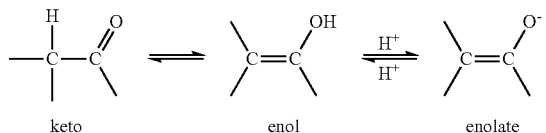

keto    enol    enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^{1}$H, $^{2}$H (D), and $^{3}$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

In one general embodiment, formula (I) and sub-formulae, sub-groups, preferences and examples thereof do not cover esters such as carboxylic acid esters and acyloxy esters.

In one particular embodiment, formula (I) and sub-formulae, sub-groups, preferences and examples thereof do not cover esters of hydroxy compounds wherein R$^2$ is hydroxy and the ester is formed with the hydroxy group R$^2$.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
(e.g., -Me, -Et, -nPr, -iPr, -nBu, —SBU, -iBu, -tBu);
$C_{1-7}$-aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Biological Activity

The compounds of the formulae (I) and sub-groups thereof are inhibitors of Hsp90 and consequently are expected to be beneficial in the treatment of wide spectrum of proliferative disorders. Examples of such proliferative disorders include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, gastrointestinal system, e.g. gastrointestinal stromal tumours, or skin, for example squamous cell carcinoma; a hematopoieitic tumour of lymphoid lineage, for example leukaemia, acute lymphocytic leukaemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkett's lymphoma; a hematopoieitic tumour of myeloid lineage, for example acute chronic myelogenous leukaemias, Imatinib sensitive and refractory chronic myelogenous leukaemias, myelodysplastic syndrome, Bortezomib sensitive and refractory multiple myeloma, myeloproliferative disease or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoacanthoma; thyroid follicular cancer; or Kaposi's sarcoma.

The cancers may be cancers which are sensitive to Hsp90 inhibition, and such cancers may be determined by a method as set out in the section headed "Methods of Diagnosis".

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma) and optionally further includes chronic myelogenous leukaemia and multiple myeloma.

A preferred sub-set of cancers consists of ErbB2-positive breast, prostate, lung, and gastric cancer; chronic myeloid leukemia; androgen receptor dependent prostate cancer; Flt3-dependent acute myeloid leukaemia; melanoma associated with Braf mutation; multiple myeloma; velcade refractory multiple myeloma; and gastrointestinal stromal tumours (GIST).

Of these, particularly preferred cancers are multiple myelomas and velcade refractory tumour types as defined herein.

Hsp90 inhibitors could also be used to treat other conditions such as viral infections, parasitic disease, autoimmune diseases, neuro-degenerative disorders, inflammation, Type I and II diabetes, and cardiac disease.

Hsp90 inhibitors could also have clinical benefit in transplantation and immunosuppression.

Hsp90 inhibitors may also have clinical benefit in the previously described diseases when used in combination with existing or new therapeutic agents.

Based on the activities of Hsp90 client proteins and experimental evidence, the following disorders may be particularly sensitive to treatment by Hsp90 inhibitors.

ErbB2-Positive Breast, Prostate, Lung, and Gastric Cancer

Overexpression of ErbB2 (HER-2) occurs in approximately 30% of breast cancers and ErbB2 receptor down-regulation by herceptin sensitized cells to Taxol. ErbB2 over-expression is linked to poor prognosis and drug resistance (Tsugawa et. al., 1993. Oncology 1993; 50: 418).

Mutant EGFR in Lung Cancer

Somatic mutations in the kinase domain of the epidermal growth factor receptor (EGFR), including L858R and exon 19 deletions, underlie responsiveness to gefitinib and erlotinib in non-small cell lung cancer (NSCLC). Acquired resistance to these tyrosine kinase inhibitors is in some cases mediated by a second mutation, T790M. Ansamycin antibiotics, such as geldanamycin, potently inhibit heat shock protein 90 (Hsp90), promoting ubiquitin-mediated degradation of oncogenic kinases that require the chaperone for proper conformational folding. Exposure of EGFR-mutant cell lines to geldanamycin induced marked depletion of phospho-Akt and cyclin D1 as well as apoptosis. These data suggest mutational activation of EGFR is associated with dependence on Hsp90 for stability and that Hsp90 inhibition may represent a novel strategy for the treatment of EGFR-mutant NSCLC.

Chronic Myeloid Leukemia

The aberrant BCR-Abl protein is created through a chromosomal translocation and results in a constitutively active Abl kinase domain. This translocation event has been shown to be causal for CML. P210BcrAbl is a known client protein for Hsp90. Treatment of the BCR-Abl cell line K562 with an hsp90 inhibitor induced apoptosis. The Bcr-Abl inhibitor Gleevec® also induces apoptosis in K562 cells; however Gleevec® resistant K562 cells still retain sensitivity towards Hsp90 inhibitors (Gorre et. al. 2002, Blood 100: 3041-3044).

Androgen Receptor Dependent Prostate Cancer

The androgen receptor kinase is an Hsp90 client protein. Hormone replacement therapy is usually adopted where surgery does not resolve the cancer. Eventually through mutation in the receptor the cancer becomes refractory to the hormone analogue. Hsp90 regulation of the receptor would still be viable post-mutation.

The same would apply to estrogen-dependent breast cancers.

Flt3-Dependent Acute Myeloid Leukaemia

Internal duplication of the tyrosine kinase receptor Flt3 leads to its constitutive activation and oncogenesis. These internal duplications are observed in 20% of all reported cases of AML and are an indication of poor prognosis. Much like the activation of the ABL kinase in CML, this represents another example of a single genetic lesion giving rise to a malignancy. Hsp90 inhibitors are predicted to be of clinical benefit to these patients as Flt3 is an Hsp90 client protein (Bali et. al., 2004 Cancer Res. 64(10):3645-52).

Melanoma Associated with Braf Mutation

Braf encodes for a serine/threonine kinase which is mutated in 70% of all melanomas. 80% of these represent a single V599E point mutation that confers elevated kinase activity to BRAF. This mutation is also transforming in NIH3T3 cells (Bignell et. al., 2002 Nature. 417(6892):949-54).

Multiple Myeloma

The Hsp90 inhibitor 17-AAG potently inhibits proliferation of Bortezomib refractory multiple myeloma cell lines. Cell surface levels of IGF-1R and IL-6R were also diminished in 17-aag treated MM-1 cells (Mitsiades et. al., Blood 107:1092-1100, 2006). Autocrine stimulation of multiple myeloma cells, as well as paracrine stimulation of bone marrow stromal cells with IL-6 is also diminished through down-regulation of the Hsp90 client IKK.

Velcade Refractory Multiple Myeloma

Compounds of the present invention can be used in the treatment of velcade refractory tumour types including treatment of patients with second line mantle cell lymphoma, indolent non-Hodgkin's lymphoma, stage IIIB and IV Bronchioloalveolar carcinoma, advanced non-small cell lung cancer, breast, prostate and ovarian cancers and non-Hodgkin's lymphoma.

Gastrointestinal Stromal Tumours (GIST)

GIST disease particularly disease dependent on growth factor activation or overexpression (e.g. c-kit)

Other conditions or disorders for which an Hsp90 inhibitor may be of clinical benefit include, but are not limited to:

Neurodegenerative Disorders

Huntington's disease (HD) is a progressive neurodegenerative disorder with no effective treatment. GA inhibition of Hsp90 and the resulting up-regulation of Hsps are effective in preventing huntington protein aggregation in neuronal cells. (Sittler et. al., 2001, Human Molecular Genetics, Vol. 10, No. 12 1307-1315). Up-regulation of HSP may also be of clinical benefit in other diseases of protein misfolding e.g., CJD and Alzheimer's.

Inflammatory Disease, Including Rheumatoid Arthritis, Asthma, Chronic Obstructive Pulmonary Disease, and Inflammatory Bowel Disease GA has been shown to dissociate HSF-1 from Hsp90 leading to the activation and nuclear translocation of HSF-1. HSF-1 subsequently acts as a transcription factor to induce HSP90 and Hsp70. The induction of Hsp70 has been implicated in the resolution of inflammation in an induced mouse model of edema (Ianaro et al., 2004 Human Molecular Genetics, 2001, Vol. 10, No. 12 1307-1315). Additionally GA treatment inhibited IkappaB kinase (IKK) activation by TNF-a or PMA. IkBa is a regulator of Nf-kB and Ap-1. (Broemer et. al. 2004). Ap-1 and Nf-kB is a major transcription factor leading to the production of pro-inflammatory cytokines (Yeo et. al., 2004 Biochem Biophys Res Commun. 30; 320(3):816-24). The stability of pro-inflammatory cytokine transcripts is also regulated through inhibition of p38 MapK (Wax et. al., 2003. Rheumatism Vol. 48, No. 2, pp 541-550).

Angiogenesis Related Disease, Including but not Limited to: Tumour Angiogenesis, Psoriasis, Rheumatoid Arthritis, and Diabetic Retinopathy Induction of angiogenesis is regulated by Hsp90 client proteins eNOS and Akt in endothelial cells (Sun and Liao, 2004 Arterioscler Thromb Vasc Biol. 24(12):2238-44). Suppression of hypoxia-inducible factor (HIF)-1a can also impair the growth, angiogenesis and vessel maturation of gastric tumours in a mouse model. (Stoeltzing et. al., 2004 J Natl Cancer Inst; 96:946-956).

Type I and type II Diabetes

Hsp90 inhibition has a profound effect on Akt signalling as well as e-nos. These are two key regulators in high glucose induced endothelial cell apoptosis in type I diabetes (Lin et. al., 2005 J Cell Biochem. 1; 94(1):194-201) and the development of hypertension in type II diabetes (Kobayashi et. al., 2004 Hypertension. 44(6):956-62).

Immunosuppression and Transplantation

Hsp90 inhibition has been shown to down regulate Lck, a T-cell specific tyrosine kinase required for T-cell activation. (Yorgin et. al., 2000 J. Immunol. 15; 164(6):2915-23.)

Cardiac Disease

Cardiac ischemic is the most common cause of death in the western world. Hsps, and notably Hsp70 (induced by radicicol treatment) have demonstrated cardioprotective activity in rat cardiomyocytes (Griffin et. al., 2004). Inhibition of Hsp90 results in the release of HSF-1 from the chaperone complex and its subsequent activation of Hsp genes. Inhibition of Hsp90 also leads to the down-regulation of HIF-1, which has been implicated in the pathogenesis of ischemic heart disease and stroke.

Infectious Disease

Hepatits C viral NS2/3 protease is an Hsp90 client protein and Hsp90 activity is required for viral processing and replication (Whitney et. al., 2001. Proc Natl Acad Sci USA. 20; 98(24):13931-5).

Parasitic Disease

GA has reported antimalarial activity against an Hsp90 ortholog of *Plasmodium falciparum*. *Plasmodium* growth was inhibited with GA at an $IC_{50}$ similar to that observed with chloroquine. GA was also effective against chloroquine resistant strains of *Plasmodium falciparum* (Kamar et. al., 2003. Malar J. 15; 2(1):30).

The biological activity of the compounds of the invention, e.g. as inhibitors of Hsp90, can be measured using the assays set forth in the examples below, for example the isothermal titration calorimetry (ITC) experiments described in Example 80 and the anti-proliferative activity assays described in Example 81. The level of activity exhibited by a given compound in the ITC assay can be defined in terms of the $K_d$ value, and preferred compounds of the present invention are compounds having a $K_d$ value of less than 1 micromolar, more preferably less than 0.1 micromolar. In the anti-proliferative activity assays, the level of activity exhibited by a given compound in an assay can be defined in terms of the $IC_{50}$ value, and preferred compounds of the present invention are compounds having an $IC_{50}$ value of less than 1 micromolar, more preferably less than 0.1 micromolar.

It has also been found that many compounds of the formula (I) have low hERG activity and a good separation between Hsp90 inhibitory activity and hERG activity.

Preferred compounds of the formula (I) have mean $IC_{50}$ values against hERG that are greater than 30 times, or greater than 40 times, or greater than 50 times the $IC_{50}$ values of the compounds in cellular proliferation assays. Preferred compounds of the formula (I) have mean $IC_{50}$ values against hERG that are greater than 5 µM, more particularly greater than 10 µM, and more preferably greater than 15 µM. Some compounds of the invention have mean $IC_{50}$ values against hERG that are greater than 50 µm.

Compounds of the invention have advantageous ADME properties and in particular better tumour distribution.

Methods for the Preparation of Compounds of the Formula (I)

In this section, as in all other sections of this application unless the context indicates otherwise, references to Formula (I) also include all sub-groups and examples thereof as defined herein. Where a reference is made to a group $R^1$, $R^2$, $R^3$, $R^4$, $R^5$, $R^6$, $R^{10}$ or any other "R" group, the definition of the group in question is as set out above and as set out in the following sections of this application unless the context requires otherwise.

Compounds of the formula (I) can be prepared in accordance with synthetic methods well known to the skilled person. For example, compounds of the formula (I) can be prepared by the reaction of a compound of the formula (X):

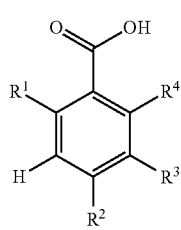

or an activated and/or protected form thereof, with an amine of the formula $HNR^5R^6$ under conditions suitable for forming an amide bond, and thereafter where necessary removing any protecting groups and optionally converting one compound of the formula (I) to another compound of the formula (I).

The amines of the formula $HNR^5R^6$ are either commercially available or can be made using methods well known to the skilled person, see for example, *Advanced Organic Chemistry*, by Jerry March, 4th edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

The carboxylic acid (X) can be converted to an amide of the formula (I) by first forming an acid chloride by treatment of the carboxylic acid with thionyl chloride, or by reaction with oxalyl chloride in the presence of a catalytic amount of dimethyl formamide, or by reaction of a potassium salt of the acid with oxalyl chloride. The acid chloride can then be reacted with the amine $HNR^5R^6$ in the presence of a non-interfering base such as triethylamine. The reaction may be carried out at around room temperature in a polar solvent such as dioxan.

As an alternative to using the acid chloride method described above, the carboxylic acid (X) can be converted to the amide (I) by reaction with the amine $HNR^5R^6$ in the presence of amide coupling reagents of the type commonly used in the formation of peptide linkages. Examples of such reagents include 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Illustrative routes to the compounds of formula (I) are described in more detail below.

Compounds of the formula (I) in which the benzoyl moiety is derived from a 2-hydroxy-5-substituted benzoic acid can be prepared by the sequence of reactions shown in Scheme 1.

The starting material for the synthetic route shown in Scheme 1 is 5-chloro-2-hydroxy benzoic acid, which can be obtained commercially. Conversion to the acid chloride is carried out by heating with thionyl chloride. The acid chloride may be used either in situ and reacted with various amines, or can be isolated as a stable white solid. Other simple 2-hydroxy-5-substituted benzoic acids may be used in this procedure to synthesise other amides of 2-hydroxy-5-substituted benzoic acids.

Scheme 1: 5-Chloro-2-hydroxybenzoic acid amides

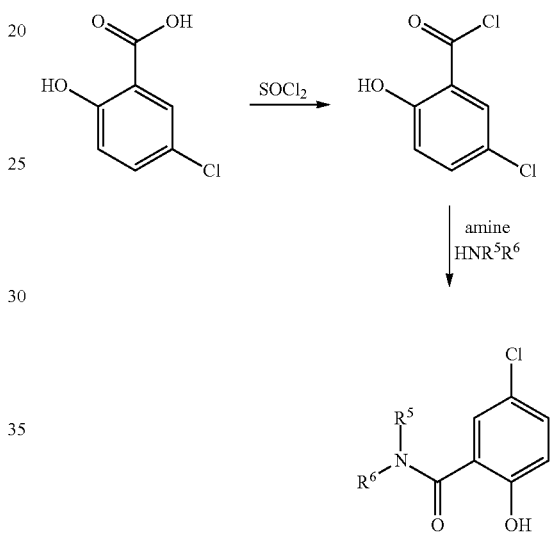

Compounds of formula (I) can also be made according to the method shown in Scheme 2. The starting material for the synthetic route shown in Scheme 2 is 4-ethyl anisole, which can be obtained commercially. Conversion to the carboxylic acid can be carried out by lithiation at low temperature, followed by quenching of the resulting anion with solid carbon dioxide. The carboxylic acid may be coupled with various amines, using standard amide coupling reagents of the type commonly used in the formation of peptide linkages as described above.

Deprotection of the methyl ether can be effected using boron tribromide (e.g. by the method described in *Synthesis* 1991, 469) to give the compound of formula (I). The method illustrated in Scheme 2 can be used to prepare other simple 2-hydroxy-5-substituted benzoic acids which can then be coupled to an appropriate amine to give the compounds of formula (I). The process of coupling intermediates acids with amines, anilines or amino-heterocyclic compounds, followed by removal of any protecting groups, is straightforward and is suitable for the synthesis of large combinatorial libraries of molecules, useful for this invention. Examples of combinatorial libraries are described in *Solid-Phase Synthesis and Combinatorial Technologies* by Pierfausto Seneci. Wiley-Interscience, New York. 2000. xii+637 pp. ISBN 0471331953).

Scheme 2

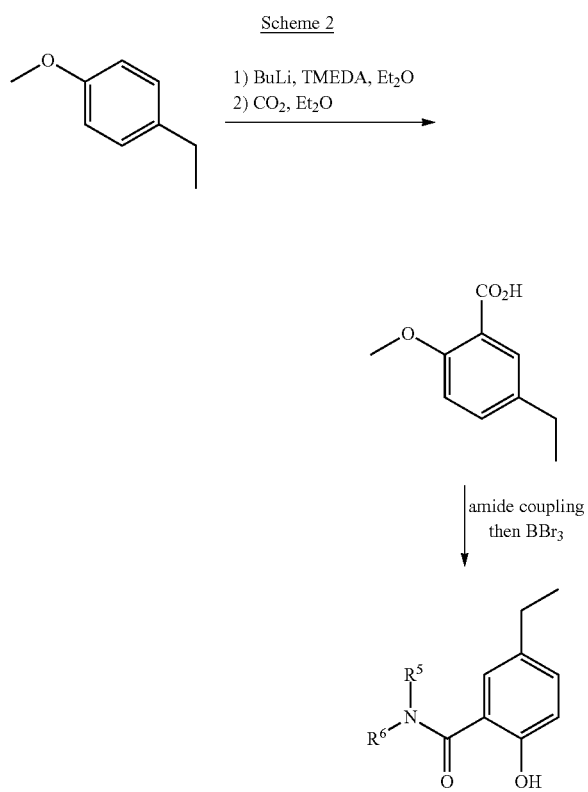

Compounds of the Formula (I) can also be made according to the methods described in Scheme 3. The starting material 3-tert-butyl-4-hydroxybenzoic acid (X=tert-butyl) is commercially available and can be coupled using the amide coupling agents (as outlined above) with a broad range of amines of the formula $HNR^5R^6$ to give compounds of the invention. The other starting material illustrated in Scheme 3, 3-isopropyl-4-hydroxybenzoic acid (X=isopropyl), can be prepared according to a modification of a literature procedure using carbon tetrachloride and copper powder in a Friedel-Crafts type reaction, in which the intermediate species is hydrolysed to the carboxylic acid (*J Chem Soc, Chem Commun* 1985, 1134). The Friedel Crafts method can be used to prepare other simple 2-hydroxy-3-substituted benzoic acids.

Scheme 3: 3-Alkyl-4-hydroxybenzoic acid amides

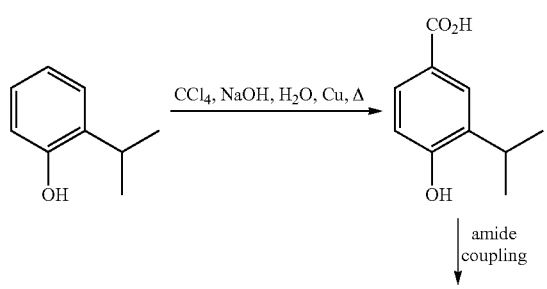

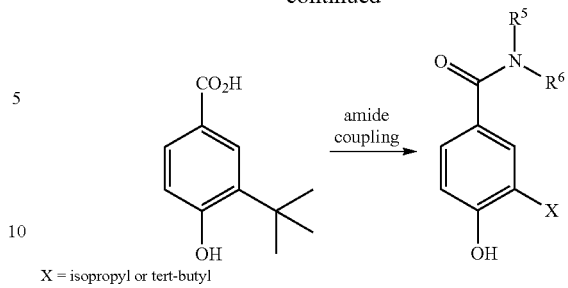

Compounds of the formula (I) can also be made according to the method described in Scheme 4. 2,4-Dihydroxy-5-isopropyl-benzoic acid amides can be prepared by amide coupling using coupling reagents (as outlined above) from a bi-benzyl ether protected intermediate, shown in the scheme, followed by catalytic hydrogenation using hydrogen gas and palladium on carbon. The benzoic acid intermediate itself is made by Friedel-Crafts acylation of 2,4-dihydroxybenzoic acid methyl ester (from commercial sources) using a literature procedure (*J. Ind. Chem. Soc.*, 1953, 30, 269). Typically, Friedel-Crafts acylation of a phenol is carried out by treatment of the phenol with an acylating agent (such as an acid chloride or acid anhydride) in the presence of a Lewis acid catalyst (such as boron trifluoride or aluminium chloride) either at room temperature or at more elevated temperatures (60-120° C.). Benzyl protection of the phenol groups, the Wittig reaction of the ketone to the olefin and ester hydrolysis (saponification) can be carried out under standard conditions, well known to those skilled in the art of organic synthesis (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8). For example, the Wittig reaction can be carried out in an inert polar solvent (such as tetrahydrofuran) and can involve treatment of an aldehyde or ketone with a phosphorus ylide species that may be prepared by the reaction of a phosphonium salt with a base (such as butyl lithium or potassium tert-butoxide). The ester hydrolysis to the carboxylic acid is usually carried out by treatment with an aqueous alkali metal hydroxide such sodium hydroxide. The saponification reaction may be carried out using an organic co-solvent such as an alcohol (e.g. methanol) and the reaction mixture is typically heated to a non-extreme temperature, for example up to about 50-60° C.

It is to be understood that other 2,4-dihydroxy-5-substituted benzoic acids could be made using this procedure to synthesise different examples of compounds of formula I not specifically exemplified herein.

In Scheme 4, as an alternative to the use of the Wittig reagent MePPH$_3$Br to form the olefin (XXVI), the ketone (XXV) can be reacted with methyl magnesium bromide under standard Grignard reaction conditions to give an intermediate hydroxy compound which is then dehydrated to the olefin by reaction with a suitable reagent such as sodium acetate and acetic acid.

The intermediate compound 2,4-bis-benzyloxy-5-isopropenyl-benzoic acid (XXVII) and its precursor compounds (XXV) and (XXVI) shown in Scheme 4 are believed to be novel and, as such, each of the compounds represents a further aspect of the invention.

The 2,4-bis-benzyloxy-5-isopropenyl-benzoic acid amides (XXVIII) are also believed to be novel and also form a further aspect of the invention.

Scheme 4: 2,4-Dihydroxy-5-isopropyl-benzoic acid amides

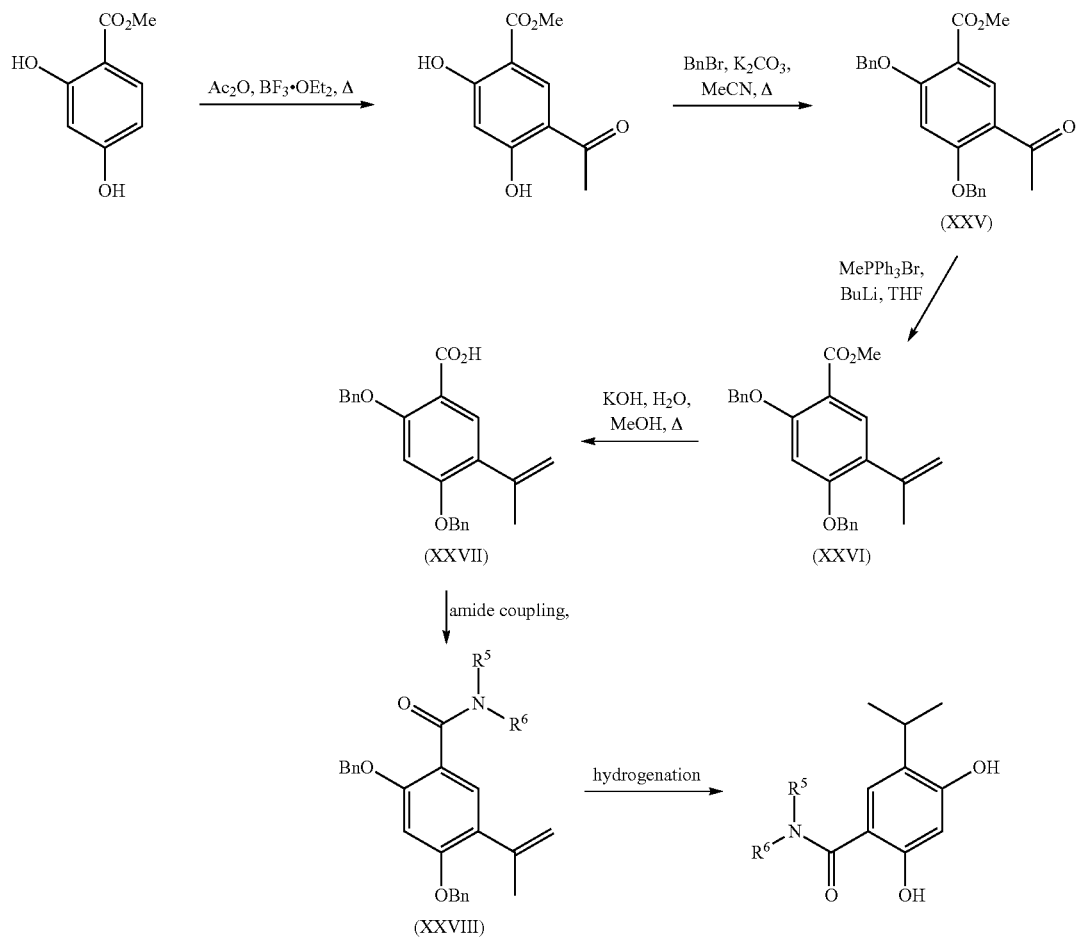

The intermediate compound 2,4-bis-benzyloxy-5-isopropenyl-benzoic acid (XXVII) in Scheme 4 can be made using a variety of methods well known to the skilled person. For example, compound (XXVII) can be made by the synthetic route illustrated in Scheme 4A.

Scheme 4A

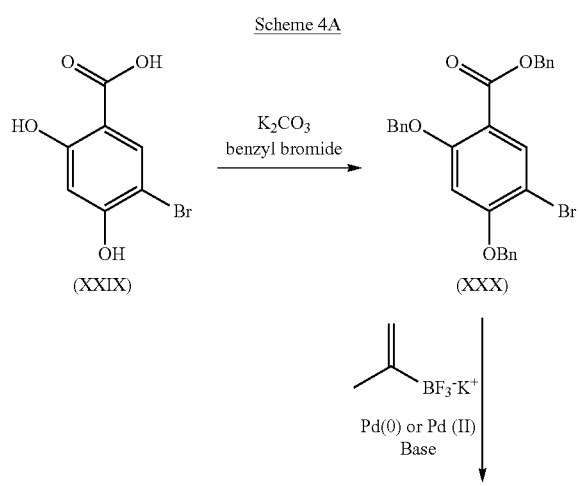

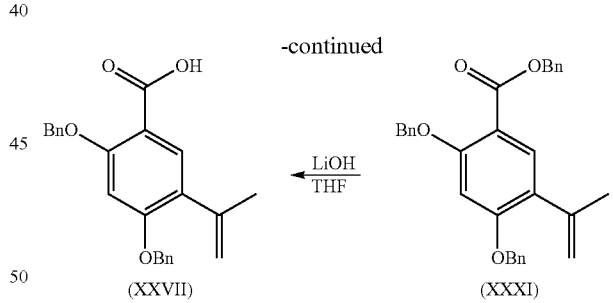

As shown in Scheme 4A, 5-bromo-2,4-dihydroxybenzoic acid is benzylated using benzyl bromide in the presence of a base such as potassium carbonate to give the bis-benzyloxy-bromobenzoic acid benzyl ester (XXX). The ester (XXX) is then reacted with potassium isoprenyl trifluoroborate in the presence of a palladium (0) or palladium (II) compound and a base to give the isopropenyl-bis benzyl ester (XXXI). The palladium compound can be a palladium (0) compound such as $Pd(PPh_3)_4$ or a palladium (II) compound such as [1,1'-bis(diphenyl-phosphino)ferrocene]dichloropalladium(II). The base can be an organic base such as n-butylamine or an inorganic base such as a metal carbonate, e.g. caesium carbonate. The reaction with potassium isoprenyl trifluoroborate is typically carried out at reflux temperature for a prolonged period, for example 15 hours or more. The resulting isopropenyl bis-benzyloxy ester (XXXI) is then hydrolysed to give the carboxylic acid (XXVII) using, for example, an alkali metal hydroxide such as lithium hydroxide, typically with heating to a non-extreme temperature.

Compounds of the formula (I) can also be made according to the route illustrated in Scheme 5. 4-Hydroxy-3-(1',2'-dimethyl-propyl)-benzoic acid amides can be prepared by amide coupling using standard coupling agents (as outlined above) from the alkyl substituted acid. The olefinic acid itself can be prepared by Claisen rearrangement of a precursor ether, as shown in the scheme, by thermal rearrangement in anisole, followed by saponification, which in this case can yield more than one isomer of the olefin, the major one being shown in the scheme. Such Claisen reactions are well known in the literature, e.g. see *J. Chem. Soc, Perkin Trans* 1 1981, 897. The ether itself can be prepared by simple alkylation of commercially available 4-hydroxy benzoic acid ethyl ester. The alkylation and saponification reactions are simple modifications that can be carried out under various conditions (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)). It is to be understood that other 4-hydroxy-3-substituted benzoic acids could be made using this procedure to synthesise different examples of compounds of formula I not specifically exemplified herein.

Scheme 5: 4-Hydroxy-3-(1', 2'-dimethyl-propyl)-benzoic acid amides

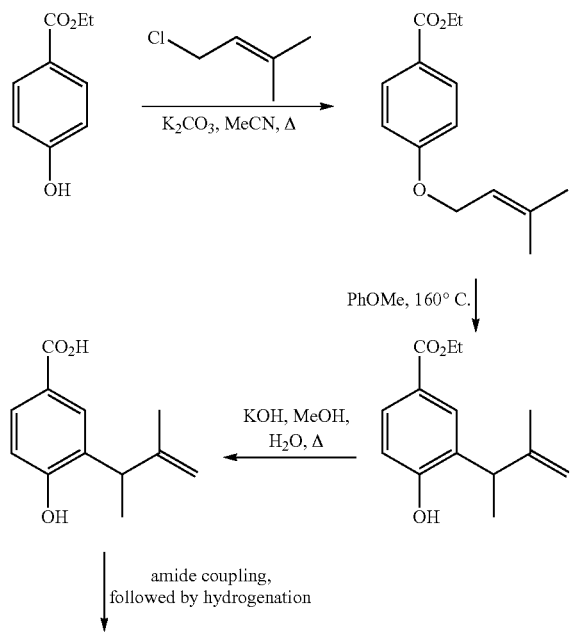

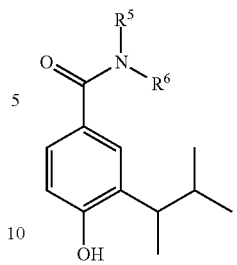

Compounds of the formula (I) can also be made according to the method shown in Scheme 6. 2,4-Dihydroxy-5-bromobenzoic acid is used as the starting material, which is commercially available. Simple protection and deprotection gives the benzoic acid precursor (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)), which can be used in amide coupling reactions with a range of amines (as outlined above). These precursor amides can be subjected to Suzuki cross coupling procedures to make alkyl substituted compounds. A broad range of Suzuki coupling conditions are described in the literature, and the ones used here were taken from *J. Am. Chem. Soc.* 2003, 11148. Suzuki coupling chemistry is also broadly applicable to synthesis of alkyl-aryl and aryl-aryl compounds. The Suzuki reaction is typically carried out in the presence of a palladium catalyst such as bis(tri-t-butylphosphine)-palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C. Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid. The final products of the reaction sequence illustrated in Scheme 6 are formed by catalytic hydrogenation (as outlined above) to remove the benzyl protecting groups and to reduce the olefin, formed in the Suzuki reaction to the alkyl substituent. It is to be understood that other 2,4-dihydroxy-5-substituted benzoic acids could be made using this procedure to synthesise different examples of compounds of formula I not specifically exemplified herein.

Scheme 6: 2,4-Dihydroxy-5-(alkyl)-benzoic acid amides

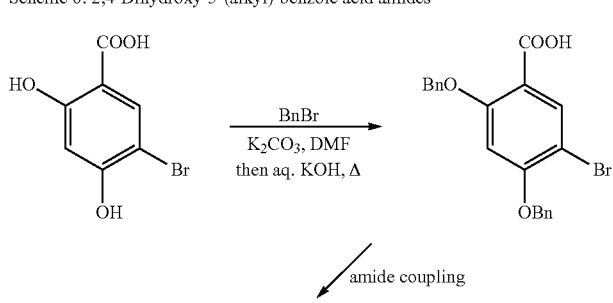

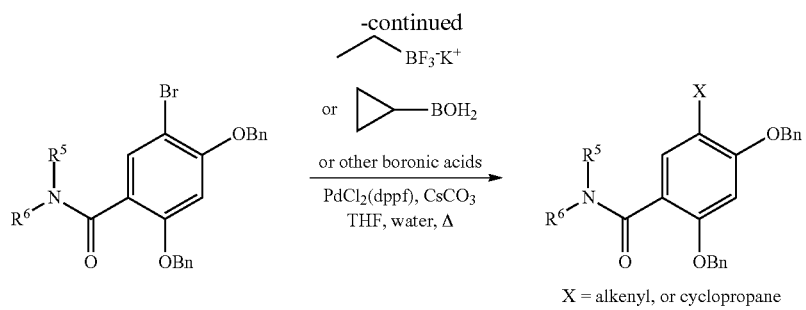

X = alkenyl, or cyclopropane

↓ hydrogenation

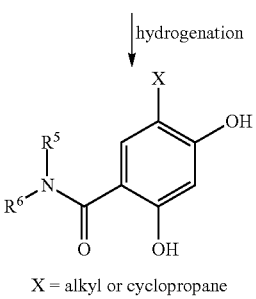

X = alkyl or cyclopropane

Compounds of the formula (I) wherein $NR^5R^6$ is an optionally substituted isoindoline group, for example as in compounds of the formulae (VII) and (VIIa), can be prepared by the methods illustrated in Scheme 7, or methods analogous thereto.

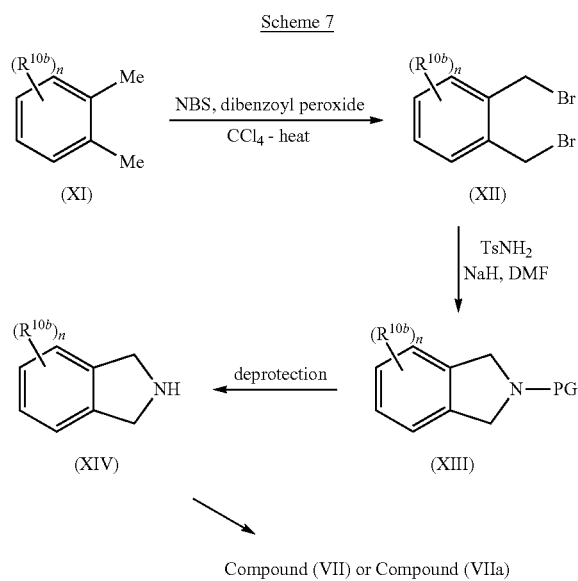

As shown in Scheme 7, an optionally substituted 1,2-dimethylbenzene (XI) is heated with N-bromosuccinimide in the presence of dibenzoyl peroxide to give the dibromo-compound (XII). The reaction is typically carried out in carbon tetrachloride with heating at reflux. The dibromo-compound (XII) is then reacted with a compound $PG\text{-}NH_2$ where PG is a protecting group such as tosyl or para-methoxybenzyl in the presence of a base such as a metal hydride (e.g. sodium hydride), when PG is a tosyl group, or an alkali metal carbonate (e.g. sodium carbonate), when PG is para-methoxybenzyl. The protecting group PG can then be removed to give the amine (XIV). Thus, for example, a tosyl group can be removed by heating with a mixture of phenol, hydrobromic acid and propanoic acid, whereas a para-methoxybenzyl group can be removed in standard manner using trifluoroacetic acid and anisole. The amine (XIV) is then coupled with a carboxylic acid of the formula (X) as described above.

In a variation on the reaction sequence of Scheme 7, one or more functional groups $R^{10b}$ present in the protected isoindoline (XIII) or the deprotected isoindoline compound (XIV) can be converted into other groups $R^{10b}$. For example, where the group $R^{10b}$ in compound (XIV) is a nitro group, it can be reduced to give the corresponding amino group, for example by catalytic hydrogenation in the presence of a palladium on charcoal catalyst. In a further example, when $R^{10b}$ in the compound (XIII) is an ester group (e.g. $CO_2Me$), it can be hydrolysed to give a carboxylic acid which can then be reacted with an amine such as morpholine to give the corresponding amide. Further functional group interconversions may subsequently be carried out (for example reduction of the amide to the corresponding aminomethyl compound with lithium aluminium hydride) before removal of the protecting group PG.

An alternative synthesis of the isoindoline compound (XIV) is shown in Scheme 8.

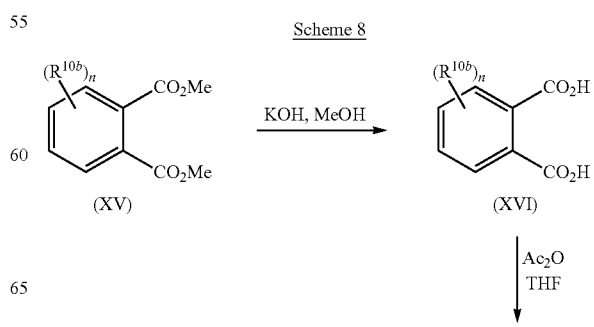

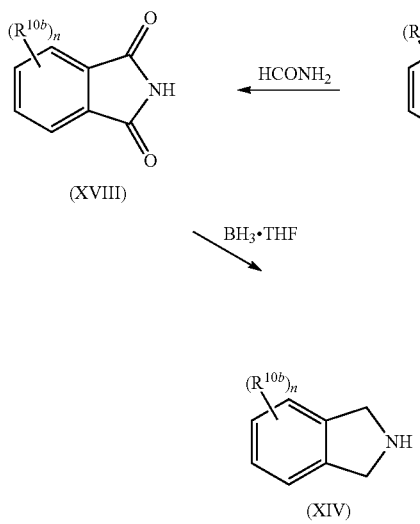

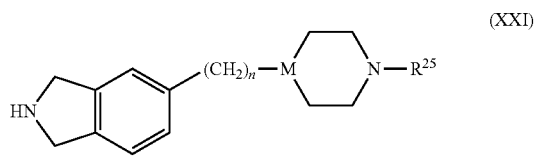

Within formula (XX), particular intermediates of the invention can be represented by the formula (XXI):

(XXI)

wherein n is 0 or 1; M is N or CHOH and $R^{25}$ is hydrogen or methyl; provided that when n is 0 and $R^{25}$ is methyl, then M is CHOH.

Particular intermediates within formula (XXI) are the compounds (XXII), (XXIII) and (XXIV) below.

(XXII)

(XXIII)

(XXIV)

The intermediates of formula (XXI) can be made by methods well known to the skilled person or methods analogous thereto. For example, intermediate XXII can be prepared by lithium-halogen exchange of a suitably N-protected 5-bromoisoindoline, quenching with 1-methyl-4-piperidone and subsequent deprotection. Intermediate XXII can be prepared by Buchwald palladium coupling of 4-BOC-piperazine and a suitably N-protected 5-bromoisoindoline followed by subsequent deprotection. One method of preparation for intermediate XXIV is from a suitably N-protected isoindoline-5-carboxylic acid, Weinreb amide formation, reduction to the aldehyde, followed by reductive amination and subsequent deprotection.

Once formed, where the substituent groups permit, one compound of the formula (I), or a protected form thereof, can be converted into another compound of the formula (I).

For example, when $R^1$ and $R^2$ are both protected hydroxy groups (e.g. benzyloxy groups), and $R^3$ is bromine, the bromine atom can be replaced by trifluoromethyl by reaction with a trifluoroacetate salt (e.g. sodium trifluoroacetate), and copper (I) iodide in a polar solvent such as dimethylformamide.

In another procedure, compounds of the formula (I) wherein $R^8$ is fluorine can be prepared from compounds of the formula (I) where $R^8$ is hydrogen by electrophilic fluorination. Electrophilic fluorination can be carried out using a fluorinating agent such as 1-(chloromethyl)-4-fluoro-1,4-diazoniabicyclo[2.2.2]octane bis(tetrafluoroborate) or similar N-fluoro-diazonia compounds.

The starting material for Scheme 8 is the ortho diester (XV) which is hydrolysed to the corresponding dicarboxylic acid (XVI) using an alkali metal hydroxide such as potassium hydroxide before being subjected to cyclisation to the phthalic anhydride (XVII) by reaction with acetic anhydride. The phthalic anhydride (XVII) can be converted to the corresponding phthalimide (XVIII) by reaction with formamide at an elevated temperature (e.g. approximately 210° C.). The phthalimide (XVIII) can then be reduced to the isoindoline (XIV) using a suitable reducing agent such as borane in tetrahydrofuran.

Compounds of the formula (VIIb) as defined herein can be prepared by the reaction of a compound of the formula (XIX) or a protected derivative thereof with a compound of the formula (XX):

(XIX)

(XX)

wherein n, $R^3$, $R^{4a}$, $R^8$ and $R^{10cc}$ are as defined herein, under amide forming conditions as described above and in the examples.

Many of the compounds of formula (XX) are novel and, as such, form another aspect of the invention. Thus, in another aspect, the invention provides a compound of the formula (XX) but excluding any and all compounds known per se in the prior art.

In a further procedure, compounds of the formula (I) wherein $R^1$ and $R^2$ are both hydroxy groups can be monomethylated to give a compound where one of $R^1$ and $R^2$ is a methoxy group by reaction with one equivalent of a methylating agent such as dimethylsulphate. The methylation reaction is typically carried out in a polar solvent such as acetonitrile in the presence of a base, for example an alkali metal carbonate such as potassium carbonate. Analogous methylation reactions may also be carried out on intermediate compounds containing two phenolic hydroxy groups.

Many of the procedures described below and used in this synthesis are well known to those skilled in the art, and examples of alkylations, acylations, functional group interconversions and reagents and conditions for carrying out such conversions can be found in, for example, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

As well as the specific examples, and the methods of preparation outlined below, it is understood that modification to the routes described would allow synthesis of many further examples of compounds claimed in Formula I. For example, alternative benzoic acid starting materials with differing or additional substitution patterns could be prepared.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc). When the hydroxy group is a phenolic hydroxy group, for example in compounds of the formula (I) wherein $R^1$ and/or $R^2$ are hydroxy, a preferred protecting group is a benzyl group.

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$alkyl ester; or a $C_{5-20}$ aryl-$C_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Methods of Purification

The compounds may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Alternatively, normal phase preparative LC based methods might be used in place of reverse phase methods. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intra-peritoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, poly-ethylene glycol 300, polyethylene glycol 400, glycerin, dim-ethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyo-philising a compound of Formula (I) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formula (I) and sub-groups as defined herein will be useful in the prophylaxis or treatment of a range of disease states or conditions mediated by Hsp90 client proteins. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined.

Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies, e.g. HDAC or HAT modulators
Radiotherapy.

For the case of Hsp90 inhibitors combined with other therapies, the two or more treatments may be given in individually varying dose schedules and via different routes.

Where the compound is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound, a patient may be screened to determine whether a disease or condition from which the patient is or may be suffering is one which would be susceptible to treatment with a compound having activity against Hsp90.

For example, a biological sample taken from a patient may be analysed to determine whether a condition or disease, such as cancer, that the patient is or may be suffering from is one which is characterised by a genetic abnormality or abnormal protein expression which leads to the mutation or over-activation of an Hsp90 client protein. Examples of such abnormalities that result in activation of Hsp90 client proteins include; Bcr-ABL translocation, Flt-3 internal duplication, and mutation of Braf, or over-expression of ErbB2.

Thus, the patient may be subjected to a diagnostic test to detect a marker characteristic of up-regulation. The term diagnosis includes screening. By marker we include genetic markers including, for example, the measurement of DNA composition to identify mutations of Braf, BCR-abl, and Flt3 or other affected client proteins. The term marker also includes proteins such as ErbB2, including levels or concentrations of the protein or some fragments or degradation product and for enzymes the enzymic activity. The protein (e.g. phosphorylated or not) and mRNA levels of the aforementioned proteins could also be assessed to characterise a change in activity. For example the level of phosphorylated AKT can be an indicator of sensitivity to HSP90 inhibitors The diagnostic tests are typically conducted on a biological sample selected from for example tumour biopsy samples, blood samples (isolation and enrichment of shed tumour cells), stool biopsies, sputum, chromosome analysis, pleural fluid, peritoneal fluid, buccal spears or biopsy or from urine.

The screening process will typically involve direct sequencing, oligonucleotide or protein microarray analysis, proteomic analysis by mass spectrometry or detection using a specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR), in-situ hybridisation or immunoblotting.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Commercially available FISH probes also exist for cytogenetic detection of chromosome rearrangements, which can be used to detect Flt3 and Bcr-Abl translocations within leukemia cell populations. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al., *BMC Cancer* 2003, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of the "philadelphia chromosome" indicative of BCR-ABL translocation.

Therefore, all of these techniques could also be used to identify tumours particularly suitable for treatment with the compounds of the invention.

EXAMPLES

The invention will now be illustrated, but not limited, by reference to the specific embodiments described in the following examples.

In the examples, the following abbreviations may be used.
AcOH acetic acid
BOC tert-butyloxycarbonyl
Bn benzyl
CDI 1,1-carbonyldiimidazole
DMAW90 Solvent mixture: DCM: MeOH, AcOH, $H_2O$ (90:18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether
h hour(s)
HOAt 1-hydroxyazabenzotriazole
HOBt 1-hydroxybenzotriazole
MeCN acetonitrile
MeOH methanol
min. minutes
P.E. petroleum ether
r.t. room temperature
$SiO_2$ silica
TBTU N,N,N',N'-tetramethyl-O-(benzotriazol-1-yl)uronium tetrafluoroborate
THF tetrahydrofuran Proton magnetic resonance ($^1$H NMR) spectra were recorded on a Bruker AV400 instrument operating at 400.13 MHz, in DMSO-$d_6$ or MeOH-$d_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

In the examples, the compounds prepared were characterised by liquid chromatography and mass spectroscopy using the system and operating conditions set out below. Where atoms with different isotopes are present and a single mass quoted, the mass quoted for the compound is the monoisotopic mass (i.e. $^{35}$Cl; $^{79}$Br etc.). Different systems were used, as described below, and these were equipped with, and were set up to run under, closely similar operating conditions. The operating conditions used are also described below.
System Description:
System 1 (Analytical System):
HPLC System: Waters 2795
Mass Spec Detector: Micromass Platform LC
PDA Detector: Waters 2996 PDA
System 2 (Preparative and Analytical System):
HPLC System: Waters Fractionlynx system
Mass Spec Detector: Waters ZQ
PDA Detector: Waters 2996 PDA System 3 (Preparative and Analytical System):
HPLC System: Agilent 1100 system
Mass Spec Detector: LC/MSD
UV Detector: Agilent MWD
Operating Conditions:
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes (over 15 minutes w/column 2)
Flow: 0.8 ml/min
Column 1: Phenomenex Synergi 4μ MAX-RP 80A, 2.0×50 mm
Column 2: Phenomenex Synergi 4μ MAX-RP 80A, 2.0×150 mm
Basic Analytical Conditions:
Eluent A: $H_2O$ (10 mM $NH_4HCO_3$ buffer adjusted to pH=9.2 with $NH_4OH$)
Eluent B: $CH_3CN$
Gradient: 5-95% eluent B over 3.5 minutes
Flow: 0.8 ml/min
Column: Phenomenex Gemini 5μ 2.0×50 mm
MS Conditions (Waters Systems):
Capillary voltage: 3.6 kV (3.40 kV on ES negative)
Cone voltage: 25 V
Source Temperature: 120° C.
Scan Range: 125-800 amu
Ionisation Mode: ElectroSpray Positive, Negative or Positive & Negative
MS Conditions (Agilent Systems):
Capillary voltage: 4000 V (3500 V on ES Negative)
Fragmentor/Gain: 150/1
Drying gas Temp/flow: 350° C./13.0 $Lmin^{-1}$
Nebuliser pressure: 50 psig
Scan Range: 125-800 amu
Ionisation Mode: ElectroSpray Positive or Negative The starting materials for each of the Examples are commercially available unless otherwise specified.

A. General Synthetic Methods

In the following general methods, the volumes stated may vary according to the scale of the reaction, as will be apparent to the skilled person.

Method A1
Amide Coupling (Acid Chloride Method)

A mixture of a carboxylic acid (1 equivalent) and thionyl chloride (1.5 equivalents) in benzene (or toluene) was stirred and held at reflux for 2 hours. Excess amine was added dropwise to the hot solution and the mixture stirred at room temperature for 15 minutes. Alternatively, the acid chloride could be isolated by evaporation and then re-dissolved in a 9:1 mixture of dichloromethane: triethylamine and the amine then added and the mixture stirred under nitrogen at room temperature for 1-18 hours. In either case, the mixture was diluted with ethyl acetate and extracted successively with water, saturated aqueous sodium bicarbonate and 2M hydrochloric acid. The organic layer was reduced to dryness in vacuo and the pure products were obtained either by trituration with ethyl acetate or by column chromatography on silica (eluting with mixtures of ethyl acetate in petroleum ether) or in a few cases by preparative HPLC/MS.

Method A2
Amide Coupling (EDC, HOBt Method)

A stirred solution of the acid (1 equivalent) in dichloromethane (10 ml) was treated successively with N-ethyl-N'-(3-dimethylaminopropyl)carbodiimide hydrochloride (1.2 equivalents), 1-hydroxybenzotriazole (1.2 equivalents) and the amine (1.5 equivalents) and the mixture was stirred at room temperature overnight. The mixture was washed successively with 2M hydrochloric acid and 2M sodium hydroxide, the organic layer was separated and the solvent removed in vacuo to afford the products. The products were either obtained pure or were purified by column chromatography on silica (eluting with mixtures of ethyl acetate in petroleum ether or methanol in ethyl acetate as appropriate).

Method A3
Anisole or Benzyl Ether Dealkylation ($BBr_3$ Method)

A stirred solution of the anisole or benzyl ether (1 equivalent) in dichloromethane at 0° C. was treated dropwise with a 1M solution of boron tribromide in dichloromethane (1.5 equivalents per group to be deprotected) and the mixture was stirred for 2 hours. The reaction was quenched by the addition of water and saturated aqueous sodium bicarbonate, the organic layer was separated and the solvent was removed in vacuo. The pure products were obtained either by trituration with diethyl ether or ethyl acetate or by column chromatography on silica (eluting with mixtures of ethyl acetate in petroleum ether).

Method A4
Amide Coupling (EDC, HOAt Method)

A stirred solution of the acid (1 equivalent) in dimethylformamide (5 ml) was treated successively with N-ethyl-N'-(3-dimethylaminopropyl)carbodiimide hydrochloride (1.2 equivalents), 1-hydroxy-7-aza-benzotriazole (1.2 equivalents) and the amine (1.5 equivalents) and the mixture was stirred at room temperature overnight. DMF was evaporated and crude dissolved in EtOAc and was washed successively with saturated sodium bicarbonate, the organic layer was separated and the solvent removed in vacuo. The products were either obtained pure or were purified by column chromatography on silica (eluting with mixtures of ethyl acetate in petroleum ether or methanol in ethyl acetate as appropriate).

Method A5
Hydrogenation

A stirred solution of protected derivative (1 equivalent) and a catalytic amount of 10% palladium on carbon (typically 30-50 mg) in ethanol (5-10 ml), methanol (5-10 ml) or methanol/DCM (3 m1/3 ml) was stirred at room temperature under an atmosphere of hydrogen for 2-16 hours. The catalyst was removed by filtration, washed with methanol (5 ml) and the solvent removed in vacuo to afford the products. Some required purification by flash chromatography, eluting typically with ether.

Method A6
Suzuki Coupling

The aryl bromide (1 equivalent, typically 0.5 mmol), boronic acid or potassium vinyl trifluoroborate derivative (1.2 equivalents) and caesium carbonate (3 equivalents) were dissolved in THF (10 ml) under nitrogen. 1,1'-Bis(diphenylphosphino)ferrocene]palladium(II) dichloride (0.1 equivalent) was added and then water (1 ml). The mixture begins to darken until black. The mixture was then heated at reflux under nitrogen until the reaction is complete (8-45 hrs). The mixture was cooled, diluted with DCM and magnesium sulphate added. The mixture was filtered and the solvent evaporated. The resulting residues were purified by flash chromatography in pet. ether/ether mixtures, and generally gave product in good yield (~60-80%).

Method A7
Resorcinol Mono-O-Methylation

Dimethyl sulphate (1 equivalent) was added to a stirred solution of the resorcinol (1 equivalent) and potassium carbonate (2.2 equivalents) in acetonitrile (10 ml per mmol of substrate) and the mixture was stirred at room temperature for 16 hours. The solvent was removed in vacuo, the residue partitioned between dichloromethane and water, the organic layer separated and the solvent removed in vacuo. The pure products were obtained either after column chromatography on silica (eluting with mixtures of petroleum ether and ethyl acetate) or by preparative HPLC/MS.

Method A8

Electrophilic Aromatic Fluorination 1-(Chloromethyl)-4-fluoro-1,4-diazoniabicyclo[2.2.2]octane bis(tetrafluoroborate) (1 equivalent) was added to a solution of the substrate (1 equivalent) in acetonitrile (15 ml per mmol of substrate) and the mixture was stirred at room temperature for 16 hours. The solvent was removed in vacuo and the residue was partitioned between ethyl acetate and water. The organic layer was separated and reduced to dryness in vacuo. The pure products were obtained either after column chromatography on silica (eluting with mixtures of petroleum ether and ethyl acetate) or by preparative HPLC/MS.

B. Synthesis of Carboxylic Acid Intermediates

Preparation B1

4-Hydroxy-3-isopropylbenzoic acid

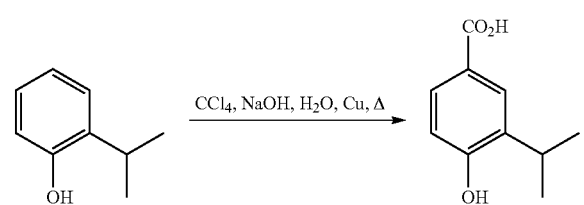

Carbon tetrachloride (28 ml, 0.26 mol) and copper powder (1.0 g) were added to a stirred solution of 2-isopropylphenol (27.2 g, 0.2 mol) in 50% aqueous sodium hydroxide (120 ml) and the mixture was held at reflux for 16 hours. Upon cooling the mixture was acidified to pH 2 or below by the addition of concentrated hydrochloric acid and was extracted with ethyl acetate. The organic layer was extracted with a saturated aqueous solution of sodium bicarbonate and the aqueous layer acidified to pH 2 or below by the very careful addition of concentrated hydrochloric acid. The solution was extracted with ethyl acetate, the organic layer was washed with water, separated and the solvent removed in vacuo to afford 4-hydroxy-3-isopropylbenzoic acid (12.5 g, 35%) as a bright red solid that was used without further purification. $^1$H NMR (DMSO-$d_6$) 12.36 (1H, br s), 10.13 (1H, br s), 7.73 (1H, d), 7.63 (1H, dd), 6.85 (1H, d), 3.22 (1H, m), 1.19 (6H, d). MS: [M−H]$^+$ 179.

Alternatively, if required, the crude product may be purified using a three step procedure involving di-benzylation [according to the conditions outlined below in Preparation B5 for the synthesis of methyl 5-acetyl-2,4-bis-benzyloxybenzoate (BnBr, $K_2CO_3$, MeCN, reflux)], column chromatography on silica to remove highly coloured impurities (eluting with 3-5% ethyl acetate in petroleum ether) and catalytic hydrogenation [according to Method A5 outlined above (10% Pd/C, EtOH, $H_2$)] to afford 4-hydroxy-3-isopropylbenzoic acid as a colourless solid.

Preparation B2

5-Ethyl-2-methoxybenzoic acid

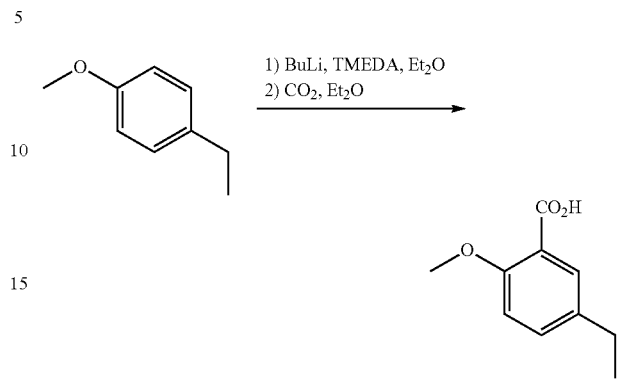

n-Butyl lithium (2.5M in hexanes, 38.5 ml, 100.0 mmol) was added dropwise under a nitrogen atmosphere to a stirred solution of 4-ethylanisole (11.7 g, 86.0 mmol) and N,N,N',N'-tetramethylethylenediamine (10 ml, 88.0 mmol) in anhydrous diethyl ether (100 ml) and the mixture was stirred and held at 30° C. for 16 hours. The mixture was cooled and poured slowly in to a mixture of excess solid carbon dioxide in anhydrous diethyl ether. Upon warming to room temperature the mixture was made basic by the addition of 2M sodium hydroxide, the aqueous layer was separated and acidified to pH 2 or below by the addition of concentrated hydrochloric acid. The mixture was extracted with diethyl ether, the organic layer separated and the solvent removed in vacuo to afford 5-ethyl-2-methoxybenzoic acid (5.7 g, 37%) as a pale yellow oil. $^1$H NMR (DMSO-$d_6$) 12.50 (1H, br s), 7.48 (1H, d), 7.33 (1H, dd), 7.03 (1H, d), 2.56 (2H, q), 1.17 (3H, q). MS: [M+H]$^+$ 181.

Preparation B3

2,4-Bis-benzyloxy-5-chloro-benzoic acid

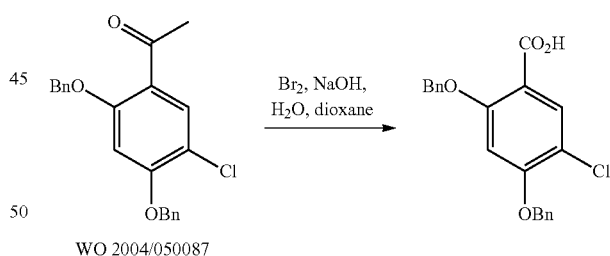

WO 2004/050087

1-(2,4-Bis-benzyloxy-5-chloro-phenyl)-ethanone [prepared as per WO 2004/0500087] (1.10 g, 3.0 mmol) was added to a stirred solution of sodium hydroxide (1.20 g, 30.0 mmol) in water (10 ml) and dioxane (10 ml). Bromine (1.44 g, 9.0 mmol) was added dropwise and the mixture stirred at room temperature for 3 hours. The dioxane was removed by evaporation in vacuo and the mixture acidified to pH 2 or below by the addition of 2M hydrochloric acid. The mixture was extracted with ethyl acetate, the organic layer separated and the solvent removed in vacuo to afford 2,4-bis-benzyloxy-5-chloro-benzoic acid (900 mg, 81%) as a pale yellow solid. $^1$H NMR (DMSO-$d_6$) 12.58 (1H, br s), 7.77 (1H, s), 7.55-7.30 (10H, m), 7.11 (1H, s), 5.31 (2H, s), 5.27 (2H, s). MS: [M+H]$^+$ 369.

Preparation B4

3-(1,2-Dimethyl-allyl)-4-hydroxy-benzoic acid

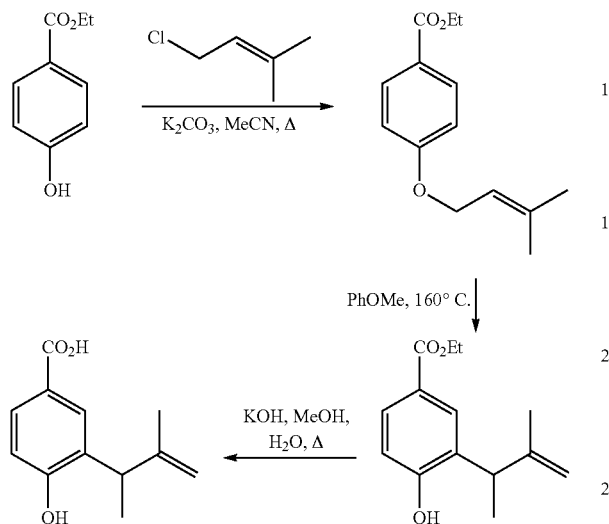

Ethyl 4-hydroxybenzoate (1.66 g, 10.0 mmol) and anhydrous potassium carbonate (2.07 g, 15.0 mmol) in acetonitrile (30 ml) was treated with 3-methyl-2-butenyl chloride (1.35 ml, 12.0 mmol) and the mixture was stirred and held at reflux for 3 hours. Upon cooling the solvent was removed in vacuo and the mixture partitioned between dichloromethane and water. The organics were separated and the solvent removed in vacuo to afford ethyl 4-(3-methyl-but-2-enyloxy)-benzoate (2.23 g, 95%) as a pale yellow liquid which was used without further purification. $^1$H NMR (DMSO-$d_6$) 7.89 (2H, d), 7.04 (2H, d), 5.44 (1H, t), 4.62 (2H, d), 4.28 (2H, q), 1.77 (3H, s), 1.73 (3H, s), 1.31 (3H, t). MS: $[M+H]^+$ 235.

Ethyl 4-(3-methyl-but-2-enyloxy)-benzoate (2.23 g, 9.53 mmol) was dissolved in anisole (8 ml) and the mixture stirred and held at reflux for 4 days. The solvent was removed in vacuo and the residue subjected to column chromatography on silica. Elution with 20% ethyl acetate in petroleum ether afforded ethyl 3-(1,2-dimethyl-allyl)-4-hydroxy-benzoate (600 mg, 27%) as a colorless solid. $^1$H NMR (DMSO-$d_6$) 10.32 (1H, br s), 7.67 (1H, dd), 7.62 (1H, s), 6.90 (1H, d), 4.90 (1H, s), 4.85 (1H, s), 4.25 (2H, q), 3.75 (1H, q), 1.61 (3H, s), 1.30 (3H, t), 1.26 (3H, d). MS: $[M+H]^+$ 235.

Ethyl 3-(1,2-dimethyl-allyl)-4-hydroxy-benzoate (600 mg, 2.56 mmol) was dissolved in methanol (20 ml), a solution of potassium hydroxide (560 mg, 10.0 mmol) in water (10 ml) was added and the mixture was stirred and held at reflux for 16 hours. Upon cooling the methanol was removed in vacuo and the solution acidified to pH 2 or below by the addition of 2M hydrochloric acid. The solution was extracted with dichloromethane, the organic layer was separated and the solvent was removed in vacuo to afford 3-(1,2-dimethyl-allyl)-4-hydroxy-benzoic acid (270 mg, 51%) as a colourless gum. $^1$H NMR (DMSO-$d_6$) 12.38 (1H, br s), 10.22 (1H, br s), 7.63 (2H, m), 6.88 (1H, d), 4.90 (1H, s), 4.87 (1H, s), 3.75 (1H, q), 1.60 (3H, s), 1.28 (3H, d). MS: $[M-H]^+$ 205.

Preparation B5

2,4-Bis-benzyloxy-5-isopropenyl-benzoic acid

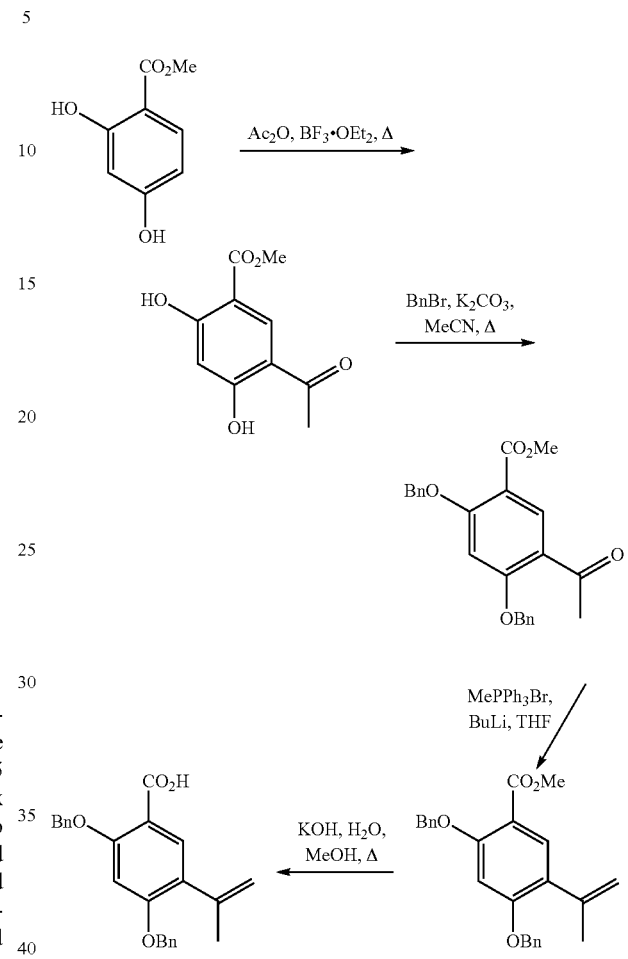

Acetic anhydride (3.06 g, 30.0 mmol) was added to methyl 2,4-dihydroxybenzoate (5.04 g, 30.0 mmol) in boron trifluoride diethyl etherate (7.6 ml) and the mixture was stirred and held at reflux for 3 hours and then allowed to cool to room temperature. Water (80 ml) was added and the mixture stirred at room temperature for 30 minutes. The resulting yellow solid was removed by filtration and sucked as dry as possible under vacuum. The solid was dissolved in dichloromethane and was washed with water, the organic layer was separated and the solvent removed in vacuo to afford methyl 5-acetyl-2,4-dihydroxybenzoate as a bright yellow solid (2.62 g, 42%) which was used without further purification. $^1$H NMR (DMSO-$d_6$) 12.58 (1H, s), 11.22 (1H, s), 8.33 (1H, s), 6.45 (1H, s), 3.90 (3H, s), 2.62 (3H, s). MS: $[M+H]^+$ 211.

Methyl 5-acetyl-2,4-dihydroxybenzoate (2.62 g, 12.48 mmol) was dissolved in acetonitrile (40 ml), anhydrous potassium carbonate (4.93 g, 35.7 mmol) was added and the stirred mixture was treated with benzyl bromide (5.09 g, 29.75 mmol) and held at reflux for 3 hours. Upon cooling the solvent was removed in vacuo and the mixture partitioned between water and dichloromethane. The organic layer was separated and the solvent removed in vacuo to afford methyl 5-acetyl-2,4-bis-benzyloxybenzoate (3.48 g, 71%) as a colourless solid which was dried at 50° C. in a vacuum oven and used without further purification. $^1$H NMR (DMSO-$d_6$)

8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]+ 391.

A stirred suspension of methyltriphenylphosphonium bromide (1.96 g, 5.5 mmol) in anhydrous tetrahydrofuran (20 ml) at 0° C. under a nitrogen atmosphere was treated dropwise with n-butyl lithium (1.6 M in hexanes, 3.5 ml, 5.5 mmol) and the resulting bright yellow solution was stirred at 0° C. for 30 minutes. A solution of methyl 5-acetyl-2,4-bis-benzyloxy-benzoate (1.95 g, 5.00 mmol) in anhydrous tetrahydrofuran (20 ml) was added dropwise and the resulting mixture was allowed to warm to room temperature and was stirred for 16 hours. Methanol (10 ml) was added and the solvent was removed in vacuo. The residues were partitioned between dichloromethane and water, the organic layer was separated and the solvent removed in vacuo to afford a brown gum that was purified by column chromatography on silica. Elution with 7% ethyl acetate in petroleum ether afforded methyl 2,4-bis-benzyloxy-5-isopropenyl-benzoate as a colourless solid (700 mg, 36%). $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]+ 389.

Methyl 2,4-bis-benzyloxy-5-isopropenyl-benzoate (700 mg, 1.80 mmol) was dissolved in methanol (20 ml), a solution of potassium hydroxide (286 mg, 5.1 mmol) in water (4 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford 2,4-bis-benzyloxy-5-isopropenyl-benzoic acid (600 mg, 89%) as a colourless solid. $^1$H NMR (DMSO-$d_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]+ 375.

Preparation B6

2,4-Bis-benzyloxy-5-bromo-benzoic acid

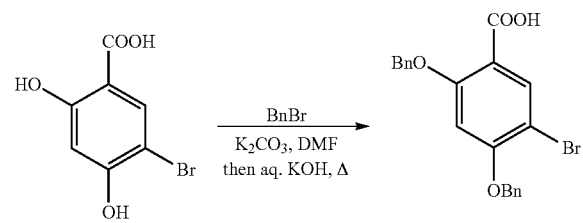 [SMILES: O=C(O)c1cc(Br)c(O)cc1O ; "BnBr" ; O=C(O)c1cc(Br)c(OCc2ccccc2)cc1OCc1ccccc1]

2,4-dihydroxy-5-bromobenzoic acid (5.16 g, 22.15 mmol) was dissolved in DMF (40 ml) and potassium carbonate (12.2 g) and benzyl bromide (8 ml) were sequentially added. The mixture was stirred at room temperature for 18 hours under nitrogen. An aqueous solution of potassium hydroxide (2 g) in water (25 ml) was then added, followed by methanol (50 ml) and the mixture heated to reflux with vigorous stirring for 24 hours. The mixture was then allowed to cool, was poured into 1N HCl (250 ml) and was then extracted with ether and then DCM. The combined organic layers were dried over magnesium sulphate and the solvent evaporated in vacuo. The resulting solid material was washed with P.E. and then Et$_2$O (3×50 ml) to yield pure product (5.2 g, 56%). $^1$H NMR (MeOH-$d_4$) 8.06 (1H, s), 7.51-7.30 (10H, m), 6.85 (1H, s), 5.22 (2H, s), 5.20 (2H, s). MS: [M+H]+ 413.

Preparation B7

Synthesis of (Z)-4-benzyloxy-3-(1-methyl-propenyl)-benzoic acid

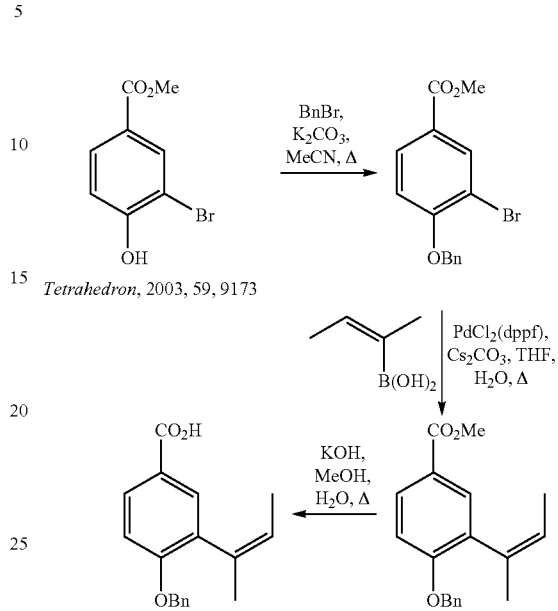

Tetrahedron, 2003, 59, 9173

Methyl 3-bromo-4-hydroxybenzoate [prepared as per *Tetrahedron*, 2003, 59, 9173] (3.47 g, 15.0 mmol) was dissolved in acetonitrile (50 ml), anhydrous potassium carbonate (3.11 g, 22.5 mmol) was added and the stirred mixture was treated with benzyl bromide (3.08 g, 18.0 mmol) and held at reflux for 5 hours. Upon cooling the solvent was removed in vacuo and the mixture partitioned between water and dichloromethane. The organic layer was separated, the solvent removed in vacuo and the residue subjected to column chromatography on silica. Elution with 10% ethyl acetate in petroleum ether afforded methyl 4-benzyloxy-3-bromobenzoate (3.6 g, 75%) as a colourless solid. $^1$H NMR (DMSO-$d_6$) 8.12 (1H, d), 7.96 (1H, dd), 7.51 (2H, m), 7.43 (2H, t), 7.35 (2H, m), 5.32 (2H, s), 3.84 (3H, s).

Methyl 4-benzyloxy-3-bromobenzoate (1.61 g, 5.0 mmol), caesium carbonate (4.89 g, 15.0 mmol), (E)-2-buten-2-yl boronic acid (600 mg, 6.0 mmol) and [1,1'-bis(diphenylphosphino)ferrocenyl]palladium (II) chloride (204 mg, 0.25 mmol) were dissolved in anhydrous tetrahydrofuran (100 ml), water (10 ml) was added and the mixture was stirred and held at reflux under an atmosphere of nitrogen for 16 hours. Upon cooling the solvent was removed in vacuo and the mixture partitioned between dichloromethane and water. The organic layer was separated, the solvent removed in vacuo and the residue subjected to column chromatography on silica. Elution with 5% ethyl acetate in petroleum ether afforded methyl (Z)-4-benzyloxy-3-(1-methyl-propenyl)-benzoate (600 mg, 41%) as a colourless solid. $^1$H NMR (DMSO-$d_6$) 7.88 (1H, dd), 7.59 (1H, d), 7.40 (4H, m), 7.34 (1H, m), 7.23 (1H, d), 5.57 (1H, q), 5.21 (2H, s), 3.82 (3H, s), 1.94 (3H, s), 1.38 (3H, d).

Methyl (Z)-4-benzyloxy-3-(1-methyl-propenyl)-benzoate (592 mg, 2.0 mmol) was dissolved in methanol (20 ml), a solution of potassium hydroxide (336 mg, 6.0 mmol) in water (7 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford (Z)-4-benzyloxy-3-(1-methyl-propenyl)-benzoic acid (460 mg, 82%) as a colourless solid. $^1$H NMR (DMSO-$d_6$) 7.85 (1H, dd), 7.57 (1H, d), 7.40 (4H, m), 7.34 (1H, m), 7.18 (1H, d), 5.57 (1H, q), 5.21 (2H, s), 1.96 (3H, s), 1.40 (3H, d). MS: [M+H]$^+$ 283.

Preparation B8

Synthesis of 2,4-bis-benzyloxy-5-tert-butyl-benzoic acid

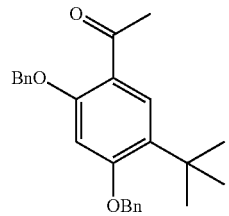

WO 2004/072051

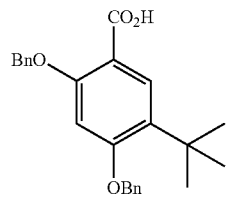

1-(2,4-Bis-benzyloxy-5-tert-butyl-phenyl)-ethanone [prepared as per WO 2004/072051] (2.02 g, 5.2 mmol) was dissolved in 1,4-dioxane (30 ml), a solution of sodium hydroxide (2.08 g, 52.0 mmol) in water (30 ml) was added and the mixture was stirred and treated dropwise with bromine (0.8 ml, 15.6 mmol). The resulting mixture was stirred at room temperature for 16 hours. The 1,4-dioxane was removed in vacuo and the mixture acidified to pH 2 or below by the addition of 2M hydrochloric acid. The mixture was extracted with ethyl acetate, the organic layer was separated, the solvent removed in vacuo and the residue subjected to column chromatography on silica. Elution with 30% ethyl acetate in petroleum ether afforded 2,4-bis-benzyloxy-5-tert-butyl-benzoic acid (1.6 g, 79%) as a pale yellow oil. $^1$H NMR (DMSO-$d_6$) 12.18 (1H, br s), 7.69 (1H, s), 7.52 (4H, t), 7.45-7.33 (6H, m), 6.93 (1H, s), 5.24 (2H, s), 5.23 (2H, s), 1.32 (9H, s). MS: [M+H]$^+$ 391.

Preparation B9

Synthesis of 2,4-bis-benzyloxy-5-isopropenyl-benzoic acid (Alternative synthesis)

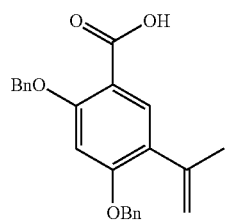 [SMILES: C=C(C)c1cc(C(=O)O)c(OCc2ccccc2)cc1OCc1ccccc1]

Step 1: Synthesis of 2,4-bis-benzyloxy-5-bromo-benzoic acid benzyl ester

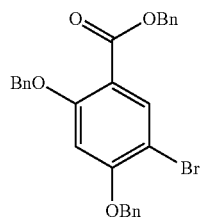

To a 10 L jacketed vessel, fitted with a flange lid containing stirrer, thermometer and dropping funnel, was charged acetone (2.5 L) followed by 5-bromo-2,4-dihydroxybenzoic acid (100 g, 0.43 mol) and potassium carbonate (356 g, 2.58 mol). To the stirring mixture at ambient was added benzyl bromide (185 mL, 1.55 mol) at a rate of ~20 ml/min. The mixture was heated at 60° C. for 18 h and then taken to 45° C. Water (1.5 L) was added and the mixture stirred for 30 min. The mixture was extracted with EtOAc (2×1 L) and the combined organic portions reduced in vacuo. To the residue was added Et$_2$O (200 mL) and petroleum ether (1 L), the mixture stirred for 30 min and the solid formed collected by filtration and dried in vacuo to give the title compound (197.2 g) as a white solid.

Step 2: Synthesis of Potassium Isopropenyl Trifluoroborate

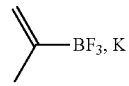

To a solution of 2-bromopropene (20 mL, 225 mmol) in anhydrous THF (250 mL) stirring under a N$_2$ atmosphere at −78° C. was added over 30 mins n-BuLi (2.5M in hexanes) (100 mL, 250 mmol) and the mixture stirred for 30 mins. To the mixture at −78° C. was slowly added triethyl borate (58 mL, 340 mmol) at a rate to ensure that the temperature of the reaction mixture did not exceed −65° C. The resulting solution was then stirred at −78° C. for 30 mins, allowed to slowly warm to ambient and stirred for a further 90 mins. Potassium hydrogen fluoride (105 g, 1.35 mol) was added to the mixture followed by water (250 mL). The mixture was stirred at ambient for 14 h and then reduced to dryness.

The procedure was repeated as above and following reduction to dryness the two residues were combined for further work-up.

To the combined residues was added acetone (800 mL), the mixture stirred for 1 h and then filtered.

The solid collected was washed with acetone (200 mL) and the combined filtrates reduced in vacuo to give a solid. This solid was triturated with Et₂O (250 mL) and then dried in vacuo to give the title compound (28.2 g) as a white solid.

Step 3: Synthesis of 2,4-bis-benzyloxy-5-isopropenyl-benzoic acid benzyl ester

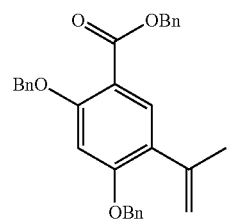 [SMILES: C=C(C)c1cc(C(=O)OCc2ccccc2)c(OCc2ccccc2)cc1OCc1ccccc1]

To a mixture of 2,4-bis-benzyloxy-5-bromo-benzoic acid benzyl ester (42.9 g, 85.7 mmol), potassium isopropenyl trifluoroborate (14.0 g, 95.2 mmol) and caesium carbonate (83.8 g, 257.1 mmol) in THF (800 mL) was added Pd(PPh₃)₄ (2.0 g) followed by water (150 mL). The mixture was heated at reflux for 72 h then allowed to cool to ambient. The mixture was reduced in vacuo to remove THF and then partitioned between water (500 mL) and EtOAc (300 mL). The organic portion was washed with brine, dried (MgSO₄), filtered and reduced in vacuo to give the title compound (40.9 g) as a brown oil.

Step 3A

Alternative Synthesis of 2,4-bis-benzyloxy-5-isopropenyl-benzoic acid benzyl ester

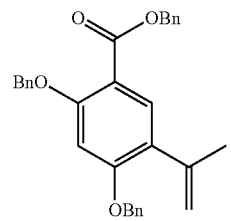

A mixture of 2,4-bis-benzyloxy-5-bromo-benzoic acid benzyl ester (10.0 g, 20 mmol), potassium isopropenyl trifluoroborate (4.0 g, 27.2 mmol) and n-butylamine (6.0 mL, 60 mmol) in 2-propanol/water (2:1, 200 mL) was purged with N₂ for 5 minutes. To this mixture was added [1,1'-bis(diphenylphosphino)ferrocene]dichloropalladium(II) (816 mg, 1.09 mmol) and the mixture was heated at reflux for 20 h. The mixture was allowed to cool to ambient then diluted with water (400 mL) and extracted with EtOAc (2×300 mL). The combined organic extracts were washed with 1M aqueous HCl, brine, dried (MgSO₄), filtered through a plug of Celite and the filtrate reduced in vacuo to give the title compound (11.1 g) as a brown gum.

Step 4: Synthesis of 2,4-bis-benzyloxy-5-isopropenyl-benzoic acid

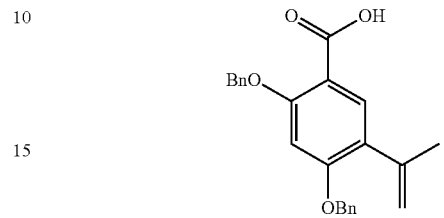

To a solution of 2,4-bis-benzyloxy-5-isopropenyl-benzoic acid benzyl ester (40.8 g, 87.9 mmol) in THF-MeOH-water (3:1:1, 300 mL total) was added lithium hydroxide (8.42 g, 352 mmol). The mixture was heated at 50° C. for 16 h, allowed to cool to ambient and then diluted with water (300 mL). The mixture was taken to pH~1 using conc. HCl (~30 mL) and then extracted with EtOAc (2×200 mL). The combined organic extracts were washed with brine, dried (MgSO₄), filtered and reduced in vacuo. The solid residue was taken up in P.E-MeOH (9:1, 300 mL total), the slurry stirred for 1 h at ambient and the solid collected by filtration. The solid was dried in vacuo to give the title compound (26.8 g) as an off-white solid. $^1$H NMR (400 MHz, DMSO-d₆) 12.30 (s, 1H), 7.61 (s, 1H), 7.53 (d, J=7.0 Hz, 2H), 7.47-7.31 (m, 8H), 6.94 (s, 1H), 5.23 (d, J=14.0 Hz, 4H), 5.08 (d, J=9.0 Hz, 2H), 2.04 (s, 3H).

Preparation B10

2,4-Bis-benzyloxy-5-isopropyl-benzoic acid

Step 1

Preparation of 1-(2-4-Bis-benzyloxy-phenyl)-ethanone

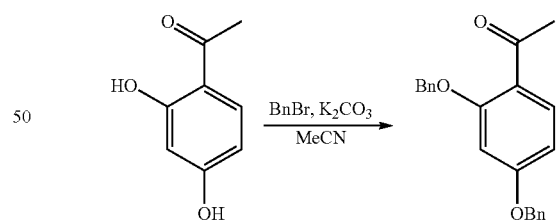

Material Inputs:

| S. No. | Item | Quantity | Eq. |
|---|---|---|---|
| 1. | 1,3 Dihydroxy acetophenone | 50 g | 1 |
| 2. | Benzyl bromide | 97 ml | 3 |
| 3. | Acetonitrile | 750 ml | 15 times |
| 4. | Potassium carbonate | 115 g | 3 |

1,3 Dihydroxy acetophenone (50 g) was placed in a 2 L single neck RB flask equipped with a reflux condenser and a guard tube. Acetonitrile (750 ml), potassium carbonate (115 g) and benzyl bromide (97 ml) were added and the mixture was heated at reflux (90° C.) for 16 hours. On completion, the acetonitrile was removed under reduced pressure. Water (200 ml) was added to the reaction mixture which was then extracted with ethyl acetate (500 ml). The organic layer was separated and dried over sodium sulphate. The solvent was removed under reduced pressure to give a residue which was washed n-hexane (600 ml) to give the product.

| Quantity of the product obtained | 105.1 g |
|---|---|
| Yield | 96.24% |
| Nature | Solid |
| Colour | Brown |

Step 2

Preparation of
2-4-Bis-benzyloxy-1-isopropenylbenzene

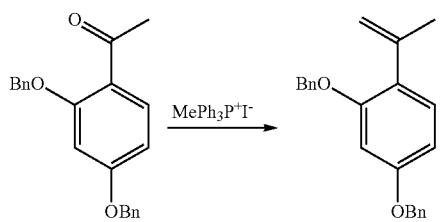

Material Inputs:

| S. No. | Item | Quantity | Eq. |
|---|---|---|---|
| 1. | Compound of Step 1 | 20 g | 1 |
| 2. | n-BuLi (1.6M) | 92.6 ml | 2.3 |
| 3. | Methyl-triphenylphosphonium iodide | 53.4 g | 2.2 |
| 4. | THF | 200 ml | 10 times |

Methyl-triphenylphosphonium iodide (53.4 g) and THF (100 ml) were introduced into a 1 L 3-neck RB flask equipped with an addition funnel and an inlet for nitrogen atmosphere and the mixture was cooled to 0° C. n-BuLi (92.6 ml) was added dropwise to the reaction mixture over a period of 15 min at 0° C. The reaction mixture was stirred for 10 min at 0° C. and further stirred at RT for 30 min. 1-(2-4-Bis-benzyloxy-phenyl)-ethanone (20 g) in THF (100 ml) was added dropwise to the reaction mixture over a period of 10 min at 0° C. and the reaction mixture was stirred overnight at RT. The progress of the reaction was monitored by TLC (10% EtOAc/n-hexane, product $R_f$~0.9). On completion, methanol (~100 ml) was added to the reaction mixture and the solvent was removed under reduced pressure to give a residue. n-Hexane (1 L) was added to the residue which was refluxed (75° C.) for 30 min. before filtering the mixture was through a Celite bed and washing the bed with n-hexane (500 ml). The solvent was removed under reduced pressure to give a residue, which was further purified by column chromatography (SiO$_2$ 2% EtOAc/n-hexane).

| Quantity of the product obtained | 12.5 g |
|---|---|
| Yield | 63.13% |
| Nature | Liquid. |
| Colour | Colorless |

Step 3

4-Isopropyl-benzene-1,3-diol

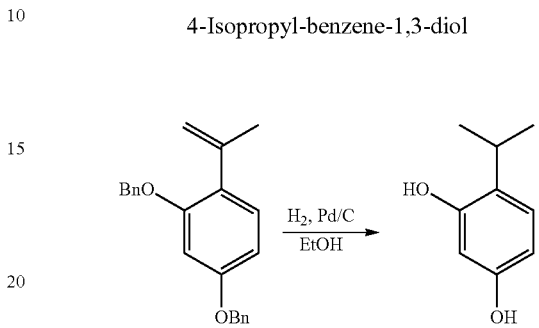

Material Inputs:

| S. No. | Item | Quantity | Eq. |
|---|---|---|---|
| 1. | 2-4-Bis-benzyloxy-1-isopropenylbenzene | 12.5 g | 1 |
| 2. | Ethanol | 125 ml | 10 times |
| 3. | 20% Palladium hydroxide | 2 g | |

To a mixture of 2-4-bis-benzyloxy-1-isopropenylbenzene (12.5 g) in ethanol (125 ml) in a 500 ml hydrogenation flask was added 20% palladium hydroxide (2 g). The reaction mixture was hydrogenated at 80 psi for 36 h. The progress of the reaction was monitored by TLC (10% EtOAc/n-hexane, product $R_f$~0.1). On completion, the reaction mixture was filtered through a bed of Celite and the bed was washed with ethanol (300 ml). The solvent was removed under reduced pressure to give a crude product, which was used as such for the next step.

| Quantity of the product obtained | 5.8 g (crude) |
|---|---|
| Nature | Solid. |
| Colour | Colourless. |

Step 4

1-(2,4-Dihydroxy-5-isopropyl-phenyl)-ethanone

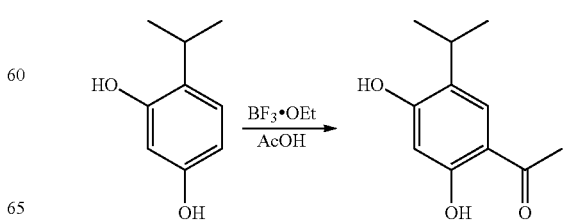

Material Inputs:

| S. No. | Item | Quantity | Eq. |
|---|---|---|---|
| 1. | 4-Isopropyl-benzene-1,3-diol | 5.8 g | 1 |
| 2. | Boron trifluoride etherate | 28.7 ml | 6 |
| 3. | Acetic acid | 4.55 ml | 2 |

4-Isopropyl-benzene-1,3-diol (5.8 g) and boron trifluoride etherate (28.7 ml) were introduced into a 250 ml single neck RB flask equipped with a reflux condenser and an inlet for nitrogen atmosphere stirred at RT for 10 min. Acetic acid (4.55 ml) was added to the reaction mixture and stirred at 90° C. for 16 h. On completion, 10% sodium acetate (300 ml) was added to the reaction mixture which was stirred at RT for 4 h before. The reaction mixture was extracted with ethyl acetate (300 ml) and washed with sat. sodium bicarbonate (100 ml) and the organic layer was dried over sodium sulphate. The reaction was monitored by TLC (10% EtOAc/n-hexane, product $R_f$~0.5). The solvent was removed under reduced pressure to give a residue, which was further purified by column chromatography (SiO$_2$, 10% EtOAc/n-hexane).

| Quantity of the product obtained | 3.2 g |
|---|---|
| Yield | 43.24% |
| Nature | Solid. |
| Colour | Colourless |

Step 5

1-(2,4-Bis-benzyloxy-5-isopropyl-phenyl)-ethanone

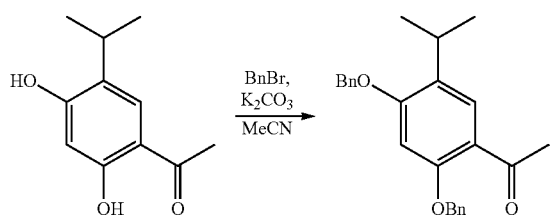 [SMILES: "MeCN" ; CC(=O)c1cc(C(C)C)c(O)cc1O ; CC(=O)c1cc(C(C)C)c(OCc2ccccc2)cc1OCc1ccccc1]

Material Inputs:

| S. No. | Item | Quantity | Eq. |
|---|---|---|---|
| 1. | 1-(2,4-Dihydroxy-5-isopropyl-phenyl)-ethanone | 3.2 g | 1 |
| 2. | Benzyl bromide | 5.89 ml | 3 |
| 3. | Potassium carbonate | 6.82 g | 3 |
| 4. | Acetonitrile | 60 ml | 20 times |

To a mixture of 1-(2,4-dihydroxy-5-isopropyl-phenyl)-ethanone (3.2 g), acetonitrile (60 ml) and potassium carbonate (10.6 g) in a a 250 ml single neck RB flask equipped with a reflux condenser and a guard tube was added benzyl bromide (9.1 ml). The reaction mixture was refluxed (90° C.) for 16 h. The progress of the reaction was monitored by TLC (10% EtOAc/n-hexane, product $R_f$~0.5). On completion, acetonitrile was removed under reduced pressure. Water (100 ml) was added to the residue obtained and the resulting mixture was extracted with ethyl acetate (200 ml). The organic layer was dried over sodium sulphate. The solvent was removed under reduced pressure to give a residue to which n-hexane (150 ml) was added to give the product.

| Quantity of the product obtained | 5.1 g |
|---|---|
| Yield | 83.6% |
| Nature | Solid. |
| Color | Colorless |

Step 6

2,4-Bis-benzyloxy-5-isopropyl-benzoic acid

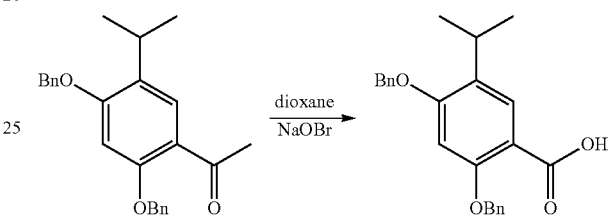

Material Inputs:

| S. No. | Item | Quantity |
|---|---|---|
| 1. | 1-(2,4-Bis-benzyloxy-5-isopropyl-phenyl)-ethanone | 7 g |
| 2. | Sodium hypobromide | 13 g in water 100 ml |
| 3. | Dioxane | 100 ml |

Procedure:

A mixture of a mixture of 1-(2,4-Bis-benzyloxy-5-isopropyl-phenyl)-ethanone (7 g) in dioxane (100 ml) in a 500 ml single neck RB flask equipped with a guard tube was cooled to 10° C. and sodium hypobromide [13 g in water (100 ml)] was added. The reaction mixture was stirred overnight at RT. The progress of the reaction was monitored by TLC (30% EtOAc/n-hexane, product $R_f$~0.5). On completion, sodium bisulphite (7 g) was added to the reaction mixture which was cooled to 0° C. The reaction mixture was then acidified with HCl (~10 ml) to pH~2, extracted with ethyl acetate (100 ml) and washed with water (25 ml). The organic layer was dried over sodium sulphate, and the solvent was removed under reduced pressure to give a residue, which was further purified by column chromatography (SiO$_2$, 10% EtOAc/n-hexane).

| Quantity of the product obtained | 3.4 g |
|---|---|
| Yield | 48.3% |
| Nature | Solid. |
| Colour | Colourless. |

C. Synthesis of Isoindoline Intermediates

Preparation C1

Synthesis of 4,7-difluoroisoindoline

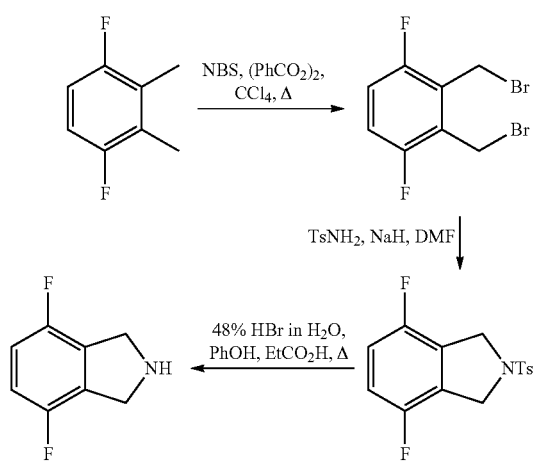

A mixture of 1,4-difluoro-2,3-dimethylbenzene (4.26 g, 30.0 mmol), N-bromosuccinimide (10.68 g, 60.0 mmol) and dibenzoyl peroxide (75 wt % in water, 120 mg) in carbon tetrachloride (50 ml) was stirred and held at reflux for 16 hours. Upon cooling to room temperature the mixture was filtered, the solids washed with carbon tetrachloride (10 ml), the organic extracts combined and the solvent removed in vacuo to afford 2,3-bis-bromomethyl-1,4-difluorobenzene (9.0 g, 100%) as a pale yellow liquid that solidified upon standing. $^1$H NMR (DMSO-$d_6$) 7.36 (2H, dd), 4.78 (4H, s).

A solution of 4-toluenesulphonamide (2.44 g, 14.28 mmol) in N,N-dimethylformamide (10 ml) was added dropwise to a vigourously stirred suspension of sodium hydride (1.2 g, 60 wt % in mineral oil, 30.0 mmol) in anhydrous N,N-dimethylformamide (60 ml). The mixture was stirred at room temperature for 1 hour, at 110° C. for 1 hour and was then cooled to 60° C. and a solution of 2,3-bis-bromomethyl-1,4-difluorobenzene (4.28 g, 14.28 mmol) in N,N-dimethylformamide (30 ml) was added dropwise. The mixture was stirred at 60° C. for 1 hour and then at room temperature for 16 hours. The solvent was removed in vacuo and the residue partitioned between dichloromethane and 1M hydrochloric acid. The organic layer was separated, washed with 5% aqueous potassium carbonate solution, the organics were separated and the solvent removed in vacuo. The residue was rinsed with diethyl ether, filtered and the solids sucked dry under reduced pressure to afford 4,7-difluoro-2-(toluene-4-sulfonyl)isoindoline (2.46 g, 56%) as a pale tan solid. $^1$H NMR (DMSO-$d_6$) 7.82 (2H, d), 7.43 (2H, d), 7.15 (2H, dd), 4.66 (4H, s), 2.36 (3H, s). MS: [M+H]$^+$ 310.

A mixture of 4,7-difluoro-2-(toluene-4-sulfonyl)isoindoline (2.36 g, 7.64 mmol), phenol (2.36 g, 25.11 mmol), 48% hydrogen bromide in water (20 ml) and propionic acid (4 ml) was stirred and held at reflux for 6 hours. Upon cooling to room temperature water (50 ml) was added and the mixture extracted with diethyl ether (2×100 ml). The aqueous layer was basified by the addition of 2M sodium hydroxide and was extracted with diethyl ether (3×100 ml). The combined extracts were evaporated to dryness in vacuo to afford 4,7-difluoroisoindoline (586 mg, 50%) as a brown oil that solidified upon standing. $^1$H NMR (DMSO-$d_6$) 7.06 (2H, dd), 4.12 (4H, s). MS: [M+H]$^+$ 156.

Preparation C2

Synthesis of 5-hydroxyisoindoline hydrobromide

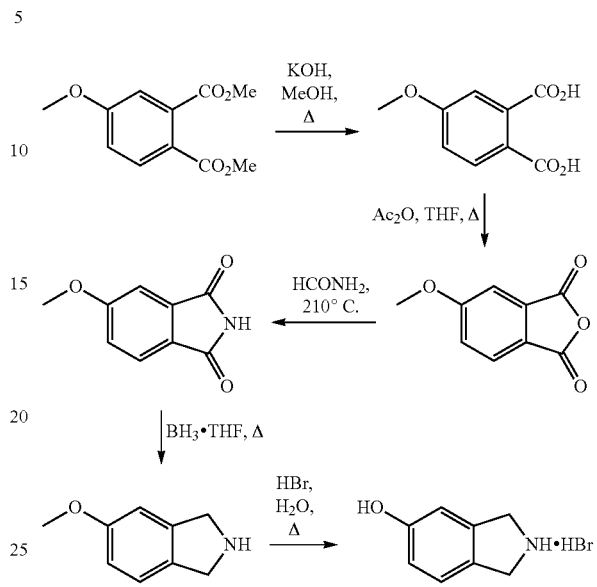

A solution of dimethyl 4-methoxyphthalate (36.75 g, 0.16 mol) in methanol (100 ml) was treated with a solution of potassium hydroxide (28.0 g, 0.5 mol) in water (50 ml) and the mixture was stirred and held at reflux for 4 hours. Upon cooling to room temperature the methanol was removed in vacuo and the mixture acidified to pH 2 or below by the addition of 5M hydrochloric acid. The solid material was filtered off, washed with water and sucked dry under reduced pressure overnight to afford 4-methoxyphthalic acid (31.8 g, 99%) as an off white solid. $^1$H NMR (DMSO-$d_6$) 12.90 (2H, br s), 7.74 (1H, d), 7.12-7.05 (2H, m), 3.84 (3H, s). MS: [M+H]$^+$ 197.

Acetic anhydride (40 ml) was added to a mixture of 4-methoxyphthalic acid (30.8 g, 0.16 mol) in anhydrous tetrahydrofuran (150 ml) and the mixture was stirred and held at reflux for 4 hours. Upon cooling to room temperature the solvent was removed in vacuo to afford 4-methoxyphthalic anhydride (27.8 g, 99%) as an off white solid. $^1$H NMR (DMSO-$d_6$) 8.02 (1H, d), 7.59 (1H, d), 7.49 (1H, dd), 3.97 (3H, s). MS: [M+H]$^+$ 179.

A mixture of 4-methoxyphthalic anhydride (27.8 g, 0.16 mol) and formamide (175 ml) was stirred and held at 210° C. for 5 hours and was then allowed to cool to room temperature overnight. The solid material was filtered off, washed sequentially with water (100 ml), 50% aqueous acetone (50 ml) and diethyl ether (200 ml) and sucked dry under reduced pressure to afford 4-methoxyphthalimide (21.3 g, 77%) as a pale yellow solid. $^1$H NMR (DMSO-$d_6$) 11.15 (1H, br s), 7.74 (1H, d), 7.33-7.28 (2H, m), 3.92 (3H, s).

A stirred solution of 4-methoxyphthalimide (21.3 g, 0.12 mol) in anhydrous tetrahydrofuran (425 ml) at 0° C. was treated dropwise with a solution of borane in tetrahydrofuran (1M, 340 ml, 0.34 mol) and the resulting mixture was stirred and held at reflux for 16 hours. The mixture was cooled to 0° C., methanol (150 ml) was added dropwise followed by 5M hydrochloric acid (150 ml) and the mixture was stirred and held at reflux for 3 hours. Upon cooling to room temperature the organic solvent was removed in vacuo, the mixture was diluted with water (750 ml) and was extracted with dichloromethane (3×750 ml). The aqueous layer was basified to pH 12 or above by the addition of 5M sodium hydroxide, extracted with dichloromethane (3×750 ml) and the combined extracts were evaporated to dryness in vacuo to afford 5-methoxyisoindoline (8.34 g, 47%) as a brown oil. $^1$H NMR (DMSO-$d_6$) 7.13 (1H, d), 6.84 (1H, d), 6.74 (1H, dd), 4.05 (2H, s), 4.01 (2H, s), 3.73 (3H, s). MS: [M+H]$^+$ 150.

5-Methoxyisoindoline (8.34 g, 55.97 mmol) in 48% aqueous hydrobromic acid (100 ml) was stirred and held at reflux for 16 hours. Upon cooling to room temperature the solvent was removed in vacuo to afford 5-hydroxyisoindoline hydrobromide (11.32 g, 93%) as a tan solid. $^1$H NMR (DMSO-$d_6$) 9.63 (1H, br s), 9.32 (2H, br s), 7.18 (1H, d), 6.79 (1H, d), 6.76 (1H, dd), 4.42 (2H, t), 4.38 (2H, t). MS: [M+H]$^+$ 136.

Preparation C3

Synthesis of 5-chloro-2,3-dihydro-1H-isoindole

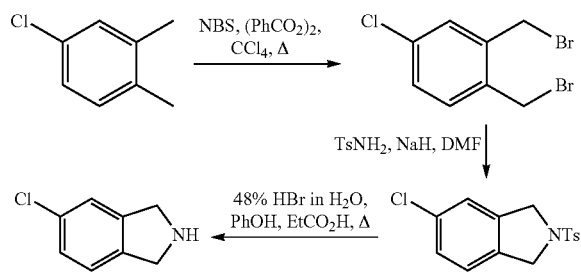

A mixture of 3,4-dimethylchlorobenzene (10 g, 71.1 mmol), N-bromosuccinimide (25 g, 142.2 mmol), and benzoyl peroxide (0.147 g, 0.6 mmol), was refluxed in 80 ml of carbon tetrachloride for 18 hours. After cooling, the insoluble material was filtered off and washed with a small amount of carbon tetrachloride. The filtrate and the washings were combined and concentrated under reduced pressure to obtain 20 g of 1,2-bis-bromomethyl-4-chloro-benzene as a pale yellow oil product as a major component.

To a suspension of 60% sodium hydride (3.0 g, 0.125 mmol) in mineral oil in 80 ml of anhydrous DMF (100 ml) was dropwise added a solution of para-toluene sulphonamide (5.6 g, 32.60 mmol) in 30 ml of DMF over 1 hour with vigorous stirring at room temperature. After the addition, the mixture was stirred for 1 hour at room temperature and another 1 hour heating at 90° C. To this mixture was added dropwise a solution of 1,2-bis-bromomethyl-4-chloro-benzene (4 g, 14.18 mmol) in 20 ml of anhydrous DMF at 60° C. and then stirred overnight at room temperature. The resultant mixture was poured onto ice and the resulting precipitate was collected by filtration. The precipitate was washed with 1N hydrochloric acid, 5% sodium carbonate and brine then dried (MgSO4), filtered and evaporated to give 2.8 g of 5-Chloro-2-(toluene-4-sulphonyl)-2,3-dihydro-1H-isoindole as a pale yellow solid. MS: [M+H]$^+$ 308

1.0 g of 2-(p-toluensulphonyl)-5-chloroisoindoline and 1.0 g of phenol were added to a mixture of 8 ml of 48% hydrobromic acid and 1.4 ml of propionic acid, and then mixture was heated at reflux for 6 hours. The resultant reaction mixture was diluted with 10 ml of water and extracted twice with 50 ml of ethyl acetate. The water layer was basified with aqueous sodium hydroxide solution and extracted with ethyl acetate three times. The extract was concentrated and the crude product was diluted with 4N HCl/dioxane and stirred for 15 minutes before evaporating the HCl and then re-evaporating with toluene three times to give 0.3 g of 5-chloro-2,3-dihydro-1H-isoindole hydrochloride as a black solid. MS: [M+H]$^+$ 153-15

Preparation C4

Synthesis of 5-chloro-6-methoxy-2,3-dihydro-1H-isoindole

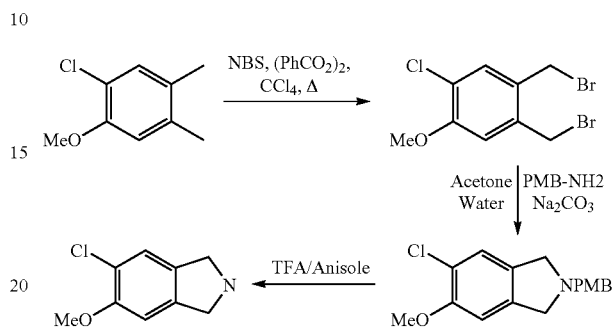

A mixture of 1-chloro-2-methoxy-4,5-dimethyl-benzene (3 g, 17.6 mmol), N-bromosuccinimide (6.3 g, 35.3 mmol), and benzoyl peroxide (0.100 g, 0.41 mmol) in carbon tetrachloride (40 ml) was heated at reflux for 18 hours. After cooling, the insoluble material was removed by filtration, washed with a small amount of carbon tetrachloride and the filtrate evaporated to give 1,2-bis-bromomethyl-4-chloro-5-methoxy-benzene as an oil product as a major component. MS: [M+H]$^+$ 329

A solution of 4-methoxybenzylamine (2.4 g, 17.6 mmol) in acetone (110 ml) was added dropwise to a mixture of 1,2-bis-bromomethyl-4-chloro-5-methoxy-benzene (assumed theoretical, 17.6 mmol) and Na$_2$CO$_3$ (12 g, 114 mmol) in acetone/water (10 ml:12.5 ml) then stirred at room temperature for 2 hours and concentrated in vacuo. The crude material was dissolved in ethyl acetate and extracted with 2N HCl. The aqueous layer was neutralized with sodium carbonate, extracted with ethyl acetate (×2), dried (MgSO$_4$) and evaporated under vacuum to give 5-chloro-6-methoxy-2-(4-methoxy-benzyl)-2,3-dihydro-1H-isoindole (0.8 g, 2.6 mmol) as a brown gum. MS: [M+H]$^+$ 304

A solution of 5-chloro-6-methoxy-2-(4-methoxy-benzyl)-2,3-dihydro-1H-isoindole (600 mg) and anisole (0.3 ml) in trifluoroacetic acid (6 ml) was heated at 180° C. (50 W) for 40 minutes in a CEM discover microwave synthesiser. The reaction mixture was evaporated and re-evaporated with toluene. The crude material was partitioned between DCM and water, the aqueous layer washed with DCM (x 3) then evaporated and re-evaporated with toluene to give 5-chloro-6-methoxy-2,3-dihydro-1H-isoindole (256 mg) as green crystals. MS: [M+H]$^+$ 184

Preparation C5

Synthesis of 2,3-dihydro-1H-isoindol-5-ylamine trifluoroacetate

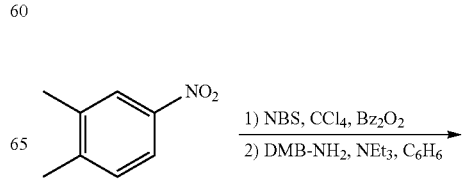

-continued

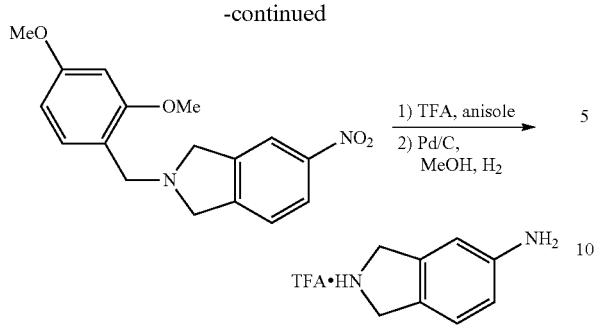

A solution of 4-nitro-o-xylene (15.1 g; 0.1 mol) in carbon tetrachloride (150 ml) was treated with N-bromosuccinimide (36 g; 0.2 mol) followed by benzoyl peroxide (1 g) then heated at reflux overnight. The reaction was allowed to cool to ambient temperature, filtered and the filtrate evaporated to give 32 g of crude 1,2-bis-bromomethyl-4-nitro-benzene as a mobile oil. The crude product was dissolved in benzene (200 ml) then treated dropwise over 30 minutes with a solution of 2,4-dimethoxybenzylamine (15 ml) and triethylamine (27.85 ml) in benzene (100 ml) then heated at 80° C. for 3 hours. The reaction was cooled, washed with water followed by saturated sodium bicarbonate. The organics were extracted with 2M HCl (×150 ml) then combined aqueous basified with 2M NaOH and extracted with EtOAc (×2). The combined EtOAc layer was dried (MgSO$_4$), evaporated then purified by flash column chromatography eluting with EtOAc/P.E. (1:3-1.2-1:1). Product containing fraction were combined and evaporated to give 10.15 g of 2-(2,4-dimethoxy-benzyl)-5-nitro-2,3-dihydro-1H-isoindole as a brown solid. $^1$H NMR (DMSO-d$_6$) 8.12 (2H, m), 7.50 (1H, d), 7.25 (1H, d), 6.55 (1H, d), 6.52 (1H, dd), 3.93 (4H, s), 3.80 (3H, s), 3.78 (2H, s), 3.75 (3H, s).

2-(2,4-dimethoxy-benzyl)-5-nitro-2,3-dihydro-1H-isoindole (13 g) in TFA (18 ml) was treated with anisole (6 ml) then heated in a CEM microwave synthesiser at 120° C. (30 Watts) for 20 minutes (carried out batch wise, 6 times). The reaction mixture was evaporated in vacuo and the residue partitioned between DCM and water. The water layer was separated, washed with DCM (×3) then evaporated and re-evaporated with toluene/MeOH (×3) to give 9.8 g of 5-nitro-2,3-dihydro-1H-isoindole trifluoroacetic acid salt as a beige solid. $^1$H NMR (DMSO-d$_6$) 9.85 (2H, br s), 8.32 (1H, d), 8.25 (1H, dd), 7.70 (1H, d), 4.68 (2H, s), 4.65 (2H, s).

A mixture of 5-nitro-2,3-dihydro-1H-isoindole trifluoroacetic acid salt (9.8 g) and 10% palladium on carbon (1 g) in methanol (75 ml) was hydrogenated at room temperature and pressure for 16 hours. The reaction was filtered through Celite™, the filtrate evaporated and re-evaporated with toluene to give 8.76 g of 2,3-dihydro-1H-isoindol-5-ylamine mono trifluoroacetic acid salt as a dark brown solid. $^1$H NMR (DMSO-d$_6$) 9.45 (2H, br s), 7.05 (1H, d), 6.60 (2H, m), 5.35 (2H, br s), 4.40 (2H, s), 4.30 (2H, s).

Preparation C6

Synthesis of 5-morpholin-4-ylmethyl-2,3-dihydro-1H-isoindole ditrifluoroacetate

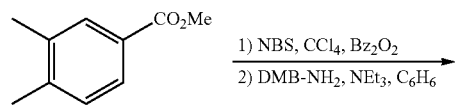

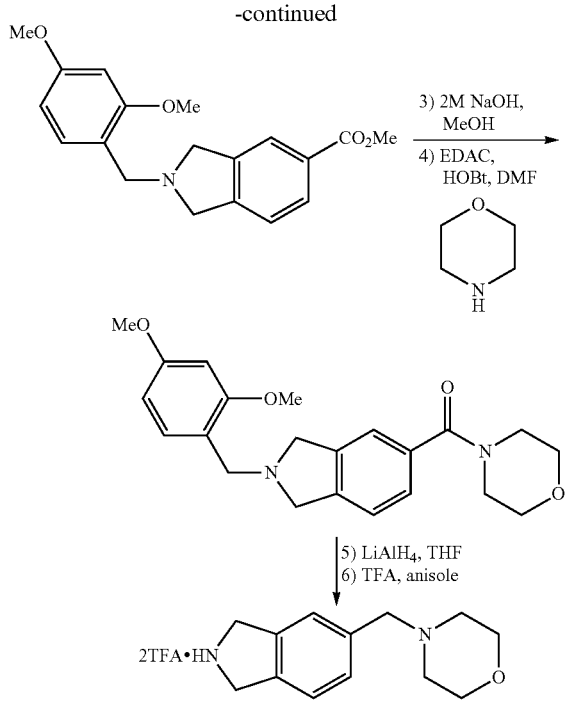

Steps 1 and 2 were carried out in a manner analogous to that described in Preparation C5 using methyl 3,4-dimethylbenzoate as the starting material.

A mixture of 2-(2,4-dimethoxybenzyl)-2,3-dihydro-1H-isoindole-5-carboxylic acid methyl ester (4.65 g; 14.2 mmol) and lithium hydroxide monohydrate (660 mg; 1.1 equiv.) in 4:1:1 THF-MeOH—H$_2$O (60 ml) was stirred at room temperature overnight. A further 170 mg of base were added and stirring continued for 7 hours. The reaction was evaporated then re-evaporated with MeOH/toluene (×2). A mixture of the crude 2-(2,4-dimethoxy-benzyl)-2,3-dihydro-1H-isoindole-5-carboxylic acid lithium salt (1.5 g; 4.7 mmol), morpholine (820 µl; 2 equiv.), EDAC (1.1 g; 1.2 equiv.) and HOBt (760 mg; 1.2 equiv.) in DMF (25 ml) was stirred at room temperature overnight then evaporated in vacuo. The residue was partitioned between EtOAc and saturated NaHCO$_3$, the EtOAc layer was separated, washed with brine, dried (MgSO$_4$) and evaporated. Purification by flash column chromatography (2% then 5% MeOH/DCM as eluant) gave 1.1 g of [2-(2,4-dimethoxybenzyl)-2,3-dihydro-1H-isoindol-5-yl]-morpholin-4-yl-methanone as a red/brown gum. $^1$H NMR (DMSO-d$_6$) 7.30-7.18 (4H, m), 6.56 (1H, d), 6.52 (1H, dd), 3.85 (4H, s), 3.78 (5H, m), 3.73 (3H, s).

A solution of [2-(2,4-dimethoxybenzyl)-2,3-dihydro-1H-isoindol-5-yl]-morpholin-4-yl-methanone (1.05 g; 2.75 mmol) in dry THF (20 ml) under a nitrogen atmosphere was treated with 1M lithium aluminium hydride solution then stirred at room temperature overnight. The reaction was quenched by the cautious addition of saturated sodium sulphate solution, then diluted with EtOAc (40 ml), filtered through Celite™ and evaporated. Purification by flash column chromatography (2% then 5% MeOH/DCM as eluant) gave 340 mg of 2-(2,4-dimethoxybenzyl)-5-morpholin-4-yl-methyl-2,3-dihydro-1H-isoindole as a pale brown gum.

A mixture of 2-(2,4-dimethoxybenzyl)-5-morpholin-4-yl-methyl-2,3-dihydro-1H-isoindole (340 mg) and anisole (350 µl) in trifluoroacetic acid (1.5 ml) was heated at 130 C in a CEM microwave synthesiser for 1 hour then evaporated and re-evaporated with toluene. The residue was partitioned between DCM and water. The water layer was separated, washed with DCM (×3) then evaporated and re-evaporated with toluene/MeOH (×3) to give 422 mg of 5-morpholin-4-ylmethyl-2,3-dihydro-1H-isoindole ditrifluoroacetate as a brown gum. $^1$H NMR (DMSO-d$_6$) 10.30 (1H, br s), 9.60 (2H, br s), 7.55-7.45 (3H, m), 4.45 (4H, s), 4.45-4.30 (2H, m), 4.20-3.88 (2H, m), 3.70-3.55 (2H, m), 3.30-3.00 (4H, m).

Preparation C7

Synthesis of ethyl-2,3-dihydro-1H-isoindole-5-carboxylate trifluoroacetate

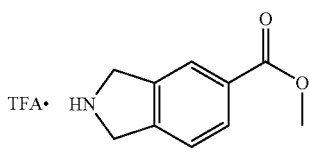

A solution of 2-(2,4-dimethoxy-benzyl)-2,3-dihydro-1H-isoindole-5-carboxylic acid methyl ester (215 mg) and anisole (200 μl) in 1 ml of TFA was heated at 140° C. for 30 minutes in a CEM discover microwave synthesiser. The reaction was partitioned between water and DCM, the water layer was separated, washed with DCM then evaporated and re-evaporated with toluene/MeOH (×2) to give 105 mg of the title compound. $^1$H NMR (DMSO-d$_6$) 9.70 (2H, br s), 8.02 (1H, s), 8.98 (1H, d), 7.57 (1H, d), 4.60 (2H, s), 4.56 (2H, s), 3.89 (3H, s).

Preparation C8

Hydroxy-2-(4-methoxy-benzyl)-isoindole-1,3-dione

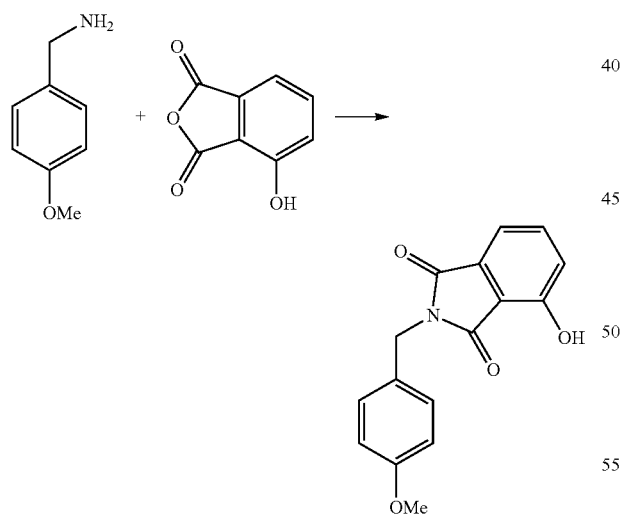

A mixture of 3-hydroxyphthalic anhydride (543 mg, 3.31 mmol), 4-methoxybenzylamine (0.43 mL, 3.31 mmol) and acetic acid (3 mL) was heated at 100° C. for 4 hours. The mixture was allowed to cool and diluted with water (20 mL). The white solid was collected by filtration, washed well with water and dried to give the title compound (760 mg, 81%). $^1$H NMR (DMSO-d$_6$) 11.03 (1H, s), 7.61 (1H, dd), 7.28 (1H, d), 7.23-7.19 (3H, m), 6.89-6.86 (2H, m), 4.63 (2H, s), 3.71 (3H, s). MS: [M−H$^+$] 282.

Preparation C9

4-Hydroxy-2-(2,4-dimethoxy-benzyl)-isoindole-1,3-dione

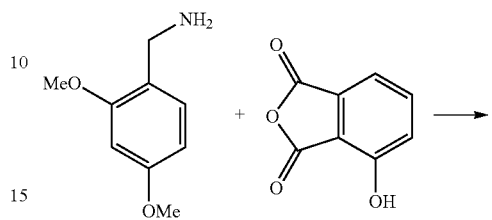

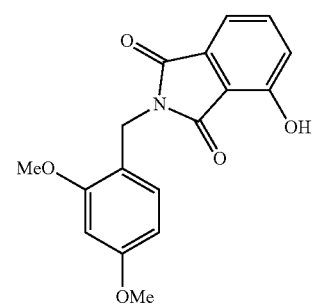

A mixture of 3-hydroxyphthalic anhydride (1.24 g, 7.6 mmol), 2,4-dimethoxybenzylamine (1.14 mL, 7.6 mmol) and acetic acid (5 mL) was heated at 80° C. for 24 hours. The mixture was allowed to cool and diluted with water (20 mL). The white solid was collected by filtration, washed well with water and dried to give the title compound (1.73 g, 73%). $^1$H NMR (DMSO-d$_6$) 11.00 (1H, s), 7.62 (1H, dd), 7.29 (1H, d), 7.21 (1H, d), 6.90 (1H, d), 6.56 (1H, d), 6.43 (1H, dd), 4.59 (2H, s), 3.79 (3H, s), 3.72 (3H, s). MS: [M−H$^+$] 314.

Preparation C10

2-(4-Methoxy-benzyl)-4-[2-(2-methoxy-ethoxy)-ethoxy]-isoindole-1,3-dione

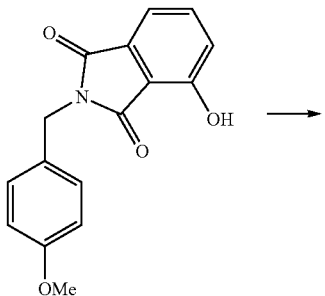

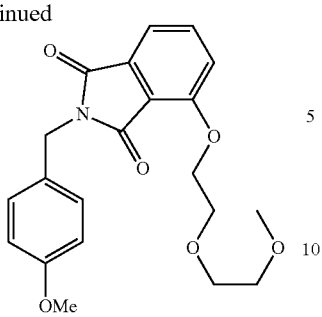

1-(2-Bromo-ethoxy)-2-methoxy-ethane (107 mg, 0.58 mmol) was added to a suspension of 4-hydroxy-2-(4-methoxy-benzyl)-isoindole-1,3-dione (150 mg, 0.53 mmol) and potassium carbonate (200 mg, 1.4 mmol) in DMF (2 mL). After 3.5 hours, a catalytic amount of potassium iodide was added. After a further 17 hours, the mixture was warmed to 60° C. After 3 hours, an additional amount of 1-(2-bromoethoxy)-2-methoxy-ethane (20 mg, 0.11 mmol) was added and the mixture maintained at 60° C. for a further 20 hours. The mixture was concentrated in vacuo then the residue was taken up in ethyl acetate and washed with potassium carbonate solution and brine. The organic phase was dried (MgSO$_4$) and concentrated to give the title compound as a yellow oil (149 mg, 73%). $^1$H NMR (methanol-d$_4$) 7.71 (1H, t), 7.43-7.40 (2H, m), 7.31-7.27 (2H, m), 6.87-6.83 (2H, m), 4.71 (2H, s), 4.37-4.34 (2H, m), 3.92-3.89 (2H, m), 3.77-3.74 (5H, m), 3.55-3.53 (2H, m), 3.33 (3H, s). MS: [M+H]$^+$ 386.

Preparation C11

2-(2,4-Dimethoxy-benzyl)-4-(2-dimethylamino-ethoxy)-isoindole-1,3-dione

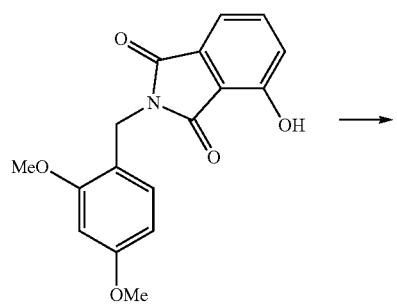

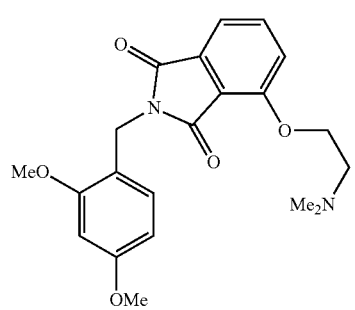

A mixture of 2-(2,4-dimethoxy-benzyl)-4-hydroxy-isoindole-1,3-dione (317 mg, 1.01 mmol), 2-dimethylaminoethyl chloride hydrochloride (160 mg, 1.11 mmol) and potassium carbonate (350 mg, 2.5 mmol) in DMF (4 mL) was heated at 60° C. for 18 hours. The mixture was concentrated in vacuo, taken up in ethyl acetate and extracted twice with 1N hydrochloric acid. The aqueous extracts were made basic with solid potassium carbonate and extracted with ethyl acetate (×2). The combined organic extracts were washed with brine, dried (MgSO$_4$) and concentrated to give the title compound (236 mg, 61%) as an off-white solid. $^1$H NMR (methanol-d$_4$) 7.73 (1H, t), 7.44-7.40 (2H, m), 7.02 (1H, d), 6.51 (1H, d), 6.42 (1H, dd), 4.72 (2H, s), 4.33 (2H, t), 3.80 (3H, s), 3.76 (3H, s), 2.87 (2H, t), 2.40 (6H, s). MS: [M+H]$^+$ 385.

Preparation C12

2-(2,4-Dimethoxy-benzyl)-4-(3-morpholin-4-yl-propoxy)-isoindole-1,3-dione

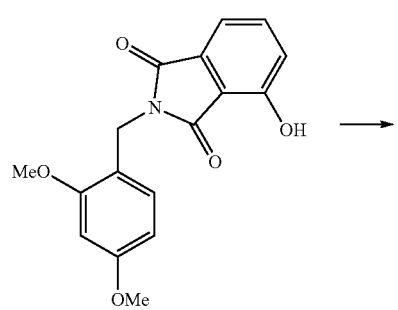

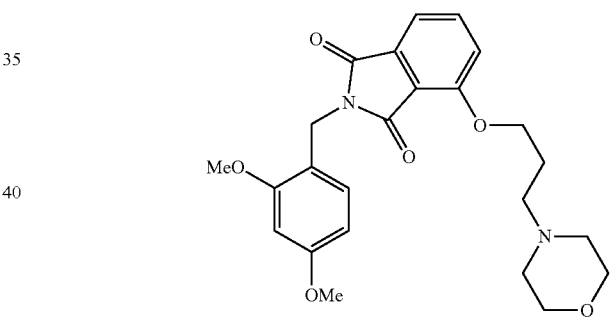

A mixture of 2-(2,4-dimethoxy-benzyl)-4-hydroxy-isoindole-1,3-dione (313 mg, 1.00 mmol), 4-(3-chloropropyl)morpholine (160 mg, 1.11 mmol) and potassium carbonate (350 mg, 2.5 mmol) in DMF (5 mL) was heated at 60° C. for 18 hours. The mixture was diluted with ethyl acetate and extracted twice with 1N hydrochloric acid. The aqueous extracts were made basic with solid potassium carbonate and extracted with ethyl acetate. The organic extract was washed with brine, dried (MgSO$_4$) and concentrated to give a yellow solid which was recrystallised from methanol/petrol then ethyl acetate/chloroform/petrol to give the title compound (298 mg, 68%) as an off-white solid. $^1$H NMR (methanol-d$_4$) 7.72 (1H, t), 7.41 (1H, d), 7.39 (1H, d), 7.02 (1H, d), 6.51 (1H, d), 6.43 (1H, dd), 4.72 (2H, s), 4.27 (2H, t), 3.81 (3H, s), 3.76 (3H, s), 3.68 (4H, t), 2.61 (2H, t), 2.50 (4H, m), 2.05 (2H, qn). MS: [M+H]$^+$ 441.

Preparation C13

2-(4-Methoxy-benzyl)-4-[2-(2-methoxy-ethoxy)-ethoxy]-2,3-dihydro-1H-isoindole

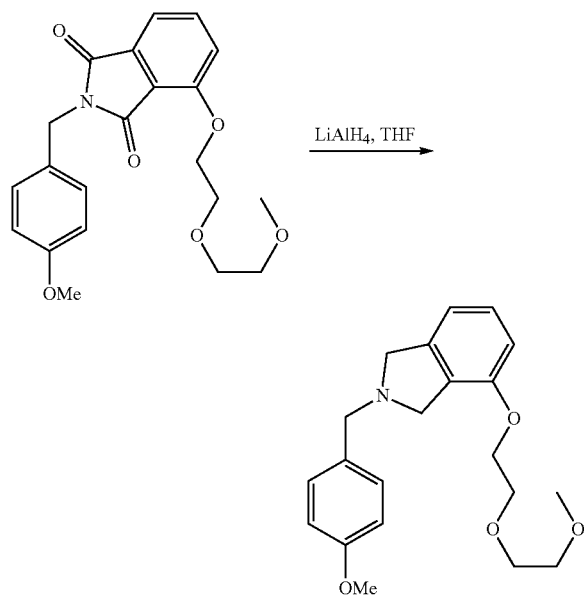 [SMILES: COCCOCCOc1cccc2c1C(=O)N(Cc1ccc(OC)cc1)C2=O ; COCCOCCOc1cccc2c1CN(Cc1ccc(OC)cc1)C2]

2-(4-Methoxy-benzyl)-4-[2-(2-methoxy-ethoxy)-ethoxy]-isoindole-1,3-dione (149 mg, 0.38 mmol) was treated with a 1M solution of lithium aluminium hydride in THF (5 mL, 5 mmol). The mixture was maintained at r.t. for 4 hours, 60° C. for 1 hour, then r.t. for a further 18 hours. The mixture was then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 15 minutes. The solids were removed by filtration, being well washed with ethyl acetate. Concentration of the filtrate gave a residue which was absorbed onto an SCX cartridge and washed with 5% methanol/dichloromethane then eluted with 10% 1M ammonia in methanol/dichloromethane to afford the title compound (134 mg, 97%). $^1$H NMR (methanol-$d_4$) 7.43-7.39 (2H, m), 7.27 (1H, t), 6.99-6.96 (2H, m), 6.90 (1H, d), 6.88 (1H, d), 4.33 (2H, s), 4.28 (2H, s), 4.23 (2H, s), 4.18-4.15 (2H, m), 3.85-3.79 (5H, m), 3.67-3.64 (2H, m), 3.54-3.51 (2H, m), 3.33 (3H, s). MS: [M+H]$^+$ 358.

Preparation C14

2-(2,4-Dimethoxy-benzyl)-4-(2-dimethylamino-ethoxy)-2,3-dihydro-1H-isoindole

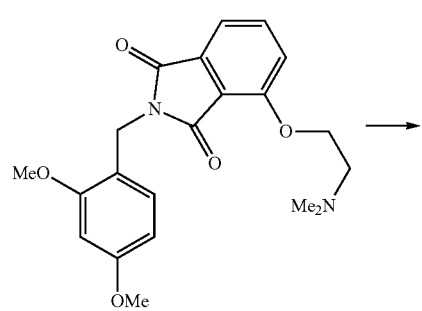

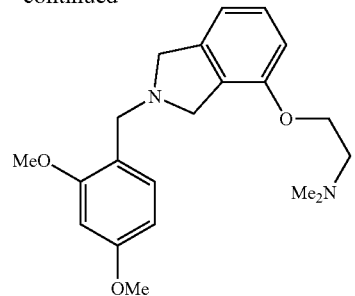

2-(2,4-Dimethoxy-benzyl)-4-(2-dimethylamino-ethoxy)-isoindole-1,3-dione (201 mg, 0.52 mmol) was treated with a 1M solution of lithium aluminium hydride in THF (5 mL, 5 mmol). After 7.5 hours at r.t. a further portion of lithium aluminium hydride solution (5 mL, 5 mmol) was added and the mixture maintained for further 18 hours. The mixture was then cooled in ice and quenched by the dropwise addition of water (0.4 mL), 2N sodium hydroxide solution (0.8 mL) and water (0.8 mL). Magnesium sulfate was added, followed by ethyl acetate and then the mixture was stirred at r.t. for 1 hour. The solids were removed by filtration, being well washed with ethyl acetate. Concentration of the filtrate gave the title compound (192 mg, 103%) as a brown oil which was carried forward without further purification. $^1$H NMR (methanol-$d_4$) 7.24 (1H, d), 7.16 (1H, t), 6.82-6.78 (2H, m), 6.55 (1H, d), 6.51 (1H, dd), 4.12 (2H, t), 3.92 (4H, s), 3.86 (2H, s), 3.82 (3H, s), 3.80 (3H, s), 2.76 (2H, t), 2.33 (6H, s). MS: [M+H]$^+$ 357.

Preparation C15

2-(2,4-Dimethoxy-benzyl)-4-(3-morpholin-4-yl-propoxy)-2,3-dihydro-1H-isoindole

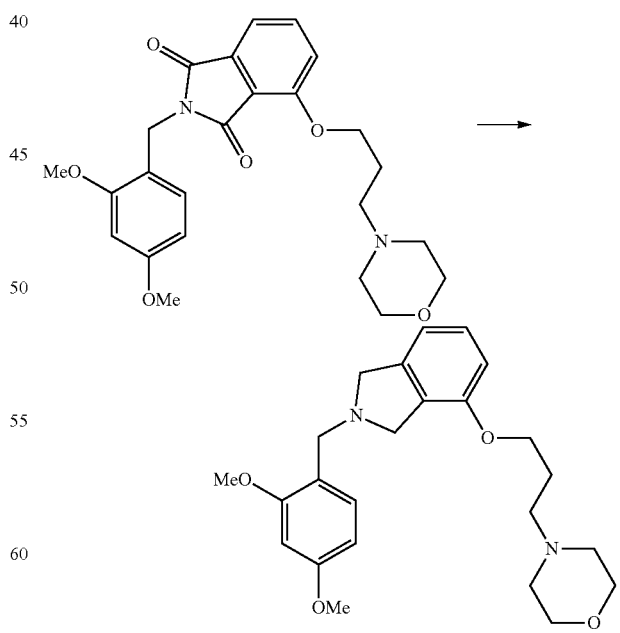

2-(2,4-Dimethoxy-benzyl)-4-(3-morpholin-4-yl-propoxy)-isoindole-1,3-dione (298 mg, 0.68 mmol) was treated with a 1M solution of lithium aluminium hydride in THF (5 mL, 5 mmol) and maintained at r.t. for 21 hours. The mixture was heated to 75° C. for 1 hour then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 1 hour. The solids were removed by filtration, being well washed with ethyl acetate. Concentration of the filtrate gave a crude product which was purified by flash chromatography on silica, eluting with 5% methanol in DCM. This afforded the title compound (233 mg, 83%) as a red oil. $^1$H NMR (methanol-$d_4$) 7.24 (1H, d), 7.15 (1H, t), 6.80 (1H, d), 6.78 (1H, d), 6.56 (1H, d), 6.52 (1H, dd), 4.05 (2H, t), 3.94 (2H, s), 3.88 (2H, s), 3.87 (2H, s), 3.83 (3H, s), 3.80 (3H, s), 3.70-3.68 (4H, m), 2.54-2.50 (2H, m), 2.49-2.47 (4H, m), 2.00-1.93 (2H, m). MS: [M+H]$^+$ 413.

Preparation C16

4-[2-(2-Methoxy-ethoxy)-ethoxy]-2,3-dihydro-1H-isoindole

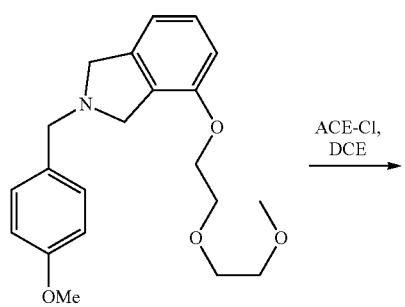

A solution of 2-(4-methoxy-benzyl)-4-[2-(2-methoxy-ethoxy)-ethoxy]-2,3-dihydro-1H-isoindole (45 mg, 0.13 mmol) in 1,2-dichloroethane (2 mL) was treated with α-chloroethyl chloroformate (0.1 mL, 0.93 mmol). After 17 hours, methanol (5 mL) was added and the mixture stirred for 3 hours. The solvents were removed in vacuo to afford the title compound as a greenish-black solid, which was used without further purification. $^1$H NMR (methanol-$d_4$) 7.36 (1H, t), 6.98 (2H, d), 4.60 (2H, s), 4.57 (2H, s), 4.23-4.21 (2H, m), 3.85-3.83 (2H, m), 3.69-3.67 (2H, m), 3.57-3.54 (2H, m), 3.36 (3H, s). MS: [M+H]$^+$ 238.

Preparation C17

[2-(2,3-Dihydro-1H-isoindol-4-yloxy)-ethyl]-dimethyl-amine

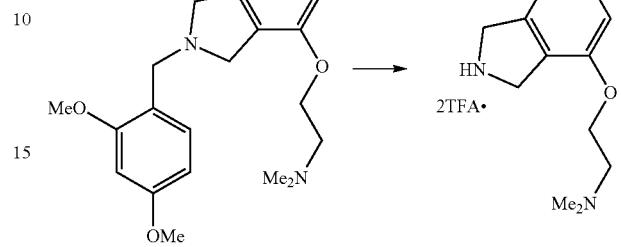

A solution of 2-(2,4-dimethoxy-benzyl)-4-(2-dimethylamino-ethoxy)-2,3-dihydro-1H-isoindole (170 mg, 0.48 mmol) in trifluoroacetic acid (0.5 mL) and anisole (0.5 mL) was heated at 150° C. under microwave irradiation for 10 minutes. The mixture was diluted with ethyl acetate and extracted twice with water. The combined aqueous extracts were concentrated to give the title compound as a purple oil (240 mg, including residual TFA and/or water). $^1$H NMR (methanol-$d_4$) 7.42 (1H, t), 7.07 (1H, d), 7.04 (1H, d), 4.64 (4H, br.s), 4.47-4.44 (2H, m), 3.65-3.63 (2H, m), 3.01 (6H, s). MS: [M+H]$^+$ 207.

Preparation C18

4-(3-Morpholin-4-yl-propoxy)-2,3-dihydro-1H-isoindole

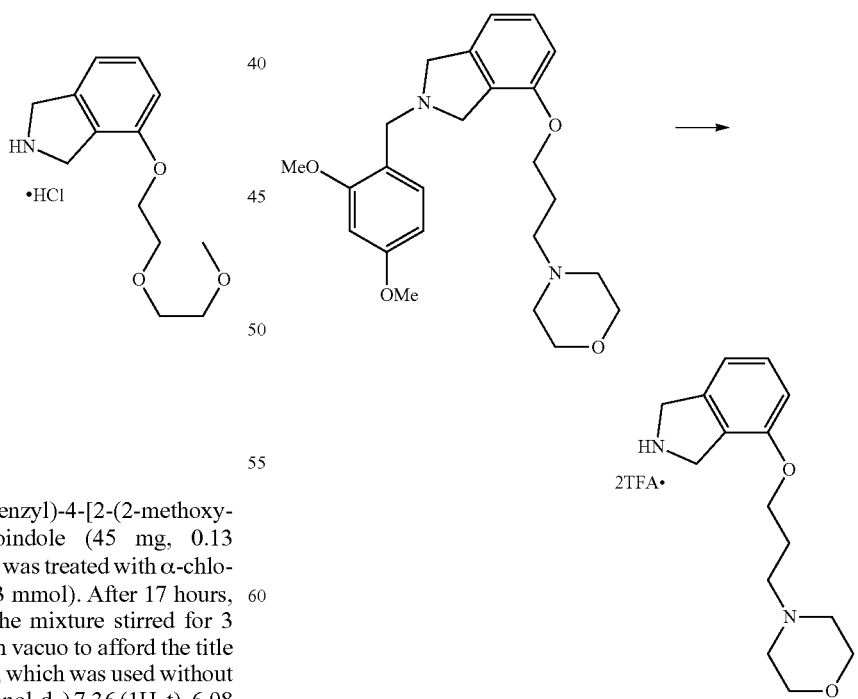

A solution of 2-(2,4-dimethoxy-benzyl)-4-(3-morpholin-4-yl-propoxy)-2,3-dihydro-1H-isoindole (233 mg, 0.56 mmol) in trifluoroacetic acid (1.0 mL) and anisole (0.5 mL) was heated at 150° C. under microwave irradiation for 10 minutes. The mixture was diluted with diethyl ether and extracted twice with water. The combined aqueous extracts were concentrated to give an oil which was dissolved in methanol and concentrated in vacuo to afford the title compound as a brown oil (348 mg, including residual TFA and/or water). $^1$H NMR (methanol-$d_4$) 7.40 (1H, t), 7.03 (1H, d), 6.99 (1H, d), 4.63 (2H, s), 4.59 (2H, s), 4.21 (2H, t), 4.14-4.04 (2H, m), 3.85-3.73 (2H, m), 3.61-3.52 (2H, m), 3.41-3.36 (2H, m), 3.25-3.13 (2H, m), 2.32-2.25 (2H, m). MS: [M+H]$^+$ 263.

Preparation C19

Synthesis of 4-bromo-2,3-dihydro-1H-isoindole trifluoroacetate

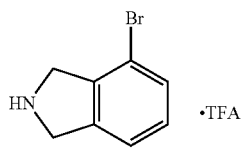

Prepared in a manner analogous to 5-nitro-2,3-dihydro-1H-isoindole (described in preparation C5). $^1$H NMR (DMSO-$d_6$) 9.73 (2H, br s), 7.60 (1H, d), 7.45 (1H, d), 7.35 (1H, t), 4.65 (2H, s), 4.55 (2H, s).

Preparation C20

Synthesis of 5-bromo-2,3-dihydro-1H-isoindole

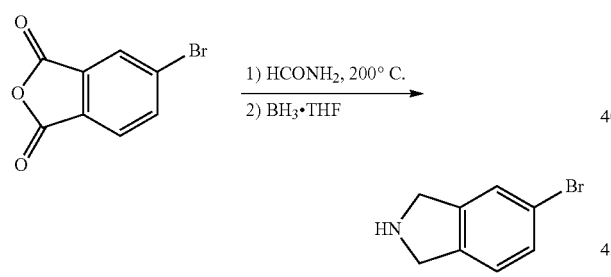

A mixture of 4-bromophthalic anhydride (25 g) in formamide (75 ml) was heated at 200° C. for 16 hours then allowed to cool to room temperature. The reaction mixture was diluted with water (200 ml), filtered, the filter cake was washed with water then diethyl ether and sucked dry to give 20.85 g of light mustard solid.

280 ml of 1M Borane-THF complex was added dropwise to a stirred solution of 4-bromophthalimide (20.85 g; 92.2 mmol) in anhydrous THF (200 ml) at 0° C. then heated at reflux overnight. The reaction was cooled to 0° C. then treated cautiously with methanol (100 ml) followed by 2M HCl (100 ml) then heated at reflux for 3 hours. The reaction mixture was cooled and the organics evaporated. The aqueous was diluted with water (100 ml) the extracted with DCM (×3). The aqueous was basified with 2M NaOH then extracted with DCM (×3). The combined DCM extracts were dried (MgSO$_4$), filtered and evaporated to give 6.99 g of 5-bromo-2,3-dihydro-1H-isoindole as a dark brown gummy solid. $^1$H NMR (DMSO-$d_6$) 7.45 (1H, s), 7.36 (1H, d), 7.20 (1H, d), 4.05 (4H, s).

Preparation C21

Synthesis of 2,3-dihydro-1H-isoindole-5-carboxylic acid methyl ester trifluoroacetate

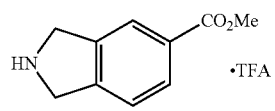

2-(2,4-Dimethoxybenzyl)-2,3-dihydro-1H-isoindole-5-carboxylic acid methyl ester (preparation C6, step 2 product) was deprotected in a manner analogous to 5-nitro-2,3-dihydro-1H-isoindole (described in preparation C5) to give the title compound. $^1$H NMR (DMSO-$d_6$) 9.70 (2H, br s), 8.00 (1H, s), 7.95 (1H, d), 7.57 (1H, d), 4.60 (4H, s), 2.88 (3H, s).

D. Synthesis of Benzylated Resorcinol Intermediates

Preparation D1

Synthesis of (2,4-bis-benzyloxy-5-isopropyl-phenyl)-[5-(2-methoxy-ethoxy)-1,3-dihydro-isoindol-2-yl]-methanone

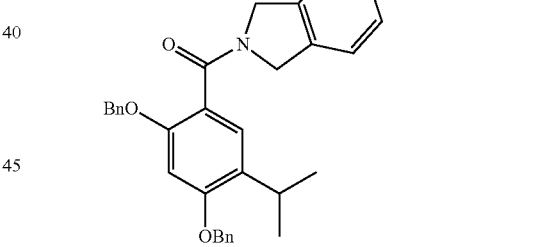

(2,4-Bis-benzyloxy-5-isopropyl-phenyl)-(5-hydroxy-1,3-dihydro-isoindol-2-yl)-methanone (A2 from 2,4-bis-benzyloxy-5-isopropyl-benzoic acid (Preparation B10) and 5-hydroxyisoindoline) (100 mg, 0.2 mmol), 1-chloro-2-methoxy-ethane (23.6 mg, 0.25 mmol) and K$_2$CO$_3$ (34.5 mg, 0.25 mmol) in DMF (4 ml) were combined and stirred for 2 hours at room temperature. A further 0.25 mmol of 1-chloro-2-methoxy-ethane and K$_2$CO$_3$ was added then heated at 90° C. for 16 hours. Reaction cooled to room temperature and diluted with EtOAc then filtered. The filtrate was reduced in vacuo then purified by flash column chromatography, eluting with 100% petroleum ether to 100% ethyl acetate to afford 115 mg of the title compound as a colourless gel. MS: [M+H]$^+$ 552

Preparation D2

Synthesis of (2,4-bis-benzyloxy-5-isopropyl-phenyl)-[5-(3-morpholin-4-yl-propoxy)-1,3-dihydro-isoindol-2-yl]-methanone

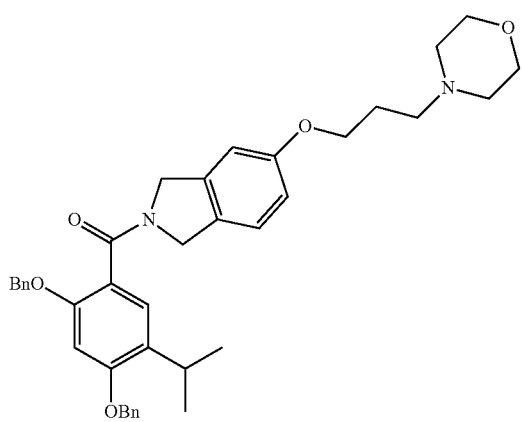 [SMILES: CC(C)c1cc(C(=O)N2Cc3ccc(OCCCN4CCOCC4)cc3C2)c(OCc2ccccc2)cc1OCc1ccccc1]

A mixture of (2,4-bis-benzyloxy-5-isopropyl-phenyl)-(5-hydroxy-1,3-dihydro-isoindol-2-yl)-methanone (100 mg, 0.2 mmol), 4-(3-chloropropyl)morpholine (82 mg, 0.5 mmol) and K$_2$CO$_3$ (104 mg, 0.75 mmol) in DMF (5 ml) was heated at 90° C. for 16 hours. The reaction mixture was diluted with EtOAc and filtered. The filtrate was reduced in vacuo and purified by flash column chromatography, eluting with 0-100% P.E./EtOAc then 0-10% MeOH/EtOAc to give the title compound as a colourless gel (90.1 mg). MS: [M+H]+ 621.

Preparation D3

Synthesis of (2,4-bis-benzyloxy-5-isopropyl-phenyl)-[5-(2-dimethylamino-ethoxy)-1,3-dihydro-isoindol-2-yl]-methanone

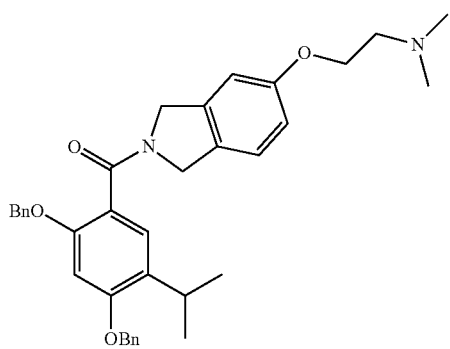 [SMILES: CC(C)c1cc(C(=O)N2Cc3ccc(OCCN(C)C)cc3C2)c(OCc2ccccc2)cc1OCc1ccccc1]

A mixture of (2,4-bis-benzyloxy-5-isopropyl-phenyl)-(5-hydroxy-1,3-dihydro-isoindol-2-yl)-methanone (100 mg, 0.2 mmol), 2-dimethylaminoethylchloride.HCl (72 mg, 0.5 mmol) and K$_2$CO$_3$ (173 mg, 1.25 mmol) in DMF (5 ml) was heated at 90° C. for 16 hours. Dilute reaction mixture with EtOAc and filtered. The reaction mixture was diluted with EtOAc and filtered. The filtrate was reduced in vacuo and purified by flash column chromatography, eluting 100% DCM then 90% DMAW 90 to give the title compound as an off white gel (79 mg). MS: [M+H]+ 565

Preparation D4

Synthesis of 2,4-bis-benzyloxy-5-isopropyl-benzoyl chloride

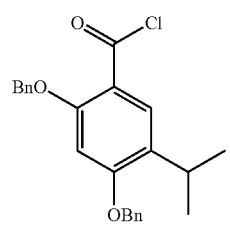

2,4-Bis-benzyloxy-5-isopropyl-benzoic acid (Preparation B10) (0.2 g, 0.53 mmol) was dissolved in DCM (10 ml) and treated with oxalyl chloride (1.5 g, 12 mmol) and a catalytic amount of DMF. The reaction mixture was stirred at room temperature for 14 hours and the solvent was then removed in vacuo. The crude material was dissolved in toluene and evaporated. Crude 2,4-bis-benzyloxy-5-isopropyl-benzoyl chloride was obtained as an oil (200 mg).

Preparation D5

Synthesis of (2,4-bis-benzyloxy-5-isopropyl-phenyl)-(5-morpholin-4-yl-1,3-dihydro-isoindol-2-yl)-methanone

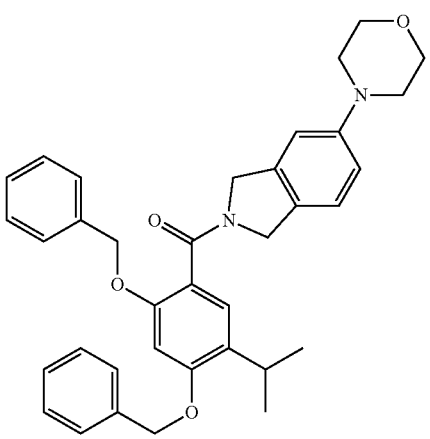 [SMILES: CC(C)c1cc(C(=O)N2Cc3ccc(N4CCOCC4)cc3C2)c(OCc2ccccc2)cc1OCc1ccccc1]

A solution of 2,4-bis-benzyloxy-5-isopropyl-benzoic acid (505 mg; 1.3 mmol) (Preparation B5), 5-nitroisoindoline, trifluoroacetate (360 mg; 1 equiv.), EDAC (300 mg; 1.2 equiv.), HOBt (210 mg; 1.2 equiv.) and NEt$_3$ (270 µA; 1.5 equiv.) in DMF (10 ml) was stirred at room temperature overnight then evaporated in vacuo. The residue was partitioned between EtOAc and 2M HCl, the EtOAc layer was separated, washed with saturated NaHCO$_3$, dried (MgSO$_4$) and evaporated. Purification by flash column chromatography (1:4 then 1:2 then 1:1 EtOAc/P.E. as eluant) gave 460 mg of (2,4-bis-benzyloxy-5-isopropyl-phenyl)-(5-nitro-1,3-dihydro-isoindol-2-yl)methanone. MS: [M+H]$^+$ 523.

A solution of (2,4-bis-benzyloxy-5-isopropyl-phenyl)-(5-nitro-1,3-dihydro-isoindol-2-yl)methanone (460 mg; 0.88 mmol) in ethanol (25 ml) was treated with tin (II) chloride dihydrate (1 g; 5 equiv.) then heated at reflux overnight then evaporated in vacuo. The residue was partitioned between EtOAc and saturated NaHCO$_3$, the EtOAc layer was separated, dried (MgSO$_4$) and evaporated to give 380 mg of (5-amino-1,3-dihydro-isoindol-2-yl)-(2,4-bis-benzyloxy-5-isopropyl-phenyl)-methanone.

A mixture of (5-amino-1,3-dihydro-isoindol-2-yl)-(2,4-bis-benzyloxy-5-isopropyl-phenyl)-methanone (100 mg; 0.2 mmol), bis(2-chloroethyl)ether (30 μl; 1.1 equiv.), Hunigs base (125 μl; 3.5 equiv.) and tetrabutylammonium iodide (10 mg) in NMP (1 ml) was heated in a CEM microwave synthesiser at 150° C. for 30 minutes. A further 30 μA of Hunigs base and 125 μl of bis(2-chloroethyl)ether were added and heating repeated for the same time. The reaction mixture was partitioned between EtOAc and saturated NH$_4$Cl solution, the EtOAc layer was separated, washed with more saturated NH$_4$Cl solution, then brine, dried (MgSO$_4$) and evaporated. Purification by flash column chromatography (1:2 then 1:1 then 2:1 EtOAc/P.E. as eluant) gave 60 mg of (2,4-bis-benzyloxy-5-isopropyl-phenyl)-(5-morpholin-4-yl-1,3-dihydro-isoindol-2-yl)-methanone. MS: [M−H]$^−$ 563.

Preparation D6

Synthesis of 2-(2,4-bis-benzyloxy-5-isopropyl-benzoyl)-2,3-dihydro-1H-isoindole-5-carboxylic acid

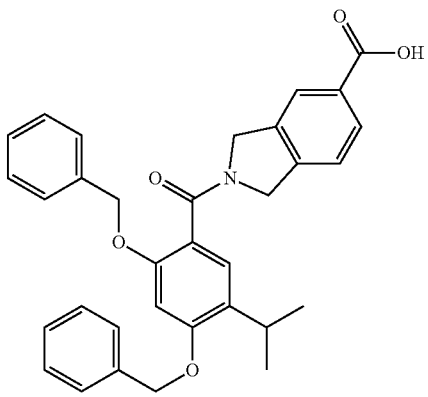 [SMILES: CC(C)c1cc(C(=O)N2Cc3ccc(C(=O)O)cc3C2)c(OCc2ccccc2)cc1OCc1ccccc1]

A solution of 2-(2,4-bis-benzyloxy-5-isopropyl-benzoyl)-2,3-dihydro-1H-isoindole-5-carboxylic acid methyl ester (390 mg) in methanol (10 ml) and 2M NaOH (10 ml) was heated at 50° C. for 48 hours then evaporated. The residue was acidified with 2M HCl, the solid collected by filtration, washed with water and sucked dry to give 255 mg of 2-(2,4-bis-benzyloxy-5-isopropyl-benzoyl)-2,3-dihydro-1H-isoindole-5-carboxylic acid as a white solid. [M+H]$^+$ 520.

EXAMPLES

By following the methods described above, the compounds set out in the Table below were prepared.

| Example Number | Compound | Chemical Name | Method | NMR Data | MS |
|---|---|---|---|---|---|
| 1 | | (5-Chloro-2-hydroxy-phenyl)-(1,3-dihydro-isoindol-2-yl)-methanone | A1. From 5-chloro-2-hydroxy-benzoic acid and isoindoline | $^1$H NMR (MeOH-d$_4$) 7.20-7.42 (6H, m), 6.92 (1H, d), 4.94 (2H, s), 4.74 (2H, s) | MS: [M + H]$^+$ 274 |
| 2 | | (3-tert-Butyl-4-hydroxy-phenyl)-(2,3-dihydro-indol-1-yl)-methanone | A2. From 3-tert-butyl-4-hydroxy-benzoic acid and indoline | $^1$H NMR (DMSO-d$_6$) 7.56 (2H, br m), 7.40 (1H, s), 7.33 (1H, d), 7.26 (1H, d), 7.13 (1H, t), 6.98 (1H, t), 6.85 (1H, d), 4.07 (2H, t), 3.08 (2H, t), 1.38 (9H, s) | MS: [M + H]$^+$ 296 |

-continued

| Example Number | Compound | Chemical Name | Method | NMR Data | MS |
|---|---|---|---|---|---|
| 3 | | (3-tert-Butyl-4-hydroxy-phenyl)-(3,4-dihydro-2H-quinolin-1-yl)-methanone | A2. From 3-tert-butyl-4-hydroxy-benzoic acid and 1,2,3,4-tetrahydro-quinoline | $^1$H NMR (DMSO-$d_6$) 11.05 (1H, br s), 8.17 (1H, d), 8.04 (2H, m), 7.88 (1H, d), 7.67 (1H, t), 7.54 (1H, t), 7.09 (1H, d), 3.39 (1H, m), 3.28 (1H, m), 1.40 (9H, s), 1.07 (3H, m), 0.84 (1H, m) | MS: [M + H]$^+$ 310 |
| 4 | | (3,4-Dihydro-1H-isoquinolin-2-yl)-(4-hydroxy-3-isopropyl-phenyl)-methanone | A2. From 3-isopropyl-4-hydroxy-benzoic acid and 1,2,3,4-tetrahydro-isoquinoline | $^1$H NMR (DMSO-$d_6$) 9.77 (1H, br s), 7.24 (1H, d), 7.17 (4H, s), 7.18 (1H, dd), 6.84 (1H, d), 4.68 (2H, s), 3.70 (2H, br s), 3.23 (1H, m), 2.87 (2H, m), 1.18 (6H, d) | MS: [M + H]$^+$ 296 |
| 5 | | (1,3-Dihydro-isoindol-2-yl)-(2,4-dihydroxy-5-isopropyl-phenyl)-methanone | A2 & A5. From 2,4-Bis-benzyloxy-5-isopropenyl-benzoic acid (B9) and isoindoline | $^1$H NMR (DMSO-$d_6$) 10.03 (1H, s), 9.63 (1H, s), 7.29 (4H, br m), 7.03 (1H, s), 6.40 (1H, s), 4.77 (4H, br s), 3.09 (1H, m), 1.14 (6H, d) | MS: [M + H]$^+$ 298 |
| 6 | | (3-tert-Butyl-4-hydroxy-phenyl)-(1,4-dioxa-8-aza-spiro[4.5]dec-8-yl)-methanone | A4. From 3-tert-butyl-4-hydroxy-benzoic acid and 4-piperidone ethylene ketal | $^1$H NMR (DMSO-$d_6$) 9.82 (1H, s), 7.22 (1H, s), 7.13 (1H, dd), 6.82 (1H, d), 3.91 (4H, s), 3.52 (4H, br m), 1.63 (4H, br m), 1.37 (9H, s) | MS: [M + H]$^+$ 320 |
| 7 | | (3-tert-Butyl-4-hydroxy-phenyl)-(1,3-dihydro-isoindol-2-yl)-methanone | A4. From 3-tert-butyl-4-hydroxy-benzoic acid and isoindoline | $^1$H NMR (DMSO-$d_6$) 9.82 (1H, s), 7.41 (1H, s), 7.38 (2H, dd), 7.29 (3H, br m), 6.82 (1H, d), 482 (4H, br m), 1.37 (9H, s) | MS: [M + H]$^+$ 296 |

-continued

| Example Number | Compound | Chemical Name | Method | NMR Data | MS |
|---|---|---|---|---|---|
| 8 | | (3-tert-Butyl-4-hydroxy-phenyl)-pyrrolo[3,2-b]pyridin-1-yl-methanone | A4. From 3-tert-butyl-4-hydroxy-benzoic acid and 1H-pyrrolo[3,2-b]pyridine | $^1$H NMR (DMSO-$d_6$) 8.57 (1H, dd), 8.43 (1H, d), 7.89 (1H, dd), 7.63 (1H, s), 7.56 (1H, dd), 7.35 (1H, m), 7.09 (1H, d), 6.84 (1H, dd), 1.37 (9H, s) | MS: [M + H]$^+$ 295 |
| 9 | | 8-(3-tert-Butyl-4-hydroxy-benzoyl)-2-methyl-2,8-diaza-spiro[4.5]decan-1-one | A4. From 3-tert-butyl-4-hydroxy-benzoic acid and 4-spiro-[3-(N-methyl-2-pyrrolidinone] piperidine hydrochloride | $^1$H NMR (DMSO-$d_6$) 9.82 (1H, s), 7.22 (1H, s), 7.13 (1H, dd), 6.82 (1H, d), 3.98 (2H, br m), 3.34 (2H, s), 3.13 (2H, m), 2.71 (3H, s), 1.92 (2H, t), 1.60 (2H, m), 1.43 (2H, m), 1.37 (9H, s) | MS: [M + H]$^+$ 345 |
| 10 | | (1,3-Dihydro-isoindol-2-yl)-(4-hydroxy-3-isopropyl-phenyl)-methanone | A4. From 3-isopropyl-4-hydroxy-benzoic acid and isoindoline | $^1$H NMR (DMSO-$d_6$) 9.82 (1H, s), 7.4 (2H, s), 7.38 (1H, dd), 7.30 (3H, m), 6.82 (1H, d), 4.82 (4H, dd), 3.23 (1H, m), 1.23 (6H, s) | MS: [M + H]$^+$ 282 |
| 11 | | (3-tert-Butyl-4-hydroxy-phenyl)-(3,4-dihydro-1H-isoquinolin-2-yl)-methanone | A4. From 3-tert-butyl-4-hydroxy-benzoic acid and 1,2,3,4-tetrahydro isoquinoline | $^1$H NMR (DMSO-$d_6$) 7.22 (1H, s), 7.13 (5H, m), 6.82 (1H, d), 4.70 (2H, s), 3.75 (2H, br s), 2.85 (2H, t), 1.37 (9H, s) | MS: [M + H]$^+$ 310 |
| 12 | | (1,3-Dihydro-isoindol-2-yl)-(5-ethyl-2,4-di-hydroxy-phenyl)-methanone | A2, A6 and A5. From 2,4-Bis-benzyloxy-5-bromo-benzoic acid, isoindoline and potassium vinyl trifluoroborate | $^1$H NMR (MeOH-$d_4$) 7.30 (4H, s), 7.15 (1H, s), 6.38 (1H, s), 4.91 (4H, s), 2.58 (2H, q), 1.18 (3H, t) | MS: [M + H]$^+$ 284 |

-continued

| Example Number | Compound | Chemical Name | Method | NMR Data | MS |
|---|---|---|---|---|---|
| 13 | | (5-Cyclopropyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and cyclopropane boronic acid | $^1$H NMR (DMSO-d$_6$) 7.40-7.23 (4H, m), 6.73 (1H, s), 6.40 (1H, s), 4.75 (4H, br s), 1.92 (1H, m), 0.78 (2H, m), 0.53 (2H, m) | MS: [M + H]$^+$ 296 |
| 14 | | (5-sec-Butyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and 2-buten-2-yl boronic acid | $^1$H NMR (MeOH-d$_4$) 7.30 (4H, s), 7.15 (1H, s), 6.39 (1H, s), 4.92 (4H, s), 3.00 (1H, q), 1.63 (2H, m), 1.18 (3H, t), 0.88 (3H, t) | MS: [M + H]$^+$ 312 |
| 15 | | (1,3-Dihydro-isoindol-2-yl)-(3-ethoxy-4-hydroxyphenyl)-methanone | Method A4. From 3-ethoxy-4-hydroxy-benzoic acid and isoindoline | $^1$H NMR (DMSO-d$_6$) 7.45 (1H, br s), 7.30 (3H, d), 7.18 (1H, d), 7.08 (1H, dd), 6.85 (1H, d), 4.85 (4H, s), 4.10 (2H, q), 1.38 (3H, t) | MS: [M + H]$^+$ 284 |
| 16 | | (1,3-Dihydro-isoindol-2-yl)-(2,4-dihydroxy-phenyl)-methanone | A2 and A5. From 2,4-Bis-benzyloxy-5-bromo-benzoic acid and isoindoline | $^1$H NMR (MeOH-d$_4$) 7.30 (5H, m), 7.15 (1H, s), 6.42 (1H, s), 6.38 (1H, s), 4.93 (4H, s) | MS: [M + H]$^+$ 256 |

Example 17

Synthesis of (5-chloro-1,3-dihydro-isoindol-2-yl)-(2,4-dihydroxy-5-isopropyl-phenyl)-methanone

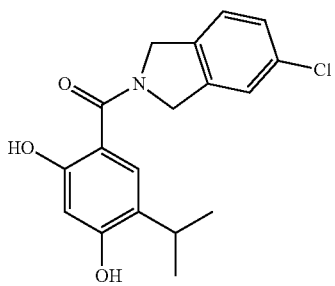 [SMILES: CC(C)c1cc(C(=O)N2Cc3ccc(Cl)cc3C2)c(O)cc1O]

A solution of 2,4-bis-benzyloxy-5-isopropyl-benzoic acid (Preparation B10) (0.451 g, 1.2 mmol), EDC (0.276 mg, 1.44 mmol), HOAt (0.196 mg, 1.44 mmol), triethylamine (0.5 ml, 3.6 mmol) and 5-chloro-2,3-dihydro-1H-isoindole (0.187 g, 1.2 mmol) (Preparation C3) in DMF (5 ml) was stirred at room temperature for 16 hours, then evaporated under vacuum. The crude material was dissolved in ethyl acetate and extracted twice with saturated $NaHCO_3$, organics washed with water three times, then evaporated under vacuum to give 0.5 g of 2,4-bis-benzyloxy-5-isopropyl-phenyl)-(5-chloro-1,3-dihydro-isoindol-2-yl)-methanone. MS: $[M+H]^+$ 512

Boron trichloride (1M in DCM) was added dropwise to a solution of 2,4-bis-benzyloxy-5-isopropyl-phenyl)-(5-chloro-1,3-dihydro-isoindol-2-yl)-methanone (0.5 g, 0.97 mmol) in dry DCM (10 ml) at 0° C. under nitrogen, then stirred for at 0° C. for 1 hour, warmed to room temperature and stirred for a further 3 hours. The reaction was quenched with ice, partitioned between DCM and water. The DCM layer was dried ($MgSO_4$), evaporated under vacuum, then purified by flash silica column chromatography eluting with 80% P.E.: EtOAc to give 0.1 g of (5-chloro-1,3-dihydro-isoindol-2-yl)-(2,4-dihydroxy-5-isopropyl-phenyl)-methanone as a white solid. MS: $[M+H]^+$ 332. $^1H$ NMR (DMSO-$d_6$) 10.0 (1H, s) 9.60 (1H, s), 7.45 (1H, br s), 7.33 (2H, br s), 7.0 (1H, s), 6.4 (1H, s), 4.80 (4H, br s), 3.10 (1H, m), 1.15 (6H, d).

Example 18

Synthesis of [5-(3-amino-propoxy)-1,3-dihydro-isoindol-2-yl]-(2,4-dihydroxy-5-isopropyl-phenyl)-methanone hydrochloride

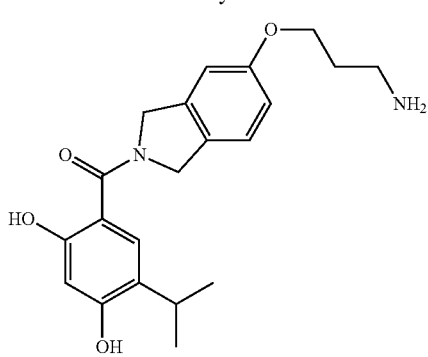

A solution of {3-[2-(2,4-dihydroxy-5-isopropyl-benzoyl)-2,3-dihydro-1H-isoindol-5-yloxy]-propyl}-carbamic acid tert-butyl ester (Example 46) (1 g) in EtOAc (10 ml) was treated with a saturated solution of HCl in EtOAC (20 ml) then stirred at room temperature for 2 hours, The reaction mixture was evaporated and re-evaporated with ethanol (×3). The title compound was isolated as a cream foam (840 mg). 1H NMR (DMSO-d6) 10.05 (1H, br s), 9.60 (1H, s), 7.88 (3H, br s), 7.30-7.18 (1H, m), 7.05 (1H, s), 7.00-6.85 (2H, m), 6.42 (1H, s), 4.75 (2H, br s) 4.70 (2H, br s), 4.05 (2H, t), 3.10 (1H, m), 3.00-2.95 (2H, m), 2.00 (2H, tt), 1.15 (6H, d). MS: $[M+H]^+$ 371.

Example 19

(5-Bromo-2,4-dihydroxy-phenyl)-(1,3-dihydro-isoindol-2-yl)-methanone

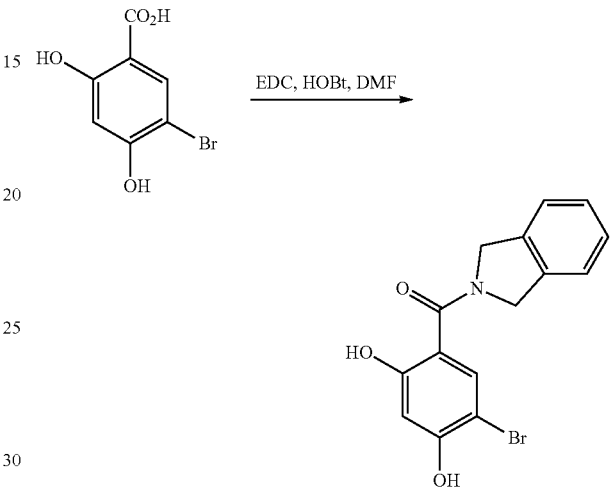

A solution of 5-bromo-2,4-dihydroxy-benzoic acid (520 mg, 2.33 mmol) in DMF (5 mL) was treated with 1-(3-dimethylaminopropyl)-3-ethylcarbodiimide hydrochloride (471 mg, 2.45 mmol) then HOBt (362 mg, 2.68 mmol). After 25 min, 2,3-dihydro-1H-isoindole (0.5 mL, 2.63 mmol) was added then the mixture was stirred at r.t. for 18 h. The solvent was removed in vacuo then the residue was taken up in ethyl acetate and washed with 1N hydrochloric acid, saturated sodium bicarbonate solution and brine then dried ($MgSO_4$) and concentrated. The residue was triturated with methanol to afford the title compound as a grey solid (328 mg, 44%). $^1H$ NMR (DMSO-$d_6$) 10.45 (1H, s), 10.32 (1H, s), 7.36 (1H, br.s), 7.35 (1H, s), 7.28 (3H, br.s), 6.59 (1H, s), 4.77 (2H, br.s), 4.71 (2H, br.s). MS: $[M+H]^+$332/334.

Example 20

(1,3-Dihydro-isoindol-2-yl)-(2,4-dihydroxy-5-trifluoromethyl-phenyl)-methanone 20A. (2,4-Bis-benzyloxy-5-bromo-phenyl)-(1,3-dihydro-isoindol-2-yl)-methanone

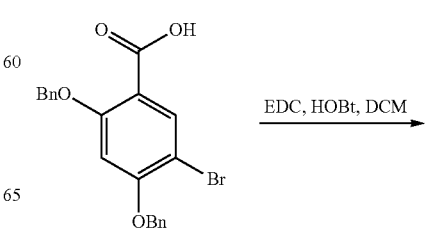

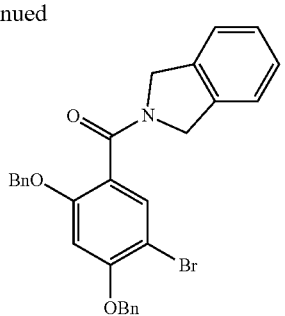

According to general method A2,2,4-bis-benzyloxy-5-bromo-benzoic acid (1.02 g, 2.47 mmol) gave a residue which was purified by flash chromatography on silica (ethyl acetate/petrol gradient, 0-20%) to afford the title compound as a white crystalline solid (501 mg, 39%). $^1$H NMR (methanol-$d_4$) 7.52 (1H, s), 7.49-7.46 (2H, m), 7.42-7.37 (2H, m), 7.34 (t, 2H), 7.30-7.24 (4H, m), 7.23-7.20 (3H, m), 7.16 (1H, d), 6.94 (1H, s), 5.24 (2H, s), 5.16 (2H, s), 4.86 (2H, s), 4.60 (2H, s). MS: [M+H]$^+$ 514/516.

20B. (2,4-Bis-benzyloxy-5-trifluoromethyl-phenyl)-(1,3-dihydro-isoindol-2-yl)-methanone

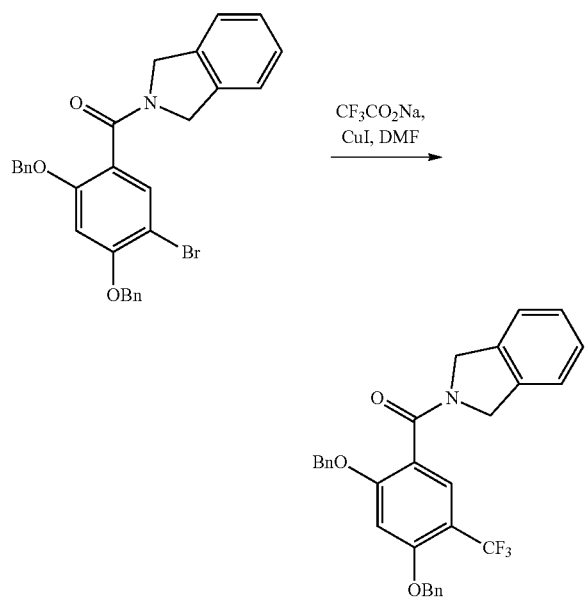

A mixture of (2,4-bis-benzyloxy-5-bromo-phenyl)-(1,3-dihydro-isoindol-2-yl)-methanone (491 mg, 0.95 mmol), sodium trifluoroacetate (649 mg, 4.8 mmol) and copper (I) iodide (364 mg, 1.91 mmol) were dried under vacuum (0.04 mbar) for 6 hours. The flask was flushed with nitrogen, DMF (5 mL) was added and the mixture heated at 150° C. for 17 hours. After cooling to r.t., the mixture was diluted with DCM (100 mL) and filtered through Celite, rinsing with DCM. The filtrate was concentrated to dryness and the residue was partially purified by flash chromatography on silica (ethyl acetate/petrol gradient, 0-20%). The purest fraction was recrystallised from methanol to afford the title compound as a white solid (140 mg, 29%). $^1$H NMR (methanol-$d_4$) 7.60 (1H, s), 7.48-7.44 (2H, m), 7.40 (2H, t), 7.37-7.21 (m, 9H), 7.17 (1H, d), 7.02 (1H, s), 5.29 (2H, s), 5.24 (2H, s), 4.88 (2H, s), 4.62 (2H, s). MS: [M+H]$^+$ 504.

20C. (1,3-Dihydro-isoindol-2-yl)-(2,4-dihydroxy-5-trifluoromethyl-phenyl)-methanone

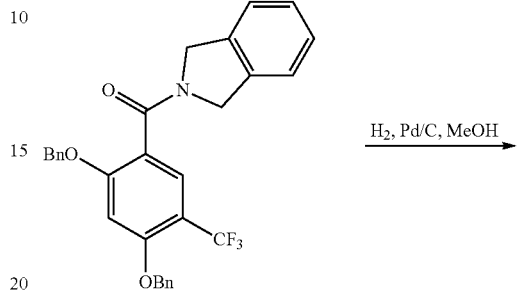

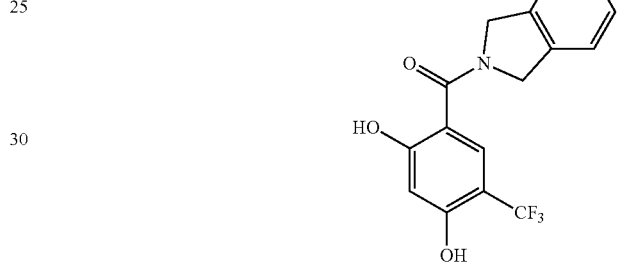

A solution of (2,4-bis-benzyloxy-5-trifluoromethyl-phenyl)-(1,3-dihydro-isoindol-2-yl)-methanone (140 mg, 0.28 mmol) in methanol (5 mL) was hydrogenated at atmospheric pressure over 10% palladium on charcoal (34 mg) for 4 hours. A further portion of catalyst was added (31 mg) and hydrogenation continued for a further 1.5 hours. The mixture was filtered through Celite, eluting with methanol, then the filtrate was concentrated in vacuo to afford the title compound as a white solid (91 mg, quant.). $^1$H NMR (DMSO-$d_6$) 10.79 (1H, s), 10.70 (1H, s), 7.40-7.35 (2H, m), 7.31-7.35 (3H, m), 6.61 (1H, s), 4.79 (2H, br.s), 4.68 (2H, br.s). MS: [M+H]$^+$ 324.

Example 21

(2,4-Dihydroxy-5-isopropyl-phenyl)-{4-[2-(2-methoxy-ethoxy)-ethoxy]-1,3-dihydro-isoindol-2-yl}methanone

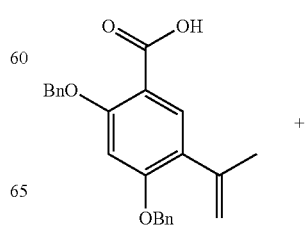

-continued

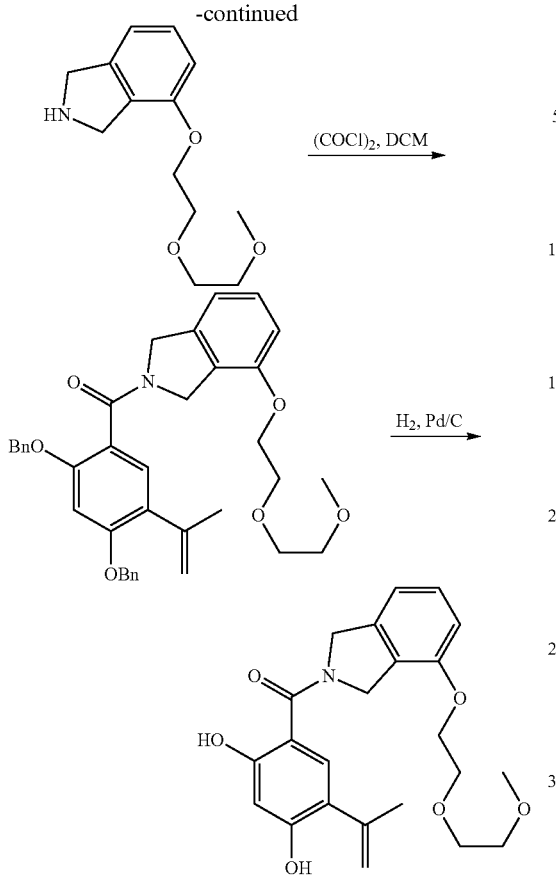

A solution of 2,4-bis-benzyloxy-5-isopropenyl-benzoic acid (96 mg, 0.26 mmol) and DMF (1 drop, cat.) in DCM (3 mL) was cooled in ice then treated with oxalyl chloride (112 µL, 1.28 mmol). After 2 hours the mixture was concentrated in vacuo then azeotroped with toluene. The resulting acid chloride was dissolved in DCM (4 mL) and added to a solution of 4-[2-(2-methoxy-ethoxy)-ethoxy]-2,3-dihydro-1H-isoindole (0.26 mmol, assuming a quantitative yield from the preceding step (debenzylation procedure C16)) and triethylamine (0.20 mL, 1.4 mmol) in DCM (1 mL). After 2 hours the mixture was diluted with ethyl acetate and washed with 1N hydrochloric acid, brine, sodium bicarbonate solution and brine. The organic phase was dried (MgSO$_4$) and concentrated to give a black residue. This was partially purified by flash chromatography on silica (ethyl acetate/petrol gradient, 20-33%) to afford an impure sample of the intermediate (2,4-bis-benzyloxy-5-isopropenyl-phenyl)-{4-[2-(2-methoxy-ethoxy)-ethoxy]-1,3-dihydro-isoindol-2-yl}-methanone.

A solution of (2,4-bis-benzyloxy-5-isopropenyl-phenyl)-{4-[2-(2-methoxy-ethoxy)-ethoxy]-1,3-dihydro-isoindol-2-yl}-methanone in methanol (5 mL) was hydrogenated at atmospheric pressure over 10% palladium on charcoal (12 mg) for 3 hours. A further portion of catalyst (12 mg) was added and hydrogenation continued for a further 7 hours. The mixture was filtered through Celite, eluting with methanol, then the filtrate was concentrated in vacuo to give a residue which was purified by preparative HPLC (basic method). This afforded the title compound as a white solid (17 mg, 16% over two steps). $^1$H NMR (methanol-d$_4$) 7.25 (1H, t), 7.17 (1H, s), 6.95-6.82 (2H, m), 6.37 (1H, s), 4.89 (2H, br.s), 4.83 (overlaps with H$_2$O, br.s), 4.16 (2H, br.s), 3.82 (2H, br.s), 3.66 (2H, br.s), 3.52 (2H, br.s), 3.39-3.28 (overlaps with MeOH, m), 3.20 (1H, sept), 1.21 (6H, d). MS: [M+H]$^+$ 416.

Example 22

(2,4-Dihydroxy-5-isopropyl-phenyl)-[4-(2-dimethylamino-ethoxy)-1,3-dihydro-isoindol-2-yl]-methanone

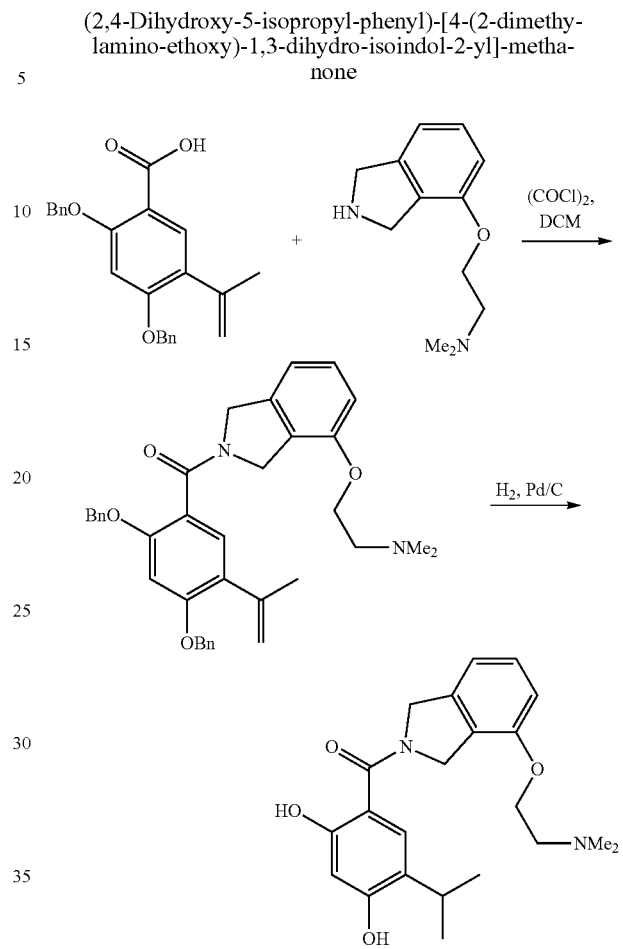

A solution of 2,4-bis-benzyloxy-5-isopropenyl-benzoic acid (189 mg, 0.50 mmol) and DMF (1 drop, cat.) in DCM (5 mL) was cooled in ice then treated with oxalyl chloride (112 µL, 1.28 mmol). After 2 hours the mixture was concentrated in vacuo then azeotroped with toluene. The resulting acid chloride was dissolved in DCM (5 mL) and added to a solution of [2-(2,3-dihydro-1H-isoindol-4-yloxy)-ethyl]-dimethyl-amine (0.48 mmol, assuming a quantitative yield from the preceding step (C17)) and triethylamine (0.50 mL, 3.6 mmol) in DCM (3 mL). After 16 hours the mixture was diluted with ethyl acetate and washed with saturated potassium carbonate solution and brine. The organic phase was dried (MgSO$_4$) and concentrated to give a residue which was partially purified by flash chromatography on silica (methanol/DCM gradient, 5-10% followed by 10% 2M methanolic ammonia/DCM) to afford an impure sample of the intermediate (2,4-bis-benzyloxy-5-isopropenyl-phenyl)-[4-(2-dimethylamino-ethoxy)-1,3-dihydro-isoindol-2-yl]-methanone.

A solution of (2,4-bis-benzyloxy-5-isopropenyl-phenyl)-[4-(2-dimethylamino-ethoxy)-1,3-dihydro-isoindol-2-yl]-methanone in methanol (5 mL) was hydrogenated at atmospheric pressure over 10% palladium on charcoal (40 mg) for 22 hours. The mixture was filtered through Celite, eluting with methanol, then the filtrate was concentrated in vacuo to give a residue which was purified by preparative HPLC (acidic method). This afforded the formate salt of the title compound as a white solid (9 mg, 5% over two steps). $^1$H NMR (methanol-d$_4$) 8.52 (0.7H, s), 7.29 (1H, t), 7.17 (1H, s), 6.98-6.86 (2H, m including 6.90 (1H, d)), 6.37 (1H, s), 4.89 (2H, br.s), 4.87 (2H, br.s), 4.28 (2H, br.s), 3.29-3.5 (3H, m including 3.20 (1H, sept)), 2.81-2.51 (6H, br.d), 1.21 (6H, d). MS: [M+H]$^+$ 385.

Example 23

(2,4-Dihydroxy-5-isopropyl-phenyl)-[4-(3-morpholin-4-yl-propoxy)-1,3-dihydro-isoindol-2-yl]methanone

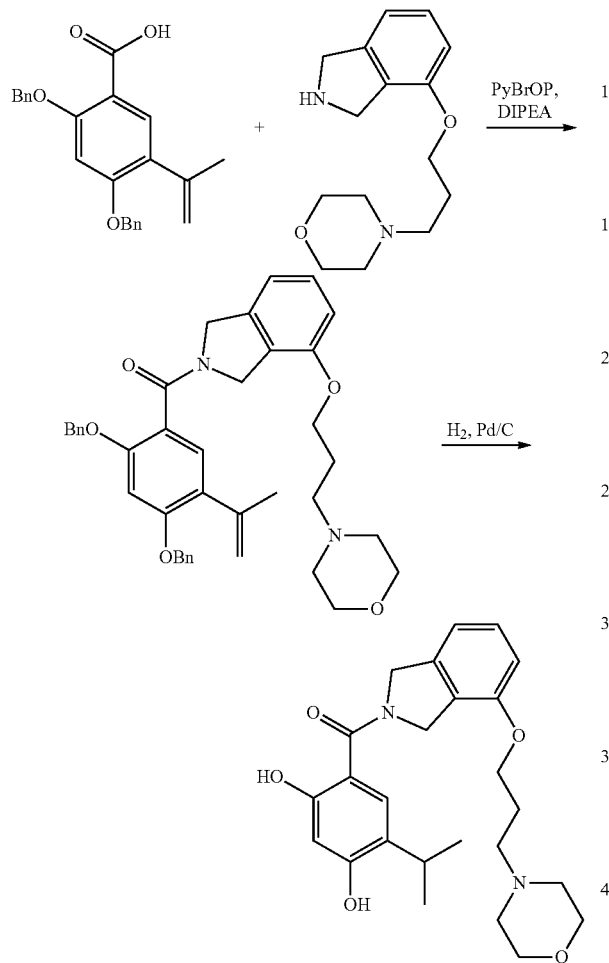

A solution of 2,4-bis-benzyloxy-5-isopropenyl-benzoic acid (210 mg, 0.56 mmol) and diisopropylethylamine (0.25 mL, 1.4 mmol) in DCM (5 mL) was treated with bromo-tris-pyrrolidino-phosphonium hexafluorophosphate (PyBrOP) (287 mg, 0.62 mmol). After 1 hour a solution of 4-(3-morpholin-4-yl-propoxy)-2,3-dihydro-1H-isoindole (0.56 mmol, assuming a quantitative yield from the preceding step (C18)) in DCM (5 mL) was added. After 4 hours the mixture was diluted with ethyl acetate and washed with water, 1N sodium hydroxide solution and brine. The organic phase was dried (MgSO$_4$) and concentrated to give a residue which was absorbed onto an SCX column. This was washed with 10% methanol/DCM then the product was eluted with 25% 2M methanolic ammonia/DCM) to afford an impure sample of the intermediate (2,4-bis-benzyloxy-5-isopropenyl-phenyl)-[4-(3-morpholin-4-yl-propoxy)-1,3-dihydro-isoindol-2-yl]-methanone.

A solution of (2,4-bis-benzyloxy-5-isopropenyl-phenyl)-[4-(3-morpholin-4-yl-propoxy)-1,3-dihydro-isoindol-2-yl]-methanone in methanol (5 mL) was hydrogenated at atmospheric pressure over 10% palladium on charcoal (45 mg) for 4 hours. The mixture was filtered through Celite, eluting with methanol, then the filtrate was concentrated in vacuo to give a residue which was purified by preparative HPLC (basic method). This afforded the title compound as a white solid (16 mg, 6% over two steps). $^1$H NMR (methanol-d$_4$) 7.24 (1H, t), 7.18 (1H, s), 6.89 (1H, d), 6.84 (1H, d), 6.37 (1H, s), 4.87 (2H, br.s), 4.78 (2H, br.s), 4.11-4.04 (2H, m), 3.72-3.66 (4H, m), 3.21 (1H, sept), 2.60-2.42 (6H, m), 2.05-1.92 (2H, m), 1.21 (6H, d). MS: [M+H]$^+$ 441.

Examples 24 to 47

By following the methods described above, the compounds of Examples 24 to 47 were prepared.

| Example Number | Compound | Chemical Name | Method | N.M.R. Data | M.S. |
|---|---|---|---|---|---|
| 24 | | (3-sec-Butyl-4-hydroxy-phenyl)-(1,3-dihydro-isoindol-2-yl)-methanone | A2 and A5. From (Z)-4-benzyloxy-3-(1-methyl-propenyl)-benzoic acid and isoindoline | $^1$H NMR (DMSO-d$_6$) 9.73 (1H, br s), 7.37 (1H, d), 7.32 (1H, dd), 7.30 (4H, br s), 6.86 (1H, d), 4.87 (2H, s), 4.82 (2H, s), 3.03 (1H, m), 1.63 (1H, m), 1.57 (1H, m), 1.19 (3H, d), 0.82 (3H, t) | MS: [M + H]$^+$ 296 |

-continued

| Example Number | Compound | Chemical Name | Method | N.M.R. Data | M.S. |
|---|---|---|---|---|---|
| 25 | 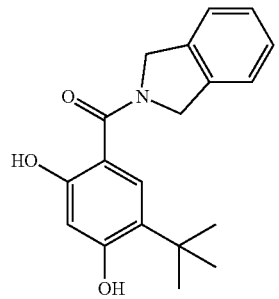 [SMILES: CC(C)(C)c1cc(C(=O)N2Cc3ccccc3C2)c(O)cc1O] | (5-tert-Butyl-2,4-dihydroxy-phenyl)-(1,3-dihydro-isoindol-2-yl)-methanone | A2 and A5. From 2,4-bis-benzyloxy-5-tert-butyl-benzoic acid and isoindoline | $^1$H NMR (DMSO-d$_6$) 7.34 (2H, m), 7.29 (2H, m), 7.10 (1H, s), 6.33 (1H, s), 4.83 (4H, s), 1.35 (9H, s) | MS: [M + H]$^+$ 312 |
| 26 | 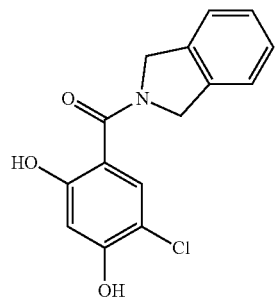 [SMILES: O=C(c1cc(Cl)c(O)cc1O)N1Cc2ccccc2C1] | (5-Chloro-2,4-dihydroxy-phenyl)-(1,3-dihydro-isoindol-2-yl)-methanone | A2 and A3. From 2,4-bis-benzyloxy-5-chloro-benzoic acid and isoindoline | $^1$H NMR (DMSO-d$_6$) 10.42 (1H, s), 10.33 (1H, s), 7.38 (2H, m), 7.30 (2H, m), 7.24 (1H, s), 6.60 (1H, s), 4.78 (2H, br s), 4.72 (2H, br s) | MS: [M + H]$^+$ 290 |
| 27 | 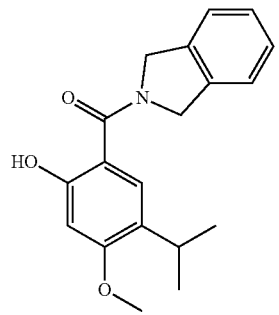 [SMILES: COc1cc(O)c(C(=O)N2Cc3ccccc3C2)cc1C(C)C] | (1,3-Dihydro-isoindol-2-yl)-(2-hydroxy-5-isopropyl-4-methoxy-phenyl)-methanone | A2, A5 & A7. From 2,4-bis-benzyloxy-5-isopropenyl-benzoic acid and isoindoline | H NMR (DMSO-d$_6$) 10.21 (1H, br s), 7.33 (2H, br s), 7.28 (2H, br s), 7.13 (1H, s), 6.50 (1H, s), 4.80 (4H, br s), 3.79 (3H, s), 3.15 (1H, m), 1.14 (6H, d) | MS: [M + H]$^+$ 312 |
| 28 | 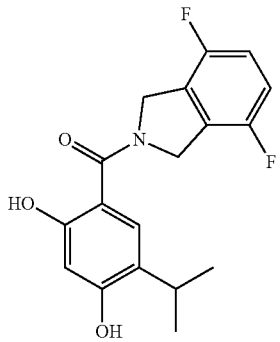 [SMILES: CC(C)c1cc(C(=O)N2Cc3c(F)ccc(F)c3C2)c(O)cc1O] | (4,7-difluoro-1,3-dihydro-isoindol-2-yl)-(2,4-dihydroxy-5-isopropyl-phenyl)-methanone | A2 and A5. From 2,4-bis-benzyloxy-5-isopropenyl-benzoic acid and 4,7-difluoro-isoindoline | H NMR (DMSO-d$_6$) 9.97 (1H, br s), 9.66 (1H, br s), 7.22 (2H, dd), 7.03 (1H, s), 6.42 (1H, s), 4.84 (4H, br s), 3.10 (1H, m), 1.13 (6H, d) | MS: [M + H]$^+$ 334 |

-continued

| Example Number | Compound | Chemical Name | Method | N.M.R. Data | M.S. |
|---|---|---|---|---|---|
| 29 | (structure) | (2,4-dihydroxy-5-isopropyl-phenyl)-(5-fluoro-1,3-dihydro-isoindol-2-yl)-methanone | A2 and A5. From 2,4-bis-benzyloxy-5-isopropenyl-benzoic acid and 5-fluoro-isoindoline [Ref. U.S. Pat. No. 5,026,856] | H NMR (DMSO-$d_6$) 10.02 (1H, br s), 9.58 (1H, s), 7.37 (1H, br m), 7.20 (1H, br m), 7.12 (1H, td), 7.04 (1H, s), 6.41 (1H, s), 4.78 (2H, br s), 4.75 (2H, br s), 3.11 (1H, m), 1.16 (6H, d) | MS: [M + H]$^+$ 316 |
| 30 | (structure) | (1,3-dihydro-isoindol-2-yl)-(3-fluoro-2,4-dihydroxy-5-isopropyl-phenyl)-methanone | A8. From (1,3-dihydro-isoindol-2-yl)-(2,4-dihydroxy-5-isopropyl-phenyl)-methanone | H NMR (DMSO-$d_6$) 12.23 (1H, br s), 7.39 (1H, m), 7.35-7.25 (3H, m), 6.84 (1H, d), 5.53 (1H, s), 4.74 (2H, s), 4.59 (2H, s), 2.52 (1H, m), 1.11 (3H, d), 0.84 (3H, d); $^{19}$F NMR (DMSO-d6) 19.3 | MS: [M + H]$^+$ 316 |
| 31 | (structure) | (1,3-dihydro-isoindol-2-yl)-(2-fluoro-4,6-dihydroxy-3-isopropyl-phenyl)-methanone | A8. From (1,3-dihydro-isoindol-2-yl)-(2,4-dihydroxy-5-isopropyl-phenyl)-methanone | H NMR (DMSO-$d_6$) 12.03 (1H, br s), 7.40-7.35 (2H, m), 7.33-7.28 (2H, m), 6.53 (1H, br d), 5.53 (1H, s), 5.07 (1H, br d), 4.98 (1H, br d), 4.79 (2H, s), 2.90 (1H, m), 1.03 (6H, m); $^{19}$F NMR (DMSO-$d_6$) 24.9 | MS: [M + H]$^+$ 316 |
| 32 | (structure) | (2,4-dihydroxy-5-isopropyl-phenyl)-(4-fluoro-1,3-dihydro-isoindol-2-yl)-methanone hydroxychloride | From 2,4-bis-benzyloxy-5-isopropyl-benzoic acid (B10) and 4-fluoro-2,3-dihydro-1H-isoindole | H NMR (DMSO-$d_6$) 7.35 (2H, m), 7.20 (1H, m), 7.1 (1H, t), 7.0 (1H, s), 6.4 (1H, s), 4.80 (4H, br s), 1.20 (6H, s) | MS: [M + H]$^+$ 316 |

-continued

| Example Number | Compound | Chemical Name | Method | N.M.R. Data | M.S. |
|---|---|---|---|---|---|
| 33 | (structure) | (5-chloro-6-methoxy-1,3-dihydro-iso-indol-2-yl)-(2,4-dihydroxy-5-isopropyl-phenyl)-methanone | A2 and A5. From 2,4-bis-benzyloxy-5-isopropyl-benzoic acid (B10) and 5-chloro-6-methoxy-2,3-dihydro-1H-isoindole | $^1$H NMR (Me-d$_3$-OD) 7.32 (1H, s), 7.17 (1H, s), 7.05 (1H, s), 6.37 (1H, s), 4.89 (2H, s), 3.89 (3H, s), 3.36 (3H, m), 1.23 (6H, d) | MS: [M + H]$^+$ 362 |
| 34 | (structure) | (2,4-dihydroxy-5-isopropyl-phenyl)-[5-(2-methoxy-ethoxy)-1,3-dihydro-isoindol-2-yl]-methanone | A5. From (2,4-bis-benzyloxy-5-isopropyl-phenyl)-[5-(2-methoxy-ethoxy)-1,3-dihydro-isoindol-2-yl]-methanone | H NMR (DMSO-d$_6$) 10.02 (1H, s), 9.60 (1H, s), 7.22 (1H, br s), 7.03 (1H, s), 690 (1H, br s), 6.85 (1H, d), 6.4 (1H, s), 4.74 (4H, br d), 4.08 (2H, br s), 3.65 (2H, t), 3.18-3.03 (1H, m), 1.15 (6H, s), 3.30 (3H, s) | MS: [M + H]$^+$ 372 |
| 35 | (structure) | (2,4-dihydroxy-5-isopropyl-phenyl)-[5-(3-morpholin-4-yl-propoxy)-1,3-dihydro-isoindol-2-yl]-methanone | A5. From (2,4-bis-benzyloxy-5-isopropyl-phenyl)-[5-(3-morpholin-4-yl-propoxy)-1,3-dihydro-isoindol-2-yl]-methanone | H NMR (DMSO-d$_6$) 10.02 (1H, s), 9.60 (1H, s), 7.22 (1H, br s), 7.03 (1H, s), 6.90 (1H, br s), 6.85 (1H, d), 6.4 (1H, s), 4.74 (4H, br d), 4.08 (2H, br s), 3.55 (4H, br s) 3.18-3.03 (1H, m), 2.40 (2H, s), 2.38 (4H, br s), 1.85 (2H, t), 1.15 (6H, s) | MS: [M + H]$^+$ 441 |
| 36 | (structure) | (2,4-dihydroxy-5-isopropyl-phenyl)-[5-(2-dimethylamino-ethoxy)-1,3-dihydro-isoindol-2-yl]-methanone | A5. From (2,4-bis-benzyloxy-5-isopropyl-phenyl)-[5-(2-dimethylamino-ethoxy)-1,3-dihydro-isoindol-2-yl]-methanone | H NMR (DMSO-d$_6$) 10.02 (1H, s), 9.60 (1H, s), 7.22 (1H, br s), 7.03 (1H, s), 6.90 (1H, br s), 6.85 (1H, d), 6.40 (1H, s), 4.74 (4H, br d), 4.08 (2H, br s), 3.18-3.03 (1H, m), 2.71 (2H, br s), 2.30 (6H, s), 1.15 (6H, s) | MS: [M + H]$^+$ 385 |

-continued

| Example Number | Compound | Chemical Name | Method | N.M.R. Data | M.S. |
|---|---|---|---|---|---|
| 37 | | (2,4-dihydroxy-5-isopropyl-phenyl)-(2-oxa-5-aza-bicyclo[2.2.1]hept-5-yl)-methanone | A2 and A5. From (2,4-bis-benzyloxy-5-isopropenyl-benzoic acid (Preparation B5) and 2-oxa-5-aza-bicyclo[2.2.1]-heptane | H NMR (DMSO-d$_6$) 9.64 (1H, s), 7.02 (1H, s), 6.31 (1H, s), 4.65 (2H, s), 3.78 (2H, dd), 3.31 (2H, s), 3.07 (1H, m), 1.77 (1H, m), 1.10 (6H, m) | MS: [M + H]$^+$ 278 |
| 38 | | (3,4-dihydro-1H-isoquinolin-2-yl)-(2,4-dihydroxy-5-isopropyl-phenyl)-methanone | A2 and A5. From (2,4-bis-benzyloxy-5-isopropenyl-benzoic acid (Preparation B5) and 1,2,3,4-tetrahydro-isoquinoline | $^1$H NMR (Me-d$_3$-OD) 7.19 (1H, s), 7.14-7.09 (1H, br s), 7.02 (1H, s), 6.37 (1H, s), 4.75 (2H, s), 3.80 (2H, t,), 3.24-3.15 (1H, m), 2.95 (2H, t), 1.19 (6H, d) | MS: [M + H]$^+$ 312 |
| 39 | | (5-amino-1,3-dihydro-isoindol-2-yl)-(2,4-dihydroxy-5-isopropyl-phenyl)-methanone | A2 & A5. From 2,4-bis-benzyloxy-5-isopropenyl-benzoic acid (Preparation B5) and 5-nitro-isoindoline. TFA (C5 but omitting hydrogenation step) | H NMR (DMSO-d$_6$) 7.05 (1H, s), 6.95-6.85 (1H, m), 6.60-6.50 (2H, m), 6.25 (1H, s), 4.6-4.5 (4H, m), 3.10 (1H, h), 1.10 (6H, d) | MS: [M + H]+ 313 |
| 40 | | (2,4-dihydroxy-5-isopropyl-phenyl)-(5-methoxy-1,3-dihydro-isoindol-2-yl)-methanone | A2 and A5. From 2,4-bis-benzyloxy-5-isopropenyl-benzoic acid (Preparation B5) and 5-methoxy-isoindoline. | H NMR (DMSO-d$_6$) 10.05 (1H, s), 9.60 (1H, s), 7.30-7.15 (1H, m), 7.05 (1H, s), 7.00-6.85 (1H, m), 6.82 (1H, d), 6.40 (1H, s), 4.75 (2H, s), 4.70 (2H, s), 3.75 (3H, s), 3.10 (1H, m), 1.13 (6H, d) | MS: [M + H]+ 328 |

-continued

| Example Number | Compound | Chemical Name | Method | N.M.R. Data | M.S. |
|---|---|---|---|---|---|
| 41 | 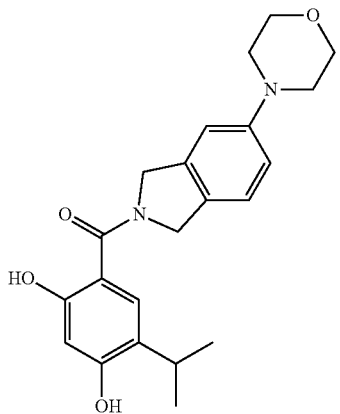 [SMILES: CC(C)c1cc(C(=O)N2Cc3ccc(N4CCOCC4)cc3C2)c(O)cc1O] | (2,4-dihydroxy-5-isopropyl-phenyl)-(5-morpholin-4-yl-1,3-dihydro-isoindol-2-yl)-methanone | A5 from (2,4-bis-benzyloxy-5-isopropyl-phenyl)-(5-morpholin-4-yl-1,3-dihydro-isoindol-2-yl)-methanone (D5). | H NMR (DMSO-d$_6$) 9.60 (1H, br s), 7.30-7.15 (1H, m), 7.05 (1H, s), 7.00-6.90 (2H, m), 6.40 (1H, s), 4.75 (2H, s) 4.70 (2H, s), 3.75 (4H, m), 3.15-3.05 (5H, m), 1.15 (6H, d) | MS: [M + H]$^+$ 383 |
| 42 | 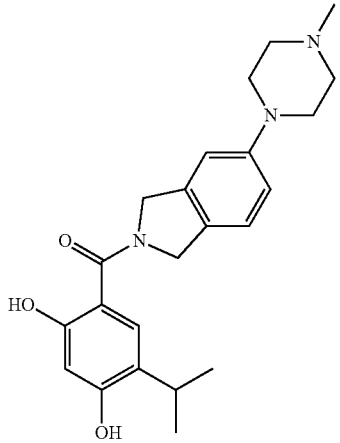 [SMILES: CC(C)c1cc(C(=O)N2Cc3ccc(N4CCN(C)CC4)cc3C2)c(O)cc1O] | (2,4-dihydroxy-5-isopropyl-phenyl)-[5-(4-methyl-piperazin-1-yl)-1,3-dihydro-isoindol-2-yl]-methanone | As for Example 41 but using bis (2-chloroethyl)-methylamine hydroxychloride in step 2. | H NMR (DMSO-d$_6$) 7.30-7.15 (1H, m), 7.05 (1H, s), 6.95-6.85 (2H, m), 6.40 (1H, s), 4.70 (2H, br s) 4.65 (2H, br s), 3.15-3.05 (5H, m), 2.45 (4H, m), 2.20 (4H, s), 1.85 (3H, s), 1.15 (6H, d) | MS: [M + H]$^+$ 396 |
| 43 | 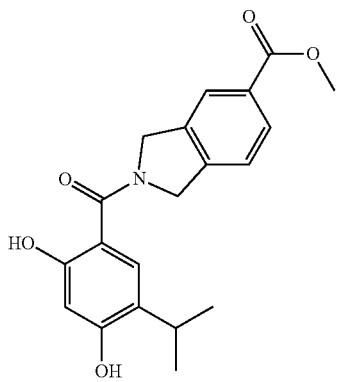 [SMILES: COC(=O)c1ccc2c(c1)CN(C(=O)c1cc(C(C)C)c(O)cc1O)C2] | 2-(2,4-dihydroxy-5-isopropyl-benzoyl)-2,3-dihydro-1H-isoindole-5-carboxylic acid methyl ester | A2 and A.5. From 2,4-bis-benzyloxy-5-isopropenyl-benzoic acid (Preparation B5) and 2,3-dihydro-1H-isoindole-5-carboxylic acid methyl ester. TFA (Preparation C21) | H NMR (DMSO-d$_6$) 10.05 (1H, br s), 9.60 (1H, s), 8.00-7.92 (1H, m), 7.90 (1H, s), 7.55-7.42 (1H, m), 7.05 (1H, d), 6.40 (1H, s), 4.85 (4H, br s) 3.85 (3H, s), 3.10 (1H, m), 1.13 (6H, d) | MS: [M + H]$^+$ 356 |

-continued

| Example Number | Compound | Chemical Name | Method | N.M.R. Data | M.S. |
|---|---|---|---|---|---|
| 44 | | 2-(2,4-dihydroxy-5-isopropyl-benzoyl)-2,3-dihydro-1H-isoindole-5-carboxylic acid | A5, from 2-(2,4-bis-benzyloxy-5-isopropyl-benzoyl)-2,3-dihydro-1H-isoindole-5-carboxylic acid. | H NMR (DMSO-$d_6$) 12.90 (1H, br s), 10.05 (1H, br s), 9.60 (1H, s), 8.00-7.92 (1H, m), 7.90 (1H, d), 7.55-7.40 (1H, m), 7.05 (1H, d), 6.45 (1H, s), 4.85 (4H, br s), 3.10 (1H, m), 1.15 (6H, d) | MS: [M + H]$^+$ 342 |
| 45 | | (2,4-dihydroxy-5-isopropyl-phenyl)-(5-morpholin-4-ylmethyl-1,3-dihydro-isoindol-2-yl)-methanone hydrochloride | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). | H NMR (DMSO-$d_6$) 11.03 (1H, br s), 10.05 (1H, br s), 9.78 (1H, br s), 7.60-7.38 (3H, m), 7.05 (1H, s), 6.45 (1H, s), 4.80 (4H, m), 4.33 (2H, d), 3.95-3.85 (2H, m), 3.32-3.22 (2H, m), 3.28-3.00 (5H, m), 1.15 (6H, d) | MS: [M + H]$^+$ 397 |
| 46 | | {3-[2-(2,4-dihydroxy-5-isopropyl-benzoyl)-2,3-dihydro-1H-isoindol-5-yloxy]-propyl}-carabamic acid tert-butyl ester | As for Example 34, A2 (from benzyloxy-5-isopropyl-benzoic acid (Preparation B5) and 5-hydroxy-isoindoline), alkylation using 3-(BOS-amino)propyl bromide, then A5. | H NMR (DMSO-$d_6$) 10.05 (1H, br s), 9.60 (1H, s), 7.30-7.15 (1H, m), 7.05 (1H, s), 6.98-6.80 (3H, m), 6.40 (1H, s), 4.75 (2H, br s), 4.70 (2H, br s), 3.95 (2H, s), 3.15-3.05 (3H, m), 1.80 (2H, tt), 1.37 (9H, s), 1.15 (6H, d) | MS: [M + H]$^+$ 471 |
| 47 | | (2,4-dihydroxy-5-isopropyl-phenyl)-(5-methyl-1,3-dihydro-isoindol-2-yl)-methanone | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). Biproduct from Example 45. | H NMR (DMSO-$d_6$) 10.05 (1H, s), 9.60 (1H, s), 7.25-7.08 (3H, m), 7.05 (1H, s), 6.40 (1H, s), 4.75 (4H, m), 3.10 (1H, m), 2.30 (1H, s), 1.15 (6H, d) | MS: [M + H]$^+$ 312 |

Example 48

Synthesis of (2,4-dihydroxy-5-isopropyl-phenyl)-[5-(2-isopropylamino-ethoxy)-1,3-dihydro-isoindol-2-yl]-methanone

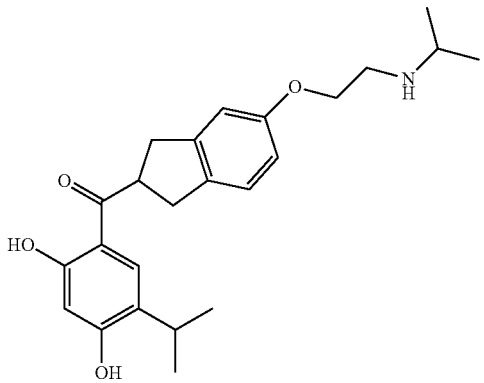 [SMILES: CC(C)NCCOc1ccc2c(c1)CC(C(=O)c1cc(C(C)C)c(O)cc1O)C2]

To a suspension of [5-(3-amino-ethoxy)-1,3-dihydro-isoindol-2-yl]-(2,4-dihydroxy-5-isopropyl-phenyl)-methanone hydrochloride (Example 57) (250 mg, 0.702 mmoles) in 1,2-dichloroethane (10 ml) was added acetone (62 µl, 0.842 mmoles), sodium triacetoxyborohydride (178 mg, 0.842 mmoles) and acetic acid (48 µl, 0.842 mmoles) and then heated at 60° C. for 24 hours. To the reaction mixture was added further acetone (52 µl, 0.702 mmoles), sodium triacetoxyborohydride (149 mg, 0.702 mmoles) and acetic acid (40 µl, 0.702 mmoles) and heated at 60° C. for a further 2 hours. The reaction mixture was then filtered and the mother liquor purified by flash chromatography [Biotage SP4: 25M, flow rate 25 ml/min, gradient 20% to 100% DMAW 90 in DCM) to give (2,4-dihydroxy-5-isopropyl-phenyl)-[5-(2-isopropylamino-ethoxy)-1,3-dihydro-isoindol-2-yl]-methanone as a light brown viscous oil (140 mg, 50%). $^1$H NMR (DMSO-d6) 10.05 (1H, br s); 9.60 (1H, br s); 7.23 (1H, br s); 7.05 (1H, s); 6.93 (1H, br s); 6.85 (1H, br d); 6.40 (1H, s); 4.70 (4H, br m); 4.00 (2H, t); 3.10 (1H, m); 2.90 (2H, t); 2.80 (1H, m); 1.15 (6H, d); 1.00 (6H, d). MS: [M+H]$^+$ 399.

Example 49

Synthesis of N-{2-[2,4-dihydroxy-5-isopropyl-benzoyl)-2,3-dihydro-1H-isoindol-5-yloxy]-ethyl}-2-morpholin-4-yl-acetamide

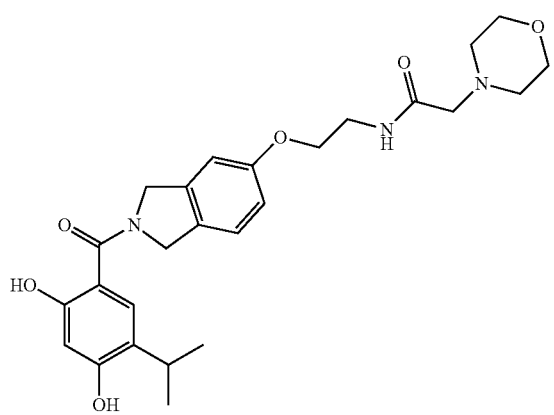 [SMILES: CC(C)c1cc(C(=O)N2Cc3ccc(OCCNC(=O)CN4CCOCC4)cc3C2)c(O)cc1O]

To a solution of [5-(3-amino-ethoxy)-1,3-dihydro-isoindol-2-yl]-(2,4-dihydroxy-5-isopropyl-phenyl)-methasone hydrochloride (100 mg, 0.255 mmoles) in DMF (10 ml) was added EDC (59 mg, 0.306 mmoles), HOBt (41 mg, 0.306 mmoles), morpholin-4-yl-acetic acid (37 mg, 0.255 mmoles) and triethylamine (43 µl, 0.306 mmoles) and stirred at ambient temperature for one hour. To the reaction mixture was added further EDC (20 mg, 0.104 mmoles), HOBt (14 mg, 0.104 mmoles), morpholin-4-yl-acetic acid (12 mg, 0.083 mmoles) and triethylamine (14 µl, 0.100 mmoles) and stirred at ambient temperature for a further 2 hours. Solvent removed in vacuo. The residue was purified by flash chromatography [Biotage SP4: 25 S, flow rate 25 ml/min, gradient 20% DMAW 90 in DCM to 100% DMAW 90] and then by preparative HPLC to give N-{2-[2,4-dihydroxy-5-isopropyl-benzoyl)-2,3-dihydro-1H-isoindol-5-yloxy]-ethyl}-2-morpholin-4-yl-acetamide as a colourless viscous oil (40 mg, 33%). $^1$H NMR (Me-d3-OD) 7.20 (1H, br s); 7.18 (1H, s); 6.90 (2H, br m); 6.40 (1H, s); 4.10 (2H, t); 3.73 (4H, m); 3.63 (2H, t); 3.20 (1H, m); 3.18 (2H, s); 2.60 (4H, m); 1.25 (6H, d). MS: [M+H]$^+$ 484.

Example 50

Synthesis of (2,4-dihydroxy-5-isopropyl-phenyl)-[5-(4-hydroxy-1-methyl-piperidin-4-yl)-1,3-dihydro-isoindol-2-yl]-methanone

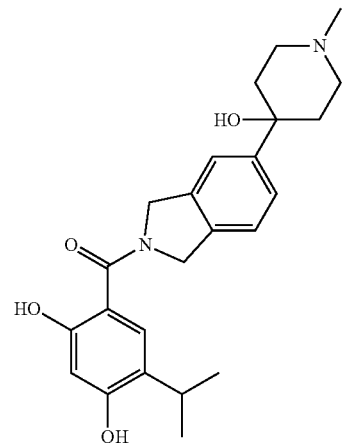 [SMILES: CC(C)c1cc(C(=O)N2Cc3ccc(C4(O)CCN(C)CC4)cc3C2)c(O)cc1O]

50A: Synthesis of 5-bromo-1,3-dihydro-isoindole-2-carboxylic acid tert-butyl ester A mixture of 5-bromo-2,3-dihydro-1H-isoindole (1.26 g; 6.4 mmol), di-tert-butyl dicarbonate (1.53 g; 1.1 equiv.) and 4-dimethylaminopyridine (catalytic amount) in DMF (20 ml) was stirred at room temperature overnight then evaporated. The residue was partitioned between EtOAc and brine, the EtOAc layer was separated, dried (MgSO$_4$) and evaporated. Purification by flash column chromatography using a Biotage SP4 (40 S, 40 ml/min) eluting with 0% to 5% MeOH/DCM gave 695 mg of 5-bromo-1,3-dihydro-isoindole-2-carboxylic acid tert-butyl ester as a brown gum. $^1$HNMR (DMSO-d6) 7.55 (1H, d), 7.48 (1H, d), 7.30 (1H, dd), 4.63-4.51 (4H, m), 1.46 (9H, s).

50B. Synthesis of 5-(4-hydroxy-1-methyl-piperidin-4-yl)-1,3-dihydro-isoindole-2-carboxylic acid tert-butyl ester 0.69 ml of n-Butyl lithium (2.5M solution in hexane) was added dropwise to a stirred solution of 5-bromo-1,3-dihydro-isoindole-2-carboxylic acid tert-butyl ester (429 mg; 1.44 mmol) in anhydrous THF (10 ml) at −78° C. under an atmosphere of nitrogen. The reaction was stirred for 50 minutes then 1-methyl-4-piperidone (212 µl; 1.2 equiv.) was added and stirred at −78° C. for a further 60 minutes then warmed to room temperature. The reaction was quenched with saturated ammonium chloride solution then extracted with EtOAc. The EtOAc layer was washed with saturated NaHCO$_3$, brine, dried (MgSO$_4$) and evaporated. Purification by flash column chromatography on SiO$_2$, gradient elution from 0% to 10% 2M methanolic ammonia/DCM gave 111 mg of 5-(4-hydroxy-1-methyl-piperidin-4-yl)-1,3-dihydro-isoindole-2-carboxylic acid tert-butyl ester as a colourless oil.

50C. Synthesis of 4-(2,3-dihydro-1H-isoindol-5-yl)-1-methpiperidin-4-ol

A solution of 5-(4-hydroxy-1-methyl-piperidin-4-yl)-1,3-dihydro-isoindole-2-carboxylic acid tert-butyl ester (107 mg; 0.32 mmol) in THF (4 ml) was treated with concentrated hydrochloric acid (1.5 ml) then heated at reflux for 4 hours, then evaporated and re-evaporated with toluene to give 4-(2,3-dihydro-1H-isoindol-5-yl)-1-methyl-piperidin-4-ol dihydrochloride as a brown gum.

50D. Synthesis of (2,4-bis-benzyloxy-5-isopropenyl-phenyl)-[5-(4-hydroxy-1-methyl-piperidin-4-yl)-1,3-dihydro-isoindol-2-yl]-methanone A solution of 2,4-bis-benzyloxy-5-isopropenyl-benzoic acid (145 mg; 1.2 equiv.) in DCM (5 ml) was treated with EDC (80 mg; 1.3 equiv.) and HOAt (66 mg; 1.5 equiv.) then stirred at room temperature for 30 minutes. This solution was then added to a mixture of 4-(2,3-dihydro-1H-isoindol-5-yl)-1-methyl-piperidin-4-ol dihydrochloride (112 mg; 0.32 mmol) and triethylamine (90 µl; 2 equiv.) in THF (5 ml) and DMF (2 ml), the reaction was then stirred at room temperature overnight. The reaction mixture was diluted with EtOAc, washed with water, 1N NaOH and brine, the EtOAc layer was separated, dried (MgSO$_4$) and evaporated. Purification by flash column chromatography on SiO$_2$, gradient elution from 0% to 5% 2M methanolic ammonia/DCM gave 104 mg of (2,4-bis-benzyloxy-5-isopropenyl-phenyl)-[5-(4-hydroxy-1-methyl-piperidin-4-yl)-1,3-dihydro-isoindol-2-yl]-methanone as a yellow glass.

50E. Synthesis of (2,4-dihydroxy-5-isopropyl-phenyl)-[5-(4-hydroxy-1-methyl-piperidin-4-yl)-1,3-dihydro-isoindol-2-yl]-methanone Hydrogenation of (2,4-bis-benzyloxy-5-isopropenyl-phenyl)-[5-(4-hydroxy-1-methyl-piperidin-4-yl)-1,3-dihydro-isoindol-2-yl]-methanone (as described in method A5) afforded 72 mg of the title compound as a cream solid. $^1$H NMR (Me-d3-OD) 7.35 (2H, m), 7.18 (1H, br m) 7.08 (1H, s), 6.25 (1H, s), 4.78 (4H, m), 3.10 (1H, m), 2.65 (2H, m), 2.45 (2H, m), 2.25 (3H, s), 2.00 (2H, m), 1.65 (2H, m), 1.10 (6H, d). MS: [M+H]$^+$ 411.

Example 51

Synthesis of (2,4-dihydroxy-5-isopropyl-phenyl)-{5-[4-(4-methyl-piperazin-1-yl)-piperidin-1-yl]-1,3-dihydro-isoindol-2-yl}-methanone

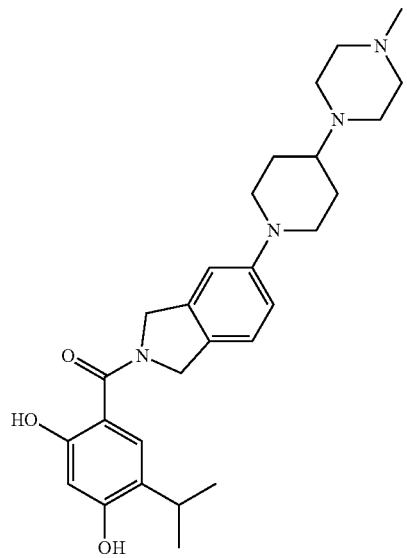 [SMILES: CC(C)c1cc(C(=O)N2Cc3ccc(N4CCC(N5CCN(C)CC5)CC4)cc3C2)c(O)cc1O]

51A. Synthesis of (2,4-bis-benzyloxy-5-isopropenyl-phenyl)-(5-bromo-1,3-dihydro-isoindol-2-yl)-methanone A solution of benzyloxy-5-isopropenyl-benzoic acid (2.85 g; 7.6 mmol), 5-bromo-2,3-dihydro-1H-isoindole (1.5 g; 1 equiv.), EDC (1.75 g; 1.2 equiv.) and HOBt (1.25 g; 1.2 equiv.) in DMF (25 ml) was stirred at room temperature overnight then evaporated. The residue was dissolved in EtOAc, washed with 2M HCl then saturated NaHCO$_3$, dried (MgSO$_4$) and evaporated. Purification using a Biotage SP4 (40 S, 40 ml/min) eluting with 1:4-1:3-1:2 EtOAc/P.E. gave 2.45 g of (2,4-bis-benzyloxy-5-isopropenyl-phenyl)-(5-bromo-1,3-dihydro-isoindol-2-yl)-methanone as a light brown solid.

51B. (2,4-bis-benzyloxy-5-isopropenyl-phenyl)-{5-[4-(4-methyl-piperazin-1-yl)-piperidin-1-yl]-1,3-dihydro-isoindol-2-yl}-methanone A solution of (2,4-bis-benzyloxy-5-isopropenyl-phenyl)-(5-bromo-1,3-dihydro-isoindol-2-yl)-methanone (200 mg; 0.36 mmol) and 1-methyl-4-(piperidin-4-yl)piperazine (80 mg; 1.2 equiv.) in toluene (5 ml) was treated with (2-biphenyl)-di-tert-butylphosphine (6 mg; 5 mol %), tris(dibenzylidene)palladium(0) (10 mg; 2.5 mol %) and sodium tert-butoxide (50 mg; 1.4 equiv.) then heated at 120° C. for 30 minutes in a CEM explorer microwave synthesiser. The reaction mixture was diluted with DCM, washed with brine, dried (MgSO$_4$) and evaporated. Purification by flash column chromatography (Biotage SP4-25 S, 25 ml/min) eluting with DMAW 240-120-90 followed by evaporation of product containing fractions gave 105 mg of (2,4-bis-benzyloxy-5-isopropenyl-phenyl)-{5-[4-(4-methyl-piperazin-1-yl)-piperidin-1-yl]-1,3-dihydro-isoindol-2-yl}-methanone as the acetic acid salt.

51C. (2,4-dihydroxy-5-isopropyl-phenyl)-{5-[4-(4-methyl-piperazin-1-yl)-piperidin-1-yl]-1,3-dihydro-isoindol-2-yl}-methanone hydrochloride A solution of (2,4-bis-benzyloxy-5-isopropenyl-phenyl)-{5-[4-(4-methyl-piperazin-1-yl)-piperidin-1-yl]-1,3-dihydro-isoindol-2-yl}-methanone acetic acid salt in methanol (10 ml) was treated with 10% palladium on carbon (wet), hydrogenated at room temperature and pressure overnight then filtered and evaporated. The crude compound was purified by flash column chromatograph (Biotage SP4-25 S, 25 ml/min) eluting with DMAW 240-120-90-60. Product containing fractions were evaporated, treated with saturated HCl/EtOAc then evaporated and re-evaporated with methanol and dried under high vacuum at 60° C. overnight. (2,4-dihydroxy-5-isopropyl-phenyl)-{5-[4-(4-methyl-piperazin-1-yl)-piperidin-1-yl]-1,3-dihydro-isoindol-2-yl}-methanone hydrochloride was isolated as a cream solid (62 mg). $^1$H NMR (DMSO-d6) 12.40-12.00 (2H, br m), 9.75-9.55 (1H, br m), 7.45-7.05 (3H, m), 7.03 (1H, s), 6.45 (1H, s), 4.70-4.55 (4H, m), 3.85-3.65 (6H, m), 3.60-3.40 (5H, m), 3.15-3.05 (1H, m), 3.0-2.78 (5H, m), 2.30-2.20 (2H, m), 2.05-1.90 (2H, m), 1.15 (6H, d). MS: [M+H]$^+$ 479.

Example 52

Synthesis of (2,4-dihydroxy-5-isopropyl-phenyl)-[5-(4-piperazin-1-yl-phenyl)-1,3-dihydro-isoindol-2-yl]-methanone

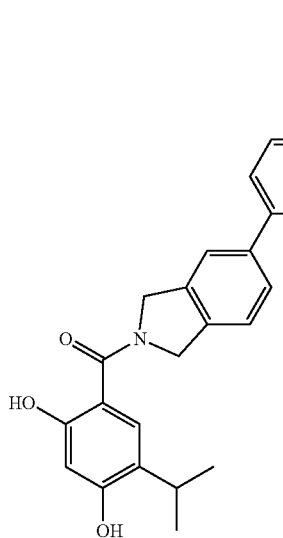

52A. Synthesis of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester A mixture of (2,4-bis-benzyloxy-5-isopropenyl-phenyl)-(5-bromo-1,3-dihydro-isoindol-2-yl)-methanone (240 mg, 0.43 mmol), t-butyl-4-[4-(4,4,5,5-tetramethyl-1,3,2-dioxaborolan-2-yl)phenyl]piperazine carboxylate (210 mg, 1.25 equiv.), bis(tri-t-butylphosphine)palladium(0) (12.5 mg, 2.5 mol %) and potassium carbonate (350 mg, 6 equiv.) in toluene/water/ethanol (1 ml: 1 ml: 4 ml) was heated at 135° C. for 30 minutes in a CEM explorer microwave synthesiser. The reaction mixture was diluted with EtOAc, washed with saturated NaHCO$_3$, dried (MgSO$_4$) and evaporated. Purification by flash column chromatography (Biotage SP4-25 S, 25 ml/min) eluting with 1:3 then 1:1 EtOAc/P.E. Evaporation of product containing fractions gave 85 mg of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester. MS: [M+H]$^+$ 736.

52B. Synthesis of (2,4-dihydroxy-5-isopropyl-phenyl)-[5-(4-piperazin-1-yl-phenyl)-1,3-dihydro-isoindol-2-yl]-methasone Hydrogenation of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester (as described in method A5), followed by BOC deprotection (as described in example 70) afforded 10 mg of the title compound as the hydrochloride salt after flash column chromatography (Biotage SP4, 25 S) eluting with DMAW 240-120-90 and evaporation from saturated HCl/EtOAc. $^1$H NMR (Me-d3-OD) 7.63 (2H, d), 7.55 (2H, m) 7.45-7.30 (1H, m), 7.25 (1H, s), 7.20 (2H, d), 5.03 (4H, m), 3.55 (4H, m), 3.47 (4H, m), 3.23 (1H, m), 1.25 (6H, d). MS: [M+H]$^+$ 458.

Example 53

Synthesis of 2,4-dihydroxy-5-isopropyl-phenyl)-[5-(1-dimethylamino-2-hydroxy-ethyl)-1,3-dihydro-isoindol-2-yl]-methanone, and dihydroxy-5-isopropyl-phenyl)-[5-(2-dimethylamino-1-hydroxy-ethyl)-1,3-dihydro-isoindol-2-yl]-methanone

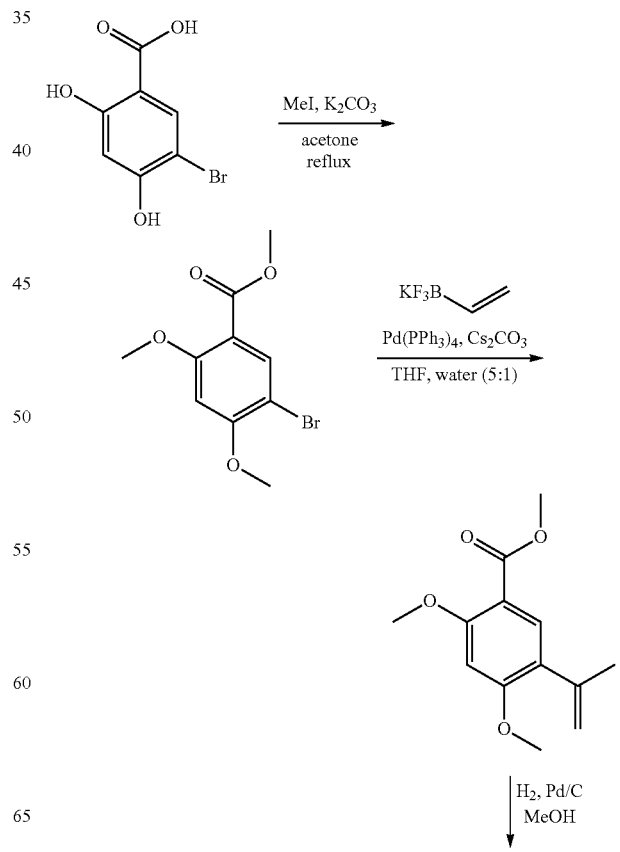

-continued

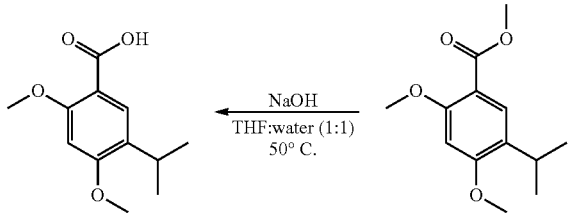

53A. Synthesis of 5-bromo-2,4-dimethoxybenzoic acid methyl ester

A solution of 5-bromo-2,4-dihydroxybenzoic acid (24.9 g, 107 mmol) in acetone (355 ml), was treated with methyl iodide (39.9 ml, 640 mmol) and $K_2CO_3$ (88 g, 640 mmol) then heated at reflux overnight. The salts were filtered off and washed with acetone. The filtrate was evaporated to dryness and the product was purified by flash column chromatography (100% DCM) to yield 5-bromo-2,4-dimethoxybenzoic acid methyl ester as a colourless solid (28 g). $^1$H NMR (Me-$d_3$-OD) 7.98 (1H, s), 6.74 (1H, s), 3.99 (3H, s), 3.94 (3H, s), 3.85 (3H, s). MS: $[M+H]^+$ 275/277.

53B. Synthesis of -isopropenyl-2,4-dimethoxy-benzoic acid methyl ester

To potassium isopropylidene trifluoroborate (4.87 g, 32.7 mmol) and 5-bromo-2,4-dimethoxybenzoic acid methyl ester (7.5 g, 27.3 mmol) in THF (195 ml) was added $Cs_2CO_3$ (26.6 g, 81.8 mmol) in water (39 ml). The reaction was degassed and $Pd(PPh_3)_4$ (1.58 g, 1.36 mmol) added. The reaction was heated at reflux for three days then quenched by adding water and extracted with EtOAc (×2). The combined organic layers were washed with brine, dried ($MgSO_4$), filtered and evaporated to leave an orange solid. The product was taken up in EtOAc again and the precipitate filtered. The filtrate was evaporated to dryness to yield 5-isopropenyl-2,4-dimethoxy-benzoic acid methyl ester (6.2 g). $^1$H NMR (Me-$d_3$-OD) 7.68 (1H, s), 6.66 (1H, s), 5.10-5.08 (1H, m), 5.02-5.00 (1H, m), 3.93 (3H, s), 3.92 (3H, s), 3.84 (3H, s), 2.08-2.06 (3H, m). MS: $[M+H]^+$ 237.

53C. Synthesis of 5-isopropyl-2,4-dimethoxy-benzoic acid methyl ester

A solution of 5-isopropenyl-2,4-dimethoxy-benzoic acid methyl ester (6.0 g, 25.4 mmol) in MeOH (85 ml) was shaken with 10% Pd/C under an atmosphere of $H_2$ at room temperature for 3 hours. The catalyst was filtered through GF/A paper but a little fine powder passed through. The filtrate was passed through a small pad of silica and evaporated to dryness to yield a colourless solid. The product was purified by flash column chromatography (DCM:Petrol gradient elution) to yield 5-isopropyl-2,4-dimethoxy-benzoic acid methyl ester a colourless solid (5.5 g). $^1$H NMR (Me-$d_3$-OD) 7.68 (1H, s), 6.64 (1H, s), 3.94 (3H, s), 3.91 (3H, s), 3.84 (3H, s), 3.23 (1H, sept), 1.20 (6H, d). MS: $[M+H]^+$ 239.

53D. Synthesis of 5-isopropyl-2,4-dimethoxy-benzoic acid

5-Isopropyl-2,4-dimethoxy-benzoic acid methyl ester (5.5 g, 23.1 mmol) and NaOH (1.38 g, 34.6 mmol) in THF (46 ml) and water (46 ml) was warmed to 50° C. overnight. The reaction was cooled and diluted with water and EtOAc. The aqueous layer was neutralised with HCl (1N, aq.). The product was extracted with EtOAc (×3) and the combined organic layers were washed with brine and dried over $MgSO_4$. The product was filtered and evaporated to dryness to yield 5-isopropyl-2,4-dimethoxy-benzoic acid as a pale peach solid (4.7 g). $^1$H NMR (DMSO-$d_6$) 12.1 (1H, br s), 7.62 (1H, s), 6.71 (1H, s), 3.95 (3H, s), 3.91 (3H, s), 3.19 (1H, sept), 1.18 (6H, d). MS: $[M+H]^+$ 225.

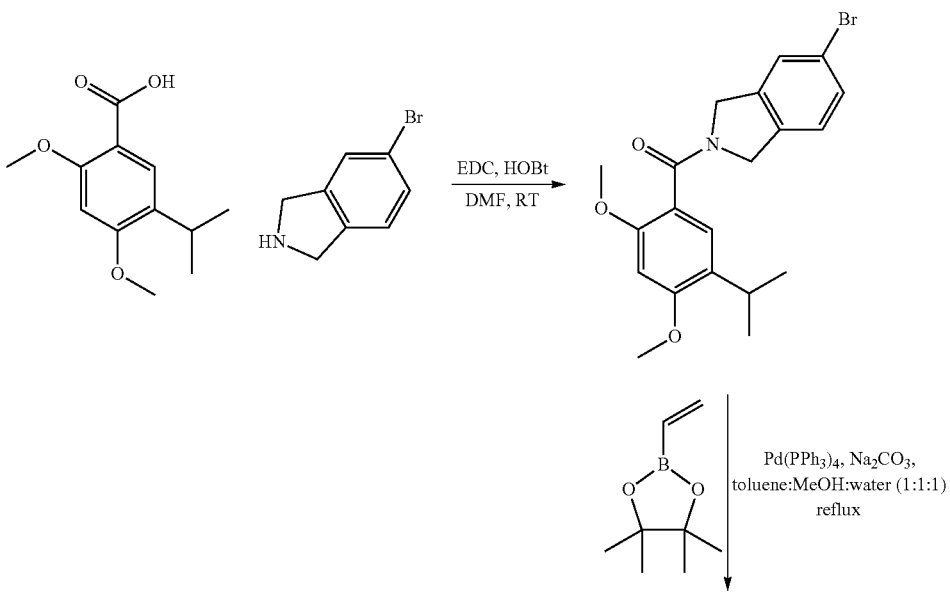

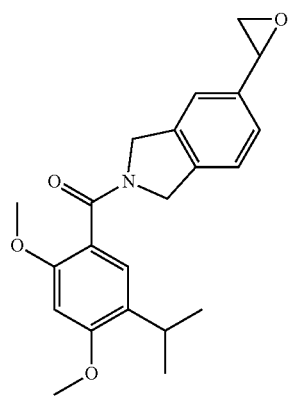 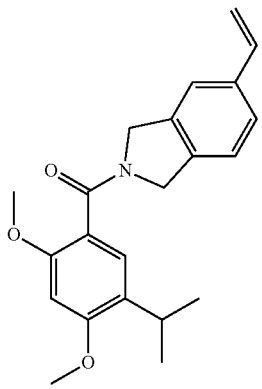

53E. Synthesis of (5-bromo-1,3-dihydro-isoindol-2-yl)-(5-isopropyl-2,4-dimethoxyphenyl)methanone To a mixture of 5-isopropyl-2,4-dimethoxybenzoic acid (2.45 g, 10.9 mmol), HOBt (1.61 g, 11.9 mmol) and EDC (1.85 g, 11.9 mmol) in anhydrous DMF (33 ml) under $N_2$ was added 5-bromo-2,3-dihydro-1H-isoindole (1.97 g, 9.95 mmol) and stirred at room temperature overnight. The reaction was quenched by diluting with NaOH (1M, aq.) and extracting the product with EtOAc (×2). The combined organic layers were washed with brine and dried over $MgSO_4$. The product was filtered and evaporated to dryness to leave a brown oil. The product was purified by flash column chromatography using gradient elution (ether/petrol) to yield (5-bromo-1,3-dihydro-isoindol-2-yl)-(5-isopropyl-2,4-dimethoxyphenyl)-methanone as a beige solid (3 g). $^1$H NMR (Me-$d_3$-OD) 7.60-7.13 (3H, m), 7.14 (1H, s), 6.71 (1H, s), 4.89 (2H, d), 4.64 (2H, d), 3.93 (3H, s), 3.90 (3H, s), 3.27 (1H, sept), 1.20 (6H, d). MS: $[M+H]^+$ 404/406.

53F. Synthesis of 5-isopropyl-2,4-dimethoxy-phenyl)-(5-vinyl-1,3-dihydro-isoindol-2-yl)-methanone To (5-bromo-1,3-dihydro-isoindol-2-yl)-(5-isopropyl-2,4-dimethoxyphenyl)methanone (2.2 g, 5.44 mmol), and 2-vinyl-4,4,5,5-tetramethyl-1,3,2-dioxaboralane (1.2 ml, 6.53 mmol) in MeOH (25 ml) and toluene (25 ml) was added $Na_2CO_3$ in water (25 ml). The reaction was degassed, $Pd(PPh_3)_4$ (0.38 g, 0.05 mmol) added then heated at 80° C. overnight. The reaction was worked up by adding water and extracting with EtOAc (×3). The combined organic layers were washed with brine and dried over $MgSO_4$. The product was filtered and evaporated to dryness then purified by flash column chromatography, gradient elution (ether:petrol) to yield 5-isopropyl-2,4-dimethoxy-phenyl)-(5-vinyl-1,3-dihydro-isoindol-2-yl)-methanone as a yellow oil (1.6 g). $^1$H NMR (Me-$d_3$-OD) 7.47-7.15 (3H, m), 7.15 (1H, s), 6.82-6.72 (1H, m), 6.71 (1H, s), 5.79 (1H, dd), 5.24 (1H, dd), 4.90 (2H, d), 4.64 (2H, d), 3.93 (3H, s), 3.91 (3H, s), 3.27 (1H, sept), 1.23 (6H, d). MS: $[M+H]^+$ 352.

53G. Synthesis of (5-isopropyl-2,4-dimethoxy-phenyl)-(5-oxiranyl-1,3-dihydro-isoindol-2-yl)-methasone To (5-isopropyl-2,4-dimethoxy-phenyl)-(5-vinyl-1,3-dihydro-isoindol-2-yl)-methanone (0.80 g, 2.28 mmol) in DCM (22 ml) was added mCPBA (0.61 g, 2.73 mmol) at 0° C. The reaction was stirred at room temperature for an hour. The reaction was diluted with NaOH (1M, aq.) and extracted the product with EtOAc. The EtOAc layer was washed with NaOH again. The organic layer was washed with brine and dried over $MgSO_4$. The product was filtered and evaporated to dryness to yield crude (5-isopropyl-2,4-dimethoxy-phenyl)-(5-oxiranyl-1,3-dihydro-isoindol-2-yl)-methanone as a very pale yellow oil. MS: $[M+H]^+$ 368.

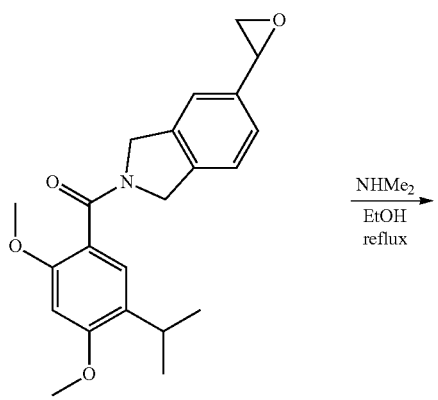

-continued

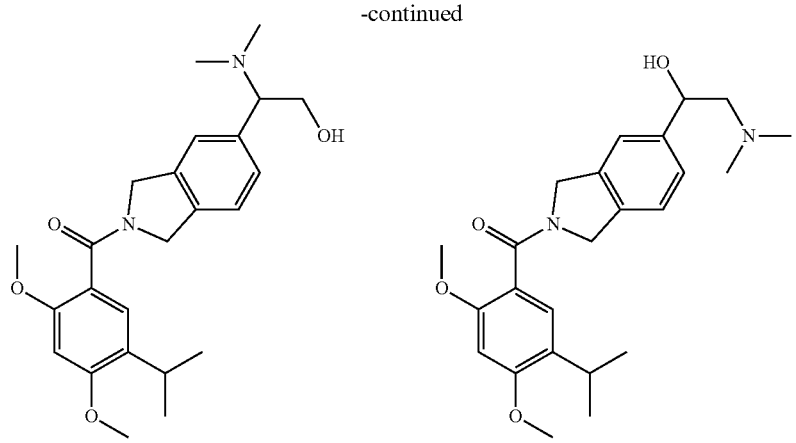

↓ BBr₃, DCM, RT

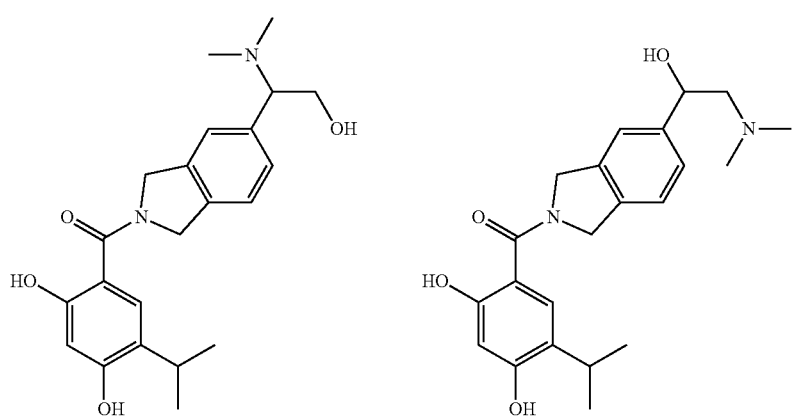

53H. Synthesis of (2,4-dihydroxy-5-isopropyl-phenyl)-[5-(1-dimethylamino-2-hydroxy-ethyl)-1,3-dihydro-isoindol-2-yl]-methasone (Compound 121H-i) and (2,4-dihydroxy-5-isopropyl-phenyl)-[5-(2-dimethylamino-1-hydroxy-ethyl)-1,3-dihydro-isoindol-2-yl]-methanone (Compound 121H-ii)

(5-Isopropyl-2,4-dimethoxy-phenyl)-(5-oxiranyl-1,3-dihydro-isoindol-2-yl)-methanone (~120 mg, crude) was dissolved in dimethylamine in EtOH (20 ml, ~33%, 5.6 M) and heated at 60° C. overnight. The reaction was evaporated to dryness and the product crudely purified by flash column chromatography MeOH:DCM (1:5) to yield impure material which was used without further purification. To a mixture of [5-(1-dimethylamino-2-hydroxy-ethyl)-1,3-dihydro-isoindol-2-yl]-(5-isopropyl-2,4-dimethoxy-phenyl)-methanone and [5-(2-dimethylamino-1-hydroxy-ethyl)-1,3-dihydro-isoindol-2-yl]-(5-isopropyl-2,4-dimethoxy-phenyl)-methanone (~100 mg) was added DCM (5 ml) and then boron tribromide (3 eq.) under $N_2$. The reaction was left to stir at room temperature until completion. The reaction was quenched with ice and diluted with water and EtOAc. The aqueous layer was extracted with EtOAc (×2). The combined organic layers were washed with brine, dried over $MgSO_4$ then filtered and evaporated to dryness, to leave a yellow residue which was purified by preparative HPLC to yield the two resorcinol isomers.

(2,4-Dihydroxy-5-isopropyl-phenyl)-[5-(1-dimethylamino-2-hydroxy-ethyl)-1,3-dihydro-isoindol-2-yl]-methanone, (Compound 121H-i) $^1$H NMR (Me-d₃-OD) 7.42-7.30 (3H, m), 7.19 (1H, s), 6.39 (1H, s), 4.98-4.87 (4H, m), 4.03-3.97 (1H, m), 3.94-3.86 (1H, m), 3.68 (1H, br s), 3.22 (1H, sept), 2.40 (6H, s), 1.23 (6H, d). MS: [M+H]⁺ 384.

(2,4-Dihydroxy-5-isopropyl-phenyl)-[5-(2-dimethylamino-1-hydroxy-ethyl)-1,3-dihydro-isoindol-2-yl]-methanone, (Compound 121H-ii) $^1$H NMR (Me-d₃-OD) 7.39-7.25 (3H, m), 7.18 (1H, s), 6.38 (1H, s), 6.94-6.88 (5H, m), 3.22

(1H, sept), 2.77-2.68 (1H, m), 2.61-2.51 (1H, m), 2.42 (6H, s), 1.23 (6H, d). MS: [M+H]+ 384.

Example 54

Synthesis of (2,4-dihydroxy-5-isopropyl-phenyl)-[5-(piperazine-1-carbonyl)-1,3-dihydro-isoindol-2-yl]-methanone hydrochloride

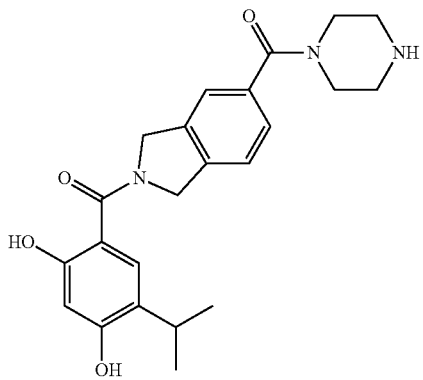 [SMILES: CC(C)c1cc(C(=O)N2Cc3ccc(C(=O)N4CCNCC4)cc3C2)c(O)cc1O]

54A. Synthesis of 4-[2-(2,4-dihydroxy-5-isopropyl-benzoyl)-2,3-dihydro-1H-isoindole-5-carbonyl]-piperazine-1-carboxylic acid tert-butyl ester A solution of 2-(2,4-bis-benzyloxy-5-isopropyl-benzoyl)-2,3-dihydro-1H-isoindole-5-carboxylic acid (Preparation D6) (0.5 g, 0.96 mmol), EDC (0.22 g, 1.15 mmol), HOBT (0.196 g, 1.15 mmol) and BOC piperazine (0.117 ml, 1.06 mmol) in DMF (10 ml) was stirred at room temperature for 48 hours, then evaporated under vacuum. The crude material was dissolved in ethyl acetate and extracted twice with saturated NaHCO$_3$, organics washed with brine, dried (MgSO$_4$), filtered then evaporated under vacuum and purified by flash column chromatography (80% EtOAc-P.E. as eluant) to give 0.5 g of 4-[2-(2,4-dihydroxy-5-isopropyl-benzoyl)-2,3-dihydro-1H-isoindole-5-carbonyl]-piperazine-1-carboxylic acid tert-butyl ester. MS: [M+H]+ 688.

54B. Synthesis of (2,4-dihydroxy-5-isopropyl-phenyl)-[5-(piperazine-1-carbonyl)-1,3-dihydro-isoindol-2-yl]-methanone hydrochloride Hydrogenation as Method A5 to give (0.2 g, 0.30 mmol) 4-[2-(2,4-dihydroxy-5-isopropyl-benzoyl)-2,3-dihydro-1H-isoindole-5-carbonyl]-piperazine-1-carboxylic acid tert-butyl ester [used crude] dissolved in EtOAc then treated with saturated EtOAc/HCl, stirred at ambient for 3 hours, reaction diluted with ether, solid filtered to give 0.19 g of (2,4-dihydroxy-5-isopropyl-phenyl)-[5-(piperazine-1-carbonyl)-1,3-dihydro-isoindol-2-yl]-methanone hydrochloride. $^1$H NMR (Me-d$_3$-OD) 7.50-7.42 (3H, m), 7.18 (1H, s), 6.39 (1H, s), 5.00-4.95 (4H, br s), 3.92-3.79 (4H, br s), 3.35-3.28 (4H, br s), 3.26-3.15 (1H, m), 1.23 (6H, d). MS: [M+H]+ 410.

Example 55

Synthesis of (2,4-dihydroxy-5-isopropyl-phenyl)-[5-(4-methyl-piperazin-1-ylmethyl)-1,3-dihydro-isoindol-2-yl]-methanone

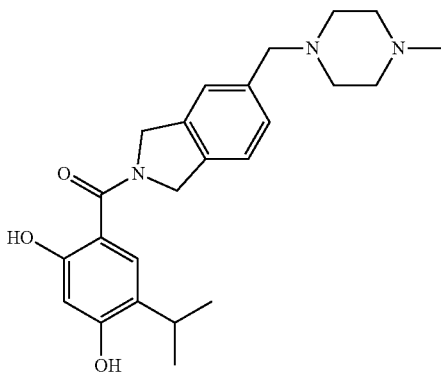 [SMILES: CC(C)c1cc(C(=O)N2Cc3ccc(CN4CCN(C)CC4)cc3C2)c(O)cc1O]

55A. Synthesis of 2-(2,4-bis-benzyloxy-5-isopropyl-benzoyl)-2,3-dihydro-1H-isoindole-5-carboxylic acid methoxy-methyl-amide A solution of 2-(2,4-bis-benzyloxy-5-isopropyl-benzoyl)-2,3-dihydro-1H-isoindole-5-carboxylic acid (Preparation D6) (1.76 g, 3.39 mmol), EDC (0.78 g, 4.06 mmol), HOBT (0.55 g, 4.06 mmol), Et$_3$N (1 ml, 6.78 mmol) and N,O-dimethylhydroxylamine hydrochloride (0.36 g, 3.72 mmol) in DMF (20 ml) was stirred at room temperature for 48 hours, then evaporated under vacuum. The crude material was dissolved in ethyl acetate and extracted twice with saturated NaHCO$_3$, organics washed with brine, dried (MgSO$_4$), filtered then evaporated to give 1.84 g of 2-(2,4-bis-benzyloxy-5-isopropyl-benzoyl)-2,3-dihydro-1H-isoindole-5-carboxylic acid methoxy-methyl-amide. MS: [M+H]+ 563.

55B. Synthesis of 2-(2,4-bis-benzyloxy-5-isopropyl-benzoyl)-2,3-dihydro-1H-isoindole-5-carbaldehyde A solution of 2-(2,4-bis-benzyloxy-5-isopropyl-benzoyl)-2,3-dihydro-1H-isoindole-5-carboxylic acid methoxy-methyl-amide (0.226 g, 0.4 mmol) in THF (5 ml) cooled to 0° C., treated with 1M LiAlH$_4$/THF (0.3 ml, 0.3 mmol), stirred 1 hour, further LiAlH$_4$ (0.05 ml) added then stirred for 30 minutes. The reaction was quenched with saturated KHSO$_4$ solution, extracted with EtOAc, dried (MgSO$_4$), filtered and evaporated to give 0.2 g of 2-(2,4-bis-benzyloxy-5-isopropyl-benzoyl)-2,3-dihydro-1H-isoindole-5-carbaldehyde. MS: [M+H]+ 504.

55C. Synthesis of (2,4-bis-benzyloxy-5-isopropyl-phenyl)-[5-(4-methyl-piperazin-1-ylmethyl)-1,3-dihydro-isoindol-2-yl]-methanone To a solution of 2-(2,4-bis-benzyloxy-5-isopropyl-benzoyl)-2,3-dihydro-1H-isoindole-5-carbaldehyde (0.316 g, 0.63 mmol) and n-methyl piperazine (63 mg, 0.63 mmol) in CH$_2$Cl$_2$ (10 ml) was added AcOH (38 mgs 0.63 mmol) and NaBH(OAc)$_3$ (0.28 g, 1.33 mmol), then stirred at ambient for 5 hours. The reaction was quenched with water, layers separated and aqueous washed CH$_2$Cl$_2$. The organics were combined, washed with brine, dried (MgSO$_4$), filtered and evaporated to give 0.32 g of (2,4-bis-benzyloxy-5-isopropyl-phenyl)-[5-(4-methyl-piperazin-1-ylmethyl)-1,3-dihydro-isoindol-2-yl]-methanone. MS: [M+H]+ 588.

55D. Synthesis of (2,4-dihydroxy-5-isopropyl-phenyl)-[5-(4-methyl-piperazin-1-ylmethyl)-1,3-dihydro-isoindol-2-yl]-methanone Hydrogenation was carried out using Method A5 but with the addition of $K_2CO_3$ (2 equiv.) in a $MeOH/H_2O$ [9.1]. After evaporation of methanol the reaction was diluted with water, neutralised using 1M HCl and extracted with $CH_2Cl_2$ (×2). Organics dried ($MgSO_4$), filtered and evaporated under vacuum then purified by preparative HPLC to give 21 mg of (2,4-dihydroxy-5-isopropyl-phenyl)-[5-(4-methyl-piperazin-1-ylmethyl)-1,3-dihydro-isoindol-2-yl]-methanone. MS: $[M+H]^+$ 410. $^1$H NMR (Me-$d_3$-OD) 7.37-7.23 (3H, br s), 7.19 (1H, s), 6.39 (1H, s), 4.94-4.87 (4H, br s), 3.57 (2H, s), 3.27-3.16 (1H, m), 2.67-2.39 (8H, m), 2.31 (3H, s), 1.23 (6H, d).

Example 56

Synthesis of (2,4-dihydroxy-5-isopropyl-phenyl)-[4-(3-morpholin-4-yl-propoxy)-1,3-dihydro-isoindol-2-yl]methanone

56A. Synthesis of 4-hydroxyisoindoline hydrobromide

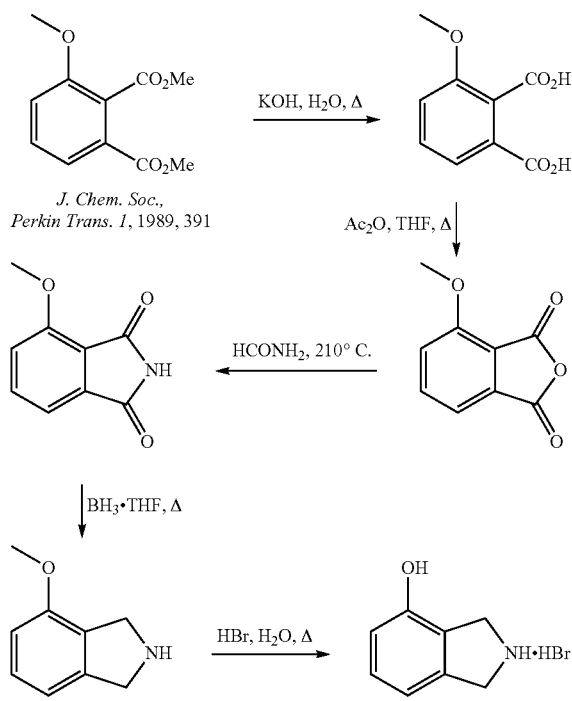

A suspension of dimethyl 3-methoxyphthalate (69.45 g, 0.31 mol) [prepared as per *J. Chem. Soc., Perkin Trans. 1*, 1989, 391] in water (300 ml) was treated with potassium hydroxide (43.7 g, 0.78 mol) and the mixture was stirred and held at reflux for 4 hours. Upon cooling to room temperature the methanol liberated during the course of the reaction was removed in vacuo, the mixture acidified to pH 2 or below by the addition of 5M hydrochloric acid and evaporated gently in vacuo to induce crystallization. The solid material was filtered off, washed with a little ice cooled water, sucked dry under reduced pressure and dried in a vacuum oven at 50° C. overnight to afford 3-methoxyphthalic acid (51.0 g, 84%) as a colourless solid. $^1$H NMR (DMSO-$d_6$) 13.05 (2H, br s), 7.48 (2H, m), 7.33 (1H, m), 3.82 (3H, s). MS: $[M+H]^+$ 197.

Acetic anhydride (70 ml) was added to a mixture of 3-methoxyphthalic acid (51.0 g, 0.26 mol) in anhydrous tetrahydrofuran (250 ml) and the mixture was stirred and held at reflux for 4 hours. Upon cooling to room temperature the solvent was removed in vacuo and the resulting solid material was dried in a vacuum oven at 50° C. overnight to afford 3-methoxyphthalic anhydride (45.9 g, 99%) as a colourless solid. $^1$H NMR (DMSO-$d_6$) 7.97 (1H, dd), 7.63 (1H, d), 7.60 (1H, d), 4.02 (3H, s). MS: $[M+H]^+$ 179.

A mixture of 3-methoxyphthalic anhydride (24.0 g, 134.8 mmol) and formamide (120 ml) was stirred and held at 210° C. for 5 hours and was then allowed to cool to room temperature overnight. Water (100 ml) was added and the solid material filtered off under reduced pressure. The crude product was washed sequentially with 50% aqueous acetone (50 ml) and diethyl ether (200 ml) and sucked dry under reduced pressure to afford 3-methoxyphthalimide (8.95 g, 37%) as an off-white solid. $^1$H NMR (DMSO-$d_6$) 11.08 (1H, br s), 7.78 (1H, dd), 7.45 (1H, d), 7.36 (1H, d), 3.93 (3H, s). MS: $[M+H]^+$ 178.

A stirred solution of 3-methoxyphthalimide (8.95 g, 50.56 mmol) in anhydrous tetrahydrofuran (200 ml) at 0° C. was treated dropwise with a solution of borane in tetrahydrofuran (1M, 150 ml, 0.15 mol) and the resulting mixture was stirred and held at reflux for 16 hours. The mixture was cooled to 0° C., methanol (60 ml) was added dropwise followed by 5M hydrochloric acid (60 ml) and the mixture was stirred and held at reflux for 4 hours. Upon cooling to room temperature the organic solvent was removed in vacuo and the mixture diluted with water (250 ml) and extracted with dichloromethane (3×250 ml). The aqueous layer was basified to pH 12 or above by the addition of 5M sodium hydroxide, extracted with dichloromethane (3×250 ml) and the combined extracts were evaporated to dryness in vacuo to afford 4-methoxyisoindoline (4.44 g, 59%) as a green oil which was used without further purification. $^1$H NMR (DMSO-$d_6$) 7.18 (1H, t), 6.83 (1H, d), 6.78 (1H, d), 4.07 (2H, s), 4.02 (2H, s), 3.78 (3H, s). MS: $[M+H]^+$ 150.

4-Methoxyisoindoline (4.4 g, 29.53 mmol) in 48% aqueous hydrobromic acid (50 ml) was stirred and held at reflux for 16 hours. Upon cooling to room temperature the solvent was removed in vacuo to afford 4-hydroxyisoindoline hydrobromide (5.0 g, 78%) as a pale orange solid. $^1$H NMR (DMSO-$d_6$) 9.95 (1H, br s), 9.37 (2H, br s), 7.19 (1H, t), 6.84 (1H, d), 6.80 (1H, d), 4.48 (2H, t), 4.40 (2H, t). MS: $[M+H]^+$ 136.

56B. Synthesis of (2,4-bis-benzyloxy-5-isopropenyl-phenyl)-(4-hydroxy-1,3-dihydro-isoindol-2-yl)-methanone

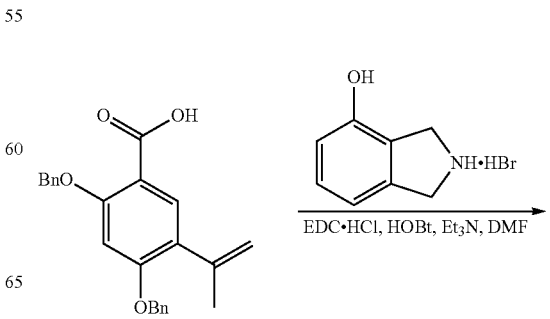

-continued

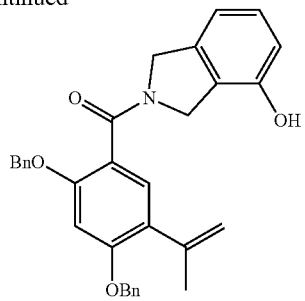

A mixture of 2,4-bis-benzyloxy-5-isopropenyl-benzoic acid (8.1 g, 21.65 mmol), 4-hydroxyisoindoline hydrobromide (4.91 g, 22.73 mmol), N-ethyl-N'-(3-dimethylaminopropyl)carbodiimide hydrochloride (5.0 g, 25.98 mmol), 1-hydroxybenzotriazole (3.5 g, 25.98 mmol) and triethylamine (6 ml, 43.3 mmol) in N,N-dimethylformamide (50 ml) was stirred at room temperature for 16 hours. The solvent was removed in vacuo and the residue was treated with a saturated aqueous solution of sodium hydrogen carbonate (200 ml). The mixture was filtered, the solid material was washed copiously with water, sucked dry under reduced pressure and dried in a vacuum oven at 50° C. overnight to afford (2,4-bis-benzyloxy-5-isopropenyl-phenyl)-(4-hydroxy-1,3-dihydro-isoindol-2-yl)-methanone (10.25 g, 96%) as a pale tan solid. $^1$H NMR (DMSO-$d_6$) (mixture of amide rotamers) 9.68 and 9.60 (1H, 2×br s), 7.45-7.25 (10H, m), 7.20-7.00 (3H, m), 6.82 and 6.72 (1H, 2×d), 6.68 (1H, m), 5.23 and 5.22 (2H, 2×s), 5.18 (2H, s), 5.11 (1H, s), 5.09 (1H, s), 4.77 and 6.67 (2H, 2×s), 4.53 and 4.44 (2H, 2×s), 2.04 (3H, s). MS: [M+H]$^+$ 492.

56C. Synthesis of (2,4-bis-benzyloxy-5-isopropenyl-phenyl)-[4-(3-morpholin-4-yl-propoxy)-1,3-dihydro-isoindol-2-yl]-methanone A mixture of (2,4-bis-benzyloxy-5-isopropenyl-phenyl)-(4-hydroxy-1,3-dihydro-isoindol-2-yl)-methanone (2 g; 4.07 mmol), 4-(3-chloropropyl)morpholine (1.66 g; 2.5 equiv.) and caesium carbonate (8.3 g; 6.25 equiv) in DMF was heated at 90° C. overnight then evaporated. The residue was dissolved in EtOAc, washed with brine, dried (MgSO$_4$) and evaporated. Purification of the crude material using a Biotage SP4 (40 S, 40 ml/min), using gradient elution form 0% to 10% MeOH/EtOAc gave 1.8 g of (2,4-bis-benzyloxy-5-isopropenyl-phenyl)-[4-(3-morpholin-4-yl-propoxy)-1,3-dihydro-isoindol-2-yl]-methanone as a pale yellow gum. MS: [M+H]$^+$ 619.

56D. Synthesis of (2,4-dihydroxy-5-isopropyl-phenyl)-[4-(3-morpholin-4-yl-propoxy)-1,3-dihydro-isoindol-2-yl]methanone

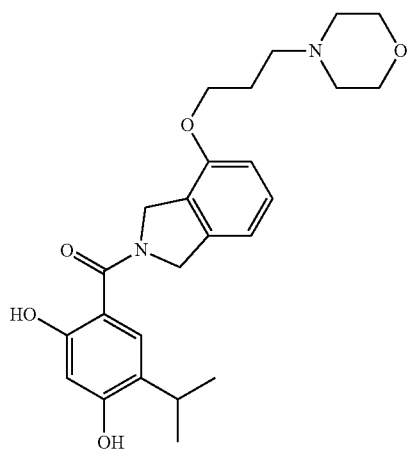 [SMILES: CC(C)c1cc(C(=O)N2Cc3cccc(OCCCN4CCOCC4)c3C2)c(O)cc1O]

Hydrogenation of (2,4-bis-benzyloxy-5-isopropenyl-phenyl)-[4-(3-morpholin-4-yl-propoxy)-1,3-dihydro-isoindol-2-yl]-methanone (as described in method A5) followed by treatment with saturated HCl/EtOAc and trituration with hot acetone afforded 890 mg of the title compound (hydrochloride salt) as a cream solid. $^1$H NMR (DMSO-$d_6$) 10.78 (1H, br s), 10.05 (1H, br s), 9.55 (1H, br s), 7.30 (1H, t), 7.08 (1H, s) 6.98-6.90 (2H, m), 6.45 (1H, s), 4.80 (2H, s), 4.75 (2H, s), 4.15 (2H, t), 3.95 (2H, br m), 2.80 (2H, br m), 3.50-3.35 (2H, br m), 3.25 (2H, br m), 3.18-3.02 (3H, br m), 2.20 (2H, br m), 1.15 (6H, d). MS: [M+H]$^+$ 441.

Examples 57 to 74

By following the methods described above, the following compounds were prepared.

| Example Number | Compound | Chemical Name | Method | N.M.R. Data | M.S. |
|---|---|---|---|---|---|
| 57 | | [5-(2-Amino-ethoxy)-1,3-dihydro-isoindol-2-yl]-(2,4-dihydroxy-5-isopropyl-phenyl)-methanone | As for Example 34, A2 (from 2,4-bis-benzyloxy-5-isopropenyl-benzoic acid (Preparation B5) and 5-hydroxy-isoindoline), alkylation using 3-(BOC-amino)ethyl tosylate, then A5. Final BOC deprotection using saturated HCl/EtOAc (Example 18). | $^1$H NMR (Me-$d_3$-OD) 8.55 (1H, s), 7.30-7.20 (1H, m), 7.15 (1H, s), 7.05-6.95 (2H, m), 6.40 (1H, s), 4.95-4.80 (4H, m) 4.25 (2H, t), 3.35 (2H, t), 3.25-3.15 (1H, m), 1.25 (6H, d) | MS: [M + H]$^+$ 357 |

-continued

| Example Number | Compound | Chemical Name | Method | N.M.R. Data | M.S. |
|---|---|---|---|---|---|
| 58 | | (2,4-Dihydroxy-5-isopropyl-phenyl)-(5-hydroxy-1,3-dihydro-isoindol-2-yl)-methanone | Isolated as a bi-product from synthesis of Example 57. | $^1$H NMR (Me-d$_3$-OD) 7.20 (1H, s), 7.15-7.05 (1H, m), 6.80-6.70 (2H, m), 6.40 (1H, s), 4.95-4.80 (4H, m), 3.25-3.15 (1H, m), 1.25 (6H, d) | MS: [M + H]$^+$ 314 |
| 59 | | (2,4-Dihydroxy-5-isopropyl-phenyl)-{5-[4-(2-hydroxy-ethyl)-piperazin-1-yl]-1,3-dihydro-isoindol-2-yl}-methanone | As for Example 51, using N-(2-hydroxyethyl)-piperazine in the Buchwald reaction. | $^1$H NMR (DMSO-d$_6$) 10.40 (1H, br s), 9.65 (1H, br s), 7.40-7.15 (1H, m), 7.05 (1H, s), 7.05-6.90 (2H, m), 6.45 (1H, s), 4.80-4.60 (4H, m), 3.85-3.70 (4H, m), 3.65-3.55 (2H, m), 3.25-3.05 (7H, m), 1.15 (6H, d) | MS: [M + H]$^+$ 426 |
| 60 | | (2,4-Dihydroxy-5-isopropyl-phenyl)-[5-(4-morpholin-4-yl-piperidin-1-yl)-1,3-dihydro-isoindol-2-yl]-methanone | As for Example 51, using 4-morpholino-piperidine in the Buchwald reaction. | $^1$H NMR (DMSO-d$_6$) 11.10 (1H, br s), 9.65 (1H, br s), 7.30-7.05 (3H, m), 7.03 (1H, s), 6.45 (1H, s), 4.80-4.65 (4H, m), 4.0-3.95 (2H, m), 3.90-3.75 (4H, m), 3.50-3.40 (2H, m), 3.40-3.30 (1H, m), 3.15-3.03 (3H, m), 2.90-2.75 (2H, m), 2.25-2.15 (2H, m), 1.95-1.80 (2H, m), 1.15 (6H, d) | MS: [M + H]$^+$ 466 |

-continued

| Example Number | Compound | Chemical Name | Method | N.M.R. Data | M.S. |
|---|---|---|---|---|---|
| 61 | (structure) | (2,4-Dihydroxy-5-isopropyl-phenyl)-[5-(1-methyl-piperidin-4-ylamino)-1,3-dihydro-isoindol-2-yl]-methanone | As for Example 51, using 4-amino-1-methyl-piperidine in the Buchwald reaction. | $^1$H NMR (DMSO-$d_6$) 10.60 (1H, br s), 9.65 (1H, br s), 7.20 (1H, m), 7.03 (1H, s), 6.95-6.80 (2H, m), 6.45 (1H, s), 4.80-4.65 (4H, m), 3.45 (2H, m), 3.25 (1H, m), 3.10 (1H, m), 3.00 (2H, m), 2.70 (3H, d), 2.15-2.05 (2H, m), 1.90-1.75 (2H, m), 1.15 (6H, d) | MS: [M + H]$^+$ 410 |
| 62 | (structure) | (2,4-Dihydroxy-5-isopropyl-phenyl)-[5-(4-isopropyl-piperazin-1-yl)-1,3-dihydro-isoindol-2-yl]-methanone | As for Example 51, using i-propyl-piperazine in the Buchwald reaction. | $^1$H NMR (DMSO-$d_6$) 10.70 (1H, br s), 9.65 (1H, br s), 7.25-7.10 (1H, m), 7.05 (1H, s), 7.00-6.90 (2H, m), 6.45 (1H, s), 4.80-4.60 (4H, m), 3.80 (2H, m), 3.55-3.40 (3H, m), 3.23-3.05 (5H, m), 1.33 (6H, d), 1.15 (6H, d) | MS: [M + H]$^+$ 424 |
| 63 | (structure) | (2,4-Dihydroxy-5-isopropyl-phenyl)-(5-piperazin-1-yl-1,3-dihydro-isoindol-2-yl)-methanone | As for Example 51, using Boc-piperazine in the Buchwald reaction. Boc deprotection using saturated HCl/dioxane (Example 18). | $^1$H NMR (DMSO-$d_6$) 9.70 (1H, br s), 9.25 (2H, br s), 7.23 (1H, br m), 7.05 (1H, s), 7.00-6.90 (2H, m), 6.45 (1H, s), 4.80-4.60 (4H, m), 3.35 (4H, m), 3.20 (4H, m), 3.10 (1H, m), 1.15 (6H, d) | MS: [M + H]$^+$ 382 |

| Example Number | Compound | Chemical Name | Method | N.M.R. Data | M.S. |
|---|---|---|---|---|---|
| 64 | | 4-[2-(2,4-Dihydroxy-5-isopropyl-benzoyl)-2,3-dihydro-1H-isoindol-5-ylamino]-piperidine-1-carboxylic acid tert-butyl ester | As for Example 51, using 1-Boc-4-amino-piperidine in the Buchwald reaciton. | $^1$H NMR (Me-d$_3$-OD) 7.20 (1H, s), 7.05 (1H, m), 6.65-6.55 (2H, m), 6.35 (1H, s), 4.85-4.75 (4H, m), 4.05 (2H, m), 3.50 (1H, m), 3.20 (1H, m), 3.00 (2H, m), 2.00 (2H, m), 1.5 (9H, s), 1.30 (2H, m), 1.15 (6H, d) | MS: [M + H]$^+$ 496 |
| 65 | | (2,4-dihydroxy-5-isopropyl-phenyl)-[5-(piperidin-4-ylamino)-1,3-dihydro-isoindol-2-yl]-methanone | BOC deprotection using saturated HCl/EtOAC (Example 18). | $^1$H NMR (DMSO-d$_6$) 7.05 (1H, s), 7.00 (1H, m), 6.55-6.45 (2H, m), 6.40 (1H, s), 4.70-4.60 (4H, m), 3.25 (1H, m), 3.10 (1H, m), 2.95 (2H, m), 2.45 (2H, m), 1.85 (2H, m), 1.75 (3H, s), 1.20 (2H, m), 1.15 (6H, d) | MS: [M + H]$^+$ 396 |
| 66 | | (2,4-dihydroxy-5-isopropyl-phenyl)-[4-(4-methyl-piperazin-1-yl)-1,3-dihydro-isoindol-2-yl]-methanone | As for Example 51, using (2,4-bis-benzyloxy-5-isopropenyl-phenyl)-(4-bromo-1,3-dihydro-isoindol-2-yl)-methanone (Prep: A2 between 2,4-bis-benzyloxy-5-isopropenyl-benzoic acid and 4-bromo-1,3-dihydro-1H-isoindoline) and N-methyl-piperazine in the Buchwald reaction. | $^1$H NMR (Me-d$_3$-OD) 7.35-7.18 (2H, m), 7.10-6.95 (2H, m), 6.95-6.85 (2H, m), 6.40 (1H, s), 4.95-4.85 (4H, m), 3.25 (1H, m), 3.20-3.05 (4H, m), 3.05-2.80 (4H, m), 2.60 (3H, m), 2.00 (3H, s), 1.25 (6H, d) | MS: [M + H]$^+$ 396 |

| Example Number | Compound | Chemical Name | Method | N.M.R. Data | M.S. |
|---|---|---|---|---|---|
| 67 | | (2,4-dihydroxy-5-isopropyl-phenyl)-[4-(piperidin-4-ylamino)-1,3-dihydro-isoindol-2-yl]-methanone | As for Example 65, using 1-Boc-4-amino-piperidine in the Buchwald reaction, followed by Boc deprotection using saturated HCl/EtOAc (Example 18). | $^1$H NMR (DMSO-d$_6$) 7.05 (1H, s), 7.00 (1H, m), 6.55-6.45 (2H, m), 6.40 (1H, s), 4.70-4.60 (4H, m), 3.25 (1H, m), 3.10 (1H, m), 2.95 (2H, m), 2.45 (2H, m), 1.85 (2H, m), 1.75 (3H, s), 1.20 (2H, m), 1.15 (6H, d) | MS: [M + H]$^+$ 396 |
| 68 | | (2,4-Dihydroxy-5-isopropyl-phenyl)-(5-dimethylaminomethyl-1,3dihydro-isoindol-2-yl)-methanone | A2 and A5. From 2,4-bis-benzyloxy-5-isopropenyl-benzoic acid (B5, and (2,3-dihydro-1H-isoindol-5-ylmethyl)-dimethyl-amine (Preparation A1) | $^1$H NMR (Me-d$_3$-OD) 7.26-7.12 (3H, m), 7.07 (1H, s), 6.27 (1H, s), 4.85-4.77 (4H, br s), 3.40 (2H, s), 3.15-3.05 (1H, m), 2.15 (6H, s), 1.11 (6H, d) | MS: [M + H]+ 355 |
| 69 | | (2,4-Dihydroxy-5-isopropyl-phenyl)-[5-(4-methyl-piperazine-1-carbonyl)-1,3-dihydro-isoindol-2-yl]-methanone | A2 and A5. From 2-(2,4-bis-benzyloxy-5-isopropyl-benzoyl)-2,3-dihydro-1H-isoindole-5-carboxylic acid (D6) and N-methyl piperazine | $^1$H NMR (Me-d$_3$-OD) 7.60-7.38 (3H, m), 7.19 (1H, s), 6.39 (1H, s), 4.96 (4H, m), 3.85-3.71 (2H, br s), 3.54-3.4 (2H, br s), 3.26-3.15 (1H, m), 2.59-2.39 (4H, br d), 2.34 (3H, s), 1.23 (6H, d) | MS: [M + H]$^+$ 424 |

| Example Number | Compound | Chemical Name | Method | N.M.R. Data | M.S. |
|---|---|---|---|---|---|
| 70 | | (2,4-Dihydroxy-5-isopropyl-phenyl)-{5-[2-(2,2-dimethyl-propylamino)-ethoxy]-1,3-dihydro-isoindol-2-yl}-methanone | As for the synthesis of (2,4-dihydroxy-5-isopropyl-phenyl)-[5-(2-isopropylamino-ethoxy)-1,3-dihydro-isoindol-2-yl]-methanone except using trimethyl acetaldehyde instead of acetone. Purified by preparative HPLC. | $^1$H NMR (Me-d$_3$-OD) 7.28 (1H, br s); 7.20 (1H, s); 7.00 (2H, br m); 6.40 (1H, s); 4.35 (2H, t); 3.50 (2H, t); 3.20 (1H, m); 3.00 (2H, s); 1.23 (6H, d); 1.10 (9H, s) | MS: [M + H]$^+$ 427 |
| 71 | | [5-(2-Cyclopentyl-amino-ethoxy0-1,3-dihydro-isoindol-2-yl]-(2,4-dihydroxy-5-isopropyl-phenyl)-methanone | As for the synthesis of (2,4-dihydroxy-5-isopropyl-phenyl)-[5-(2-isopropylamino-ethoxy)-1,3-dihydro-isoindol-2-yl]-methanone except using cyclopentanone instead of acetone. Purified by preparative HPLC. | $^1$H NMR (DMSO-d$_6$) 10.05 (1H, br s); 9.60 (1H, br s); 7.23 (1H, br s); 7.05 (1H, s); 6.95 (1H, br s); 6.88 (1H, br d); 6.40 (1H, s); 4.72 (4H, br m); 4.02 (2H, t); 3.10 (2H, m); 2.93 (2H, t); 1.78 (2H, m); 1.63 (2H, m); 1.48 (2H, m); 1.35 (2H, m); 1.15 (6H, d) | MS: [M + H]$^+$ 425 |
| 72 | | (2,4-Dihydroxy-5-isopropyl-phenyl)-(5-piperidin-1-ylmethyl-1,3-dihydro-isoindol-2-yl)-methanone | As for the synthesis of (2,4-dihydroxy-5-isopropyl-phenyl)-[5-(4-methyl-piperazin-1-ylmethyl)-1,3-dihydro-isoindol-2-yl]-methanone (Example 56) except using piperidine instead of N-methyl-piperazine. | $^1$H NMR (Me-d$_3$-OD) 7.35-7.24 (3H, m), 7.19 (1H, s), 6.39 (1H, s), 4.94-4.49 (4H, br s), 3.54 (2H, s), 3.27-3.18 (1H, m), 2.51-2.41 (4H, br s), 1.66-1.58 (4h br m), 1.53-1.42 (2H, br s), 1.23 (6H, d). | MS: [M + H]$^+$ 395. |

| Example Number | Compound | Chemical Name | Method | N.M.R. Data | M.S. |
|---|---|---|---|---|---|
| 73 | | (2,4-Dihydroxy-5-isopropyl-phenyl)-[5-(4-hydroxypiperidin-4-yl)-1,3-dihydro-isoindol-2-yl]-methanone | As for the synthesis of (2,4-dihydroxy-5-isopropyl-phenyl)-[5-(4-hydroxy-1-methyl-piperidin-4-yl)-1,3-dihydro-isoindol-2-yl]-methanone (Example 50) except using N-benzyloxy-carbonyl-piperidin-4-one in step 2. | $^1$H NMR (Me-d$_3$-OD) 7.47 (2H, m), 7.30 (1H, br m) 7.20 (1H, s), 6.40 (1H, s), 4.90 (4H, d), 3.22 (1H, m), 3.15 (2H, m), 2.95 (2H, m), 2.05 (2H, m), 1.75 (2H, m), 1.25 (6H, d) | MS: [M + H]$^+$ 397 |
| 74 | | (5-chloro-6-hydroxy-1,3-dihydro-isoindol-2-yl)-(2,4-dihydroxy-5-isopropyl-phenyl)-methanone | Isolated as a bi-product during the preparation of Example 33. | $^1$H NMR (DMSO-d$_6$) 10.00 (1H, s), 9.58 (1H, s), 7.48-7.38 (1H, m), 7.02 (1H, s), 7.97-6.85 (1H, m), 6.40 (1H, s), 4.68 (4H, br s), 3.10 (1H, m), 1.15 (6H, d) | MS: [M + H]+ 348 |

Example 75

(5-Chloro-2,4-dihydroxy-phenyl)-[5-(4-methyl-piperazin-1-yl)-1,3-dihydro-isoindol-2-yl]-methanone

75A. 5-(4-Methyl-piperazin-1-yl)-1,3-dihydro-isoindole-2-carboxylic acid tert-butyl ester

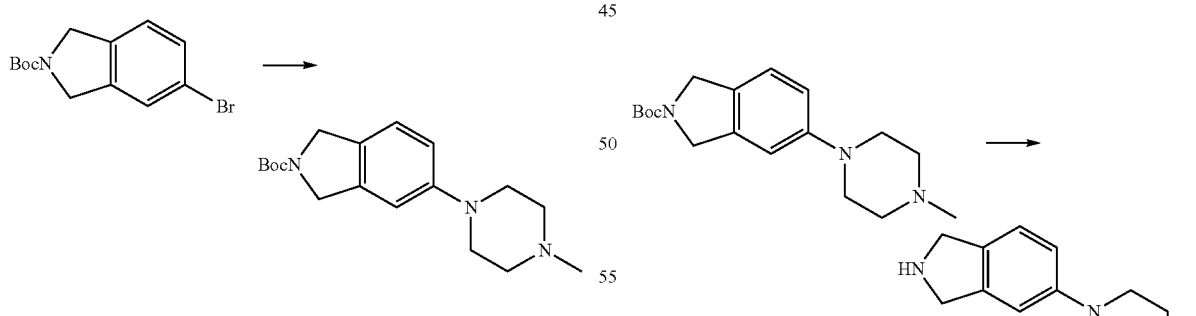

5-Bromo-1,3-dihydro-isoindole-2-carboxylic acid tert-butyl ester (2.97 g, 10 mmol) was azeotropically dried by evaporation from toluene. Tris(dibenzylideneacetone)dipalladium (0) (228 mg, 0.25 mmol), 2-(di-tert-butylphosphino)biphenyl (149 mg, 0.50 mmol) and sodium tert-butoxide (1.34 g, 13.9 mmol) were added and the flask was purged with nitrogen. Toluene (25 mL) then N-methylpiperazine (1.33 mL, 12 mmol) were added and the mixture was heated to 80° C. for 2 hours. After allowing to cool to r.t. the mixture was diluted with ether, filtered through Celite and concentrated to give a residue that was purified by flash chromatography on silica (2M methanolic ammonia/dichloromethane, 1% to 3% gradient). This afforded the title compound as a brown solid (1.45 g, 46%). $^1$H NMR (MeOH-d$_4$) 7.15 (1H, m), 6.94-6.88 (2H, m), 4.60-4.54 (4H, m), 3.20-3.17 (4H, m), 2.63-2.60 (4H, m), 2.34 (3H, s), 1.52 (9H, s). MS: [M+H]$^+$ 318.

75B. 5-(4-Methyl-piperazin-1-yl)-2,3-dihydro-1H-isoindole dihydrochloride 5-(4-Methyl-piperazin-1-yl)-1,3-dihydro-isoindole-2-carboxylic acid tert-butyl ester (247 mg, 0.78 mmol) was treated with 4M HCl in dioxane (4 mL, 4 mmol) for 24 hours. Concentration in vacuo afforded the title compound quantitatively, which was used directly in the coupling reaction. $^1$H NMR (DMSO-d$_6$) 11.13 (1H, br.s), 9.99 (2H, br.s), 7.27 (1H, d), 7.02-7.00 (2H, m), 4.43-4.37 (4H, m), 3.82-3.75 (2H, m), 3.49-3.43 (2H, m), 3.15-3.10 (4H, m), 2.79-2.78 (3H, s), 1.52 (9H, s). MS: [M+H]+ 218.

75C. (5-Chloro-2,4-dihydroxy-phenyl)-[5-(4-methyl-piperazin-1-yl)-1,3-dihydro-isoindol-2-yl]-methanone

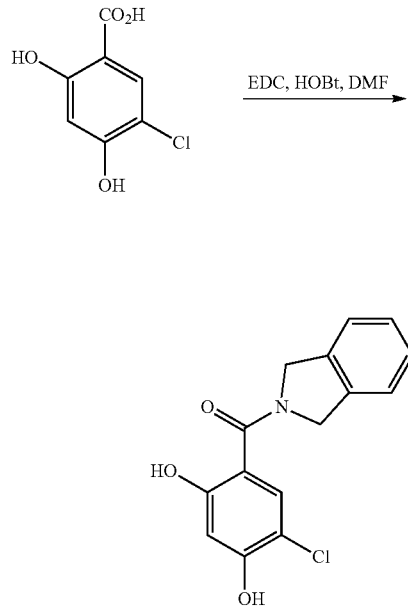

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 min, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried (MgSO4), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). $^1$H NMR (DMSO-d$_6$) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]+ 386/388.

Example 76

(2,4-dihydroxy-5-isopropyl-phenyl)-[5-(4-methyl-piperazin-1-yl)-1,3-di-hydro-isoindol-2-yl]-methanone

76A. Synthesis of (2,4-bis-benzyloxy-5-isopropenyl-phenyl)-(5-bromo-1,3-dihydro-isoindol-2-yl)-methanone

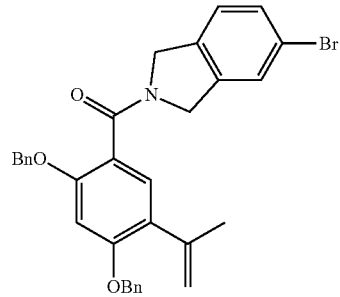 [SMILES: C=C(C)c1cc(C(=O)N2Cc3ccc(Br)cc3C2)c(OCc2ccccc2)cc1OCc1ccccc1]

Coupling of 2,4-bis-benzyloxy-5-isopropenyl-benzoic acid (5.0 g, 13.4 mmol) (Preparation B9) and 5-bromo-2,3-dihydro-1H-isoindole (Preparation C20) was completed according to method A4, using CH$_2$Cl$_2$ as the reaction solvent to give the title compound (8.34 g) as a beige solid.

76B. Synthesis of (2,4-bis-benzyloxy-5-isopropenyl-phenyl)-[5-(4-methyl-piperazin-1-yl)-1,3-dihydro-isoindol-2-yl]-methanone

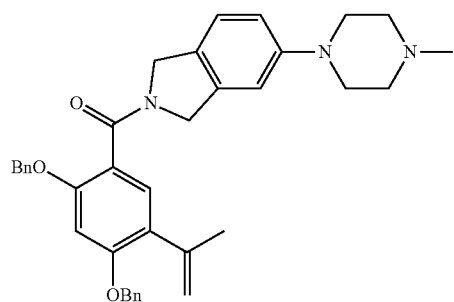 [SMILES: C=C(C)c1cc(C(=O)N2Cc3ccc(N4CCN(C)CC4)cc3C2)c(OCc2ccccc2)cc1OCc1ccccc1]

To a mixture of (2,4-bis-benzyloxy-5-isopropenyl-phenyl)-(5-bromo-1,3-dihydro-isoindol-2-yl)-methanone (8.30 g, 15.0 mmol), 2-(di-t-butylphosphino)biphenyl (223 mg, 0.75 mmol), tris(dibenzylideneacetone)dipalladium (344 mg, 0.38 mmol), sodium tert-butoxide (2.17 g, 22.5 mmol) and 1-methyl-piperazine (2.16 mL, 19.5 mmol) under a N$_2$ atmosphere was added anhydrous toluene (100 mL). The mixture was taken to 80° C. and heated at this temperature for 16 h. The mixture was allowed to cool to ambient temperature, diluted with ether (150 mL) and filtered through a plug of Celite, washing with ether. The filtrate was reduced in vacuo and the residue purified by column chromatography using an eluant of $CH_2Cl_2$-DMAW120 (1:0-0:1) to give the title compound (9.39 g) as a red gum.

76C. (2,4-dihydroxy-5-isopropyl-phenyl)-[5-(4-methyl-piperazin-1-yl)-1,3-di-hydro-isoindol-2-yl]-methanone

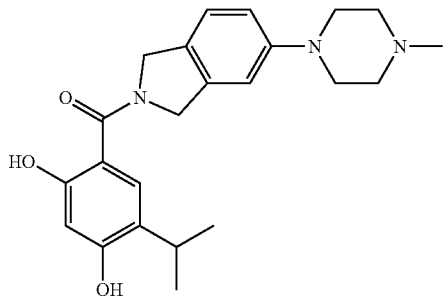 [SMILES: CC(C)c1cc(C(=O)N2Cc3ccc(N4CCN(C)CC4)cc3C2)c(O)cc1O]

A mixture of (2,4-bis-benzyloxy-5-isopropenyl-phenyl)-[5-(4-methyl-piperazin-1-yl)-1,3-dihydro-isoindol-2-yl]-methanone (8.61 g, 15.0 mmol) and 10% Pd/C (1.0 g) in methanol (200 mL) was stirred vigorously under a hydrogen atmosphere (~1 atm) for 18 h at ambient temperature. The mixture was filtered through a plug of Celite and reduced in vacuo to give a purple oil. This residue was purified by column chromatography using an eluant of DMAW120 to give the title compound as its acetate salt. This salt was taken up in MeOH (30 mL) and to the solution was added saturated HCl in EtOAc (20 mL). This mixture was stirred at ambient for 2 h and the solid formed collected by filtration and dried in vacuo to give the title compound as its hydrochloride salt (2.64 g) as a white solid.

Example 77

(5-Chloro-2,4-dihydroxy-phenyl)-[5-(4-methyl-piperazin-1-yl)-1,3-dihydro-isoindol-2-yl]-methanone

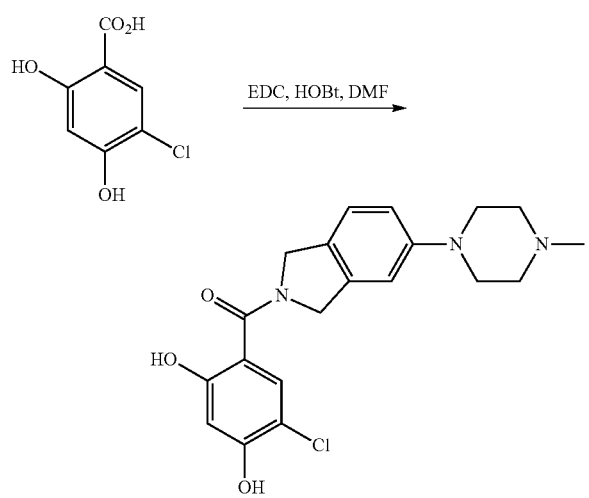

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 minutes, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried ($MgSO_4$), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). $^1$H NMR (DMSO-$d_6$) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]$^+$ 386/388.

Example 78

Alternative Synthesis of (2,4-Dihydroxy-5-isopropyl-phenyl)-[5-(4-hydroxy-1-methyl-piperidin-4-yl)-1,3-dihydro-isoindol-2-yl]-methasone

78A. 5-bromo-2-trityl-2,3-dihydro-1H-isoindole

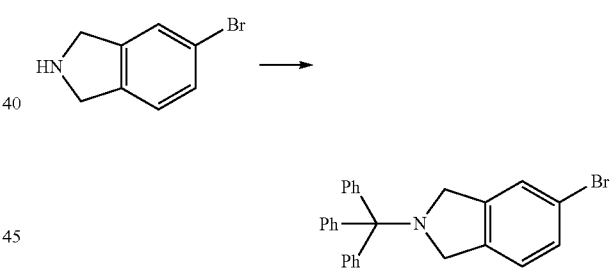

Trityl chloride (2.30 g, 8.23 mmol) was added to a solution of 5-bromo-2,3-dihydro-1H-isoindole (1.64 g, 8.23 mmol) and triethylamine (1.4 mL, 9.9 mmol) in dichloromethane (20 mL). After 18 hours the solvent was removed in vacuo, the residue taken up in ethyl acetate and washed with water (×2) and brine, dried ($MgSO_4$) and concentrated. The crude material was purified by flash chromatography on silica eluting with 1% triethylamine/10% ethyl acetate/petrol to give 5-bromo-2-trityl-2,3-dihydro-1H-isoindole as a reddish-brown solid (3.10 g, 85%). $^1$H NMR (CDCl$_3$) 7.91-7.84 (1H, m), 7.57 (6H, d), 7.45-7.41 (1H, m), 7.33-7.14 (9H, m), 6.95 (1H, d), 3.90 (2H, s), 3.86 (2H, s). MS: Ph$_3$C$^+$ 243.

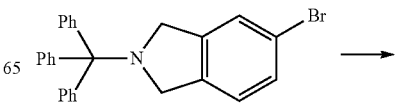

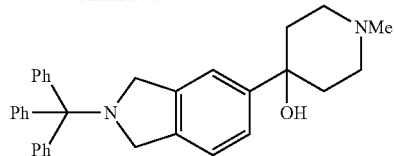

Under nitrogen, a solution of 5-bromo-2-trityl-2,3-dihydro-1H-isoindole (2.03 g, 4.6 mmol) in THF (20 mL) was cooled to −78° C. n-Butyllithium solution (2.5M in hexanes, 2.0 mL, 5 mmol) was added over 5 minutes, then after 10 minutes, 1-methyl-4-piperidone was added dropwise. After a further hour, the cooling bath was removed and the reaction quenched with sodium bicarbonate solution. The mixture was extracted with ethyl acetate then the organic phase was washed with brine, dried (MgSO$_4$) and concentrated. The residue was purified by flash chromatography on silica (gradient elution with 2M methanolic ammonia/dichloromethane, 0% to 5%) to afford 1-methyl-4-(2-trityl-2,3-dihydro-1H-isoindol-5-yl)-piperidin-4-ol as a pink foam (1.25 g, 57%). $^1$H NMR (MeOH-d$_4$) 7.56 (6H, dd), 7.28 (6H, t), 7.25-7.21 (2H, m), 7.15 (3H, t), 7.03 (1H, d), 3.92 (2H, s), 3.91 (2H, s), 2.70 (2H, d), 2.53 (2H, td), 2.33 (3H, s), 2.06 (2H, td), 1.70 (2H, d). MS: [M+H]$^+$ 475.

78C. 4-(2,3-Dihydro-1H-isoindol-5-yl)-1-methyl-piperidin-4-ol dihydrochloride

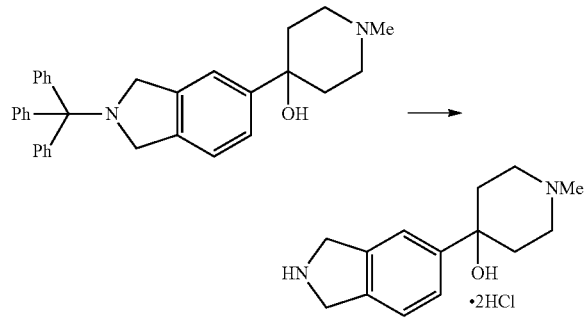

A mixture of 1-methyl-4-(2-trityl-2,3-dihydro-1H-isoindol-5-yl)-piperidin-4-ol (1.42 g, 3.0 mmol), 5N hydrochloric acid (5 mL) and methanol (10 mL) was placed under nitrogen then heated to reflux for 80 minutes. After cooling, the mixture was concentrated in vacuo to remove methanol, diluted with water and washed with ethyl acetate (×2). The aqueous phase was concentrated to dryness to afford the title compound in quantitative yield as a black solid. $^1$H NMR (MeOH-d$_4$) 7.62 (1H, s), 7.57 (1H, d), 7.45 (1H, d), 4.64 (2H, s), 4.63 (2H, s), 3.49-3.46 (4H, m), 2.95 (3H, s), 2.40-2.32 (2H, m), 1.97 (2H, dd).

78D. (2,4-Bis-benzyloxy-5-isopropenyl-phenyl)-[5-(4-hydroxy-1-methyl-piperidin-4-yl)-1,3-dihydro-isoindol-2-yl]-methanone

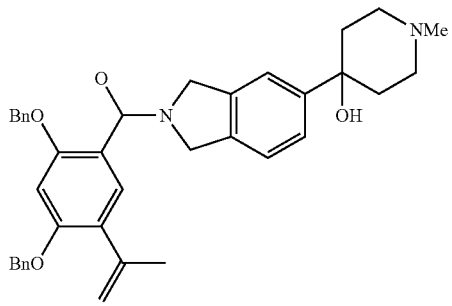 [SMILES: C=C(C)c1cc(C(O)N2Cc3ccc(C4(O)CCN(C)CC4)cc3C2)c(OCc2ccccc2)cc1OCc1ccccc1]

2,4-Bis-benzyloxy-5-isopropenyl-benzoic acid (1.65 g, 4.4 mmol), 1-[3-(dimethylamino)propyl)]-3-ethylcarbodiimide hydrochloride (843 mg, 4.4 mmol) and 1-hydroxybenzotriazole (595 mg, 4.4 mmol) were dissolved in DMF (20 mL). After 35 minutes, the solution was added to a suspension of 4-(2,3-dihydro-1H-isoindol-5-yl)-1-methyl-piperidin-4-ol dihydrochloride (1.22 g, 4.0 mmol) in DMF (5 mL) and triethylamine (1.4 mL, 10 mmol). The mixture was stirred for 3 hours then concentrated in vacuo. The residue was taken up in ethyl acetate and washed with a mixture of water (adjusted to pH 14 with 2N sodium hydroxide solution) and brine. The aqueous phase was extracted twice further with ethyl acetate then the combined organic extracts were washed with sodium bicarbonate solution and brine, dried (MgSO$_4$) and concentrated. The crude product was purified by flash chromatography (gradient elution with 2M methanolic ammonia/dichloromethane, 2% to 10%) to afford the title compound as a brown foam (1.62 g, 69%). $^1$H NMR (methanol-d$_4$) 7.51-7.14 (14H, m), 6.85 (0.5H, s), 6.84 (0.5H, s), 5.16 (2H, s), 5.15 (2H, s), 5.10-5.08 (1H, m), 5.07-5.05 (1H, m), 4.87 (1H, s), 4.86 (1H, s), 4.61 (2H, br.s), 2.78-2.70 (2H, m), 2.57 (1H, td), 2.54 (1H, td), 2.36 (1.5H, s), 2.34 (1.5H, s), 2.16-2.05 (5H, m including 2.09 (3H, s)), 1.78-1.70 (2H, m). MS: [M+H]$^+$ 589.

78E. (2,4-Dihydroxy-5-isopropyl-phenyl)-[5-(4-hydroxy-1-methyl-piperidin-4-yl)-1,3-dihydro-isoindol-2-yl]-methanone

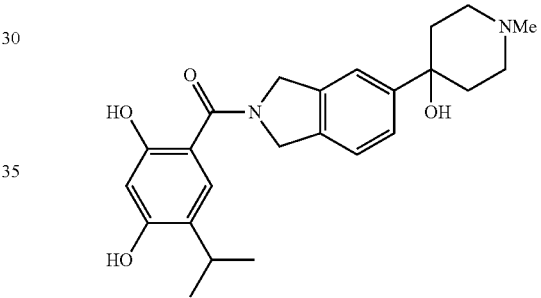

(2,4-Bis-benzyloxy-5-isopropenyl-phenyl)-[5-(4-hydroxy-1-methyl-piperidin-4-yl)-1,3-dihydro-isoindol-2-yl]-methanone (Example 50F) (1.62 g, 2.75 mmol) was dissolved in methanol (50 mL) and hydrogenated at 50° C. over 10% palladium on charcoal using an H-cube hydrogenation apparatus, under free hydrogen conditions. Concentration afforded the title compound (1.14 g, 100%) as a yellow solid, the NMR and mass spectrometric data of which were as set out in Example 50E.

Example 79

(2,4-Dihydroxy-5-isopropyl-phenyl)-[5-(2-dimethylamino-ethoxy)-7-methyl-1,3-dihydro-isoindol-2-yl]-methasone 79A. 7-Methyl-2,3-dihydro-1H-isoindol-5-ol hydrobromide

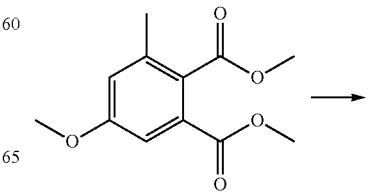

-continued

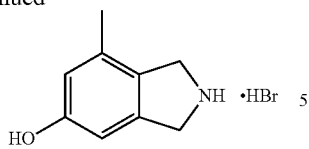

Using the method of preparation C2,5-methoxy-3-methyl-phthalic acid dimethyl ester (prepared according to Tam and Coles, *Synthesis* 1988, 383) was hydrolysed to 5-methoxy-3-methyl-phthalic acid. $^1$H NMR (DMSO-d$_6$) 12.95 (2H, br.s), 7.15 (1H, d), 7.04 (1H, d), 3.80 (3H, s), 2.29 (3H, s). MS: [M–H]$^+$ 209.

5-Methoxy-3-methyl-phthalic acid was converted to 5-methoxy-3-methyl-phthalic anhydride. $^1$H NMR (DMSO-d$_6$) 7.40 (1H, d), 7.34-7.33 (1H, m), 3.94 (3H, s), 2.58 (3H, s).

5-Methoxy-3-methyl-phthalic anhydride was used to prepare 6-methoxy-4-methyl-isoindole-1,3-dione. $^1$H NMR (DMSO-d$_6$) 11.05 (1H, br.s), 7.13 (1H, d), 7.10 (1H, d), 3.88 (3H, s), 2.55 (3H, s). Reduction of 6-methoxy-4-methyl-isoindole-1,3-dione according to the method of preparation C2 afforded 6-methoxy-4-methyl-isoindole. $^1$H NMR (DMSO-d$_6$) 6.64 (1H, s), 6.57 (1H, s), 4.05 (2H, s), 3.96 (2H, s), 3.70 (3H, s), 2.16 (3H, s). MS: [M+H]$^+$ 164. 6-Methoxy-4-methyl-isoindole was demethylated to give the title compound as its hydrobromide salt. $^1$H NMR (DMSO-d$_6$) 9.52 (1H, br.s), 9.29 (2H, br.s), 6.59 (1H, s), 6.56 (1H, s), 4.41 (2H, t), 4.34 (2H, t), 2.17 (3H, s).

79B. (2,4-Bis-benzyloxy-5-isopropenyl-phenyl)-(5-hydroxy-7-methyl-1,3-dihydro-isoindol-2-yl)-methanone

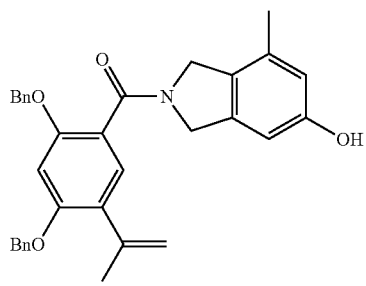 [SMILES: C=C(C)c1cc(C(=O)N2Cc3cc(O)cc(C)c3C2)c(OCc2ccccc2)cc1OCc1ccccc1]

2,4-Bis-benzyloxy-5-isopropenyl-benzoic acid (248 mg, 0.66 mmol), 1-[3-(dimethylamino)propyl)]-3-ethylcarbodiimide hydrochloride (127 mg, 0.66 mmol) and 1-hydroxybenzotriazole (89 mg, 0.66 mmol) were dissolved in DMF (5 mL). After 20 minutes, 7-methyl-2,3-dihydro-1H-isoindol-5-ol hydrobromide (152 mg, 0.66 mmol) and triethylamine (0.14 mL, 0.99 mmol) were added. After a further 3.5 hours the mixture was concentrated in vacuo and the residue was treated with 1N hydrochloric acid and ethyl acetate. The aqueous phase was removed, brine was added and the title compound was collected by filtration as a grey solid (168 mg, 57%). $^1$H NMR (DMSO-d$_6$) 9.30 (0.47H, s), 9.24 (0.53H, s), 7.48-7.25 (10H, m), 7.09 (0.47H, s), 7.08 (0.53H, s), 6.99 (0.47H, s), 6.98 (0.53H, s), 6.56 (0.47H, s), 6.50 (0.53H, s), 6.48 (0.47H, s), 6.44 (0.53H, s), 5.24 (0.47H, s), 5.22 (0.53, s), 5.18 (2H, s), 5.10-5.07 (2H, m), 4.70 (0.47H, s), 4.61 (0.53H, s), 4.46 (0.47H, s), 4.36 (0.53H, s), 2.17 (1.41H, s), 2.04 (3H, s), 1.99 (1.59H, s). MS: [M+H]$^+$ 506.

79B. (2,4-Bis-benzyloxy-5-isopropenyl-phenyl)-[5-(2-dimethylamino-ethoxy)-7-methyl-1,3-dihydro-isoindol-2-yl]-methanone

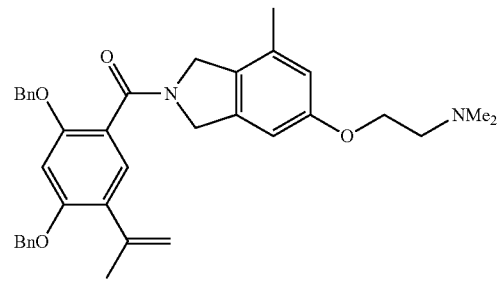 [SMILES: C=C(C)c1cc(C(=O)N2Cc3cc(OCCN(C)C)cc(C)c3C2)c(OCc2ccccc2)cc1OCc1ccccc1]

A mixture of (2,4-bis-benzyloxy-5-isopropenyl-phenyl)-(5-hydroxy-7-methyl-1,3-dihydro-isoindol-2-yl)-methanone (164 mg, 0.32 mmol), potassium carbonate (112 mg, 0.81 mmol) and 2-(dimethylamino)ethyl chloride hydrochloride (93 mg, 0.64 mmol) in DMF (5 mL) was heated at 60° C. for 17 hours then 90° C. for 6 hours. Further portions of potassium carbonate (112 mg, 0.81 mmol) and 2-(dimethylamino)ethyl chloride hydrochloride (93 mg, 0.64 mmol) were added and the mixture maintained at 60° C. for 72 hours and finally, a further 24 hours at 90° C. The mixture was concentrated in vacuo then the residue was partitioned between ethyl acetate and 0.5N aqueous sodium hydroxide. The organic phase was washed with brine (×2), dried (MgSO$_4$) and concentrated to give a residue which was purified by preparative HPLC (acidic method) to afford the title compound as a formate salt (37 mg, 20%). $^1$H NMR (MeOH-d$_4$) 8.51 (1H, br.s), 7.43-7.27 (7H, m), 7.24-7.20 (3H, m), 7.17 (0.5H, s), 7.16 (0.5H, s), 6.85 (0.5H, s), 6.84 (0.5H, s), 6.81 (0.5H, s), 6.77 (0.5H, s), 6.74 (0.5H, s), 6.62 (0.5H, s), 5.16 (1H, s), 5.14 (3H, s), 5.09 (1H, m), 5.06 (1H, m), 4.83 (1H, s), 4.74 (1H, s), 4.60 (1H, s), 4.48 (1H, s), 4.28 (1H, t), 4.23 (1H, t), 3.41 (1H, t), 3.37 (1H, t), 2.84 (3H, s), 2.81 (3H, s), 2.27 (1.5H, s), 2.09 (3H, s), 2.07 (1.5H, s). MS: [M+H]$^+$ 577.

79C. (2,4-Dihydroxy-5-isopropyl-phenyl)-[5-(2-dimethylamino-ethoxy)-7-methyl-1,3-dihydro-isoindol-2-yl]-methanone

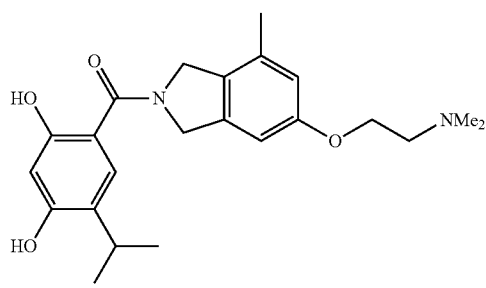 [SMILES: Cc1cc(OCCN(C)C)cc2c1CN(C(=O)c1cc(C(C)C)c(O)cc1O)C2]

(2,4-Bis-benzyloxy-5-isopropenyl-phenyl)-[5-(2-dimethylamino-ethoxy)-1,3-dihydro-isoindol-2-yl]-methanone (37 mg, 0.06 mmol) was hydrogenated in methanol at 50° C.

over 10% palladium on charcoal using an H-cube hydrogenation apparatus, under free hydrogen conditions. The product was purified by preparative HPLC (basic method) to give the title compound as an off-white solid (9 mg, 35%). $^1$H NMR (MeOH-$d_4$) 7.18 (1H, s), 6.77-6.65 (2H, br.m), 6.37 (1H, s), 4.85 (water obscuring $CH_2$), 4.77 (2H, s), 4.08 (2H, t), 3.20 (1H, sept), 2.81 (2H, t), 2.39 (6H, s), 2.22 (3H, br.s), 1.21 (6H, d). MS: $[M+H]^+$ 399.

Biological Activity

Example 80

Isothermal Titration Calorimetry

The ability of the compounds of the invention to bind to human Hsp90 proteins was determined using isothermal titration calorimetry.

Isothermal titration calorimetry (ITC) experiments were performed with a VP-ITC titration calorimeter (Microcal Inc., Northampton, Mass., USA). Cloning, expression, and purification of the Human Hsp90α N-terminal domain were performed according to published methods (Jez, J. M. et al, Chem. Biol. 2003 April; 10(4):361-8.) Solutions of the human Hsp90α N-terminal domain and compound were prepared in a buffer comprising 25 mM Tris, 100 mM NaCl, 1 mM $MgCl_2$, 1 mM TCEP, 5% DMSO, pH 7.4. All solutions were filtered and degassed prior to a titration being carried out. The enthalpy change resulting from each injection of ligand was obtained through integration of the calorimetric signal. Data were analysed using Origin 7.0 (Microcal Software Inc., Northampton, Mass.). Heats of dilution were estimated using the final injections of each individual titration and subtracted before data fitting. Different ITC experimental formats were employed in order to obtain compound dissociation constants (Kd's) over a wide range of affinities. For weakly binding compounds a low c-value ITC method was used (Turnbull W. B. & Daranas A. H. J. Am. Chem. Soc. 2003 Dec. 3; 125(48): 14859-66) in which the protein was present at 10-20 µM in the calorimetric cell and the compound concentration was 1-20 mM in the injection syringe. In this type of experiment the stoichiometry parameter (N) was locked at 1 for data fitting. For Kd's in the 20-0.004 µM range the experiment was configured such that the binding site concentration divided by the Kd (c-value) was between 5 and 1000. For the majority of these experiments the protein concentration in the calorimetric cell was in the range 4-100 µM and the ligand concentration in the injection syringe ranged from 50-1500 µM. In rare cases where compound solubility was limiting, the compound solution was placed in the calorimetric cell and titrated with protein from the injection syringe, maintaining a c-value between 5 and 1000. Competition ITC experiments were used to access Kd's<4 nM by performing the titration in the presence of a weaker binding competitor according to the method described in Sigurskjold B. W. Anal Biochem. 2000 Jan. 15; 277(2):260-6.

The compounds of examples 5, 10, 11, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 52, 53, 54, 55, 59, 60, 61, 62, 63, 65, 66, 67, 68, 69, 70, 71, 72, 73, 74 and 75 were tested and were found to have $K_d$ values of less than 1 micromolar.

The compounds of examples 5, 10, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 53, 54, 55, 59, 60, 61, 62, 63, 65, 66, 67, 68, 69, 70, 71, 72, 73, 74 and 75 have $K_d$ values of less than 0.1 micromolar and most of these compounds have $K_d$ values of less than 0.01 micromolar.

Example 81

Anti-Proliferative Activity

The anti-proliferative activities of compounds of the invention can be determined by measuring the ability of the compounds to inhibition of cell growth in a number of cell lines such as the human colon cancer cell line HCT116. Inhibition of cell growth is measured using the Alamar Blue assay (Nociari, M. M, Shalev, A., Benias, P., Russo, C. Journal of Immunological Methods 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines can be obtained from the ECACC (European Collection of cell Cultures).

The compounds of examples 5, 12, 13, 14, 17, 18, 19, 21, 22, 23, 25, 28, 29, 32, 33, 34, 35, 36, 37, 38, 39, 40, 41, 42, 43, 45, 48, 49, 50, 51, 52, 53, 54, 55, 59, 60, 61, 62, 63, 65, 66, 67, 68, 69, 70, 71, 72, 74 and 75 were tested and were found to have $IC_{50}$ values of less than 1 micromolar against the HCT116 cell line.

Pharmaceutical Formulations

Example 82

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of formula (I) (e.g.

in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

We claim:

1. A combination comprising:
(i) an Hsp90 inhibitor compound of the formula (VII):

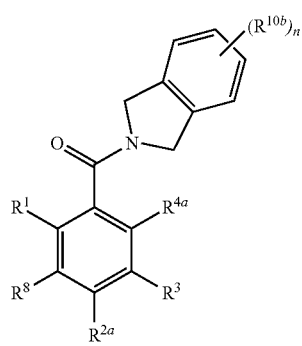

(VII)

or tautomer thereof;
wherein n is 1, 2 or 3;
$R^1$ and $R^{2a}$ are both hydroxy;
$R^3$ is selected from isopropyl and tert-butyl;
$R^{4a}$ is hydrogen;
$R^8$ is hydrogen;
$R^{10b}$ is selected from a group consisting of halogen, OH, $NH_2$, $CH_2OH$, $CH_2NH_2$, O—$C_{1-6}$-alkyl, NH—$C_{1-6}$ alkyl, aryl, heteroaryl, $C_{3-7}$ cycloalkyl, heterocyclyl, O-heteroaryl, O—$C_{3-7}$ cycloalkyl, O-heterocycloalkyl, C(=O)$C_{1-6}$ alkyl, C(=O) O$C_{1-6}$ alkyl, C(=O)$NH_2$, C(=O)NH$C_{1-6}$ alkyl, C(=O)N ($C_{1-6}$ alkyl)$_2$, NH($C_{1-6}$ alkyl), N($C_{1-6}$ alkyl)$_2$, NC(=O)$C_{1-6}$ alkyl, $C_6$ aryl, O$C_6$ aryl, C(=O)$C_6$aryl, C(=O)O$C_6$aryl, C(=O)$NH_2$, C(=O)NH$C_6$aryl, C(=O)N($C_6$ aryl)$_2$, NH($C_6$ aryl), N($C_6$ aryl)$_2$, NC(=O)$C_6$ aryl, $C_{5-6}$ heterocyclyl, O$C_{5-6}$ heterocyclyl, C(=O)$C_{5-6}$ heterocyclyl, C(=O)O$C_{5-6}$ heterocyclyl, C(=O)NH$C_{5-6}$ heterocyclyl, C(=O)N($C_{5-6}$ heterocyclyl)$_2$, NH($C_{5-6}$ heterocyclyl), N($C_{5-6}$ heterocyclyl)$_2$, NC(=O)$C_{5-6}$ heterocyclyl, C(=O)NH$C_{1-6}$ alkyl, $C_{5-6}$ aryl, S(=O)$C_{1-6}$ alkyl, S(=O)N—$C_{1-6}$ alkyl and $SO_2N$—$C_{1-6}$ alkyl; and a group [sol], $CH_2$[sol] or OCH$_2$CH$_2$[sol] where [sol] is selected from the following groups

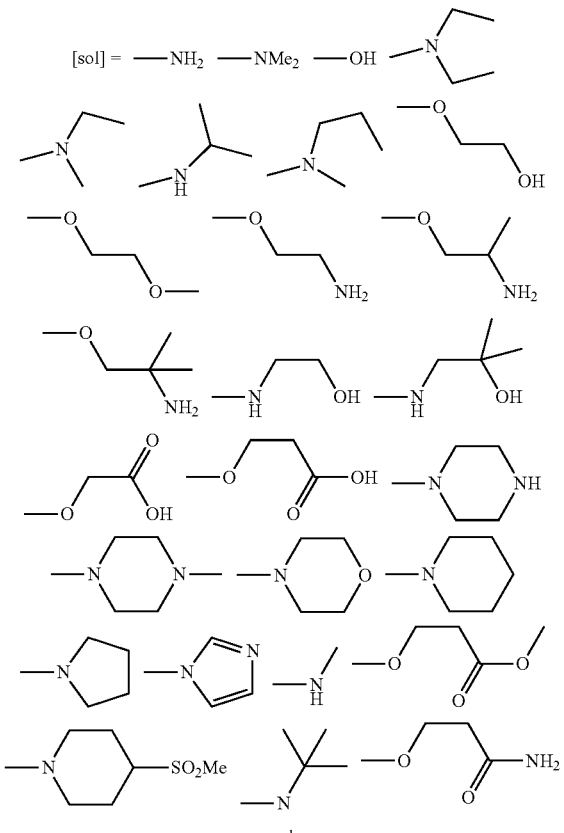

and:

(ii) one or more therapeutic agents selected from topoisomerase I inhibitors; antimetabolites; tubulin targeting agents; DNA binder and topoisomerase II inhibitors; alkylating agents; monoclonal antibodies; anti-hormones; signal transduction inhibitors; proteasome inhibitors; DNA methyl transferases; cytokines; retinoids and HDAC or HAT modulators.

2. A combination according to claim 1 wherein $R^{10b}$ is selected from a group $R^{10c}$ consisting of [sol], $CH_2$[sol] or OCH$_2$CH$_2$[sol] where [sol] is selected from the following groups:

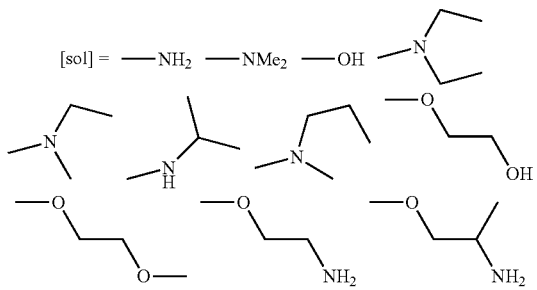

-continued

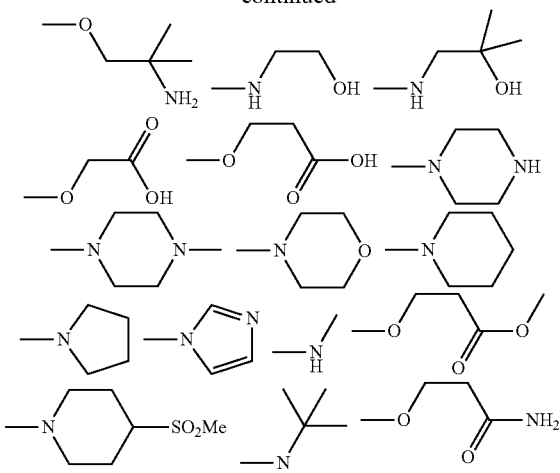

3. A combination according to claim 1 wherein R³ is isopropyl.

4. A combination according to claim 1 wherein n is 1.

5. A combination according to claim 3 wherein n is 1.

6. A combination according to claim 1 wherein the Hsp90 inhibitor compound is selected from:
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-[5-(4-methyl-piperazin-1-yl)-1,3-dihydro-isoindol-2-yl]-methanone;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[5-(1-methyl-piperidin-4-ylamino)-1,3-dihydro-isoindol-2-yl]-methanone;
(2,4-dihydroxy-5-isopropyl-phenyl)-(5-piperazin-1-yl-1,3-dihydro-isoindol-2-yl)-methanone; and
(2,4-dihydroxy-5-isopropyl-phenyl)-(5-dimethylaminomethyl-1,3dihydroisoindol-2-yl)-methanone;
and tautomers thereof.

7. A combination according to claim 6 wherein the Hsp90 inhibitor compound is selected from:
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone; or
(2,4-dihydroxy-5-isopropyl-phenyl)-[5-(1-methyl-piperidin-4-ylamino)-1,3-dihydro-isoindol-2-yl]-methanone;
and tautomers thereof.

8. A combination according to claim 7 wherein the Hsp90 inhibitor compound is:
(2,4-dihydroxy-5-isopropyl-phenyl)-[5-(4-methyl-piperazin-1-ylmethyl)-1,3-dihydro-isoindol-2-yl]-methanone;
and tautomers thereof.

9. A combination according to claim 1 wherein the Hsp90 inhibitor compound is in the form of a salt.

10. A combination according to claim 6 wherein the Hsp90 inhibitor compound is in the form of a salt.

11. A combination according to claim 7 wherein the Hsp90 inhibitor compound is in the form of a salt.

12. A combination according to claim 8 wherein the Hsp90 inhibitor compound is in the form of a salt.

13. A combination according to claim 1 wherein the one or more therapeutic agents are selected from antimetabolites; tubulin targeting agents; alkylating agents; anti-hormones; signal transduction inhibitors and proteasome inhibitors.

14. A combination according to claim 6 wherein the one or more therapeutic agents are selected from antimetabolites; tubulin targeting agents; alkylating agents; anti-hormones; signal transduction inhibitors and proteasome inhibitors.

15. A combination according to claim 8 wherein the one or more therapeutic agents are selected from antimetabolites; tubulin targeting agents; alkylating agents; anti-hormones; signal transduction inhibitors and proteasome inhibitors.

16. A combination according to claim 1 wherein the one or more therapeutic agents comprises an antimetabolite.

17. A combination according to claim 1 wherein the one or more therapeutic agents comprises a tubulin targeting agent.

18. A combination according to claim 1 wherein the one or more therapeutic agents comprises an alkylating agent.

19. A combination according to claim 1 wherein the one or more therapeutic agents comprises an anti-hormone.

20. A combination according to claim 1 wherein the one or more therapeutic agents comprises a signal transduction inhibitor.

21. A combination according to claim 1 wherein the one or more therapeutic agents comprises a proteasome inhibitor.

* * * * *